(12) United States Patent
Simpson et al.

(10) Patent No.: US 10,410,538 B2
(45) Date of Patent: Sep. 10, 2019

(54) SYSTEM AND METHOD FOR EDUCATING USERS, INCLUDING RESPONDING TO PATTERNS

(71) Applicant: DexCom, Inc., San Diego, CA (US)

(72) Inventors: Peter C. Simpson, Cardiff, CA (US); Robert J. Boock, Carlsbad, CA (US); David DeRenzy, San Diego, CA (US); Laura J. Dunn, San Diego, CA (US); Matthew Lawrence Johnson, Encinitas, CA (US); Katherine Yerre Koehler, Solana Beach, CA (US); Apurv Ullas Kamath, San Diego, CA (US); Andrew Attila Pal, San Diego, CA (US); David Price, Carlsbad, CA (US); Eli Reihman, San Diego, CA (US); Mark Wu, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 402 days.

(21) Appl. No.: 15/148,757

(22) Filed: May 6, 2016

(65) Prior Publication Data
US 2016/0324463 A1 Nov. 10, 2016

Related U.S. Application Data

(60) Provisional application No. 62/158,463, filed on May 7, 2015.

(51) Int. Cl.
*A61B 5/1495* (2006.01)
*A61B 5/145* (2006.01)
(Continued)

(52) U.S. Cl.
CPC ............ *G09B 19/00* (2013.01); *A61B 5/0022* (2013.01); *A61B 5/0077* (2013.01);
(Continued)

(58) Field of Classification Search
CPC .. G09B 19/00; G09B 19/0092; A61B 5/0022; A61B 5/0077; A61B 5/1112;
(Continued)

(56) References Cited

U.S. PATENT DOCUMENTS 5,251,126 A * 10/1993 Kahn ............... G01N 35/00871
600/309
7,440,786 B2 * 10/2008 Hockersmith ..... A61B 5/14532
600/316
(Continued)

FOREIGN PATENT DOCUMENTS

WO WO 2012-142502 10/2012

OTHER PUBLICATIONS

Cobellí et al. 2014. Diabetes 63:1203-1213. The Oral Minimal Model Method.
(Continued)

*Primary Examiner* — Navin Natnithithadha
(74) *Attorney, Agent, or Firm* — Knobbe Martens Olson & Bear, LLP

(57) ABSTRACT

Provided are systems and methods using which users may learn and become familiar with the effects of various aspects of their lifestyle on their health, e.g., users may learn about how food and/or exercise affects their glucose level and other physiological parameters, as well as overall health. In some cases the user selects a program to try; in other cases, a computing environment embodying the system suggests programs to try, including on the basis of pattern recognition, i.e., by the computing environment determining how a user could improve a detected pattern in some way. In this way, users such as type II diabetics or even users who are only prediabetic or non-diabetic may learn healthy habits to benefit their health.

11 Claims, 66 Drawing Sheets

(51) Int. Cl.
    *G09B 19/00* (2006.01)
    *G16H 50/50* (2018.01)
    *G16H 15/00* (2018.01)
    *G06F 19/00* (2018.01)
    *A61B 5/11* (2006.01)
    *A61B 5/00* (2006.01)

(52) U.S. Cl.
    CPC ........... *A61B 5/1112* (2013.01); *A61B 5/1118* (2013.01); *A61B 5/1495* (2013.01); *A61B 5/14532* (2013.01); *A61B 5/14546* (2013.01); *A61B 5/486* (2013.01); *A61B 5/4833* (2013.01); *A61B 5/4866* (2013.01); *A61B 5/4872* (2013.01); *A61B 5/742* (2013.01); *A61B 5/7435* (2013.01); *A61B 5/7475* (2013.01); *G06F 19/3456* (2013.01); *G09B 19/0092* (2013.01); *A61B 2562/0219* (2013.01); *G06F 19/3475* (2013.01); *G06F 19/3481* (2013.01); *G16H 15/00* (2018.01); *G16H 50/50* (2018.01); *Y02A 90/26* (2018.01)

(58) Field of Classification Search
    CPC .............. A61B 5/1118; A61B 5/14532; A61B 5/14546; A61B 5/1495; A61B 5/4833; A61B 5/486; A61B 5/4866; A61B 5/4872; A61B 5/742; A61B 5/7435; A61B 2562/0219; G16H 50/50; G16H 15/00; Y02A 90/26; G06F 19/3475; G06F 19/3481
    USPC ......................................... 600/309, 345–365
    See application file for complete search history.

(56) References Cited

U.S. PATENT DOCUMENTS

| | | | |
|---|---|---|---|
| 8,233,959 B2 | 7/2012 | Karnath et al. | |
| 8,690,769 B2 | 4/2014 | Edman et al. | |
| 8,744,828 B2* | 6/2014 | Albisser | G06F 19/3418 703/11 |
| 8,756,043 B2* | 6/2014 | Albisser | A61B 5/14532 703/11 |
| 8,768,673 B2* | 7/2014 | Albisser | G06F 19/3418 703/11 |
| 9,330,237 B2 | 5/2016 | Cohen et al. | |
| 2005/0159656 A1* | 7/2005 | Hockersmith | A61B 5/14532 600/315 |
| 2007/0100222 A1* | 5/2007 | Mastrototaro | A61B 5/01 600/365 |
| 2008/0139910 A1* | 6/2008 | Mastrototaro | G06F 19/3456 600/365 |
| 2009/0076360 A1 | 3/2009 | Brister et al. | |
| 2011/0004085 A1 | 1/2011 | Mensinger et al. | |
| 2011/0024307 A1 | 2/2011 | Simpson et al. | |
| 2011/0077490 A1 | 3/2011 | Simpson et al. | |
| 2012/0227737 A1* | 9/2012 | Mastrototaro | G06F 19/3456 128/203.14 |
| 2013/0053665 A1 | 2/2013 | Hughes et al. | |
| 2013/0338629 A1 | 12/2013 | Agrawal et al. | |
| 2013/0338630 A1 | 12/2013 | Agrawal et al. | |
| 2013/0345663 A1 | 12/2013 | Agrawal et al. | |
| 2014/0107450 A1 | 4/2014 | Simpson et al. | |
| 2014/0118138 A1 | 5/2014 | Cobelli et al. | |
| 2014/0156204 A1 | 6/2014 | Taub et al. | |
| 2014/0213866 A1 | 7/2014 | Simpson et al. | |
| 2014/0278189 A1 | 9/2014 | Vanslyke et al. | |
| 2014/0297246 A1* | 10/2014 | Albisser | A61B 5/14532 703/11 |
| 2014/0303995 A1* | 10/2014 | Albisser | G06F 19/3418 705/2 |
| 2014/0316759 A1* | 10/2014 | Albisser | G06F 19/3418 703/11 |
| 2014/0343861 A1 | 11/2014 | Edman et al. | |
| 2015/0119655 A1 | 4/2015 | Mayou et al. | |
| 2015/0289821 A1 | 10/2015 | Rack-Gomer et al. | |
| 2015/0335272 A1* | 11/2015 | Natale | A61B 5/0022 600/365 |
| 2016/0081597 A1 | 3/2016 | Bhavaraju et al. | |
| 2016/0328990 A1* | 11/2016 | Simpson | A61B 5/742 |
| 2016/0328991 A1* | 11/2016 | Simpson | A61B 5/742 |

OTHER PUBLICATIONS

Kudva et al. 2014. Diabetes Care 37:1184-1190. Closed-Loop Artificial Pancreas Systems: Physiological Input to Enhance Next-Generation Devices.

Schiavon et al. 2014. Diabetes Care 37: 1216-1223. Quantitative Estimation of Insulin Sensitivity in Type 1 Diabetic Subjects Wearing a Sensor-Augmented Insulin Pump.

Zeevi et al. 2015. Cell 163:1079-1094. Personalized Nutrition by Prediction of Glycemic Responses.

* cited by examiner

Current Blood Glucose

Trend Arrow

Status Message

Your blood sugar is
Good

Daily Progress

Today's Time in Goal

90%

Event Logging

What happened 2 hours ago?

Food  Activity  Other

Action Indicator

Act now
to raise your blood sugar

CGM Activity

Go for a short walk

-40 mg/dL   Walk for 30 minutes   >

SYSTEM AND METHOD FOR EDUCATING USERS, INCLUDING RESPONDING TO PATTERNS

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 62/158,463, filed on May 7, 2015. The aforementioned application is incorporated by reference herein in its entirety, and is hereby expressly made a part of this specification.

TECHNICAL FIELD

The present embodiments relate to continuous analyte monitoring, and, in particular, to control of operation of an analyte monitor upon changes in available data in a continuous analyte monitoring system.

BACKGROUND OF THE INVENTION

Diabetes mellitus is a disorder in which the pancreas cannot create sufficient insulin (Type I or insulin-dependent) and/or in which insulin is not effective (Type II or non-insulin-dependent). In the diabetic state, the patient or user suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose—lowering agent accompanied by extraordinary exercise or insufficient food intake.

Conventionally, a person with diabetes carries a self—monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. It is not only unlikely that a person with diabetes will become aware of a dangerous condition in time to counteract it, but it is also likely that he or she will not know whether his or her blood glucose concentration value is going up (higher) or down (lower) based on conventional methods. Diabetics thus may be inhibited from making educated insulin therapy decisions.

Another device that some diabetics used to monitor their blood glucose is a continuous analyte sensor, e.g., a continuous glucose monitor (CGM). A CGM typically includes a sensor that is placed invasively, minimally invasively or non-invasively. The sensor measures the concentration of a given analyte within the body, e.g., glucose, and generates a raw signal using electronics associated with the sensor. The raw signal is converted into an output value that is rendered on a display. The output value that results from the conversion of the raw signal is typically expressed in a form that provides the user with meaningful information, and in which form users have become familiar with analyzing, such as blood glucose expressed in mg/dL.

Commercial CGM systems are designed for Type I patients and/or intensively managed insulin-dependent type II patients. These systems are designed for accuracy and reliability, but are generally expensive and complicated, requiring significant technical knowledge. Such systems commonly provide more information than may be necessary for the broader population, e.g., type II patients on oral medications as well as patients with pre-diabetes, gestational diabetes, and the like.

In addition, many such people are interested not only in control of their diabetes, or in reversing their progression toward diabetes, but also in weight loss, optimizing sports regimes, including participation in performance sports, optimizing diet and food intake, and other aspects. Indeed, such monitoring may be important factors in reversing the progression toward diabetes. While certain current systems allow users to enter data about meals and exercise, such are not integrated into the rest of the monitoring ecosystem, and such systems lack both the technical integration as well as useful ways to utilize such integrated knowledge. In addition, active input of such variables by users is low.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY OF THE INVENTION

Systems and methods according to present principles provide convenient ways in which users may learn and become familiar with the effects of various aspects of their lifestyle on their health. Users may learn about how food and/or exercise affects their glucose level and other physiological parameters, as well as overall health. In some cases, the user selects a program or a challenge to try; in other cases, a computing environment embodying the system suggests programs to try, including on the basis of pattern recognition, i.e., by the computing environment determining how a user could improve a detected pattern in some way. In this way, users such as type II diabetics or even users who are nondiabetic or prediabetic may learn healthy habits to benefit their health. Systems and methods according to present principles address the technical limitations of current systems; in particular, that such systems are not optimized to provide the most effective monitoring to Type II individuals or other more casual users. More specifically, prior systems cannot provide programmatic learning. A system that provides programmatic coaching and self-learning can better engage users and be a more effective tool to achieve the desired benefit and clinical outcomes. Such effectiveness can also reduce certain inefficiencies, causing the computing environment implementing the monitoring to require fewer cycles, causing less battery drain, and so on.

Continuous analyte sensing can also be applied beyond diabetics to general weight loss, wellness, sports optimization, medication management and more. Applications of the systems and methods described are also applicable for non-type-I users, athletes or other users who desire to optimize their training for sports and fitness endeavors. Other applications include weight loss optimization. It will be understood that the systems and methods according to present principles may be applied to any users, including Type I diabetics, Type II diabetics, pre-diabetics, those with gestational diabetes, non-diabetics, users with interests in optimizing sports or fitness routines or eating habits, users interested in losing weight or otherwise increasing their health, or indeed any other user interested in bettering their health or learning more about how their habits and actions affect their health. Other applications will be understood given the description herein.

Systems and methods according to present principles may also be employed to ease the input of event data such as meal and exercise data, making entry of the same more convenient to type II users. In particular, such may be passively determined in a reliable either through additional sensors, e.g., lactate sensor, accelerometer, or via analytics, e.g., pattern recognition of a meal combined with geolocation data.

In a first aspect, the embodiments are directed towards a method of evaluating a user against a program, including: displaying a user interface, the user interface including one or more graphical elements representing respective programs, the one or more programs configured to guide a user in treating diabetes; receiving a selection of a program from the user interface; monitoring and storing glucose concentration data of the user; analyzing the monitored and stored glucose concentration data of the user; evaluating the analyzed glucose concentration data of the user against the selected program; and displaying an output responsive to the evaluating step.

Implementations may include one or more of the following. The displaying a user interface may further include analyzing retrospective data of a user and basing the one or more graphical elements at least in part on the analysis. The method may further include, after the receiving a selection of a program, displaying an indication on the user interface, the indication representing initial guidance for following the program. The displaying an indication may include displaying suggested meals, foods, or recipes, helpful in performing the program; and/or displaying suggested exercise routines helpful in performing the program. The method may further include, after the receiving a selection of a program: displaying one or more graphical elements representing respective subprograms, the one or more subprograms configured to further guide a user in treating the disease; and receiving a selection of a selected subprogram. The monitoring and storing may be performed by a continuous glucose monitor. The method may further include, monitoring other data about the user, and the analyzing or evaluating steps, or both, may be based on the glucose concentration data and the other data. The other data may include activity data, such as where the activity data is received from an accelerometer or GPS device. The activity data may indicate an activity level, where the activity level is selected from the group consisting of: sleeping, sedentary, light activity, medium activity, or strenuous activity. The evaluating may include evaluating an effect of the activity data on the glucose concentration data. The displaying may include displaying the effect of the activity data on the glucose concentration data. The data may include data about one or more other analytes, such as ketones, lactic acid, lactate, glycerol, triglycerides, cortisol, and testosterone.

The glucose concentration data may be measured by a glucose sensor, and the data about one or more other analytes may be received from one or more other analyte sensors, and the one or more other analyte sensors may be calibrated based on a calibration of the glucose sensor.

The other data may include meal data, e.g., received from a social network, user entry, a food app, or photographic data, or inferred from known parameters of the individual and their CGM curve. Meal data may also be inferred beforehand in real time by scanning a meal.

The method may further include, following the receiving of meal data: querying a user to enter a prediction of a measured glucose concentration value following a duration of time; receiving user input of the prediction; subsequent to the duration of time, displaying an indication of the prediction and an actual current measured glucose concentration value.

The analyzing and evaluating may include determining a glycemic impact of the meal data, and the displaying may include displaying the glycemic impact of different meals. The displaying the glycemic impact of different meals may include displaying the different meals in order from lowest to highest or highest to lowest of glycemic impact. The evaluating may include evaluating the effect of the meal data on the glucose concentration data. The evaluating may include comparing the glucose concentration value over time with data about typical or actual mealtimes of the user. The displaying may include displaying an effect of the meal data on the glucose concentration data. The user interface may include at least one graphical element pertaining to a meal program and at least one graphical element pertaining to an exercise program. If the receiving a selection of a program includes receiving a selection of a meal program, then the method may further include displaying one or more graphical elements representing respective subprograms pertaining to different meals, the one or more subprograms configured to further guide a user in treating the disease. The method may further include receiving a selection of one of the respective subprograms, such that the user is instructed to vary a meal choice for a particular meal over a predetermined time period, such as one week.

If the receiving a selection of a program includes receiving a selection of an exercise program, then the method may further include displaying one or more graphical elements representing respective subprograms pertaining to different exercise programs, the one or more subprograms configured to further guide a user in treating the disease. The method may further include receiving a selection of one of the respective subprograms, such that the user is instructed to perform an exercise activity of a predetermined intensity level and/or duration over a predetermined time period. If the receiving a selection of a program includes receiving a selection of an exercise program, then the method may further include: receiving retrospective user data; analyzing the received retrospective user data to determine if a prior user activity similar to the exercise program has been performed, and if a glycemic event has occurred after such determined prior user activity; if a glycemic event has occurred after such determined prior user activity, then determining a suggestion which may be employed to counteract an effect of such glycemic event; and displaying an indication of the suggestion as initial guidance. The monitoring other data may include monitoring metabolism data.

The monitoring of other data may include receiving data from a cloud-connected source, and the cloud-connected source may be a social network, a caregiver network, or a network of diabetes patients. The selected program may be associated with a difficulty level, and the evaluating against the selected program may include evaluating against the associated difficulty level. The difficulty level may be set by the program or by the user.

The output may include a color indicating if a goal associated with the program was met. The output may include an avatar indicating if a goal associated with the program was met. The output may include a trend graph indicating at least a trace signal representing the glucose concentration value over a time period associated with the program. The trend graph further may include a desired glucose concentration value or range of values over the time period. The desired glucose concentration value or range of values may be based on a modeled, ideal, or predicted glucose concentration value or range of values. The selected program may be associated with a difficulty level, and the desired glucose concentration value or range of values may be further based on the difficulty level. The method may further include transmitting the output to a cloud connected entity. The method may further include, prior to a displaying of an actual current measured glucose concentration value, querying a user to enter a prediction of the current glucose concentration value; receiving user input of the prediction; and displaying an indication of the prediction and the actual current measured glucose concentration value. The output may include an indication of a predicted or projected A1C value.

The method may further include determining if the actual current measured glucose concentration value meets predefined criteria; and if the predefined criteria is met, displaying an indication that the predefined criteria has been met. The predefined criteria may be a threshold glucose concentration value or a projected average glucose level or projected A1C.

In a second aspect, the embodiments are directed towards a method of alerting a user to a pattern, and providing a program to address the pattern, including: evaluating user data to determine a pattern; comparing the pattern against a criteria to determine if the determined pattern is a pattern for which improvement is desired; determining a program to improve the pattern; monitoring and storing glucose concentration data of the user; analyzing the monitored and stored glucose concentration data of the user; evaluating the analyzed glucose concentration data of the user against the determined program; and displaying an output responsive to the evaluating step.

Implementations may include one or more of the following.

The determining a program to improve the pattern may further include: determining a set of potential programs to improve the pattern; displaying a user interface, the user interface including one or more graphical elements respectively representing the set of potential programs; and receiving a selection of one of the potential programs from the user interface, where the determined program is defined as the received selection.

The displaying a user interface may further include analyzing retrospective data of a user and basing the user interface at least in part on the analysis. The method may further include, after the step of determining a program, displaying an indication on the user interface, the indication representing initial guidance for following the determined program. The displaying an indication may include: displaying suggested meals, foods, or recipes, helpful in performing the program; and/or displaying suggested exercise routines helpful in performing the program. The monitoring and storing may be performed at least in part by a continuous glucose monitor. The interface may further allow for analyzing potential meals, activities, or actions, in real time, and providing insight on what would happen if the action were taken.

The method may further include monitoring other data about the user, and the analyzing or evaluating steps, or both, may be based on the glucose concentration data and the other data. The other data may include activity data, such as may be received from an accelerometer or a GPS device. The activity data may indicate an activity level, and the activity level may be selected from the group consisting of: sleeping, sedentary, light activity, medium activity, or strenuous activity. The criteria may be received from a cloud-connected source. The evaluating may include evaluating an effect of the activity data on the glucose concentration data. The displaying may include displaying the effect of the activity data on the glucose concentration data. The other data may include data about other analytes, such as ketones, lactic acid, lactate, glycerol, triglycerides, cortisol, and testosterone. The glucose concentration data may be measured by a glucose sensor, and the data about one or more other analytes may be received from one or more other analyte sensors, and the one or more other analyte sensors may be calibrated based on a calibration of the glucose sensor.

The other data may include meal data, such as may be received from a social network, user entry, a food app, or photographic data. The analyzing and evaluating may include determining a glycemic impact of the meal data, and the displaying may include displaying the glycemic impact of different meals. The evaluating may include evaluating an effect of the meal data on the glucose concentration data.

The displaying may include displaying the effect of the meal data on the glucose concentration data, both retrospectively and prospectively (prospectively being the ability to predict a response before it happens). The user interface may include at least one graphical element pertaining to a meal program and at least one graphical element pertaining to an exercise program. If the receiving a selection of a potential program includes receiving a selection of a potential meal program, then the method may further include determining the program to be a meal program. The meal program may be configured to instruct the user to vary a meal choice for a particular meal over a predetermined time period, e.g., one week. If the receiving a selection of a potential program includes receiving a selection of a potential exercise program, then the method may further include determining the program to be an exercise program. The exercise program may be configured to instruct the user to perform an exercise activity of a predetermined intensity level and duration over a predetermined time period, such as over one week. The monitoring other data may include receiving data from a cloud connected source, such as a social network, a caregiver network, or a network of patients. The determined program may be associated with a difficulty level, and the evaluating against the determined program may include evaluating against the associated difficulty level. The difficulty level may be set by the program based at least in part on a retrospective history of the patient. The difficulty level may be selected by the user.

The output may include a color indicating if a goal associated with the program was met. The output may include an avatar indicating if a goal associated with the program was met. The output may include a trend graph indicating at least a trace signal representing the glucose concentration value over a time period associated with the program. The trend graph further may include a desired glucose concentration value or range of values over the time period. The desired glucose concentration value or range of values may be based on a modeled, ideal, or predicted glucose concentration value or range of values. The determined program may be associated with a difficulty level, and the desired glucose concentration value or range of values may be further based on the difficulty level. The evaluated user data may include retrospective glucose concentration data. The evaluated user data may include retrospective meal data. The displaying an output may include displaying an indicator of the determined pattern. The determined pattern may be selected from the group consisting of: overnight lows, postprandial spikes, a type of discriminated fault, a pattern of high glucose variability, a consistent pattern of weekly highs or lows. The method may further include determining a baseline glucose concentration pattern for the user, and the determined pattern may be a consistent variation from the baseline pattern.

The evaluating user data to determine a pattern step may further include initiating a discovery mode, where in the discovery mode, one or more questions are posed on the user interface, user responses to the one or more questions constituting additional user data, and the evaluating user data step further may further include evaluating the additional user data along with the monitored and stored glucose concentration data to determine a pattern.

The additional user data may be meal data, activity data, and so on. The method may further include transmitting the output to a cloud connected entity.

In a third aspect, the embodiments are directed towards a method of optimizing a diabetes therapy involving a medicament, including: receiving data about a first medicament to be ingested by a user in a first regimen; monitoring and storing glucose concentration data of the user; analyzing the monitored and stored glucose concentration data of the user; evaluating the analyzed glucose concentration data of the user against the first regimen; and displaying an output responsive to the evaluating step.

Implementations may include one or more of the following.

The method may further include receiving data from a cloud connected source, the data pertaining to medicaments and/or regimens attempted by a plurality of other users, the plurality of other users determined by having similar demographics to the user, such that the diabetes therapy is optimized for the user in an efficient way. The similar demographics may include one or more similar demographic parameters selected from the group consisting of: age, ethnicity, weight, BMI, and type of diabetes. The evaluating may include determining either the first medicament or the first regimen to be non-optimal for the user, and further including: determining a second medicament or a second regimen, or both, for the user; and displaying an output indicating the second medicament, or the second regimen, or both. The regimen may include data about a dosage of a respective medicament and the timing of ingestion of the respective medicament.

The method may further include monitoring other data about the user, and the analyzing or evaluating steps, or both, may be based on the glucose concentration data and the other data. The other data may include activity data, meal data, or data about other analytes, and the meal data may be received from sources described above. The other data may also include data about job type, education status, age, sex, marital status, buying preferences, ethnic background, history of heart disease, whether the user is a smoker, and so on, all of which being significant predictors of diabetes risk. The data about other analytes may be about the analytes described above. The method may further include determining user compliance with the regimen. The method may further include transmitting an indication of the output to a cloud connected entity, along with demographic data about the user.

In a fourth aspect, the embodiments are directed towards a method of optimizing user activity for sports performance, including: displaying a user interface, the user interface including one or more graphical elements representing respective programs, the one or more programs configured to guide a user in optimizing an exercise routine; receiving a selection of a program from the user interface; monitoring and storing activity data of the user; monitoring and storing an analyte concentration data of the user; analyzing the monitored and stored activity and analyte concentration data of the user; evaluating the analyzed data against the selected program; and displaying an output responsive to the evaluating step.

Implementations may include one or more of the following.

The activity data may indicate an activity level as stratified or categorized in the levels noted above. The analyte may be selected from the group consisting of: glucose, lactic acid, lactate, ketones, glycerol, testosterone, cortisol, and combinations thereof. In some cases two analytes may be measured, a first analyte and a second analyte, the first analyte being glucose measured by a glucose sensor, and the second analyte may be measured by an analyte sensor calibrated based on a calibration of the glucose sensor. In another implementation, the first analyte may be glucose measured by a glucose sensor, and the second analyte may be lactate measured by a lactate sensor. The lactate sensor may be calibrated based on the glucose sensor.

The method may further include monitoring a parameter indicative of a metabolic level of the user, and the evaluating may further include evaluating the metabolic level along with the analyzed data. The activity data may be received from an accelerometer or GPS. The activity data may be received from an exercise machine or a heart rate monitor or the like. The optimizing an exercise routine may include optimizing a building of muscle mass. The optimizing an exercise routine may include optimizing cardiovascular health. The method may further include monitoring other user data, and the evaluating step may further include evaluating the other user data along with the analyzed data. The other data may include a ratio of VCO2 and VO2. The other data may also include meal data received from sources noted above. The displaying may include displaying the effect of the meal data on the exercise routine to be optimized. The selected program may include a goal having predetermined criteria, and the evaluating step may include determining if the analyzed data meets or matches the predetermined criteria. The predetermined criteria may include an envelope of acceptable analyte traces. The analyzed data may be represented by a trace graph, and the predetermined criteria may include whether the trace graph is within the envelope of acceptable analyte traces. The selected program may be associated with a difficulty level, and the evaluating against the selected program may include evaluating against the associated difficulty level. The difficulty level may be set by the program or by the user. The output may include a color or avatar indicating a level of optimization. The output may include a trace graph indicating a level of optimization. The output may include a column, row, or tachometer diagram having a needle pointing at a range corresponding to the output. Where the output indicates metabolism, the diagram may have ranges of: calorie intake greater than calorie expenditure; and calorie intake less than calorie expenditure. The output may indicate whether the metabolism is fat burning or carbohydrate burning. The output may indicate proximity to a lactate threshold. The method may further include transmitting an indication of the output to a cloud connected entity.

In a fifth aspect, the embodiments are directed towards a system for sports optimization, including: a sports sensor; a sports transmitter; and a sports receiver, the sports receiver configured to perform the methods described above.

Implementations may include one or more of the following.

The kit may further include a circuit for determination of activity data. The circuit may include an accelerometer or a module for determination of location data using GPS. The circuit may include a receiver for receiving activity data from an external source, such as a mobile device. The circuit may be disposed within the sports receiver. The circuit may be disposed within the sports transmitter. The analyte may be selected from the group consisting of: glucose, lactic acid, lactate, ketones, glycerol, and combinations thereof.

In a sixth aspect, the embodiments are directed towards a method of optimizing weight loss, including: displaying a user interface, the user interface including one or more graphical elements representing respective programs, the one or more programs configured to guide a user in optimizing weight loss; receiving a selection of a program from the user interface; monitoring and storing meal data of the user; monitoring and storing an analyte concentration data of the user; analyzing the monitored and stored meal data and analyte concentration data of the user; evaluating the analyzed data against the selected program; and displaying an output responsive to the evaluating step.

Implementations may include one or more of the following.

The method may further include monitoring and storing activity data of the user, and where the evaluating further may include evaluating the activity data along with the analyzed data. The analyte may be selected from the group consisting of: glucose, insulin lactic acid, lactate, ketones, glycerol, and combinations thereof. Two analytes may be measured, a first analyte and a second analyte, the first analyte being glucose measured by a glucose sensor, and the second analyte measured by an analyte sensor calibrated based on a calibration of the glucose sensor. The first analyte may be glucose and may be measured by a glucose sensor, and the second analyte may be insulin and may be measured by an insulin sensor, and the output may indicate a measure of calories ingested and calories expended. The method may further include monitoring a parameter indicative of a metabolic level of the user, and the evaluating further may include evaluating the metabolic level along with the analyzed data. The monitoring a parameter indicative of a metabolic level may include receiving data from a metabolic sensor. The metabolic sensor may measure an analyte involved in conversion of food into fat storage or intermediaries between dietary inputs and fat. The analyte involved in conversion of food into fat storage or intermediaries between dietary inputs and fat may be selected from the group consisting of: glucose, glucagon, insulin, glycogen, starch, free fatty acid, triglycerides, monoglycerides, proteins involved in fat storage, glycerol, pyruvate, lipids, acetyl Co A, intermediates in the citric acid cycle, ketone bodies including acetone, acetoacetic acid, and beta hydroxybutyric acid, lactate, molecules involved in aerobic or anaerobic metabolic pathways, or combinations of these. The activity data may indicate an activity level, and the activity level may be stratified or categorized as noted above. The activity data may be received from an accelerometer or GPS, from an exercise machine, from a heart rate monitor, and so on. The optimizing weight loss may include optimizing a metabolic rate. The optimizing weight loss may include optimizing fat consumption. The meal data may be received from sources noted above.

The displaying may include displaying the effect of the meal data on the weight loss to be optimized. The selected program may include a goal having predetermined criteria, and the evaluating step may include determining if the analyzed data meets or matches the predetermined criteria. The method may further include monitoring and storing metabolic level data of the user, and the predetermined criteria may include an envelope of acceptable metabolic levels. The metabolic level data may be represented by a trace graph, and the predetermined criteria may include whether the trace graph is within the envelope of acceptable metabolic levels. The method may include displaying initial guidance, the initial guidance based on the selected program. The monitoring and storing an analyte concentration data of the user may further include monitoring and storing glucose or lactic acid concentration data, or both. Where the selected program is to lose a predetermined number of pounds, the method may further include receiving data about a weight of the user prior to the program, and the evaluating step may evaluate a current weight of the user and the weight of the user prior to the program against the predetermined number of pounds. Where the selected program is to lose a predetermined percentage of body fat, the method may further include receiving data about a body fat percentage of the user prior to the program, and the evaluating step may evaluate a current body fat percentage of the user and the body fat percentage of the user prior to the program against the predetermined percentage of body fat. Where the selected program is to achieve a predetermined metabolic level over a duration of time, the method may further include receiving data about a metabolic level over the duration of time, and the evaluating step may evaluate the metabolic level over the duration of time against the predetermined metabolic level over the duration of time. Where the selected program is to achieve a predetermined fat consumption level over a duration of time, the method may further include receiving a fat consumption level over the duration of time, and the evaluating step may evaluate the fat consumption level over the duration of time against the predetermined fat consumption level over the duration of time.

The receiving data about a fat consumption level may include: receiving data selected from the group consisting of: a lactate level and a heart rate, a ratio of VO2 and VCO2, a level of glycerol, a level of ketones, or a level of free fatty acids, or a combination of the above, associated with the user; and determining a fat consumption level from the received data. The determined fat consumption level may indicate a source of calorie expenditure, from fat or from carbohydrates.

The receiving data about a fat consumption level may include receiving data about a lactate level and data from an accelerometer, and the lactate level and the accelerometer data may be evaluated against the selected program to determine if the predetermined fat consumption level has been achieved. Where the selected program is to achieve a predetermined energy expenditure, the method may further include receiving data about a current energy expenditure, and the evaluating step may evaluate the current energy expenditure against the predetermined energy expenditure. The selected program may be associated with a difficulty level, and the evaluating against the selected program may include evaluating against the associated difficulty level. The difficulty level may be set by the program or by the user. The output may include a color or an avatar or a trace graph indicating a level of optimization. The output may also include a column, row, or tachometer diagram having a needle pointing at a range corresponding to the output. Where the output indicates metabolism, the diagram may have ranges of: calorie intake greater than calorie expenditure; and calorie intake less than calorie expenditure. The method may further include transmitting an indication of the output to a cloud-connected entity. The method may further include displaying multiple parameters on the user interface, the multiple parameters including at least two of the group consisting of: fat consumption, percentage of max fat consumption, lactate level, or total fat consumption during workout.

In an seventh aspect, the embodiments are directed towards a method of using retrospective data to determine guidance on a user interface, including: evaluating retrospective user data to determine a suboptimal data arrangement in an analyte concentration value of a user; determining a program to improve the suboptimal data arrangement; displaying an indication of the determined program on a user interface; receiving an indication to start the determined program entered by a user on the user interface; monitoring and storing analyte concentration data of the user; evaluating the monitored and stored analyte concentration data of the user against the determined program; and displaying an output responsive to the evaluating step.

Implementations may include one or more of the following.

The suboptimal data arrangement may constitute a pattern, and the determining a program may be initiated upon an unambiguous determination that a pattern exists. The analyte may be glucose.

In an eighth aspect, the embodiments are directed towards a method of optimizing exercise, including: displaying a user interface, the user interface including one or more graphical elements representing respective programs, the one or more programs configured to guide a user in optimizing weight loss; receiving a selection of a program from the user interface; monitoring and storing activity data of the user; monitoring and storing lactate concentration data of the user; analyzing the monitored and stored activity data and lactate concentration data of the user; evaluating the analyzed data against the selected program; and displaying an output responsive to the evaluating step.

Implementations may include one or more of the following.

The method may further include displaying an output indicating if the user is in a carbohydrate-burning zone. The method may further include displaying an output indicating how close a user is to a lactate threshold. The method may further include: monitoring and storing glucose concentration data of the user; analyzing the monitored and stored glucose concentration data along with the monitored and stored activity data and lactate concentration data; evaluating the analyzed data including the glucose concentration data against the selected program; and displaying an output responsive to the evaluating step. The method may further include displaying an output indicative of a source of calories expended, including whether from fat or from carbohydrates.

In a ninth aspect, the embodiments are directed towards a method of determining net calories relative to a user, including: displaying a user interface, the user interface including one or more graphical elements representing respective programs, the one or more programs configured to guide a user in optimizing weight loss; receiving a selection of a program from the user interface; monitoring and storing a glucose concentration data of the user; monitoring and storing an insulin concentration data of the user; analyzing the monitored and stored glucose and insulin concentration data of the user to determine a number of calories ingested and a number of calories expended; and displaying an output responsive to the analyzing step.

Implementations may include one or more of the following.

The method may further include monitoring and storing data corresponding to fat content, and analyzing the monitored and stored data corresponding to fat content along with the glucose and insulin concentration data. The fat content data may correspond to data about ketones, glycerol or triglycerides.

In an tenth aspect, the embodiments are directed towards a method of optimizing weight loss, including: displaying a user interface, the user interface including one or more graphical elements representing respective programs, the one or more programs configured to guide a user in optimizing weight loss; receiving a selection of a program from the user interface; monitoring and storing activity data of the user; monitoring and storing lactate concentration data of the user; analyzing the monitored and stored activity data and lactate concentration data of the user; evaluating the analyzed data against the selected program; and displaying an output responsive to the evaluating step, where the displaying may include indicating to a user if the user is in a fat burning zone.

Implementations may include one or more of the following.

The method may further include displaying an output indicating a value selected from the group consisting of: a fat burning rate, a carbohydrate-burning rate, a total fat expended, a total carbohydrates expended, a calorie burning rate, a total calories expended, and combinations thereof.

In a eleventh aspect, the embodiments are directed towards a sensor array for measuring an analyte concentration, the sensor array including: a plurality of sensor devices each configured for insertion through the skin, where each sensor device may include a sensor unit and a mounting unit configured to support the sensor device on an exterior surface of the host's skin, the sensor unit including an in vivo portion having a tissue piercing element and a sensor body, the sensor body including at least one electrode and a membrane covering at least a portion of the at least one electrode; where the plurality of sensor devices may include a first sensor device and a second sensor device, where the first sensor device may include a first sensor configured to measure a first analyte, and where the second sensor device may include a second sensor configured to measure a second analyte; and where the second sensor device is calibrated using a calculation based on at least a calibration parameter of the first sensor device.

Implementations may include one or more of the following.

Where one or more calibration parameters of the second sensor device bear a known relationship with one or more calibration parameters of the first sensor device, calibration parameters of the second sensor device may be determined based on the calibration parameters of the first sensor device. The calibration parameters may include a sensitivity of the sensor device. The calculation may be a linear calculation. The first sensor device may be configured to measure glucose and the second sensor device may be configured to measure an analyte selected from the group consisting of: ketones, triglycerides, glycerol, lactate, lactic acid, cortisol, testosterone, and combinations thereof. The first sensor device may be configured to measure uric acid and the second sensor device may be configured to measure glucose. The first sensor device may be configured to measure glucose and the second sensor device may be configured to measure an analyte selected from the group consisting of: glucagon, insulin, other hormones involved in metabolic processes, glycogen, starch, free fatty acids, triglycerides, monoglycerides, troponin, cholesterol, proteins involved in fat storage, glycerol, pyruvate, lipids, other carbohydrates, molecules involved in breaking down fat, glucagon, acetyl Co A, triglycerides, fatty acids, intermediaries in the citric acid cycle, ketone bodies, acetone, acetoacetic acid, beta hydroxybutyric acid, lactate, molecules involved in aerobic or anaerobic metabolic pathways, or combinations of the above. The first sensor device may be configured to be calibrated using a blood measurement.

In a thirteenth aspect, the embodiments are directed towards a method of evaluating a user against a program, including: displaying a user interface, the user interface including one or more graphical elements representing respective programs, the one or more programs configured to guide a user in treating diabetes; receiving a selection of a program from the user interface; monitoring and storing analyte concentration data of the user; analyzing the monitored and stored analyte concentration data of the user; evaluating the analyzed analyte concentration data of the user against the selected program; and displaying an output responsive to the evaluating step.

Implementations may include one or more of the following. The displaying a user interface may further include analyzing retrospective data of a user and basing the one or more graphical elements at least in part on the analysis. The method may further include, after the receiving a selection of a program, displaying an indication on the user interface, the indication representing initial guidance for following the program. The displaying an indication may include: displaying suggested meals, foods, or recipes, helpful in performing the program; and/or displaying suggested exercise routines helpful in performing the program. The method may further include, after the receiving a selection of a program: displaying one or more graphical elements representing respective subprograms, the one or more subprograms configured to further guide a user in treating a physiological condition; and receiving a selection of a selected subprogram. The monitoring and storing may be performed by a continuous analyte monitor. The method may further include monitoring other data about the user, and the analyzing or evaluating steps, or both, may be based on the analyte concentration data and the other data. The other data may include activity data, such as may be received from an accelerometer or a GPS device. The activity data may indicate an activity level, and the same may be selected from the group consisting of: sleeping, sedentary, light activity, medium activity, or strenuous activity.

The evaluating may include evaluating an effect of the activity data on the analyte concentration data. The displaying may include displaying the effect of the activity data on the analyte concentration data. The other data may include data about one or more other analytes, and the other analytes may be selected from the group consisting of: ketones, lactic acid, lactate, glycerol, triglycerides, cortisol, and testosterone.

The analyte concentration data may be measured by an analyte sensor, and the data about one or more other analytes may be received from one or more other analyte sensors. The one or more other analyte sensors may be calibrated based on a calibration of the analyte sensor. The other data may also include meal data, such as may be received from one or more of the group selected from: a social network; user entry; a food app; or photographic data. The method may further include, following the receiving of meal data: querying a user to enter a prediction of a measured analyte concentration value following a duration of time; receiving user input of the prediction; and subsequent to the duration of time, displaying an indication of the prediction and an actual current measured analyte concentration value.

The user interface may include at least one graphical element pertaining to a meal program and at least one graphical element pertaining to an exercise program. If the receiving a selection of a program includes receiving a selection of a meal program, the method may further include displaying one or more graphical elements representing respective subprograms pertaining to different meals, the one or more subprograms configured to further guide a user in treating the disease. The method may further include receiving a selection of one of the respective subprograms, whereby the user is instructed to vary a meal choice for a particular meal over a predetermined time period, e.g., one week.

If the receiving a selection of a program includes receiving a selection of an exercise program, the method may further include displaying one or more graphical elements representing respective subprograms pertaining to different exercise programs, the one or more subprograms configured to further guide a user in treating the disease. The method may further include receiving a selection of one of the respective subprograms, whereby the user is instructed to perform an exercise activity of a predetermined intensity level and/or duration over a predetermined time period, e.g., one week.

If the receiving a selection of a program includes receiving a selection of an exercise program, the method may further include: receiving retrospective user data; analyzing the received retrospective user data to determine if a prior user activity similar to the exercise program has been performed, and if a physiological event has occurred after such determined prior user activity; if a physiological event has occurred after such determined prior user activity, then determining a suggestion which may be employed to counteract an effect of such physiological event; and displaying an indication of the suggestion as initial guidance.

The monitoring other data may include monitoring metabolism data. The monitoring other data may also include receiving data from a cloud connected source, such as a social network, a caregiver network, or a network of diabetes patients or a support group.

The selected program may be associated with a difficulty level, and the evaluating against the selected program may include evaluating against the associated difficulty level. The difficulty level may be set by the program or by the user.

The output may include a color indicating if a goal associated with the program was met or is on track to being met. The output may also or alternatively include an avatar indicating if a goal associated with the program was met. The output may include a trend graph indicating at least a trace signal representing the analyte concentration value over a time period associated with the program. The trend graph may include a desired analyte concentration value or range of values over the time period. The desired analyte concentration value or range of values may be based on a modeled, ideal, or predicted analyte concentration value or range of values. The selected program may be associated with a difficulty level, and the desired analyte concentration value or range of values may be further based on the difficulty level.

The method may include transmitting the output to a cloud connected entity.

The method may further include, prior to a displaying of an actual current measured analyte concentration value, querying a user to enter a prediction of the current analyte concentration value; receiving user input of the prediction; and displaying an indication of the prediction and the actual current measured analyte concentration value.

The method may further include: determining if the actual current measured analyte concentration value meets predefined criteria; and if the predefined criteria is met, displaying an indication that the predefined criteria has been met. The predefined criteria may be a threshold analyte concentration value.

In a fourteenth aspect, the embodiments are directed towards a method of alerting a user to a pattern, and providing a program to address the pattern, including: evaluating user data to determine a pattern; comparing the pattern against a criteria to determine if the determined pattern is a pattern for which improvement is desired; determining a program to improve the pattern; monitoring and storing analyte concentration data of the user; analyzing the monitored and stored analyte concentration data of the user; evaluating the analyzed analyte concentration data of the user against the determined program; and displaying an output responsive to the evaluating step.

Implementations may include one or more of the following. The determining a program to improve the pattern may further include: determining a set of potential programs to improve the pattern; displaying a user interface, the user interface including one or more graphical elements respectively representing the set of potential programs; receiving a selection of one of the potential programs from the user interface, where the determined program is defined as the received selection.

The displaying a user interface may further include analyzing retrospective data of a user and basing the user interface at least in part on the analysis. The method may further include, after the step of determining a program, displaying an indication on the user interface, the indication representing initial guidance for following the determined program. The displaying an indication may include: displaying suggested meals, foods, or recipes, helpful in performing the program; and/or displaying suggested exercise routines helpful in performing the program.

The monitoring and storing may be performed at least in part by a continuous analyte monitor. The method may further include monitoring other data about the user, and the analyzing or evaluating steps, or both, may be based on the analyte concentration data and the other data. The other data may include activity data. The activity data may be received from an accelerometer or GPS device, and may indicate an activity level, e.g., an activity level selected from the group consisting of: sleeping, sedentary, light activity, medium activity, or strenuous activity.

The criteria may be received from a cloud-connected source. The evaluating may include evaluating an effect of the activity data on the analyte concentration data. The displaying may include displaying the effect of the activity data on the analyte concentration data. The other data may include data about other analytes, such as: ketones, lactic acid, lactate, glycerol, triglycerides, cortisol, and testosterone. The analyte concentration data may be measured by an analyte sensor, and the data about one or more other analytes may be received from one or more other analyte sensors, and the one or more other analyte sensors may be calibrated based on a calibration of the analyte sensor.

The other data may include meal data, which may be received from: a social network; user entry; a food app; or photographic data.

The determined program may be associated with a difficulty level, and the evaluating against the determined program may include evaluating against the associated difficulty level. The difficulty level may be set by the program based at least in part on a retrospective history of the patient, or selected by the user.

The output may include a color indicating if a goal associated with the program was met. The output may also include an avatar indicating if a goal associated with the program was met. The output may include a trend graph indicating at least a trace signal representing the analyte concentration value over a time period associated with the program. The trend graph may include a desired analyte concentration value or range of values over the time period, where the desired analyte concentration value or range of values is based on a modeled, ideal, or predicted analyte concentration value or range of values. The determined program may be associated with a difficulty level, and the desired analyte concentration value or range of values may be further based on the difficulty level. The evaluated user data may include retrospective analyte concentration data for retrospective meal data.

The displaying an output may include displaying an indicator of the determined pattern. The determined pattern may be selected from the group consisting of: overnight lows, postprandial spikes, a type of discriminated fault, a pattern of high analyte variability, or a consistent pattern of weekly highs or lows. The method may further include determining a baseline analyte concentration pattern for the user, and the determined pattern may be a consistent variation from the baseline pattern. The evaluating user data to determine a pattern step may further include initiating a discovery mode, where in the discovery mode, one or more questions are posed on the user interface, user responses to the one or more questions constituting additional user data, and the evaluating user data step may further include evaluating the additional user data along with the monitored and stored analyte concentration data to determine a pattern. The additional user data may be meal data or activity data. The method may further include transmitting the output to a cloud connected entity.

In further aspects and embodiments, the above method features of the various aspects are formulated in terms of a system as in various aspects. Any of the features of an embodiment of any of the aspects, including but not limited to any embodiments of any of the first through fourteenth aspects referred to above, is applicable to all other aspects and embodiments identified herein, including but not limited to any embodiments of any of the first through fourteenth aspects referred to above. Moreover, any of the features of an embodiment of the various aspects, including but not limited to any embodiments of any of the first through fourteenth aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the first through fourteenth aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the first through fourteenth aspects referred to above.

Advantages of one or more Implementations may include one or more of the following. Users may be enabled to learn how to better their health through the use of programs, both self-selected and system-determined on the basis of user data. Users may further be enabled to optimize sports and weight loss efforts through the use of the described principles. Other advantages will be understood from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The present embodiments now will be discussed in detail with an emphasis on highlighting the advantageous features. These embodiments depict the novel and non-obvious systems and methods according to present principles, for use in educating users and other purposes, shown in the accompanying drawings, which are for illustrative purposes only. These drawings include the following figures, in which like numerals indicate like parts.

Like reference numerals refer to like elements throughout. Elements are not to scale unless otherwise noted.

DETAILED DESCRIPTION

Definitions

Figure 1:
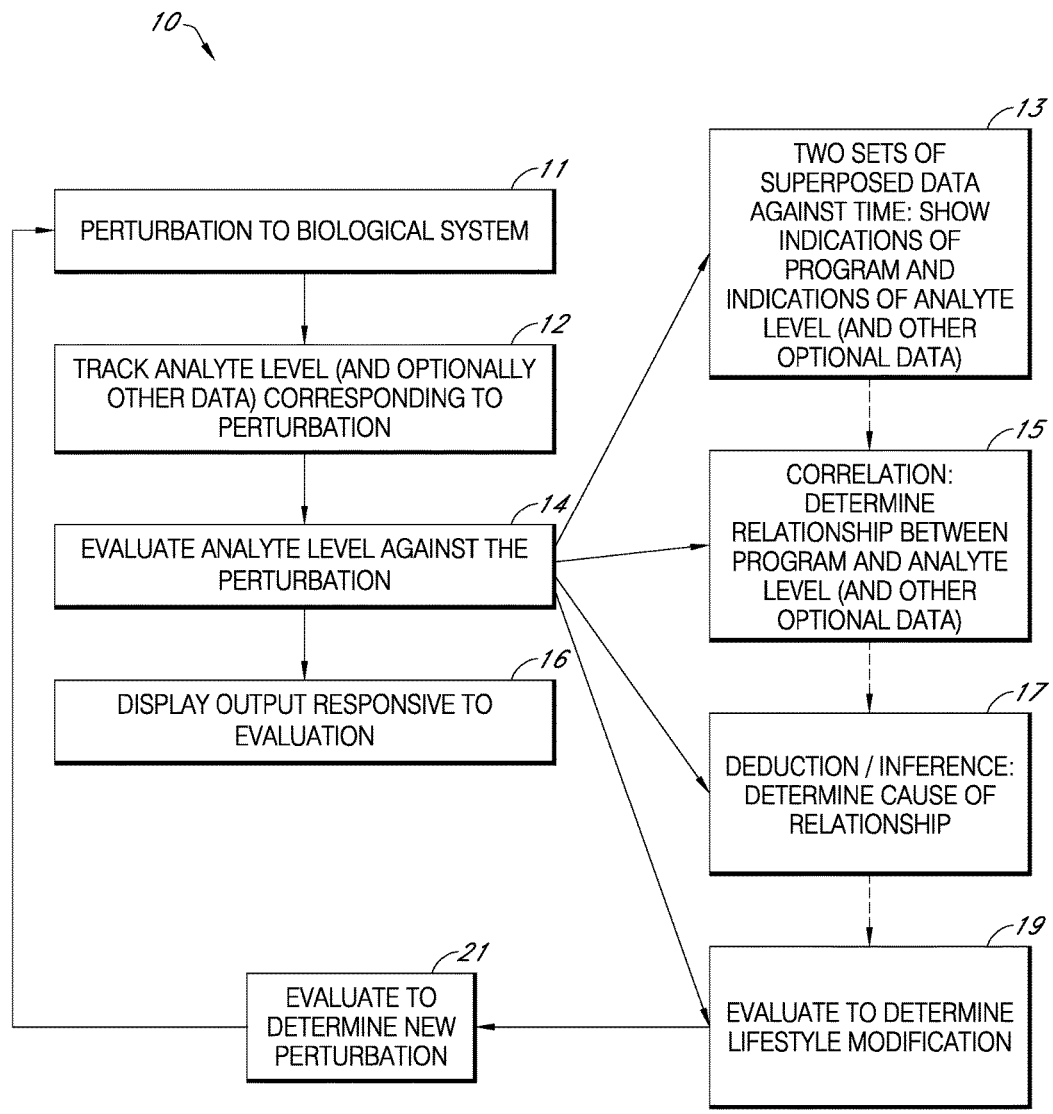
FIG. 1 is a flowchart according to present principles.

In order to facilitate an understanding of the preferred embodiments, a number of terms are defined below.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle)), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxy-progesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxy-tyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "calibration" as used herein is a broad term, and is to be given its ordinary and customary meaning to a person of ordinary skill in the art (and is not to be limited to a special or customized meaning), and refers without limitation to the process of determining the relationship between sensor data and corresponding reference data, which can be used to convert sensor data into meaningful values substantially equivalent to the reference data, with or without utilizing reference data in real time. In some embodiments, namely, in continuous analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like.

The terms "calibrated data" and "calibrated data stream" as used herein are broad terms, and are to be given their ordinary and customary meaning to a person of ordinary skill in the art (and are not to be limited to a special or customized meaning), and refer without limitation to data that has been transformed from its raw state (e.g., digital or analog) to another state using a function, for example a conversion function, to provide a meaningful value to a user.

The term "algorithm" as used herein is a broad term, and is to be given its ordinary and customary meaning to a person of ordinary skill in the art (and is not to be limited to a special or customized meaning), and refers without limitation to a computational process (for example, programs) involved in transforming information from one state to another, for example, by using computer processing. In many cases such an algorithm serves to transform a computing environment into a special purpose computing environment to solve one or more technological challenges.

The term "counts" as used herein is a broad term, and is to be given its ordinary and customary meaning to a person of ordinary skill in the art (and is not to be limited to a special or customized meaning), and refers without limitation to a unit of measurement of a digital signal. In one example, a raw data stream (or just "raw" data) measured in counts is directly related to a voltage (e.g., converted by an A/D converter), which is directly related to current from the working electrode.

The term "sensor" as used herein is a broad term, and is to be given its ordinary and customary meaning to a person of ordinary skill in the art (and is not to be limited to a special or customized meaning), and refers without limitation to the component or region of a device by which an analyte can be quantified.

The term "glucose sensor" as used herein is a broad term, and is to be given its ordinary and customary meaning to a person of ordinary skill in the art (and is not to be limited to a special or customized meaning), and refers without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction: Glucose+$O_2$→Gluconate+$H_2O_2$ Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms, and are to be given their ordinary and customary meaning to a person of ordinary skill in the art (and are not to be limited to a special or customized meaning), and refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "in vivo portion" as used herein is a broad term, and is to be given its ordinary and customary meaning to a person of ordinary skill in the art (and is not to be limited to a special or customized meaning), and refers without limitation to the portion of the device (for example, a sensor) adapted for insertion into and/or existence within a living body of a host. Conversely, "ex vivo portion" relates to a portion outside the living body.

The term "variation" as used herein is a broad term, and is to be given its ordinary and customary meaning to a person of ordinary skill in the art (and is not to be limited to a special or customized meaning), and refers without limitation to a divergence or amount of change from a point, line, or set of data. In one embodiment, estimated analyte values can have a variation including a range of values outside of the estimated analyte values that represent a range of possibilities based on known physiological patterns, for example.

The terms "physiological parameters" and "physiological boundaries" as used herein are broad terms, and are to be given their ordinary and customary meaning to a person of ordinary skill in the art (and are not to be limited to a special or customized meaning), and refer without limitation to the parameters obtained from continuous studies of physiological data in humans and/or animals. For example, a maximal sustained rate of change of glucose in humans of about 4 to 5 mg/dL/min and a maximum acceleration of the rate of change of about 0.1 to 0.2 mg/dL/min$^2$ are deemed physiologically feasible limits; values outside of these limits would be considered non-physiological. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along a glucose signal data stream over a certain time period (for example, about 20 to 30 minutes) is a straight line, which can be used to set physiological limits. These terms are broad enough to include physiological parameters for any analyte.

The term "measured analyte values" as used herein is a broad term, and is to be given its ordinary and customary meaning to a person of ordinary skill in the art (and is not to be limited to a special or customized meaning), and refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, and the like).

The term "estimated analyte values" as used herein is a broad term, and is to be given its ordinary and customary meaning to a person of ordinary skill in the art (and is not to be limited to a special or customized meaning), and refers without limitation to an analyte value or set of analyte values, which have been algorithmically extrapolated from measured analyte values.

As employed herein, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); L (microliters); cm (centimeters); mm (millimeters); µm (micrometers); nm (nanometers); h and hr (hours); min. (minutes); s and sec. (seconds); ° C. (degrees Centigrade).

The phrase "continuous glucose sensor" as used herein is a broad term, and is to be given its ordinary and customary meaning to a person of ordinary skill in the art (and is not to be limited to a special or customized meaning), and refers without limitation to a device that continuously or continually measures the glucose concentration of a bodily fluid (e.g., blood, plasma, interstitial fluid and the like), for example, at time intervals ranging from fractions of a second up to, for example, 1, 2, or 5 minutes, or longer.

The phrases "continuous glucose sensing" or "continuous glucose monitoring" as used herein are broad terms, and are to be given their ordinary and customary meaning to a person of ordinary skill in the art (and are not to be limited to a special or customized meaning), and refer without limitation to the period in which monitoring of the glucose concentration of a host's bodily fluid (e.g., blood, serum, plasma, extracellular fluid, tears etc.) is continuously or continually performed, for example, at time intervals ranging from fractions of a second up to, for example, 1, 2, or 5 minutes, or longer. In one exemplary embodiment, the glucose concentration of a host's extracellular fluid is measured every 1, 2, 5, 10, 20, 30, 40, 50 or 60 seconds.

The term "substantially" as used herein is a broad term, and is to be given its ordinary and customary meaning to a person of ordinary skill in the art (and is not to be limited to a special or customized meaning), and refers without limitation to being largely but not necessarily wholly that which is specified, which may include an amount greater than 50 percent, an amount greater than 60 percent, an amount greater than 70 percent, an amount greater than 80 percent, an amount greater than 90 percent, or more.

The terms "processor" and "processor module" as used herein are broad terms, and are to be given their ordinary and customary meaning to a person of ordinary skill in the art (and are not to be limited to a special or customized meaning), and refer without limitation to a computer system, state machine, processor, or the like, designed to perform arithmetic or logic operations using logic circuitry that responds to and processes the basic instructions that drive a computer. In some embodiments, the terms can include ROM and/or RAM associated therewith.

Exemplary embodiments disclosed herein relate to the use of a glucose sensor that measures a concentration of glucose or a substance indicative of the concentration or presence of another analyte. In some embodiments, the glucose sensor is a continuous device, for example a subcutaneous, transdermal, transcutaneous, non-invasive, intraocular and/or intravascular (e.g., intravenous) device. In some embodiments, the device can analyze a plurality of intermittent blood samples. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor capable of measuring the concentration of glucose in a host, the systems and methods of embodiments can be applied to any measurable analyte. Some exemplary embodiments described below utilize an implantable glucose sensor. However, it should be understood that the devices and methods described herein can be applied to any device capable of detecting a concentration of analyte and providing an output signal that represents the concentration of the analyte.

In some embodiments, the analyte sensor is an implantable glucose sensor, such as described with reference to U.S. Pat. No. 6,001,067 and U.S. Patent Publication No. 2011/0027127-A1. In some embodiments, the analyte sensor is a transcutaneous glucose sensor, such as described with reference to U.S. Patent Publication No. 2006/0020187-A1. In yet other embodiments, the analyte sensor is a dual electrode analyte sensor, such as described with reference to U.S. Patent Publication No. 2009/0137887-A1. In still other embodiments, the sensor is configured to be implanted in a host vessel or extracorporeally, such as is described in U.S. Patent Publication No. 2007/0027385-A1. These patents and publications are incorporated herein by reference in their entirety.

The following description and examples describe the present embodiments with reference to the drawings. In the drawings, reference numbers label elements of the present embodiments. These reference numbers are reproduced below in connection with the discussion of the corresponding drawing features.

FIG. 1 is a flowchart 10 illustrating a basic method according to present principles. The basic method of flowchart 10 is exemplified and applied below in the specification, and in particular within subsequent flowcharts of FIGS. 37, 38, 39, 3, 41, 42, 45, 47, 51, and 52. In this basic method, a perturbation is applied to a biological system (step 11). An analyte level is tracked corresponding to the perturbation (step 12). The analyte level is then evaluated, and in particular with respect to the perturbation (step 14). An output is then displayed responsive to the evaluation (step 16). Various types of outputs will be understood and are described below.

In more detail, and as will be described below in greater detail with respect to other flowcharts, the perturbation to a biological system will often include a program followed by a user in the treatment of a disease, e.g., diabetes, but may also be employed to prevent (or reverse) such diseases, e.g., when a user is prediabetic or non-diabetic. Systems and methods according to present principles are not limited to predetermined programs, however. For example, a user may start wearing the sensors described here, and the systems and methods may learn from the user's responses, and from such learning a program or suggested perturbation may be suggested. Alternatively, the systems and methods may recommend other actions, or simply give feedback. In such implementations, by having the system and method learn by user data, whether user entered or sensor measured, the system and method configure a computing environment such as an analyte monitor to operate better, faster, and more efficiently, as less computing cycles are required to provide the same (or better) output to a user. Applications of the systems and methods may include sports and health optimization, as well as weight loss and other areas.

In these applications, various analyte levels may be tracked in the second step above (step 12), and commonly glucose will be one such analyte. Other analytes will also be understood and are described below. For example, lactate may be tracked, as well as insulin and/or triglycerides. The program may further include determining a program for a user to follow, e.g., a meal program or an exercise program, and tracking an analyte level over a period of time, e.g., a week, to see how the analyte level, and thus the user's health, is affected by the prescribed program. Outputs may be provided to provide comment on the evaluation, to provide numerous types of evaluative outputs, to suggest other programs for the user to try, and so on.

The perturbation, as noted, is often a program to try which provides a perturbation or change to a user's "normal" routine. By seeing how the change to the user's routine affects the analyte level or other aspects of a patient's health, conclusions may be drawn as to the usefulness of the change to the user, and such conclusions can be manifested within the various outputs. As such, the perturbation can be initiated by the user who interacts with the computing environment, the computing environment in signal communication with the analyte sensor and receiving data therefrom, and in this way the user can initiate a program to learn how to better their health. For example, a user may desire to learn more about the effect of food on their health. Alternatively, the user may desire to learn more about the effect of exercise on their health.

In the above systems, perturbations are initiated by the user. However, in some cases, the system including an appropriate computing environment can detect a pattern in a physiological parameter of a patient, e.g., their glucose level, and as a result the system may prompt the user to try a system-generated program, i.e., to try a perturbation (program) so as to affect the detected pattern or its consequences. As a particular example, the system may detect a pattern of overnight lows (in glucose level), and may suggest a program for a user to try to treat the same.

By the suggestion and implementation of a program to perturbation, systems and methods according to present principles are configured to both (a) turn the computing environment of a continuous analyte monitor into a special purpose computing environment configured for user programmatic learning, and (b) allow the computing environment to automatically learn (or prepare to learn), in an efficient way, user parameters, thus freeing the user (and a HCP) from having to enter and iterate suggested parameters in an ad hoc and haphazard manner.

In some cases, even without the detection of a pattern, the systems and methods according to present principles may suggest programs for the user to try, either based on a past history of the patient or starting with a default program. With respect to either of these, the system may make a determination as to a suitable program on which to start the user. In this way, even a neophyte user with no knowledge of the system, and little knowledge of their own biological response to meal and exercise routines, may be enabled to start a program. In some cases, the systems and methods may use retrospective user information and in some implementations contemporaneous user input so as to select potential programs for a user to try. Alternatively, one or more default programs may be provided which the system displays to users as potential starting points. In any case, these methods provide significant technological advantages over prior systems in which no programs were provided to a user, much less personalized and customized programs.

As an example of the use of retrospective data, if previously measured user data indicates the patient is prone to overnight lows in glucose concentration level, even if the same do not constitute a pattern per se, the systems and methods may suggest altering the evening meal and evaluating the effect of different evening meals on the occurrence of overnight lows. In the same way, the systems and methods may suggest a program for exercising during the day, instead of at night, to achieve the same purpose. Other variations will also be understood. Using such facilities, the user is relieved from having to hypothesize programs on their own.

As an example of the use of default programs, systems and methods may be "preloaded" with default program options, particularly for the case where the system, using retrospective analysis, can discern no particular single unambiguous program to suggest, or where no such suggestion algorithm is in place. In this case, the system might provide a default option of varying a single meal for a weeklong predetermined period, or proposing an exercise routine to be carried out three times per week.

In certain implementations according to present principles, the systems and methods may start sua sponte in the determination of data and information required for the performance of the flowchart 10. In other implementations, the systems and methods may include analysis of user data. For example, the determinations of detected patterns may include analysis of retrospective glucose data over time to determine a user profile. In yet other implementations, the systems and methods may initiate by beginning a period of measurement in which patterns are determined corresponding to a baseline glucose profile. In the latter, a user may be instructed to conduct themselves according to their normal habits, eating their typical meals and exercising with their typical frequency and intensity. The systems and methods can define such as a baseline profile, and may construct the same from patterns using appropriate pattern recognition software. Then, the systems and methods may detect patterns or events representing deviations from the same in subsequent periods of measurement. For example, from the baseline pattern, the system may detect a pattern of overnight lows. However, if the user starts having hyperglycemic excursions on, e.g., Sunday afternoons, either as measured sua sponte or as measured with respect to the measured baseline profile, then the system may start to detect an unhealthy pattern as may be caused by, e.g., watching football and consuming unhealthy snacks. The same may then be used as a pattern to address with a program.

However the program is determined, use of the program leads to eventual more efficient processing within the computing environment of the analyte monitor, as problematic patterns and events are minimized or reduced in frequency.

The tracking of analyte levels (step 12) may encompass the tracking of one analyte level or multiple analyte levels. In some cases, multiple analyte levels may be measured with a single sensor assembly, although commonly distinct sensor technologies are employed, e.g., using another analyte sensor/transmitter, or different portions of a single sensor assembly. That is, multi-analyte sensors may be co-located or use similar sensing technologies, e.g., from a single manufacturer, or the same may be embodied by discrete and separate sensing technologies from different manufacturers, where the data is aggregated in a single source, e.g., a smart phone or other electronic device.

Where analyte levels are provided by signals measured by a sensor, the same are often entered into a monitoring device such as a smart phone or other mobile device running monitoring applications, including, e.g., dedicated CGM devices. However, in some implementations, where sensors are not signally coupled to the monitoring device, a user may enter an analyte value himself or herself, e.g., after reading the same from a sensor display.

Exemplary types of analytes or other physiological data which may be monitored include glucose, ketones, lactic acid, lactate, glycerol, insulin, VCO2, VCO, free fatty acids, cortisol, testosterone, biochemical indicators of mental health, body temperature, blood urea, nitrogen, bicarbonate, oxidants, oxidizing species, and the like. Exemplary analytes will also be described below in connection with respective applications. Other types of biological measurements may also be employed, including measurements of metabolism by a sensor 34, and other physiological quantities employed may not necessarily involve measurement of an analyte.

Figure 2:
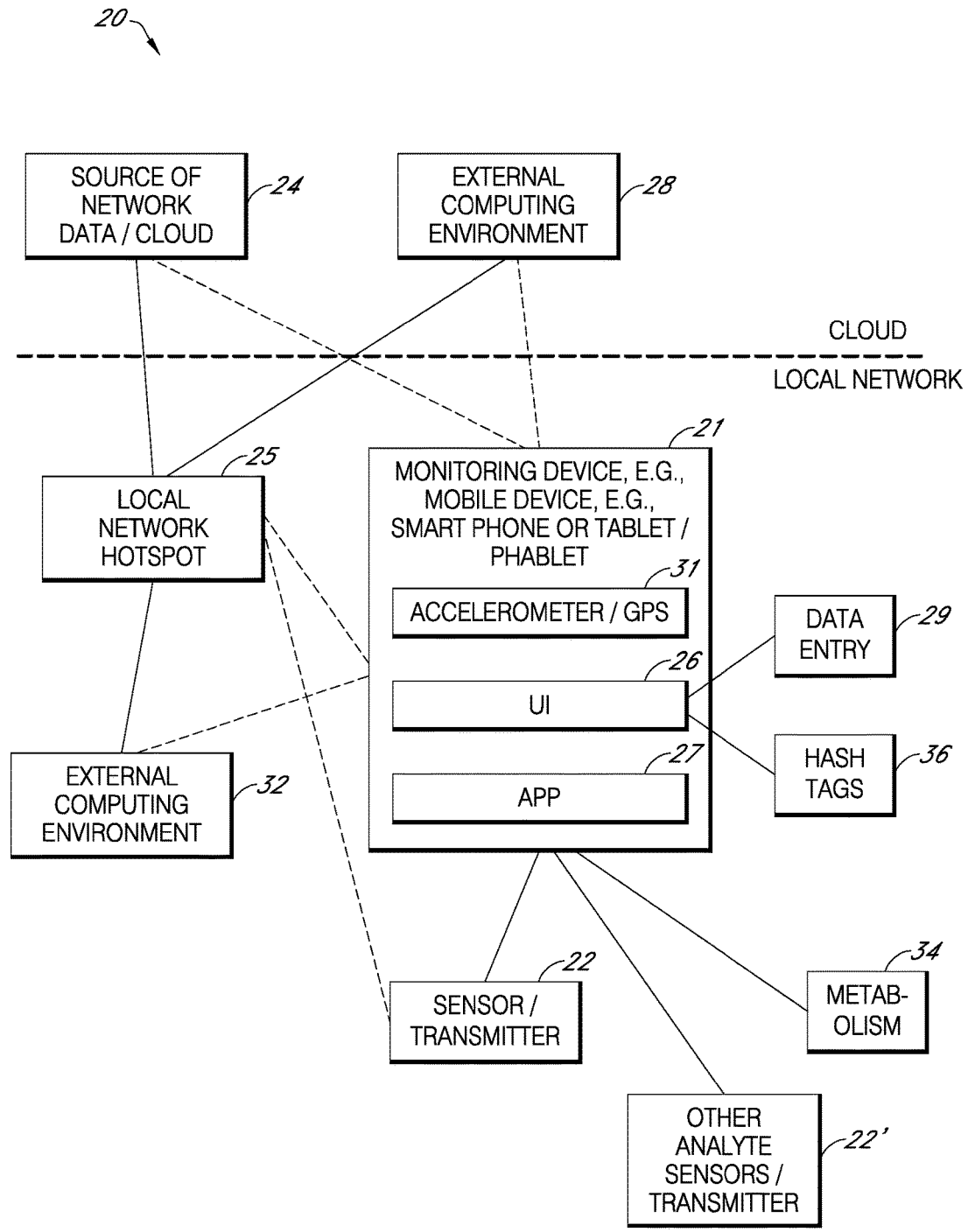
FIG. 2 is a schematic of an exemplary system according to present principles.

In some cases, and referring to the system 20 of FIG. 2, a monitoring device 21 may receive data from a sensor and transmitter 22 and may be connected via a local network hotspot 25 (or using a cellular network) to a network or other cloud-based source of data 24. The monitoring device is often a mobile device 21, but the same may also be a dedicated device such as a CGM receiver. In this case the source of data 24 as well as the sensor/transmitter 22 may provide data as needed by the described methods. In some cases the monitoring device 21 will perform the steps, and in such cases it may receive the data or may receive a copy of the data. In other cases an external computing environment 28 (within the cloud) or 32 (within the local network) may perform calculations and thus may receive the data from the source of data 24 or the sensor/transmitter 22 (in this case the monitoring device 21 provides the data from the sensor to the external computing environment 28 or 32). The monitoring device 21 may further include non-transitory computer readable memory running an application or "app" 27. The app 27 may include functionality for receiving data from sensors 22 and 22' or the like, as well as analyzing such and other data to perform the methods described herein with respect to flowcharts 37, 38, 39, 3, 41, 42, 45, 47, 51, and 52.

As will be described in greater detail below, the cloud may source significant amounts of data, and in such cases the monitoring device 21 may receive the same using the configuration of FIG. 2.

Returning to the tracking of analyte levels (step 12) of FIG. 1, even where just one analyte level is monitored, other associated data may be accumulated and stored. For example, besides an analyte level value, generally an analyte concentration value and a timestamp of the analyte data point may be returned. From such data, the frequency of analyte data points may be calculated, as well as the frequency of how often the user checks the analyte data, e.g., via screen refreshes, user's screen element activations, or the like, calibration values, the timestamps of calibration values, the frequency of calibrations, and so on. The analysis of an analyte data level over time can lead to additional data as well, e.g., time rates of change of the analyte level, e.g., velocities, accelerations, and so on.

Data about one or more analyte levels may be accompanied by other data useful in the evaluation step (step 14). Such data may include activity data, including data about the intensity and duration of activity. Exemplary such activity data include exercise data, although other activity may also be measured and quantified. For example, activity data may be stratified into multiple levels including: heavy exercise, medium exercise, light exercise, a sedentary state, and a sleeping state.

Activity may be measured in various ways, particularly by use of an accelerometer 24 within the mobile device 21 (see again FIG. 2). External accelerometers may also be employed, e.g., as may be available within a running watch or the like. In some cases, an accelerometer may be built into the sensor or sensor electronics including transmitter. In some cases, e.g., where a user is exercising by running or jogging, GPS data may also be determined and used. GPS data may also be employed to determine a velocity of the user, and may be able in that way to determine an intensity of the running or jogging. Other activity monitors may include, e.g., heart rate monitors, pulse meters, and so on. Activity may also be directly entered by a user, e.g., by direct data entry 29 on a user interface 26, such as "I ran 3 miles". In an indirect user entry technique, the use of hash tags 36 may be employed to allow convenient entry by a user of common entries. For example, if a user eats the same size and type of cereal every day, entering "#cereal" may input data of a datatype "food" and may also automatically enter a glycemic index and/or a calorie count appropriate to the bowl of cereal. In the same way, entering "#3 miles" may enter data of a datatype "activity:exercise" and with a value suitable to 3 miles of running. The timing of the entry may automatically timestamp the occurrence of the event, e.g., eating a bowl of cereal or running 3 miles, if the hash tag is entered at substantially the same time as the event.

Other aspects of sizes and types may also be entered. For example, the user may enter "I ate a bowl of cereal" but may also enter "I ate a 1-cup bowl of brand X cereal". Other types of data which may be entered by a user can include a report of best days, e.g., least time in hypoglycemia, worst days, e.g., most time in hypoglycemia, best meals, or the like. Such data can also be sourced from the system and reported as part of the output.

The output of the system may be tied to the evaluation and thus to the data entered. Accordingly, if data such as "I ate a bowl of cereal" is entered as a text string, the same may be evaluated with the resulting glucose (or other analyte) trace. In this case, one exemplary output may be to display the effect of that day's meal, i.e., cereal, via a glucose trace, with a textual legend or other indicator associated with the entry, e.g., "result of a 'bowl of cereal'". However, the data entry may also be more quantified, in which case the glucose trace can be shown with a numerical or graphical indicator of the meal, rather than just a text string. For example, if it is known that the bowl of cereal in question has a certain number of calories, or a certain glycemic index, such may be displayed as a more accurate indicator in lieu of the text string. The text string may be symbolized in a convenient way, allowing the user a more "ready" reference of the cause of the glucose trace. Such symbolizations may include photographs taken of the food at the time of eating, e.g., which may be associated via an appropriate mobile device application with the entry about the food. In this regard it is noted that in some cases applications may be employed which, using a photograph of food, can estimate or otherwise approximate a number of calories of pictured food or a glycemic index thereof. In this case, additional user entry may not be needed beyond the capture of the photograph. The use of such pictorial representations is described in greater detail below with respect to displayed outputs.

In this regard it is noted that users commonly eat similar meals over time. For example, a user may commonly eat a particular type of fast food hamburger several times a week.

By creating a hash tag or other entry element which is convenient to enter, and which can be quantified by generally known information about fast food nutritional statistics, the user may be provided with a convenient way to enter meal data of high accuracy.

Systems and methods according the present principles may also deduce meal data, given location data. For example, a method may be employed of determining meal information using location data, including determining one or more meal sources, e.g., restaurants, associated with the location, and further determining one or more likely meal choices given a user's meal history associated with the location. The system can either posit a meal, given the precise GPS location, and prompt the user for confirmation, or can present the user with various meal options and have the user select which is the current meal choice. In one example, the computing environment being provided with GPS data may be enough to deduce meal information. For example, if a particular fast food restaurant is at a particular GPS location, and the user is detected to be at that GPS location, then meal data may be deduced according to the user's usual menu choice, e.g., subject to user confirmation. Alternatively, if the user sometimes orders different options, the user may be presented on the user interface 26 of the mobile device with the various options, and the user may conveniently choose which option they ordered that day. A default choice may be selected if it is the user's predominant choice or is, e.g., a common choice for the user on that particular day of the week. Such a user interface facility may allow the computing environment of the mobile device 21 to operate in a more efficient manner, as accurate data is immediately obtained, e.g., via a lookup table associated with the hash tag, without the need for significant user interaction with the device to obtain an accurate recording of the food eaten. Alternatively, purchase information could be employed to determine such information. For example, if a user eats at a restaurant and pays for the meal with an online system, e.g., ApplePay, the system can use data about the transaction to deduce meal information. In some implementations, the meal information may be populated using the electronic transaction data and offered as a choice for the user to confirm that the same is correct and intended to constitute meal data. Using systems and methods according to present principles, implementation of the above options allows the entry of data in a way that is more accurate than prior attempts, leading to the transformation of data (via algorithmic processing) being performed in a more accurate way, which in turn leads to more accurate outputs.

Various other data can be sourced from cloud-based or other network sources. Such may include data noted above as well. For example, in some cases an analyte sensor might send measurement data to a cloud-based source, which is only later pulled down to a mobile device 21. In this case, even analyte data may be sourced from the cloud.

Other cloud or network data which may be employed in evaluation steps may include demographic and other such data. In this usage "other data" may be broadly construed, and may include data about the proximity of a user to a clinic or hospital, the user's ability to transport themselves or to use public transportation, user health data, and the like.

Other significant types of cloud or network data include data about other users, particularly other users with similar demographics to a subject user. By consideration of such users with similar demographics, and in particular aspects about such users' responses to perturbations, additional data about the subject user may be inferred, deduced, or otherwise gleaned. In particular, such additional information allows tailoring or personalization of suggested or proposed programs to the subject user, as it may be expected that if users have similar profiles, similar programs might be appropriate for them. This type of personalization significantly enhances the efficiency of the underlying computer environment, as the same is enabled to undergo far fewer computations in order to arrive at a suitable therapy for the subject user.

Returning to FIG. 1, the evaluation of the analyte level (and other optional data) (step 14) is generally made against the perturbation 10. In some cases the evaluation may be preceded by an optional step of analyzing the signal corresponding to the analyte level (or analyzing other received data). Such may include the derivation of associated data, e.g., time rates of change, signal analysis, or performing other processing on the analyte signal trace.

Step 14 provides an evaluation of the analyte level and other optional data against the perturbation. More particularly, data about the analyte, which may include values, time rates of change, or the like, as well as optionally other data, is evaluated against the perturbation. For example, where the perturbation is a program being followed by the biological system, i.e., a user, then the evaluation is some association of the response of the biological system, e.g., analyte levels, as a result of the program.

While specific outputs are discussed below, here it is noted that the response of the biological system, as measured by analyte levels and other data, may take several forms. These are generally discussed below in order of increasing sophistication, and subsequent levels generally build on information and data received or determined in lower levels. For example, a deduction or inference may build on a correlation.

In more detail, in one form, the evaluation may be to evaluate the data against time, in this case two sets of superposed data (step 13). In other words, to show an indication of the program as well as an indication of the analyte level or other data. In many cases these indications will be shown with respect to a timeline, as each represents events occurring in time, and generally the analyte level will have some relationship to the program. Showing both with respect to a time axis may bring out this relationship, even if, as is commonly seen, the analyte trace is time-shifted with respect to program events. For example, if the program includes varying the type of breakfast consumed by the user, this type of evaluation would be to receive and store both sets of data, i.e., food data and analyte level data, as a function of time, over a common time period.

In a more complex evaluation, a correlation may be evaluated between the two sets of data (step 15), and the correlation may then be displayed or indicated in the output step. In this case the evaluation step may include not only plotting the data against time but also determining that a relationship exists and what the relationship consists of. In the above example, this type of evaluation may include evaluating a relationship between food consumed and the analyte level data, e.g., that different foods affect the analyte level differently. In some cases the evaluated relationship results in the obtaining or determination of information indicative of, or insights about, the effect of one set of data on the other. The determination of the relationship leads to subsequently more efficient processing as the relationship allows the use of deductions and inferences which are more efficient for a computing environment to calculate than the case where no relationship is used.

In a still more complex evaluation, a deduction or inference may be made (step 17), at least about an underlying cause of the relationship noted in step 15. In this step, the deduction or inference evaluated may then provide (in the output step) additional information to the user about the underlying cause of the relationship. In the above example, the evaluation, which can be displayed to the user in a number of forms, may be that high glycemic index breakfast food items cause the analyte level to significantly increase. As with the relationship data, the evaluated cause may result in the obtaining or determination of information indicative of, or insights about, the effect of one set of data on the other or a cause related to each.

In a still more complex evaluation, but which may again build on prior evaluation steps, the evaluation may include suggesting a lifestyle modification (step 19). In this step, the cause is addressed and a suggestion is made to the user, and in most cases the suggestion is actionable, i.e., provides an act for the user to perform to better their health. The lifestyle modification may be determined on a basis of a lookup table tied to various causes, but may also be more personalized to the user based on retrospective user data as well as, in some cases, cloud sourced data. In some cases the lifestyle modification is a new perturbation (step 33), i.e., a new program for the user to follow, and in this case the process may simply repeat. Importantly, the new perturbation may be based on the suggested lifestyle modification of step 19, the relationship of step 17, the correlation of step 15, or the data of step 13, or combinations of the above. The new perturbation may further be based on retrospective or other prior user data, as well as cloud-based data. By doing so, systems and methods according to present principles can more efficiently converge on a solution (modification), thus saving computing cycles, battery power, and so on. In some implementations, the new perturbation may be that the same program is followed but with a lower tolerance for deviations, e.g., to challenge the user to follow a tighter analyte response envelope. For example, adaptive target glucose levels may be set for patients. The target levels that would display and potentially alert would be based on the previous history and the goals the patient was trying to achieve, e.g., as part of the program. Rather than setting a static level for a goal, the same may dynamically change to reflect improvements and changes to a target healthy level, e.g., may require the user to perform greater analyte control if the user has indicated, e.g., by their success, the ability to do so.

By tying one or more types of data to a program, performing a suitable evaluation, and providing the user with an informative output, the computing environment performing these steps operates in a more efficient manner as the computing environment is able to "home in on" a solution for a healthier lifestyle for a user in a rapid manner, eliminating programs not of use to the user and providing the user with actionable information in an efficient manner.

Figure 17:
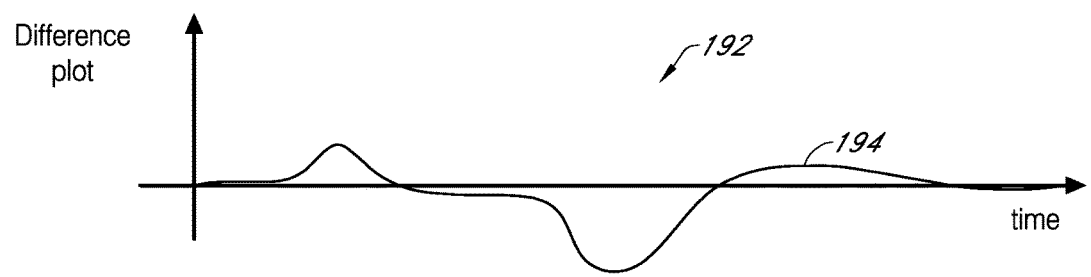
FIG. 17 shows an exemplary difference plot against time.

Various types of outputs are now described. It will be understood that while the evaluations above are described in terms of analyte and other data sets, the results of the evaluations, and in particular the outputs pertaining thereto, may be in a number of forms based on the data, but not necessarily data traces themselves. In particular, the outputs may be specifically geared to, in the case of diabetes, non-insulin-dependent type II users, or newly-diagnosed type I users, who may not have as much experience receiving and analyzing glucose levels as their type I and type II insulin-dependent counterparts. In this sense, outputs will generally provide overall or summary data, as opposed to providing so much data that the user becomes overwhelmed. For example, data may be provided in such a way so as to indicate differences, e.g., how far from the norm the user is, including in a qualitative way, as the user may not be familiar with absolute values or desired ranges. In an implementation of this concept, the display may show a trend graph (see FIG. 17, illustrating a plot 192 with a difference curve 194 as a function of time) that is the difference between the actual values from that expected from a healthy individual. For example, if "healthy" is defined as 70 and 120 mg/dL, then the plot would show the difference between the actual and the average, e.g., 90 mg/dL. The definition of "healthy" could also change if the system detects a glucose peak during lunch, e.g., if a user is often running "high", then systems and methods according to present principles may indicate a worse result than if the user is only temporarily showing a high number. Such systems may be generated from simple algorithms or from more complex ones, employing retrospective information to generate the plotted values.

Figure 18:
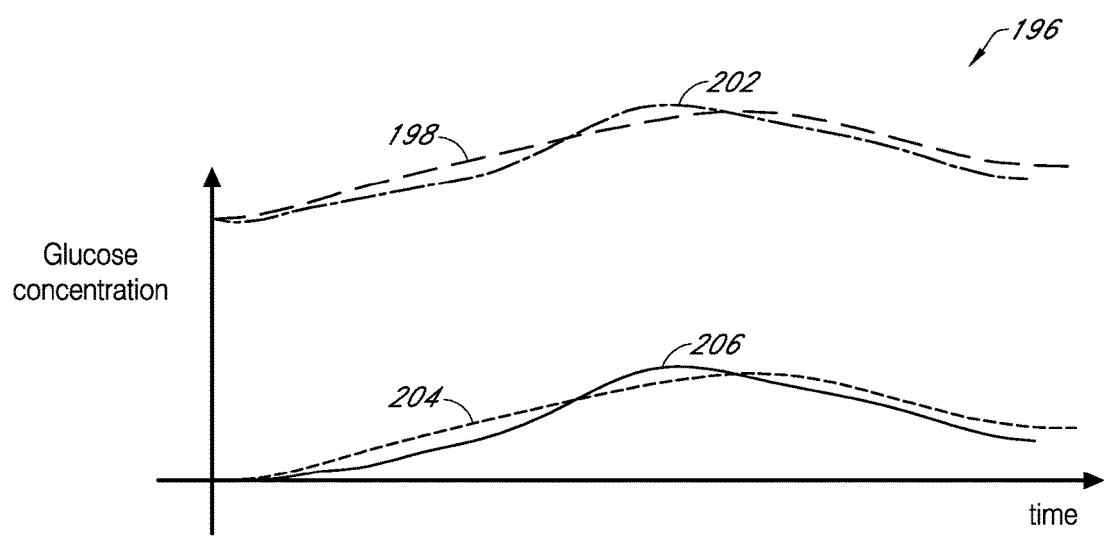
FIG. 18 shows an exemplary user interface in which glucose concentrations are plotted against time.

In a related implementation, where exemplary and/or average glucose values are portrayed to the user, e.g., to convey to the user the effect of a meal (which may also be portrayed against a desired or ideal glucose trace), a glucose concentration value may be illustrated at the start of the meal as if the user was starting from a zero glucose concentration. Such may significantly clarify the presentation of data on a graph, and thus convey the meaning of the glucose trace more clearly to an inexperienced user. For example, referring to FIG. 18, a graph 196 is shown in which an actual glucose concentration trace 202 is plotted superposed on an ideal glucose trace 198, an event, indicated by the traces, being consumption of a meal. By subtracting out the glucose concentration value at the beginning of the meal, e.g., by starting both traces from zero, as illustrated by the glucose trace 206 plotted with the superposed ideal glucose trace 204, the effect of the meal may be more easily seen by the user. In this case, the meal trace follows the ideal trace well.

For portrayal as part of a program, such traces may indicate average values, and the averages may be taken over various time periods, e.g., 1, 3, 6, 12, 24 hours, and so on. In other cases, glucose traces may be displayed to the user as example depictions of glucose events occurring within or as a result of the program or other perturbation.

As examples of qualitative ways of providing data, colors or the use of range indicators (in lieu of value indicators) may be employed to provide information to a user. Other examples include the use of ranges or zones, textual verbiage, actions or comments by avatars, and the like, as will be described below.

The displayed outputs may thus be simple, intuitive, and easy to understand, e.g., the outputs may be configured such that it is easy to understand what type of action is being requested of the user, and may be easily relatable to everyday life. In one implementation, "low-resolution" data may be initially provided to the user, e.g., a color indicating whether a goal associated with the program has been met, or showing, e.g., the impact of exercise on a glucose level. "High resolution" data may be provided in the background, e.g., available to the user via a swiping action. In some cases the low resolution data may be action based, instead of a color or value, providing a comment or an action performable by the user. High-resolution data may also be provided to the cloud for subsequent use by a healthcare practitioner ("HCP") or other users.

Figure 3:
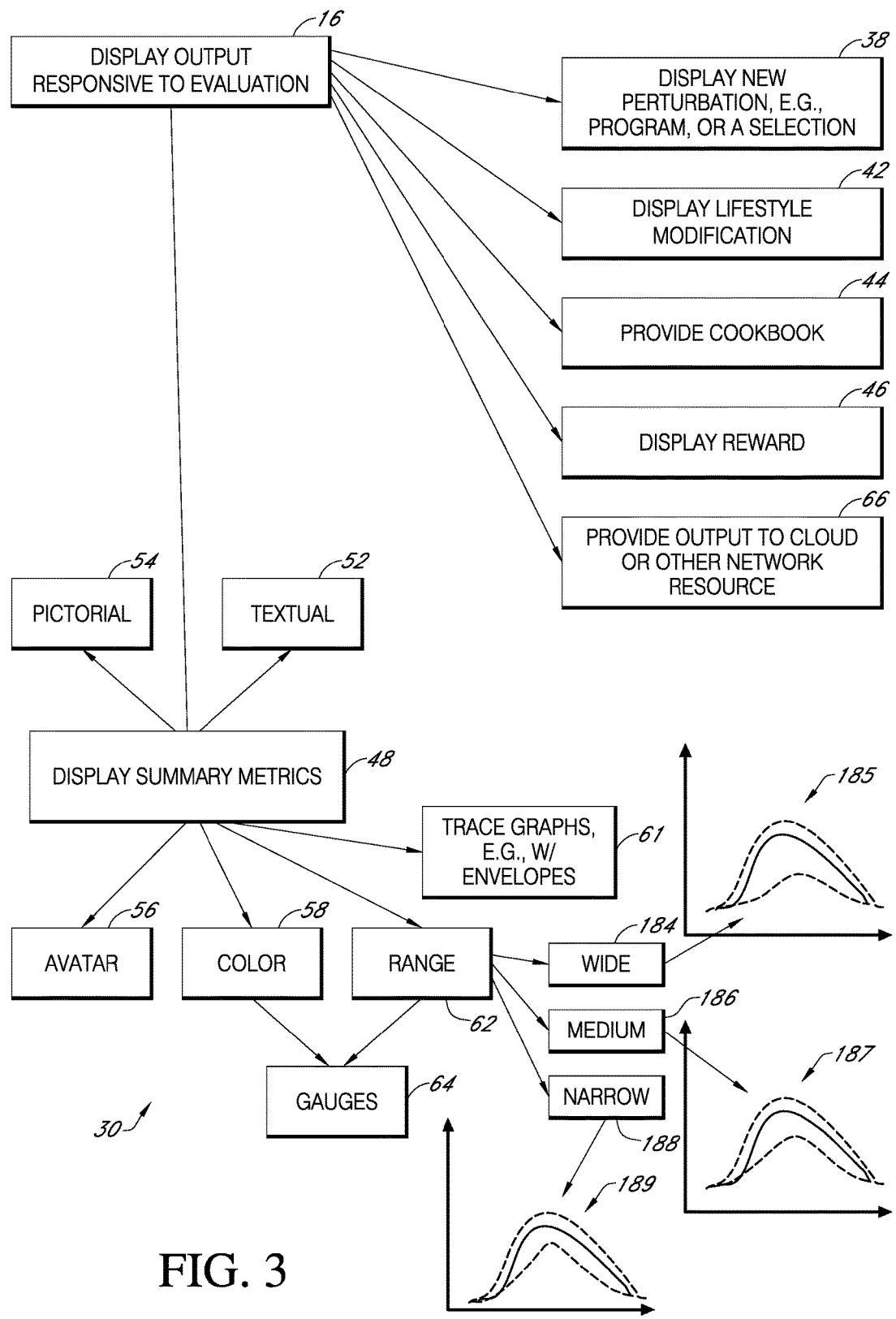
FIG. 3 illustrates various exemplary types of displayed outputs.

In more detail, referring to the diagram 30 of FIG. 3, and as one example of an output, systems and methods according to present principles may provide a new perturbation, e.g., a new program for the user to follow, or a selection of several such potential or proposed programs for a user to select (step 38). The new perturbation may generally be at least partially based on the evaluation step noted above. For example, a new program according to step 38 may include a change to a prior regimen, a new protocol to follow, or a variation of a prior protocol. The efforts of such iterative programming are to move a user toward improvements in health management in a rapid fashion. A further benefit is to make more efficient the operation of the computing environment by saving computing cycles and battery power.

As another example of an output, a lifestyle modification may be displayed (step 42). The lifestyle modification displayed is commonly the result of the step 19 noted above, i.e., to evaluate to determine lifestyle modification. For example, a lifestyle modification may be an indication such as "You did well on your attempt to control your glucose during breakfast, but maybe you should try eating half as much on your Wednesday meal, or walking a half hour before you eat."

As yet another example of an output for display, a cookbook, such as in electronic form, may be provided which is personalized to the user with recipes determined to be likely favored by the same (step 44). The recipes can be personalized to the user, on the basis of data about prior foods eaten, e.g., using retrospective user analysis, and may be further tailored to the user by use of a questionnaire or other contemporaneous data input by the user about preferred meal choices. Recipes can be selected for inclusion by their glycemic index or glycemic impact. For example, if systems and methods determine the user's Wednesday meal to have a higher-than-usual glycemic index, a recipe may be proposed for the user for that Wednesday meal to lower the same.

The cookbook may also indicate exemplary glycemic indices of various meals, thus allowing the user to compare the effects of one meal choice with the effects of another. Besides showing the effects of different meals, the effects of a single meal may be displayed as the same would be experienced by a nondiabetic person, and in some implementations as compared to how the same would be experienced by persons at different stages of diabetes. The cookbook could also adaptively show what impact a meal would have on the user's glucose. For instance a glycemic index of a meal will have different effect between different people. The app could tailor the glycemic impact to the user, or may alternatively show what the profile would look like if the user were exercising routinely or not.

The cookbook recipes may be advantageously employed as part of a perturbation to a biological system, e.g., as part of a program, as the system may incorporate and use the known nutritional characteristics of the recipes as part of the entered food data, and thus the program may be enabled to quantify the program perturbation and better evaluate results vis-a-vis measured data.

As another example of an output, a reward may be displayed (step 46). For example, if the user has shown significant levels of control, a reward may be displayed indicating that the user may consume an item of their choice. Other variations of rewards will also be understood given this teaching. For example, users may accumulate points or other counters for exercising or exhibiting significant glucose control, and the same may be the basis of achievements, prizes, posts to social networking systems, or the like.

In many cases the displayed output will include summary metrics (step 48). As noted these need not be quantitative, but rather can also be qualitative, and can provide an observance on the evaluation, and in some cases commentary on the user's result of following the selected program. For example, the display of summary metrics may include displaying text (step 52), e.g., "Eating breakfasts according to the cookbook recipes was effective for you.", "Eating those lunches with your selected limits on glycemic index foods really helped your control.", or "Wednesday's breakfast may not be your best meal." While in some cases pertinent actual glucose values can be displayed, the same can also be suppressed in many implementations for simplicity.

The displayed output may include consideration and display of glycemic index or other data about food, e.g., caloric content. The displayed output may also include data in which such are personalized to a user. For example, if it is known that a certain food or exercise has a particularly good or bad effect on a user's control, as determined by historical or other retrospective data, then an indication of such a particular sensitivity may be included in the displayed output.

The displayed output may further include comparisons to other users, e.g., using data sourced from the cloud or other network source, so that a user may be enabled to compare their control with those of others, e.g., either generally or within a specified peer group, e.g., Facebook® friends. The type of display (of compared data) may be as noted elsewhere herein, e.g., via avatars, colors, text, trace data, or the like.

Other types of outputs will also be understood, including those that are not necessarily the subject of a display on the UI 26 of the monitoring device 21 (see FIG. 2). For example, data may be sourced or output to the cloud or other network source (step 66). This data may then be analyzed by an HCP and/or may be used in the calculation or use of compared data for other users, e.g., within the subject user's peer group. As part of a calculation, such data may be employed to transform one set of data into a different set, allowing deductions to be calculated which were previously unavailable without such data and such transformations.

Providing the output to the cloud may be performed for a number of purposes. First, the same may be employed to transmit via an appropriate transmissions protocol feedback to caregivers, family members, loved ones, peer groups, or the patient themselves. For example, where program goals are monitored on a network or other cloud-based source, the same can be employed to determine if the user has met a goal, e.g., a goal of a program set by the perturbation 11 (see FIG. 1), or a goal set by caregivers, physicians, friends, or family. Besides providing information, such cloud-based data enables social and competitive activities, e.g., within peer groups or on social networking websites. Providing outputs to the cloud, with this type of "social" character, can also be employed to improve compliance. For example, if a subject user has a glucose level in a danger zone, or is suffering from a severe excursion, the "share" functionality may be employed by either the subject user or a caregiver to contact the subject user and help motivate them to make better or alternate behavior choices. Such may be particularly pertinent for elderly users. The social character allows the creation of an online community where users can act as "buddies" and help each other with motivation, such as exist in other behavior modification programs. Such allows significant savings in computational processing over the case where such communications have to be transmitted via email or other techniques.

Where outputs are sent to a cloud connected HCP, the same can determine if the user is responding to therapy, e.g., a meal program, exercise program, or medicament programs including drugs, e.g., for diabetes, metformin (or other drug indicated for type II diabetes). The HCP can determine if the user is a responder to medication based on a series of blood tests and knowledge, e.g., via metadata, of other responders, e.g., other users on the same medications. Additional details of such medication aspects are described below in connection with FIGS. 41 and 42.

In the use of cloud or other network sources, a CGM profile and cultural background can be shared, and can be used as guidance for improvement, both by the subject user and by other connected users. For example, subject users can research how users similar to them, e.g., with similar ethnic backgrounds, body types, ages, etc., were able to improve their health. In particular, providing outputs to the cloud also allows the construction of profile information which allows personalization of therapies as noted above. For example, if particular exercises or meal choices have been found appropriate and well-liked by demographically similar users, such may be provided as potential options for a subject user. Such analysis is particular data-intensive and may require analysis and computation of a large number of users, using transmitted data from around the world.

Users also may be provided with generic comparisons where such can be calculated, e.g., "You are in the top 10% of your peers.", which can serve as motivational aids to the subject user. The overall available population data may be employed to see where the individual is situated, e.g., to determine and display if the user is typical or atypical. This comparison may be made in different situations, e.g., the user may only be atypical during holiday seasons. Calculated or computed correlations may be made to historical data, and comparisons may be further narrowed by considering a user's best days, worst days, or the like.

Outputs can also be transmitted via an appropriate communications protocol to cloud-connected health insurance carriers or administrators of wellness programs. The outputs can indicate the effects of, e.g., medication, diet, exercise, or other aspects of a user's lifestyle. Outputs can further be transmitted to cloud-connected manufacturers or pharmaceutical companies, ACOS, EMR storage facilities, or the like. In some cases, insurance companies may be enabled to lower premiums or increase benefits or provide other benefits to users if the users show a certain level of glycemic performance, e.g., if the users meet a predetermined threshold criterion for glycemic performance as measured and determined by systems and methods according to present principles.

Figure 4:
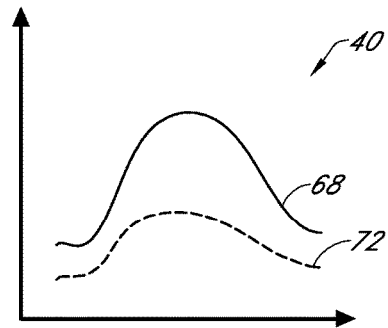
FIG. 4 illustrates an output in which an analyte trace is plotted along with an ideal or modeled analyte response.
Figure 5:
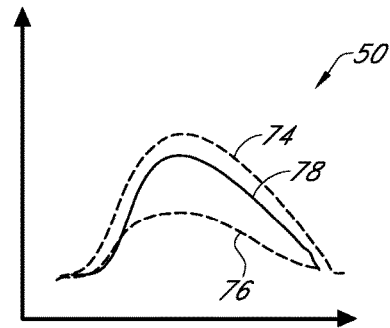
FIG. 5 illustrates a displayed output in which an analyte trace is plotted along with an envelope of an ideal or modeled analyte response.

Returning to FIG. 3 and in particular to non-cloud-based outputs, another type of output that may be of use to users is the display of a trace graph with an envelope (step 61) (or just one or more guide traces). In particular, this type of output may provide the measured analyte response to a meal along with an ideal response. For example, referring to FIG. 4, a trace graph 40 is shown in which an analyte response 68 is illustrated along with an ideal or preferred response 72 for a meal. In the same way, the graph 50 of FIG. 5 illustrates an analyte trace 78 is generally within an envelope formed by the ideal or model traces 74 and 76. In these graphs, the user's resulting analyte value is qualitatively indicated in an easy-to-understand fashion. It will be understood that, for uses in programmatic learning, such may generally represent averages, and that the averages may be determined using data accumulated during the time period in which the program is followed. These graphs may also be replaced with various surrogates, e.g., colors or avatars, indicating whether the user is "in control", within an envelope of control, or the like. For example, the color green may indicate that a user is in control (e.g., within an envelope), while the color red may indicate the user is out-of-control. Similarly, a smiling avatar may indicate control, while a frowning one may indicate a lack of control.

Figure 6:
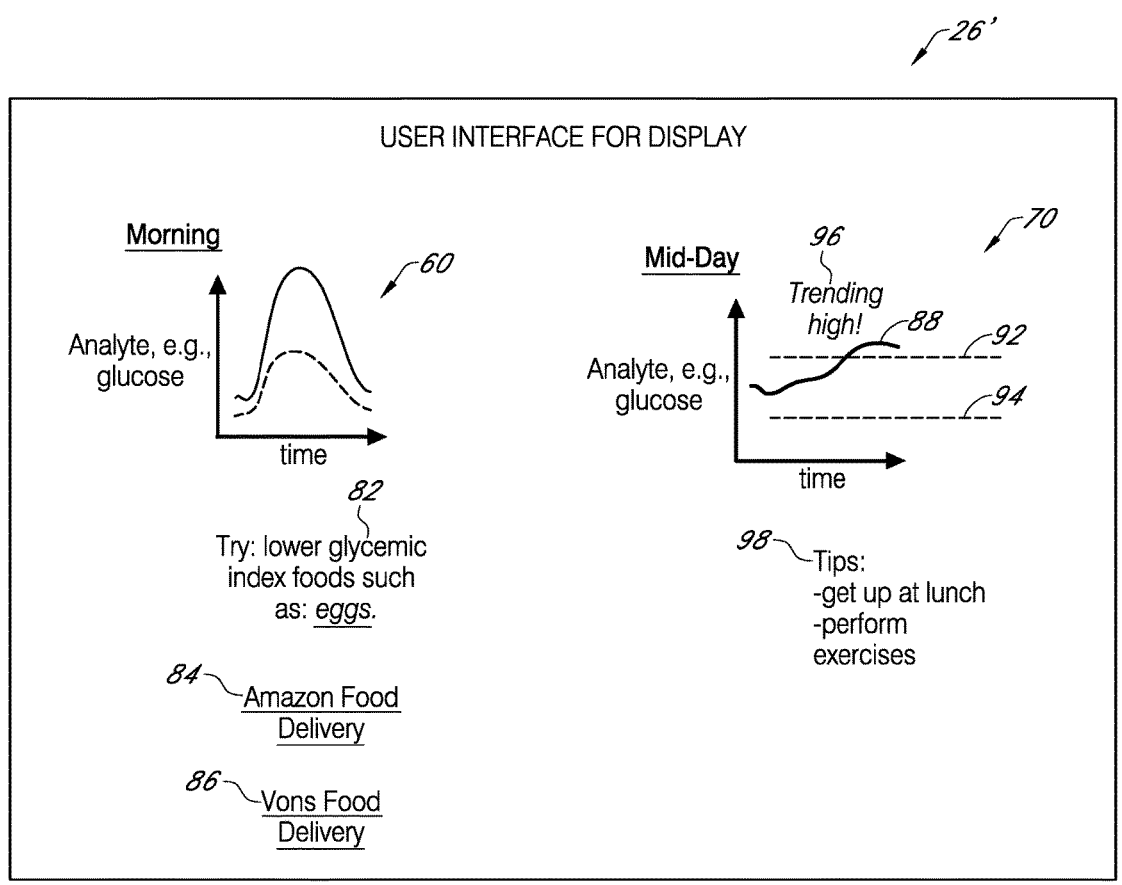
FIG. 6 illustrates an exemplary user interface in which a combination of types of outputs is displayed. It will be understood that combinations of other outputs are encompassed by present principles (in this and in other figures).

FIG. 6 illustrates a user interface 26' in which a combination of types of outputs are provided. With the user interface 26', a single screen may be employed to review numerous data from a given day or part of a day. The data displayed are generally with respect to a program or recognized pattern. For example, the user interface 26' displays a trace graph 60 with a morning analyte response shown with a solid line (aspects of this graph 60 are similar to those of the graph 40 of FIG. 4, and such details are not repeated here). The analyte response may then be compared to a desired analyte response according to the program, pictured with a dotted line.

The trace graph output 60 may then be combined with other outputs, including a textual output 82, which is a recommendation or suggestion in this example to try lower glycemic index foods. The user interface 26' may also provide convenient links 84 and 86 to sources for such foods, and by following the links, appropriate such foods may be displayed in the UI 26' for purchase by the user.

The user interface 26' also shows a mid-day analyte trace graph 70, in which an analyte level 88 is plotted with respect to time, with one or more threshold levels shown, e.g., a threshold 94 for hypoglycemia and a threshold 92 for hyperglycemia. A textual indication 96 is displayed, indicating conveniently to the user a present summary status. Potential lifestyle modifications 98 are shown, in the form of tips, such as to "get up at lunch" and/or perform "exercises". In this case the potential lifestyle modifications may be personalized to the user, as well as to time of day. For example, exercises may be suggested (not shown) which are appropriate for the workplace, if the output is being displayed during the workday. Users may also enter preferred exercises, and such may then be preferentially displayed. For example, a user may enter a preference for walking for 45 minutes rather than swimming four laps.

Figure 7:
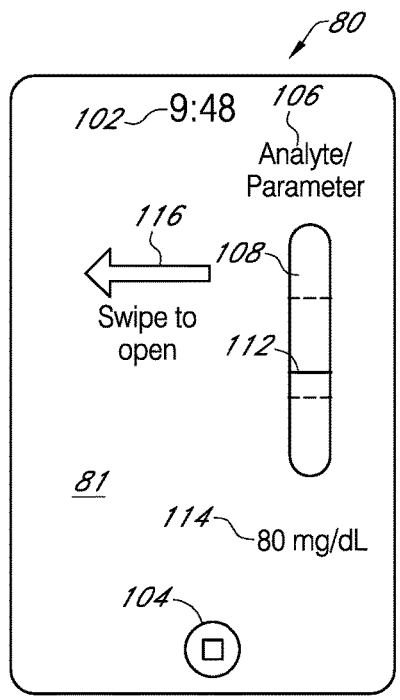
FIG. 7 is an exemplary user interface in which a combination of types of outputs is displayed.
Figure 8:
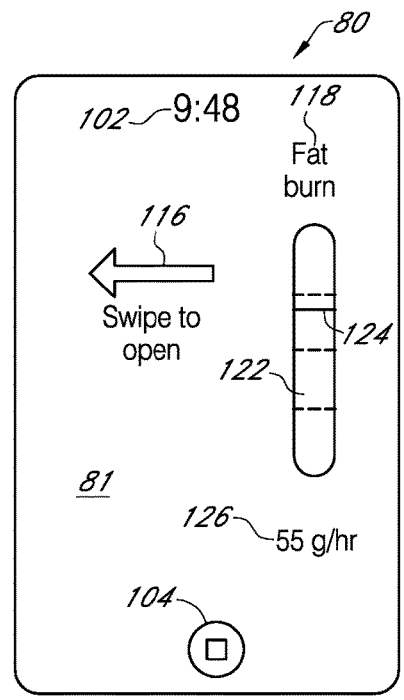
FIG. 8 is another exemplary user interface in which a combination of types of outputs is displayed.

Other combination views will also be understood. For example, referring to FIG. 7, a user interface 81 for a typical smart phone 80 is displayed where manipulation of the user interface may be via a touchscreen as well as by one or more buttons 104. A clock 102 is shown as part of the user interface, as well as an initial indication of an analyte or other data value. For example, in FIG. 7, an analyte value is shown on a thermometer-type scale 108, the parameter value being shown by a line 112. Dotted lines indicate threshold values for alerts. In some implementations, a more precise or quantitative value 114 may also be displayed. Such constitutes low-resolution data, and by a swiping motion 116, additional data may be retrieved, determined, and/or displayed, such constituting higher resolution data. In FIG. 8, another parameter is shown, e.g., "fat burn" 118, and the same indicated by a similar thermometer type scale 122 with the current value indicated by a line 124, e.g., corresponding to metabolic rate. A numerical value is also shown by text box 126, which can be used to indicate various metrics such as the estimated fat burn rate in g/hr, lbs/hr, the total fat burn since initiation of exercise or from the start of day, percent of maximal fat burn rate, lactate level, carbohydrate burn rate, or the like. Dotted lines divide the thermometer-type scale into four zones, which may be similar to those described below in connection with FIG. 9. Such metrics are generally only calculable using an appropriately-configured computing environment with suitable input data, generally from sensor data but also user-entered data.

Figure 9:
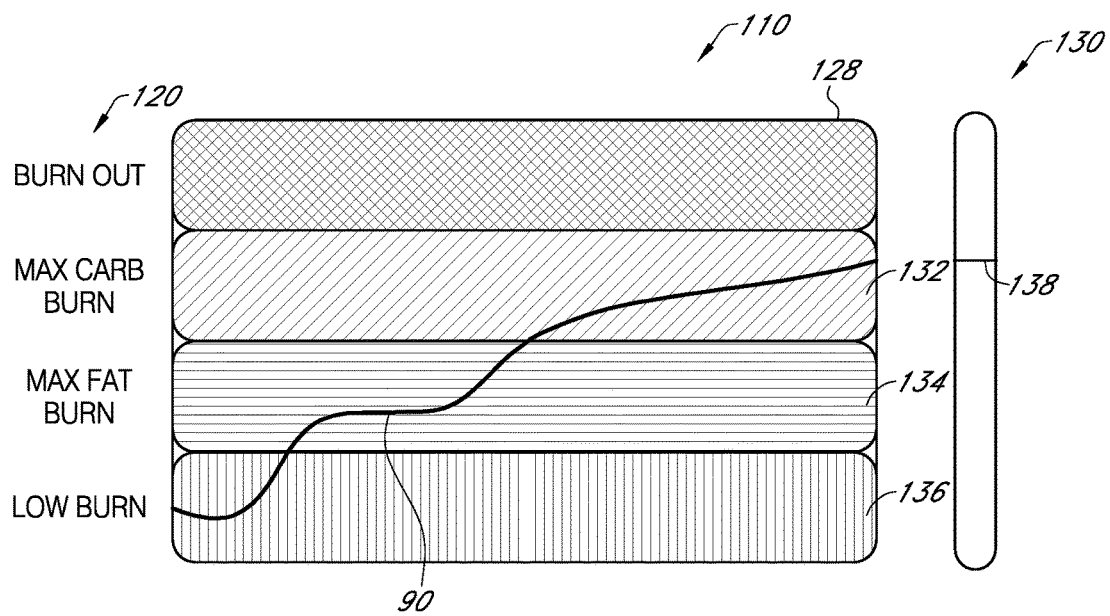
FIG. 9 is an exemplary user interface in which various ranges of fat/carbohydrate burn rates are displayed.

Following a swiping gesture, additional data may be shown, e.g., trend and history graphs, as illustrated by the exemplary FIG. 9. In this figure, the thermometer type scale of FIG. 8 is expanded into various zones 110, e.g., a low fat burning zone 136 (low physical activity), a maximum fat burn zone 134 (optimal fat burn, lipid metabolism), a maximum carbohydrate burning zone 132 (optimal cardiovascular intensity, aerobic carbohydrate metabolism), and a burnout zone 128 (anaerobic metabolism due to lactate buildup). Textual descriptions of the zones maybe displayed by elements 120. A trace graph 90 is seen, which in this case traverses three of the zones. Finally, an instantaneous value is illustrated by the thermometer-type scale 130, in which zones or gradients may be indicated, and in particular a current or instantaneous value is indicated by line 138.

The above-noted displays are beneficial for, in case of diabetes, the type II population, for a number of reasons. For example, particularly with respect to FIG. 7 and FIG. 8, there are limited or no numbers. A bar moves up and down in the column which has different zones to indicate metabolic levels. The bar may have a width to indicate range if applicable. An arrow can be displayed (not shown) to indicate a rate or direction of change. Alerting or alarming may be minimized for such patients, and may only be present for particular purposes, e.g., to indicate if an athlete has reached a lactate threshold. Predictive alarms may also be implemented for these purposes.

Figure 10:
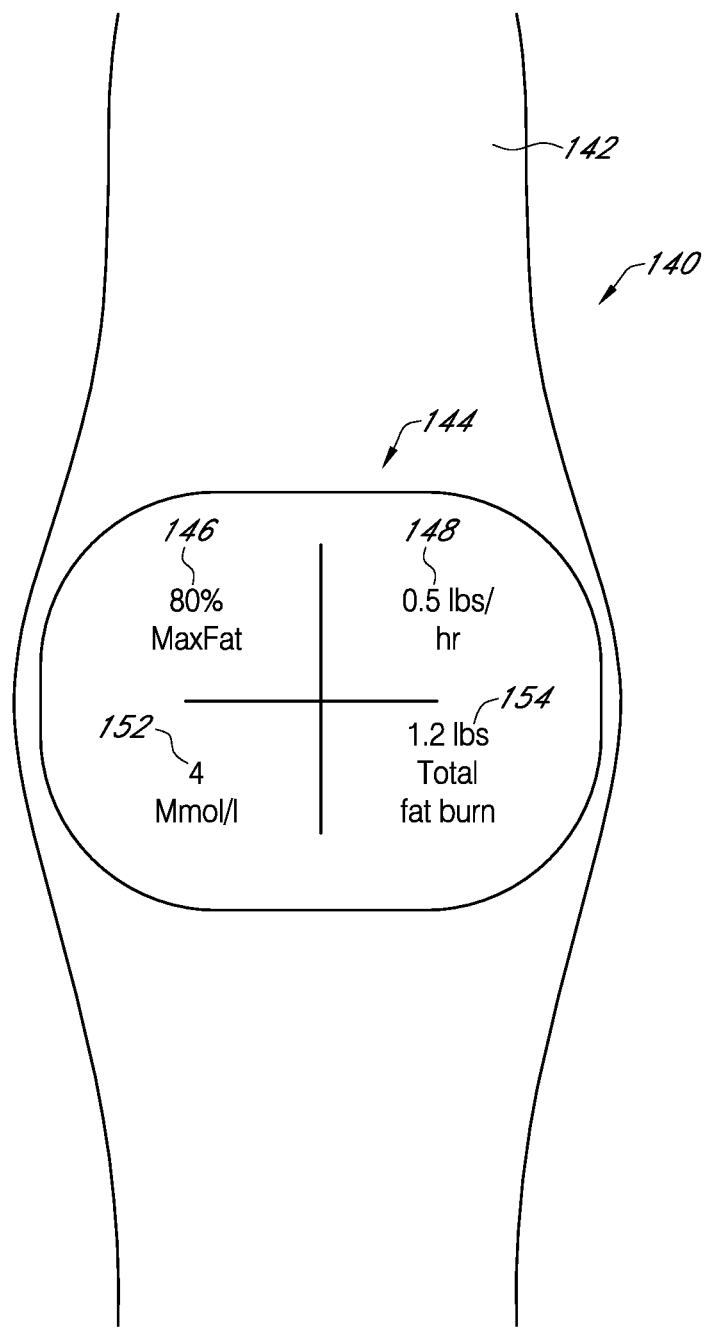
FIG. 10 is a user interface of a watch, illustrating various types of outputs.

Referring to FIG. 10, metrics may also be displayed as combined on the face of a watch or other similar display. In FIG. 10, a watch 140 is illustrated with a band 142 and interface 144. Exemplary options are shown, and it will be understood that other options may be displayed on such a combination interface.

In the figure, metrics are shown including a percentage of maximum fat burn rate 146, a numerical indication of the fat burn rate 148, a numerical indicator of a lactate level 152, and a total amount of fat burned during the workout or session 154. As noted, numerous other options will be understood.

Figure 11:
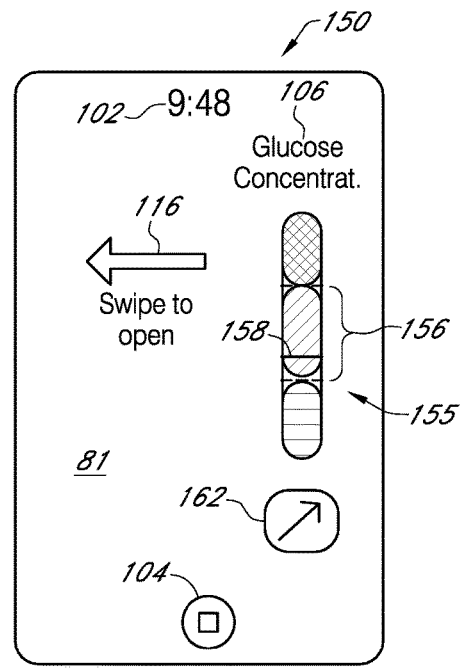
FIG. 11 is an exemplary user interface in which various ranges of glucose concentration level are displayed, along with other performance parameters.

FIG. 11 illustrates another user interface 150 which may be employed in displaying continuous glucose information to a user. Certain aspects are similar to FIGS. 7 and 8 and the discussion of such aspects is not repeated here. In FIG. 11, the analyte is represented by a glucose concentration 106, which is again indicated by a thermometer-type gauge 155. Thresholds 156 separate the gauge into three ranges or zones, and it is seen that the current level 158 is within the center range or zone, e.g., a euglycemic range. A directional indicator 162 is provided to give the user an indication of a rate of change, e.g., if the glucose level is rising, falling, or staying the same. In this case, an arrow pointing up indicates that the glucose value is rising.

Such a displayed output provides numerous beneficial elements and aspects. For example, the complexity of actual glucose values is eliminated. In FIG. 11, no glucose value is given. Rather, the bar 158 moves up and down in a column which has different zones to indicate glucose level. For example, the bottom zone may be red and may indicate a hypoglycemic zone. The middle zone may be colored green and may indicate a target glucose zone. The top portion may be colored yellow and may indicate a hyperglycemic zone. The location of the bar indicates the current glucose range of the user.

In some cases, the bar may be provided with a significant width to indicate the range which the user's glucose is in, rather than an exact value. That is, in this simplified version, an exact value is no longer emphasized. A wide bar or gradient of color indicates the range of glucose for the user.

Figure 12:
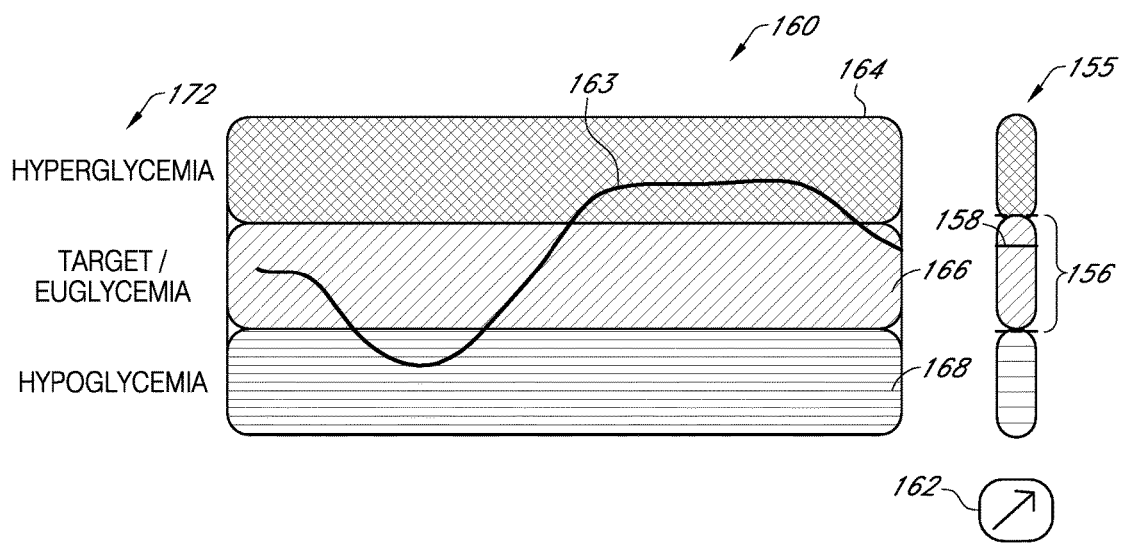
FIG. 12 is an exemplary user interface in which various ranges of glycemia are displayed.

By swiping the user interface (on a touchscreen), the trend graph may be displayed, which is indicated in FIG. 12. A center section 160 provides ranges of glycemic zones, e.g., hyperglycemic range 164, euglycemic range 166, and hypoglycemic range 168. To remind the user, textual indicators 172 may also be employed. A similar thermometer type gauge 155, along with rate of change indicator 162, may also be employed in this implementation. Superposed on the center section 160 may be a trace graph 163 illustrating recent values of the analyte, e.g., glucose.

Figure 13:
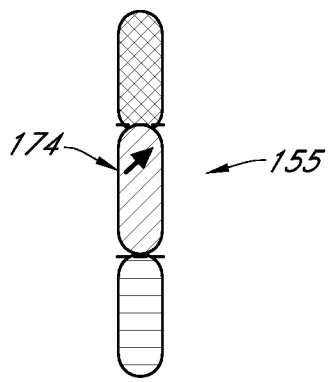
FIG. 13 is a more abbreviated exemplary user interface in which various ranges of glycemia are displayed.

If the device is oriented to type II or nondiabetic users, limited or no alarms may be configured. Alternatively, predictive alarms may be used and may be indicated using a blinking red or yellow arrow when the patient is predicted to cross into a hypoglycemic range or hyperglycemic range, respectively. An alternative way of predicting direction or rate of change may be to include an arrow 174 on the thermometer type gauge 155, which indicates direction and rate of change (see FIG. 13).

Figure 14:
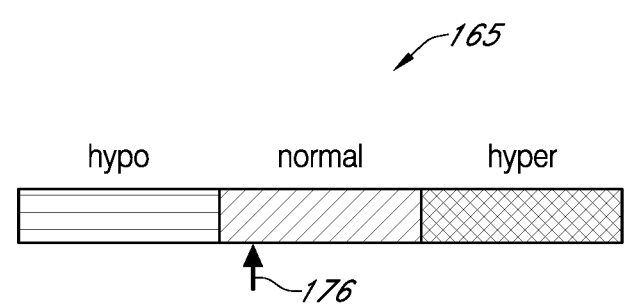
FIG. 14 is another more abbreviated exemplary user interface in which various ranges of glycemia are displayed.

As noted above, a color indicator can be conveniently employed to indicate if the user is above or below a threshold. For example, as indicated in FIG. 14, an arrow 176 may point at a location on a color strip 165 indicating in what range a glucose value is located. While the color indicator of FIG. 14 is illustrated in a horizontal orientation, the same may also be disposed vertically.

As noted above, in some cases a user population will not require as detailed a data presentation as in prior systems. For example, and returning to FIG. 3, colors, avatars, or other range indicators may be sufficient.

A number of elements, e.g., on a mobile device, may be provided in certain colors (step 58) to indicate an output. For example, the icon color of the monitoring application may indicate a current status, e.g., if the user is meeting the goals of the program or not. A background color of the smart phone itself, e.g., a wallpaper or desktop, may be provided with a color for the same purpose. Such color indicators can reinforce good behaviors, e.g., a user may wish to continue to see the green color indicator, indicating they are meeting the goals of the program, and such may then influence user actions, e.g., meals consumed and/or exercise performed. The system can also use a color to indicate a summary of a post-meal glucose level. For example, if following a meal a user continues to be in good glucose control, the system may indicate such by a suitable color scheme. In the same way, a color indicator can be employed to show the impact of exercise on the analyte level. For example, a color indicator may show a yellow color, but may indicate that the same is transitioning to green as a result of user exercise, modulating or otherwise controlling a high blood sugar level.

Figure 15:
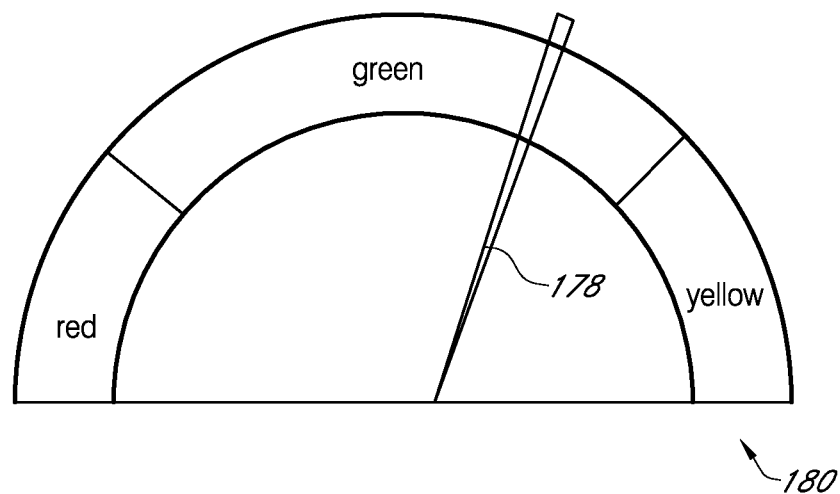
FIG. 15 is an exemplary user interface in which various ranges are displayed, in a tachometer format.
Figure 16:
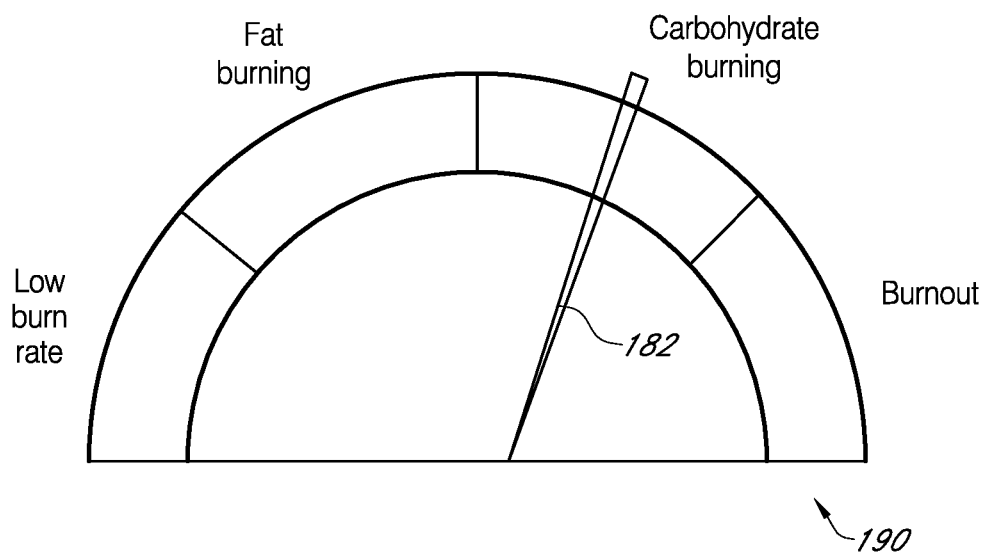
FIG. 16 is an exemplary user interface in which various ranges of fat/carbohydrate burn rates are displayed, in a tachometer format.

In another implementation, referring to FIG. 15, a tachometer or gauge type indicator 180 may be employed (see also step 64 in FIG. 3), again divided into different glycemic zones (in the case of glucose), with the needle 178 indicating a current zone. In this case both colors and ranges may be employed in a displayed output. FIG. 16 indicates an alternative such tachometer diagram 190, where a needle 182 indicates various fat burning zones as may be measured by a metabolic monitor. A coarser implementation may indicate just two ranges, e.g., whether a subject user is consuming more calories than are being expended, or vice versa. Other implementations will also be understood. Each of these implementations provides certain technological advantages and improvements as the computing environments implementing the same operate in a more efficient manner by providing users with desired information without requiring the user to traverse many screens and enter many button presses or other user interactions to achieve or view similar results.

However displayed, where ranges are employed, the same may be configurable by the user or by an HCP. Depending on the analyte response with respect to the range, as noted, rewards, congratulations, or other feedback may be provided to a user.

In some cases, and again referring to FIG. 3, ranges may be configurable based on how well a user has learned to control their glucose. As users employ the systems and methods according to present principles described herein, the ability to control analyte and other glucose levels generally increases. For a new user, ranges may be made wider (step 184) so that a measure of success for the user is more easily attained. Once the user becomes more skilled at controlling their analyte levels, ranges may be narrowed to a "medium" level (step 186). Finally, to challenge advanced users, with the goal of even better increasing their healthy lifestyle, acceptable ranges may be made narrow for such users (step 188). Such again causes the systems and methods to operate more efficiently, increasing technological efficiency of the computing system.

The terms "wide", "medium", and "narrow", are used here to refer to a level of analyte control. In some implementations the terms may thus refer to the width of a band or envelope of acceptable analyte readings measured while following a program (see graphs 185, 187, and 189, adjacent steps 184, 186, and 188, respectively), or subsequent to an event. Other definitions may also be employed, including those that take account of, i.e., are partially based on, threshold alerting and alarming values, e.g., for hypoglycemia and hyperglycemia.

Where methods include steps of modifying, e.g., tightening or loosening ranges, the modification of the range can occur in the step of determining a new perturbation, e.g., by selecting a program with the modified range. The modification may also occur at other points in the method as well.

Given the above teaching, various other types of displayed outputs will also be understood. For example, heat maps may be employed to plot analyte values. In another variation, where a user is following a program and a deviation from an expected trace graph is seen, e.g., a data arrangement outside an envelope as portrayed in FIG. 5, then the user may be provided with an image (graph or otherwise) of the deviation, e.g., a sudden rise or drop. In this way, the user may efficiently and rapidly be provided useful and actionable information without having to provide significant amounts of user interaction.

Figure 19:
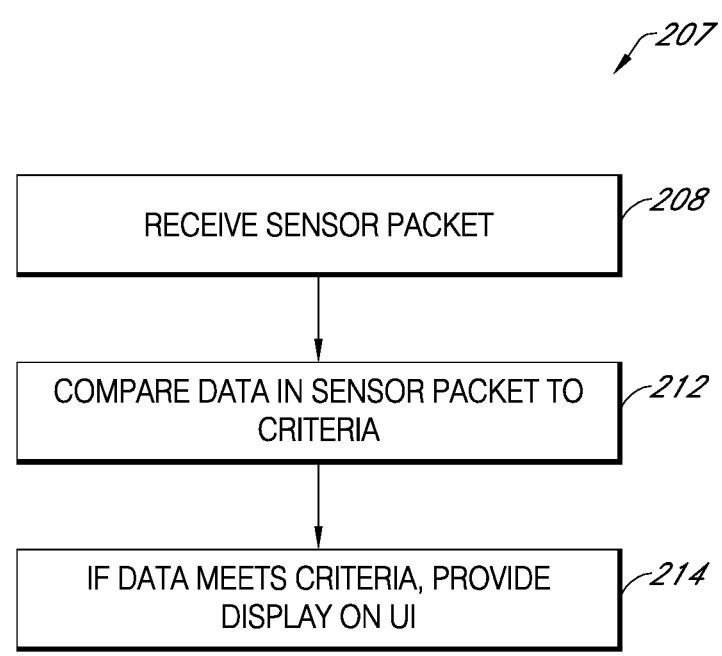
FIG. 19 is a flowchart indicating a method according to present principles.

For example, and referring to the flowchart 207 of FIG. 19, an algorithm, or a portion of the application 27 (see FIG. 2), may receive (step 208) and monitor incoming sensor packets and review the same for minima or maxima in the data. To do so, the data can be compared to criteria (step 212), including potentially predetermined thresholds or thresholds based on retrospective data analysis, e.g., the sorts of excursions the user has seen in the past. If data in the incoming sensor packet is determined to match or meet the criteria, e.g., to exceed a threshold, then an alert or alarm may be caused and the same displayed on, e.g., the UI 26 of the monitoring device 21 (step 214). The alert or alarm displayed may depend on several factors, including the criteria met, the size of the excursion, and other factors.

Figure 20:
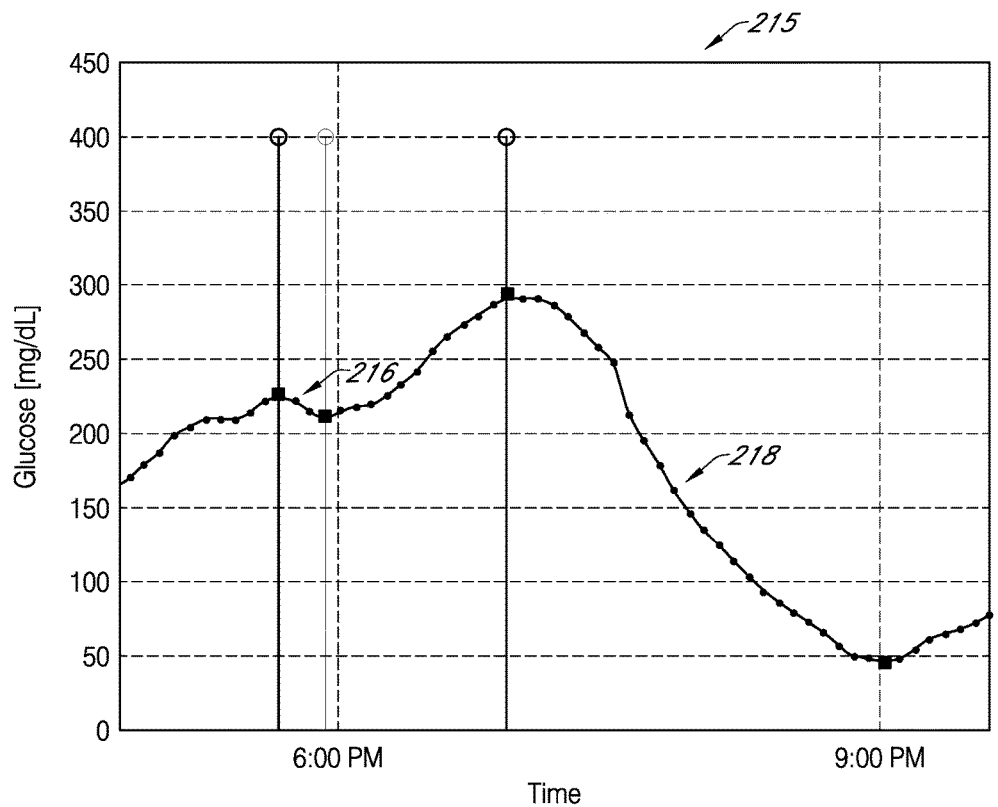
FIG. 20 shows an exemplary glucose plot against time.

An example is shown in FIG. 20. An algorithm, which may be a retrospective algorithm, may look for minima and maxima any time a new sensor packet arrives. In FIG. 20, two events are shown. A first event 216 starts at 227 mg/dL and ends at 213 mg/dL. A second event starts at 294 mg/dL and ends at 46 mg/dL. The retrospective algorithm may check whether the current event excursion falls outside of threshold. In this example, thresholds may be defined as a certain milligrams per deciliter difference or a percentage difference between the start and the end of an event. Another threshold definition may be if an excursion is at least one standard deviation outside of a typical excursion (or other measure related to standard deviation). In any case, thresholds may be defined so as to ensure that only meaningful events are displayed to the user, and that nuisance alerts are minimized. Such systems and methods clearly provide technological advantages not capable of being provided by the prior art.

Meaningful events, e.g., those that meet the criteria, trigger an alert, e.g., a push notification, an icon on a trend graph, a badge number increase, or the like. As noted, depending on the type of event, e.g., a high glucose value traversing to hypoglycemia, or the like, the alert displayed may differ. For example, if the event is an excursion from a high glucose state to hypoglycemia, e.g., 294 mg/dL to 46 mg/dL, the message might be "We noticed a wide glucose excursion, would you like to enter meal and/or insulin information for this event?". To provide further information about the event, the trend graph segment may be highlighted in a different color while the alert is active, e.g., meaning the user has not yet cleared the alert.

The output can also serve, in some implementations, e.g., in the diabetes control area, as a "glucose coach", i.e., as part of a lifestyle modification program. In this way, the output can provide positive feedback when the user is in good control of their glucose, and can provide teaching feedback when the user is in lesser control. Good control in this context generally means the user's glucose concentration value is as expected or within a predefined envelope. The glucose coach systems and methods according to present principles can provide rewards upon the demonstration of sufficient control, e.g., allowing high glycemic foods a certain number of times per week, upon the attainment of sufficient control by the user. Upon the occurrence of insufficient glucose control, teaching feedback may be provided, so as to cause dietary habit changes, e.g., to motivate the user to incur fewer post meal spikes. For example, a textual output may be indicated such as "In the future when you go here, order something different like X". The glucose coach may also in this instance prompt for additional user information, e.g., asking the user for information about activities over the last predetermined time frame, e.g., six hours. For example, did the user eat high carbohydrates, did the user fail to exercise, did the user miss a medication, or the like. Thus, upon receipt and evaluation of data indicating insufficient glucose control, the system automatically can prompt for data entry to explain the insufficient glucose control. Similar aspects are described below in the context of a "discovery mode" employed in certain implementations.

Other implementations will also be understood. For example, the glucose coach can further provide user feedback on weight loss, e.g., as determined by weight, measured ketones, calorie burn, fat burn, or the like.

Outputs appropriate to certain users, e.g., the type II diabetes population, may have a simpler form than those for the type I population since the former generally have different needs. Consequently, and returning to FIG. 3, the displayed output of summary metrics may include displaying data in a pictorial form (step 54). In particular, images of food consumed by the subject user may be portrayed in various ways as part of the displayed output. The images may be either those captured by the subject user, or may be generic images corresponding to food entered by the user. For example, the user may indicate that a lunch included a chicken salad sandwich. The images shown in the displayed output according to step 54 may include an actual image of the chicken salad sandwich captured by the user, or a generic image of a chicken salad sandwich retrieved by the application 27 from a library, either local or online. Thus, to address the technological difficulty of displaying meal data, systems and methods according to present principles may use images captured by the subject user or generic images to address this technical difficulty.

Figure 21:
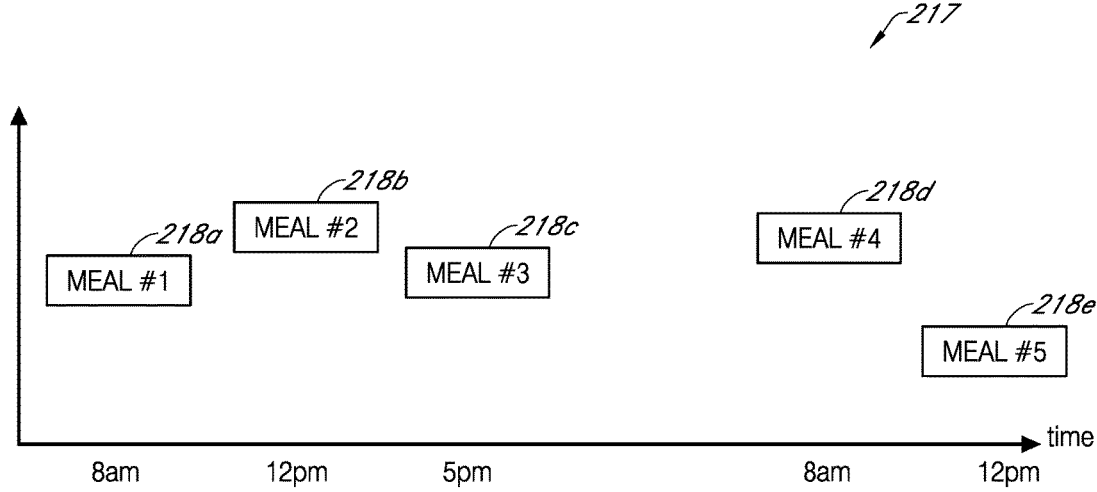
FIG. 21 shows an exemplary user interface in which meals are plotted against time, and with respect to glucose levels.

In one implementation of a displayed output, as illustrated by the graph 217 in FIG. 21, images of meals may be portrayed against a time axis. For example, meals 218a-218e are plotted against a time axis, generally representing breakfast, lunch, and dinner of a first day and breakfast and lunch on a second day. The meals are shown at different heights on a vertical axis. The height of each meal can be based on a glycemic index of the meal, a peak glucose response observed following the meal, or on other bases which may be useful to a subject user. For example, instead of placing the meal image at a vertical axis distance corresponding to glycemic index or glucose response, the size of the image may be used to convey this information, e.g., with meals of greater glycemic index or causing a larger excursion in glucose value being portrayed with a larger image. Thus, in this way, meal data is transformed into a particularly cogent visual rendering.

In a related implementation, not shown, the displayed output may be a time-lapse movie where the food is shown as an image with a corresponding effect also illustrated on the UI 26, e.g., with a size, color, or brightness, mapped to its glycemic response. In this implementation, the glycemic response may also be displayed as a trace graph, with a "current location in time" head shown moving along the trace graph in time along with the pictured image of the food consumed, both with respect to the passage of time.

Figure 22:
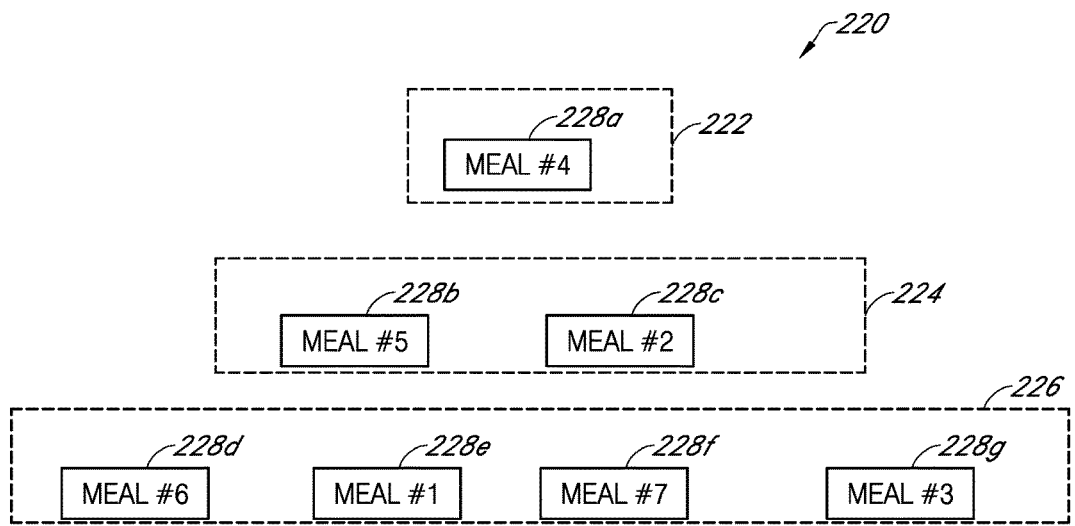
FIG. 22 shows an exemplary user interface in the form of a food pyramid.

In another implementation of a displayed output, as illustrated by the diagram 220 of FIG. 22, meal images or other indicators may be sorted into a food pyramid or other organizational scheme, e.g., "Weight Watcher®" bins. In diagram 220, users may be informed that items in the bottom zone 226 are most preferred for glucose control, items in the middle zone 224 are lesser preferred, and that items in the top zone 222 should only be eaten sparingly. The displayed output may then sort the foods eaten by the user, entered into the application as noted above, into the various zones. An indication may be given as to whether the result is a success or failure. A successful result would be if the user's meals 228a-228g occurred in the proper proportions according to the sizes of zones 222, 224, and 226. An unsuccessful result would be if the user's meals were, e.g., "top-heavy", in which a majority, or too many, of the user's meals occurred in the top zone 222. This implementation can give the user positive feedback, even if some of the user's meal choices were not always preferred.

In variations of the diagram 220, the images of meals 228a-228g may be accompanied by an indication of the time the meal was consumed.

Figure 23:
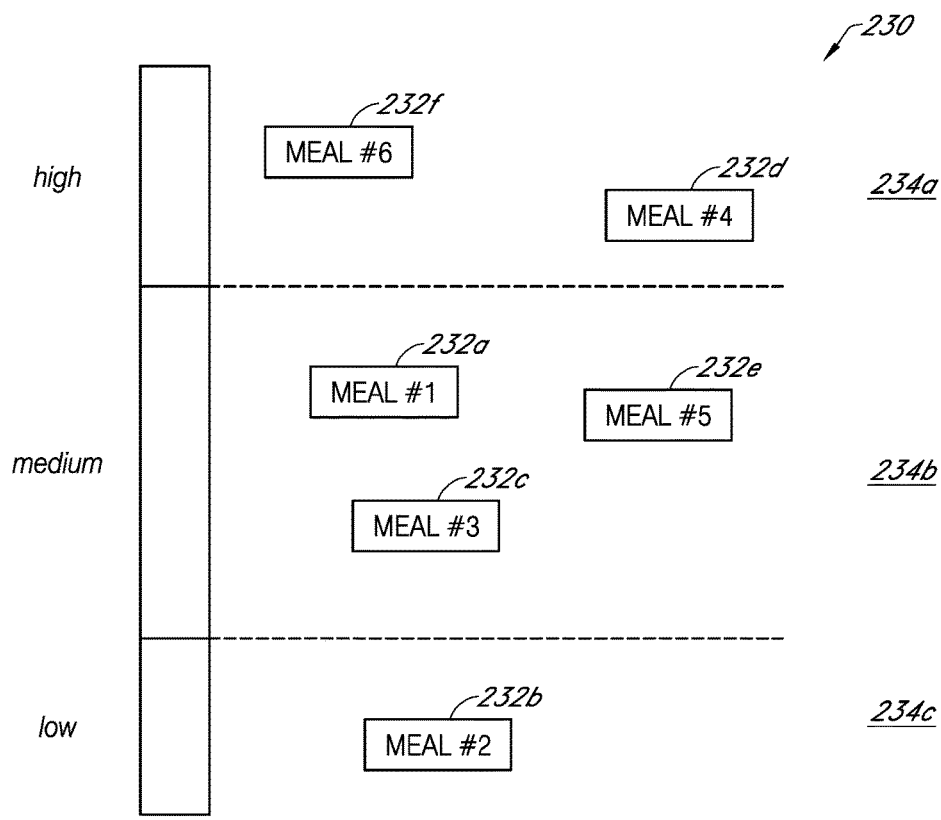
FIG. 23 shows an exemplary user interface in which meals are displayed as a function of their glycemic effect on a user.

In another implementation of a displayed output including pictures or images, as illustrated by the diagram 230 of FIG. 23, a number of meals 232a-232f are illustrated in various zones 234a-234c corresponding to meal categories of high glycemic index, medium glycemic index, and low glycemic index, respectively. Similar categories may apply to high, medium, and low glucose responses following meals. The same may also be sorted into caloric zones.

While a limited number of meals are displayed here, and in, e.g., FIGS. 22 and 21, it will be understood that such diagrams may include all meals pertaining to a particular program (or other perturbation), a subset of meals chosen as a representative sample, or another subcombination of known meals. Common meals may be combined and stacked in the display to save screen real estate. The determination of which meals are "common" may include analysis of hash tag information or other data entered by the user.

Combinations of the above pictorial types of displayed outputs will also be understood. For example, a number of food pyramids may be displayed along a timeline, each food pyramid corresponding to a day, a meal, or the like. In another variation, besides glucose, other analytes or physiological data may be portrayed, e.g., metabolic rate indicators, weight loss indicators, and the like. Other graphical techniques may also be employed for displaying outputs, e.g., heat maps, pie charts, histograms, and so on. The determination of how much data to include in a particular displayed output may vary, but is generally based on the data obtained during the current program, i.e., perturbation. In certain implementations, additional historical or retrospective data, from other sources, may be employed in a displayed output.

Other types of outputs will also be understood, including outputs tailored for type II users. In particular, certain technical challenges have been encountered in past analyte monitoring efforts related to understandability and context of the displayed data. Prior displays to have caused users to have to scroll or touch their way across numerous interface screens to obtain desired data and such present additional computing efforts required. Thus, in certain implementations according to present principles, calculations may be performed to display data on a user interface that is tailored to type II users, and may in some cases depend in part on user configurable settings.

In more detail, quantities which may be familiar to a type I user, such as a glucose concentration in mg/dL, may be difficult for type II users to understand as they may lack training in the same. In many cases, such users are unaware of the difference between, e.g., 55 mg/dL and 325 mg/dL. Accordingly, a user interface may be more "relative" for a type II patient, and may also be more explicit about status updates and actions to take. For example, instead of displaying 55 mg/dL, the user interface may state "you are low". Instead of displaying 325 mg/dL, the user interface may state "you are high". Instead of displaying 120 mg/dL, the user interface may state "you are in target". Different colors may be employed, using color schemes described above, e.g., red/yellow/green, where a user prompt in a red area indicates that action is required, a user prompt in a yellow area indicates a warning, and a user prompt in a green area indicates the user is in target. In some cases the intensity of the color may change, with the intensity of the area in which the user is situated being made more intense or bright. That is, the bar the user is in would be brighter than the other bars.

Figure 24:
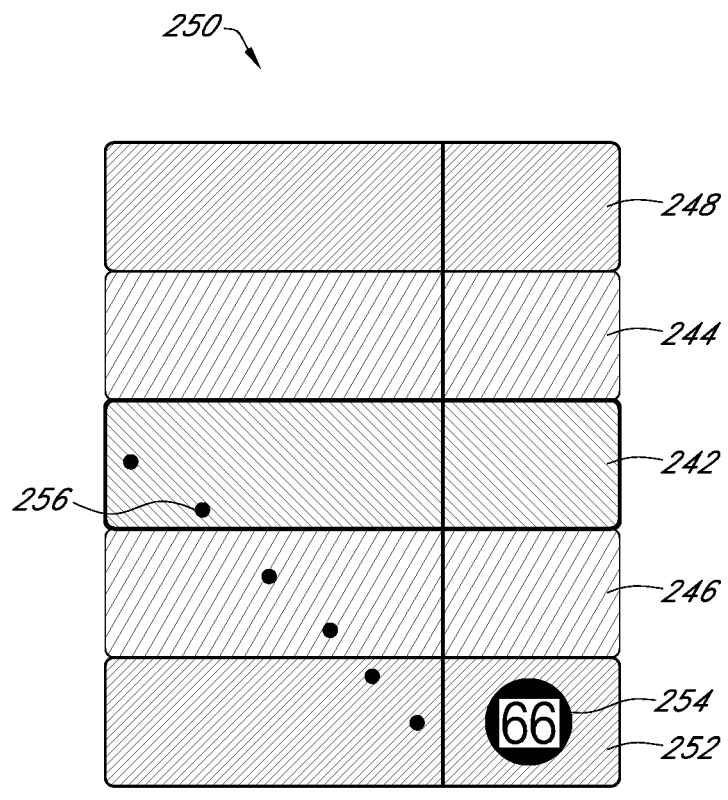
FIG. 24 shows an exemplary user interface simplified for type II users.
Figure 25:
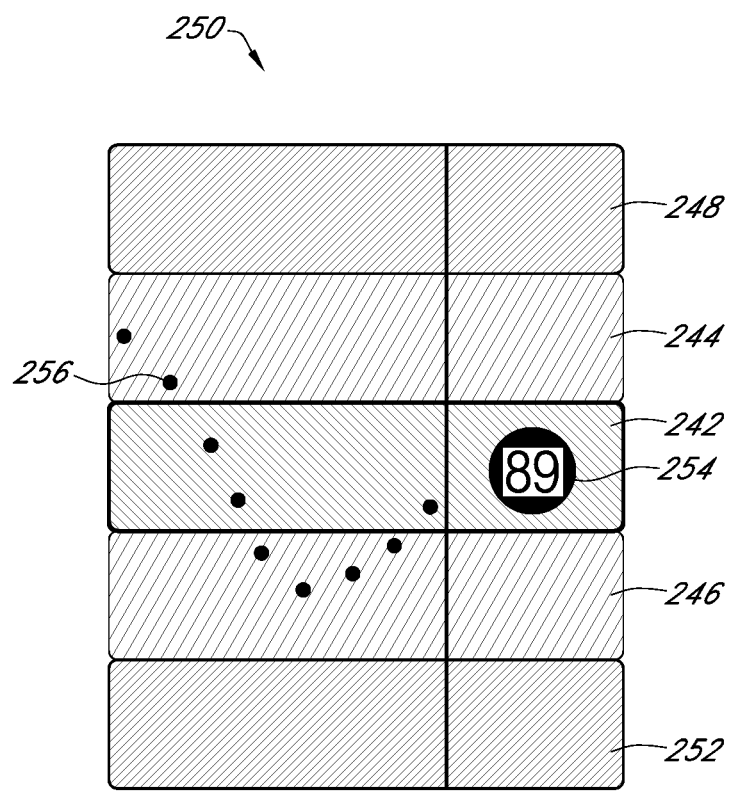
FIG. 25 shows another exemplary user interface simplified for type II users.

An exemplary such user interface is shown by the user interface 250 of FIG. 24. In this figure, points 256 on a trace graph are shown, along with a glucose value of 66 (element 254). These elements are relatively deemphasized, however, in favor of the colored bars indicating various ranges. Shown are a target range (euglycemia) 242 which is colored green, yellow warning ranges (impending hypoglycemia 246 and impending hyperglycemia 244, typically informing the user to watch and wait), and red danger zones (hypoglycemia 252 and hyperglycemia 248, typically informing the user to take action right away). In some implementations the range corresponding to the current glucose value may be made brighter or enlarged. In FIG. 24 the user is in hypoglycemia, and a textual indicator is provided to notify the user of potential actions to take. The same user interface with the user in euglycemia is illustrated in FIG. 25.

FIG. 26 illustrates alternative user interfaces useful for type II patients, and in particular varieties of home screens for a continuous monitoring application. The screen 258 of FIG. 26A illustrates an A1c estimator. As before, a green range indicates the user is in target and shades of red may be used for out of target occurrences. A share functionality can share if medication was taken or not. The user can also enter a time delay, such that so long as medication is taken within the time delay, an alert will not be sent to a follower. If medication is not taken within the time delay, the alert is sent.

Figure 26A:
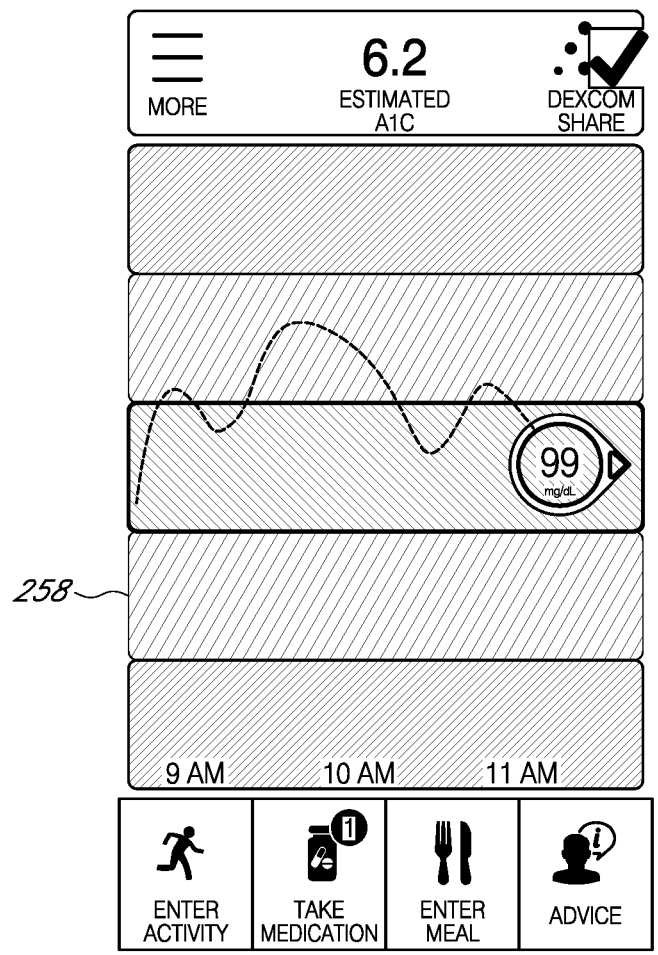
FIGS. 26A-26F illustrate other exemplary user interfaces, particularly suitable for type II users.
Figure 26B:
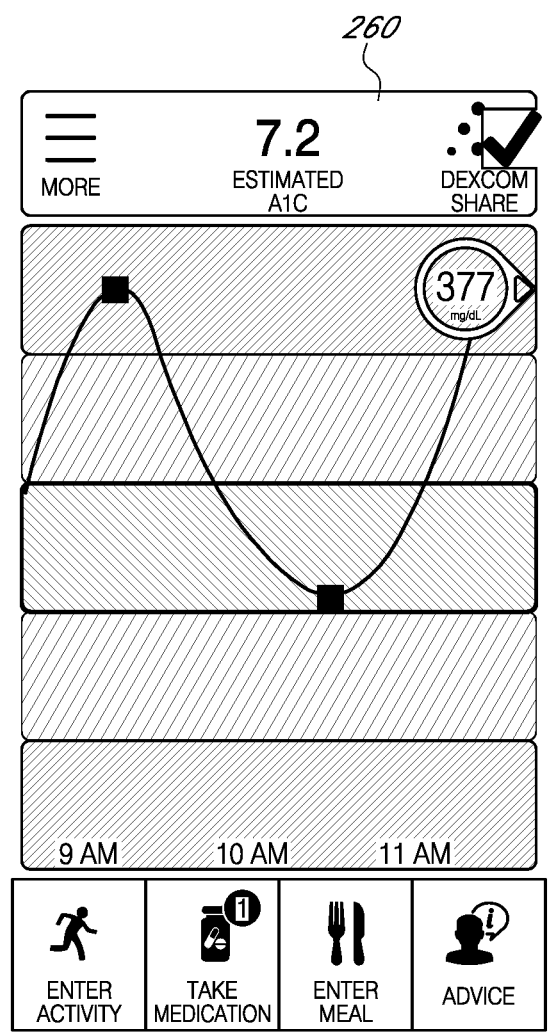
Figure 26C:
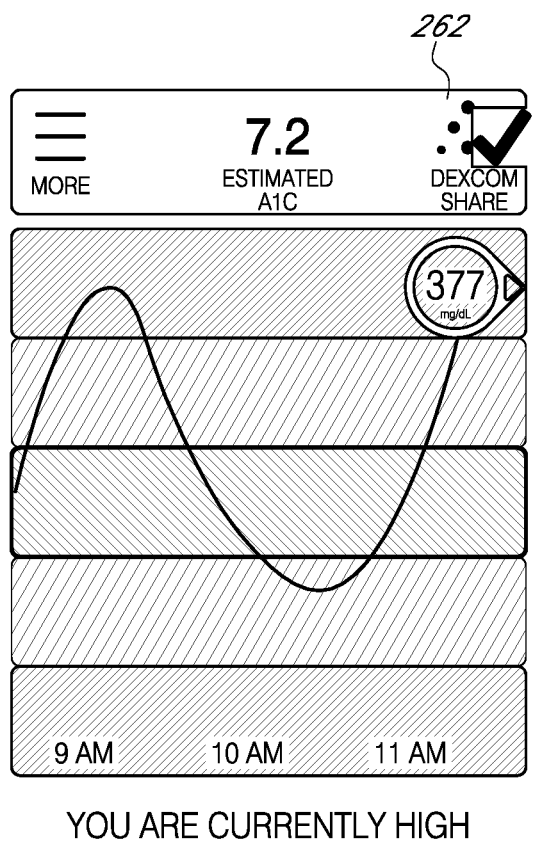

The current glucose zone may be highlighted as compared to other zones, e.g., may appear brighter. As seen in FIG. 26C, the application may communicate the current zone with a textual notification, e.g., "you are currently high" or without such (FIG. 26B). Such may be especially pertinent when lows (hypoglycemia) for type II users, as such are generally rarer than hyperglycemic situations.

Figure 26D:
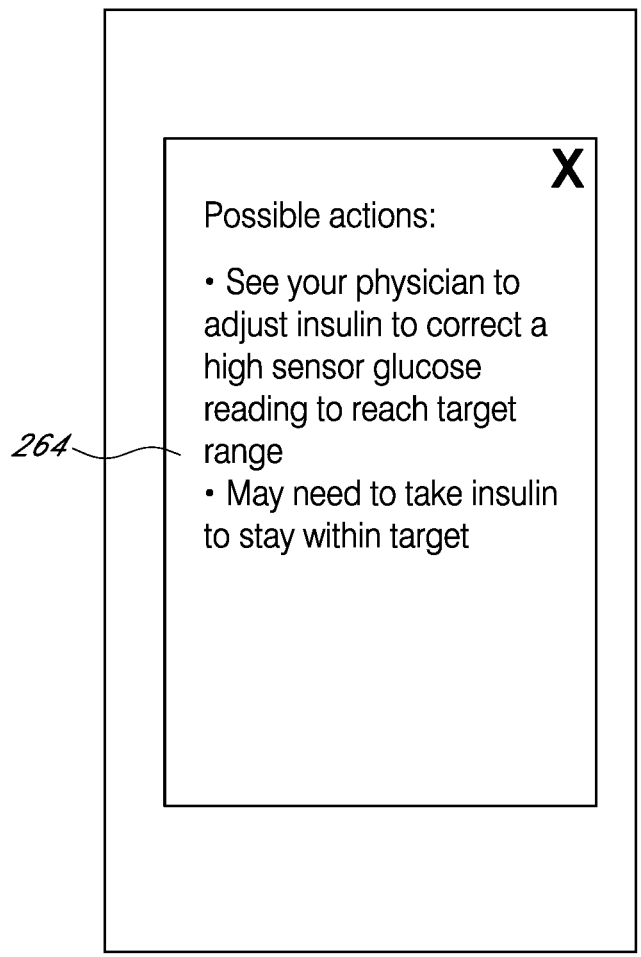

Activation of the advice button leads to a screen as illustrated in FIG. 26D. In this screen, doctor and/or IFU advice may be provided. The advice may be specified to the glucose state, time of day, GPS location, and so on.

Figure 26E:
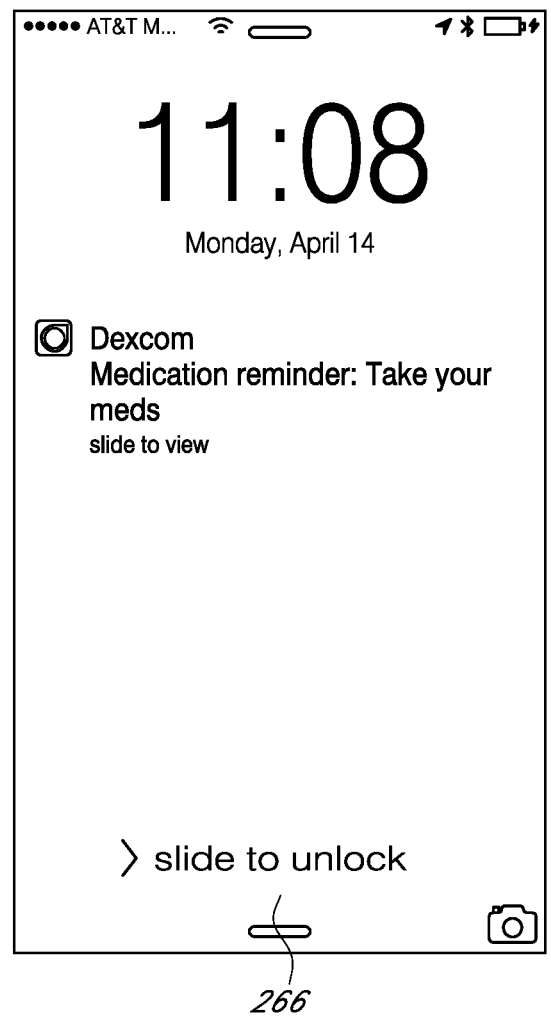

FIG. 26E illustrates a reminder on an initial wake screen.

Figure 26F:
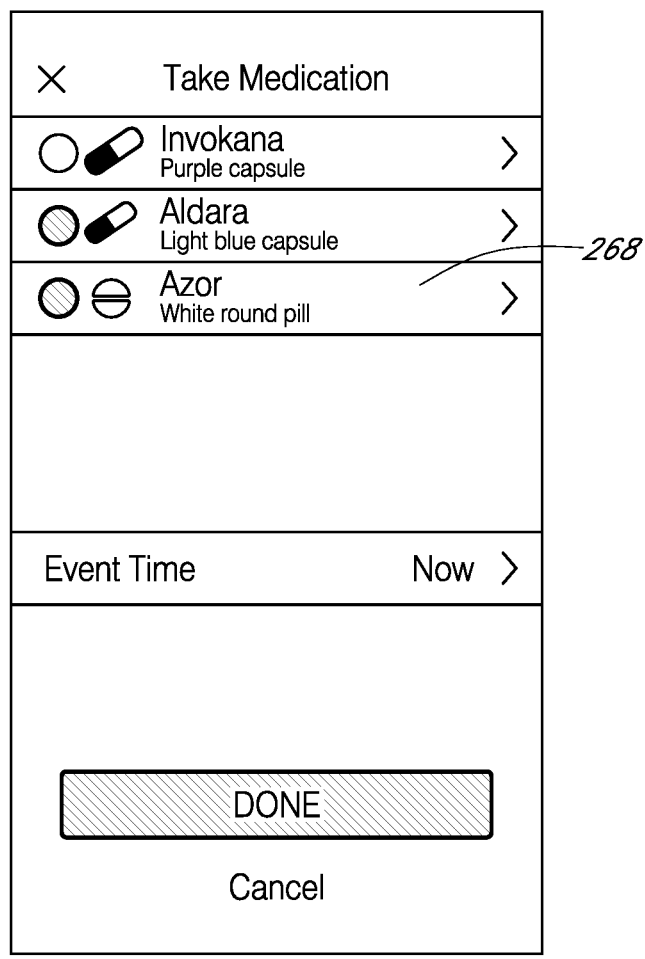

FIG. 26F illustrates a screen following activation of a "take medication" button. Such functionality typically provides benefits for behavioral modification. For example, a user or caretaker may set the time medication is to be taken, along with the name of the drug and a description of the drug. If the notification (such as may be seen in FIG. 26E) is ignored, a notification may be sent to a follower. From the notification shown in FIG. 26E, a user can acknowledge any and all drugs taken at the current, past, or future time. This action also enters an event on the trend graph. An additional reminder is seen by a badge on the "take medication" button, indicating that medications are scheduled to be taken.

Figure 27:
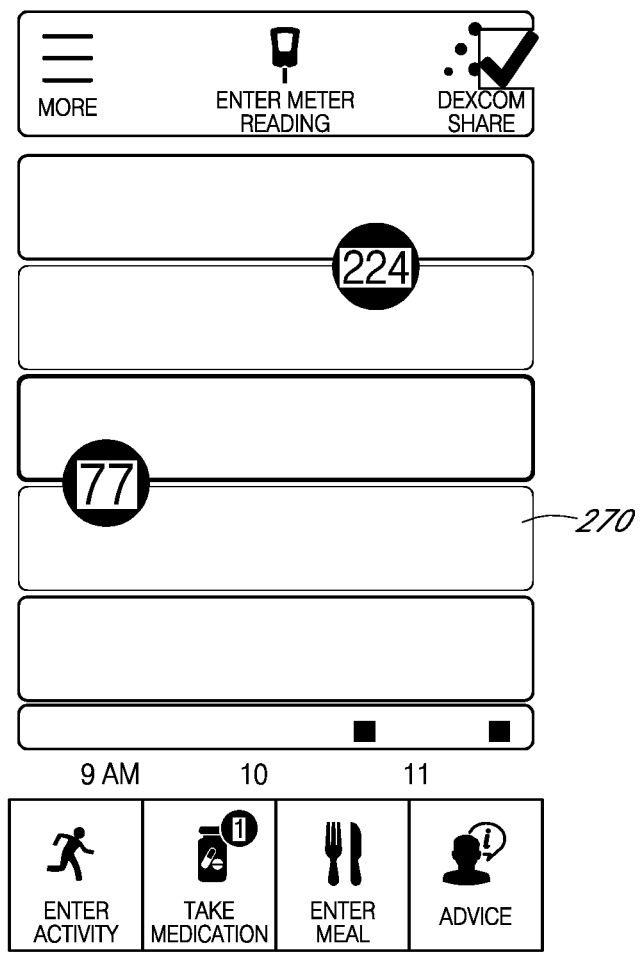
FIG. 27 shows an exemplary user interface simplified for type II users.

FIG. 27 illustrates a screen which may be employed when the user is out of or between sensor sessions. With an appropriate button, the user can add meter readings from an SMBG. In this way, additional functionality may be added to monitoring applications, to monitor glucose readings even when a continuous glucose monitor sensor is not available.

Variations will be understood of these above described user interfaces. For example, turning the smart phone may lead to a landscape mode graph, which may be pinchable/zoomable.

FIGS. 28-36 illustrate other aspects of user interfaces which may be particularly appropriate for type II users.

Figure 28A:
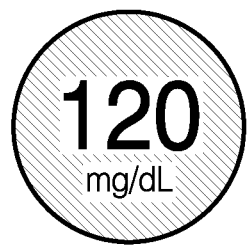
FIGS. 28A-28H illustrate exemplary elements which may be advantageously rendered on user interfaces, particularly suitable for type II users.
Figure 28B:
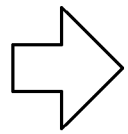
Figures 28C, 28D:
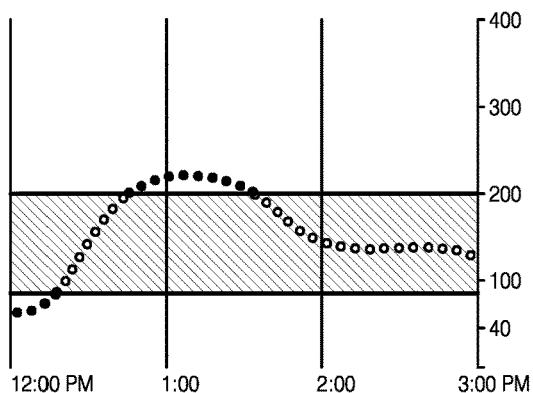

FIGS. 28A-28H illustrate various types of indicators which may be present on user interfaces, and which may also appear in various combinations on a given user interface. FIG. 28A illustrates a current blood glucose level. FIG. 28B illustrates a trend arrow, which in this example is horizontal, indicating the user is maintaining their level, but which may be pointed upwards or downwards to indicate a trend. FIG. 28C illustrates a trace graph, which can have discrete data points or a continuous curve. The background color may be used to indicate whether the user is in range or out of range. FIG. 28D illustrates a status message, in the form of text, which can be particularly useful for type II users as the same are often not used to determining the meaning of glucose concentration numeric values. It is noted that the particular text to show may be varied from patient to patient, and may also vary depending on the historical impact of glucose parameters vis-a-viz that individual patient. In other words, a number which may lead to one status message for a first patient may lead to a different status message for a second patient. For example, for one patient a glucose value and rate of change may be indicated as "you're doing okay", whereas for another patient, the glucose value and rate of change are associated with a more problematic diabetic state and thus the status message may be a warning to "take action before you go low".

Figure 28E:
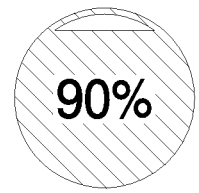
Figure 28F:

FIG. 28E illustrates daily progress, and in the implementation shown illustrates how much time in the current day the user has spent within the target range. FIG. 28F indicates various events, which may have been logged or entered by the user or which may have been detected automatically by the system. Where the system detects events automatically, such provides technical improvements to the system as events are generally logged more rapidly and accurately. This solves a problem of the prior art, the problem related to a late entry of data, late occurrence of necessary calculations, late display of action items, and so on. Such also allows the ability to build a knowledge base over a period of time, e.g., two weeks, in order to build a deeper understanding of cause-and-effect for the given patient.

Figure 28G:
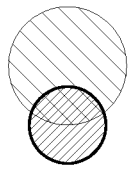
Figure 28H:
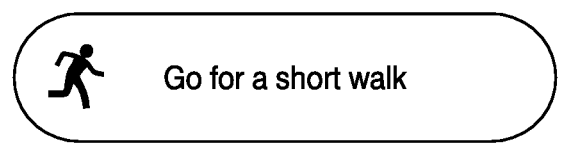
Figure 28H:
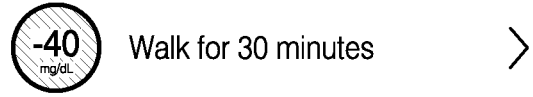

FIG. 28G illustrates an action indicator, with a current status "bubble" or "circle" depicted in red and offset from a neutral target circle. That the red circle is offset in a downward direction from the neutral circle indicates that the user is below the target range. The color of the circle, i.e., red, indicates that action needs to be taken right away. A textual indicator is also provided to reinforce this message. If the remedial action cures the situation, then the smaller circle color will change to green and the smaller circle will move to within the larger neutral target circle. FIG. 28H illustrates exemplary suggested activities useful for type II users, who again may be unfamiliar with specific remedial actions to take to address certain glucose situations.

These indicators, including in one or more combinations, have been shown to significantly induce behavioral modification in type II users.

Figure 29A:
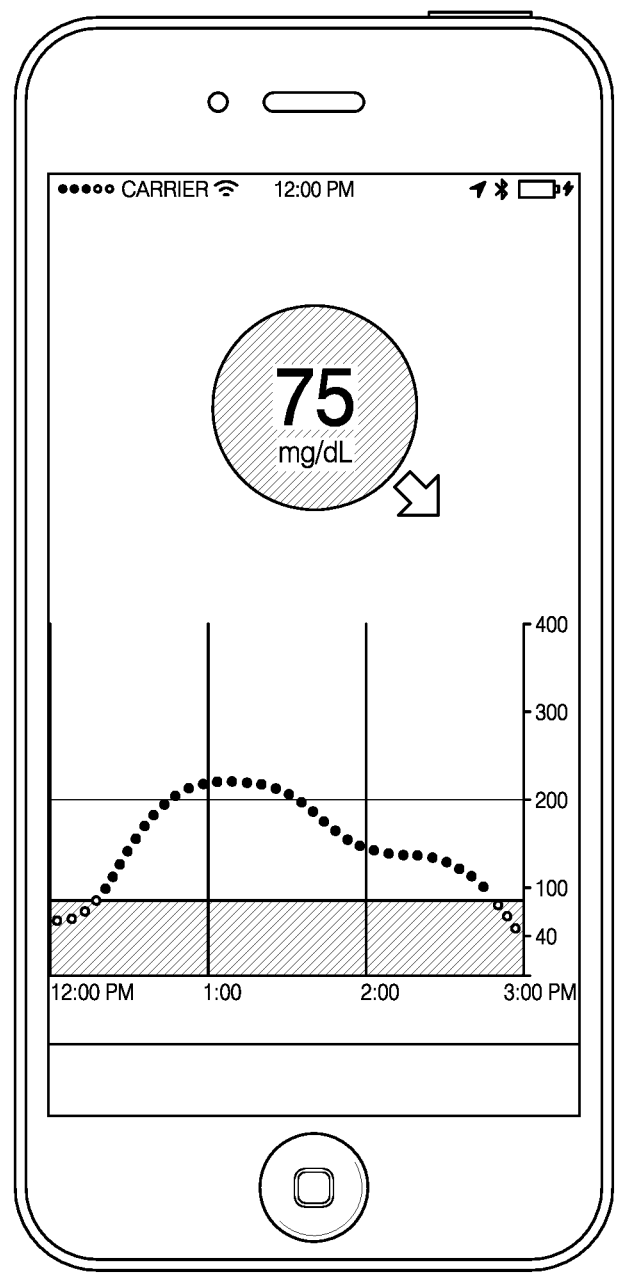
FIGS. 29A-29C illustrate other exemplary user interfaces, particularly suitable for type II users.
Figure 29B:
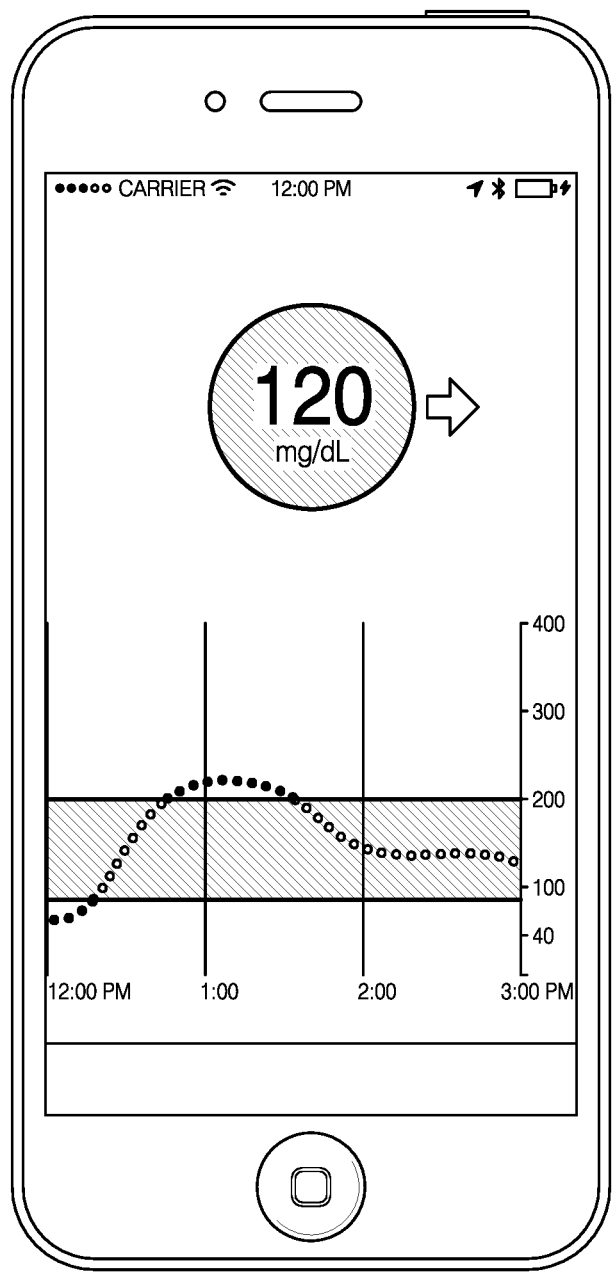
Figure 29C:
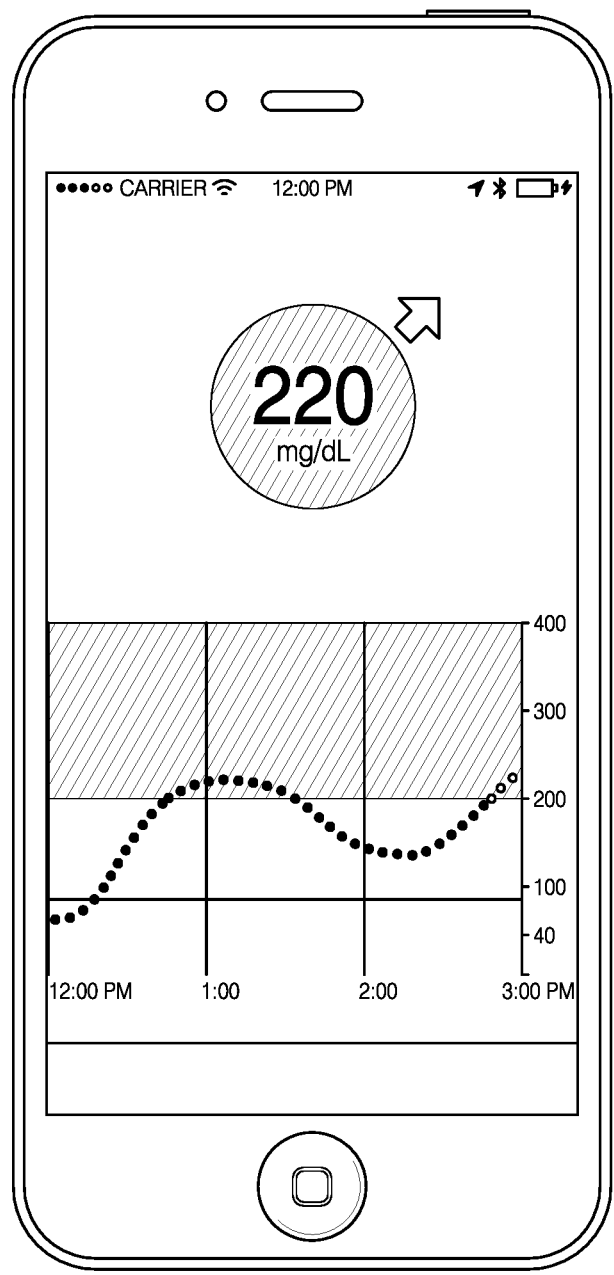

One combination of the above components is illustrated in FIGS. 29A-29C. In FIGS. 29A-29C, the user interface shows the current blood glucose value, a color to indicate urgency and a graph, e.g., covering a three-hour historical past period. In addition, it will be noted that in FIGS. 29A-29C, only one colored band is shown at a time, this band corresponding to the current state of the user.

Figure 32A:
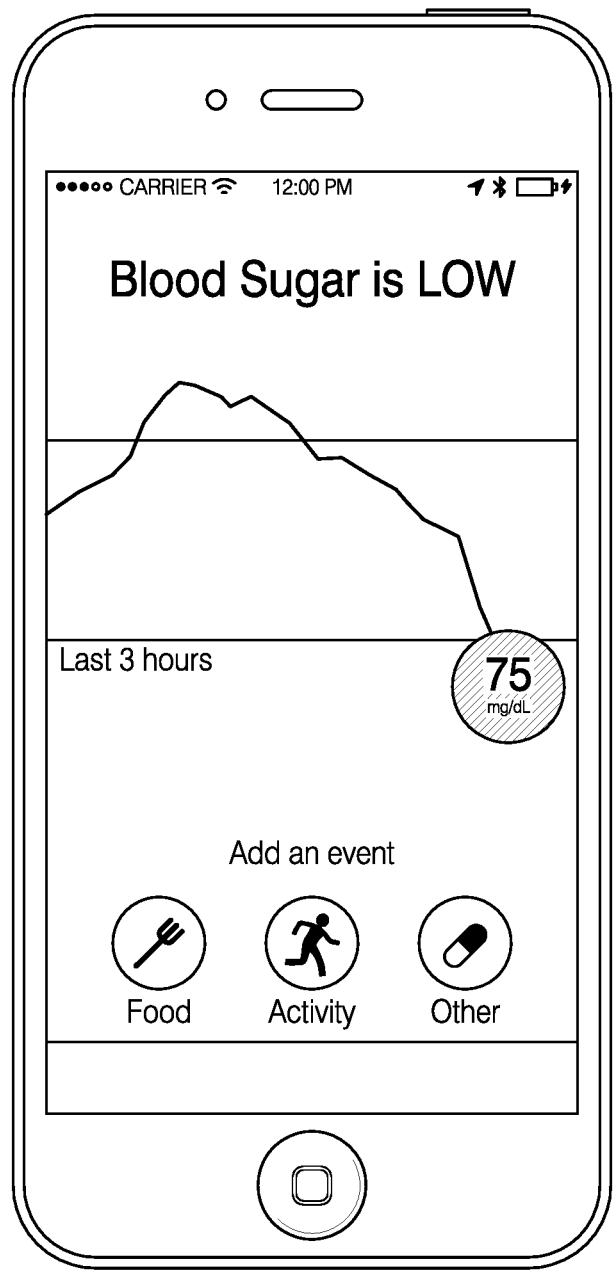
FIGS. 32A-32C illustrate other exemplary user interfaces, particularly suitable for type II users.
Figure 32B:
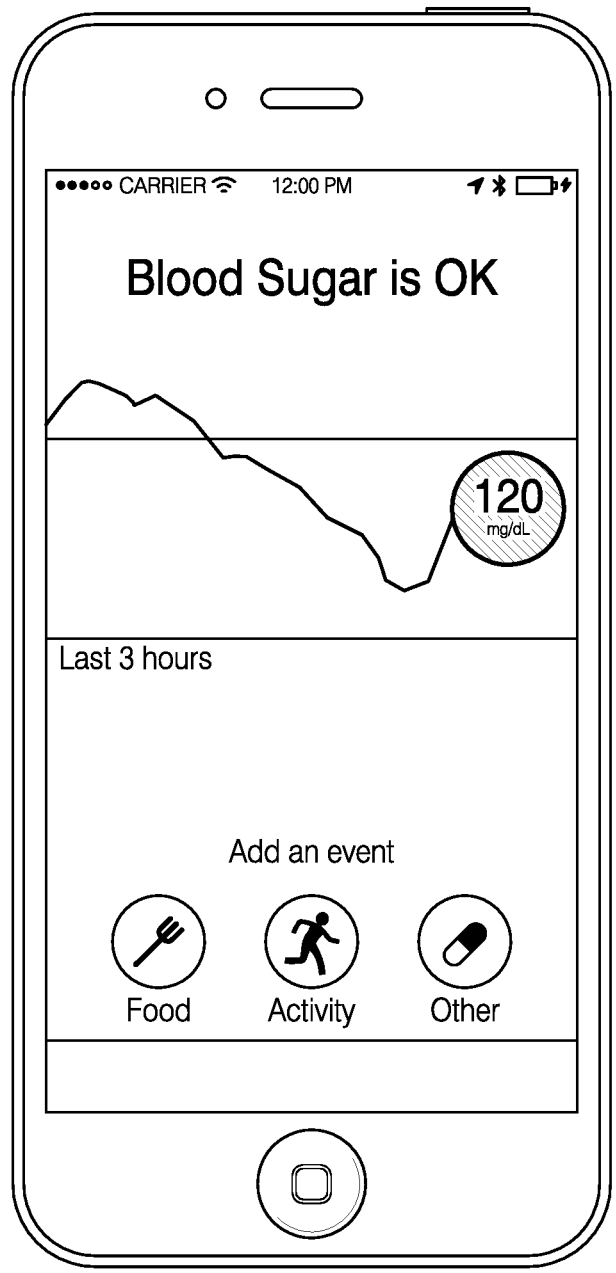
Figure 32C:
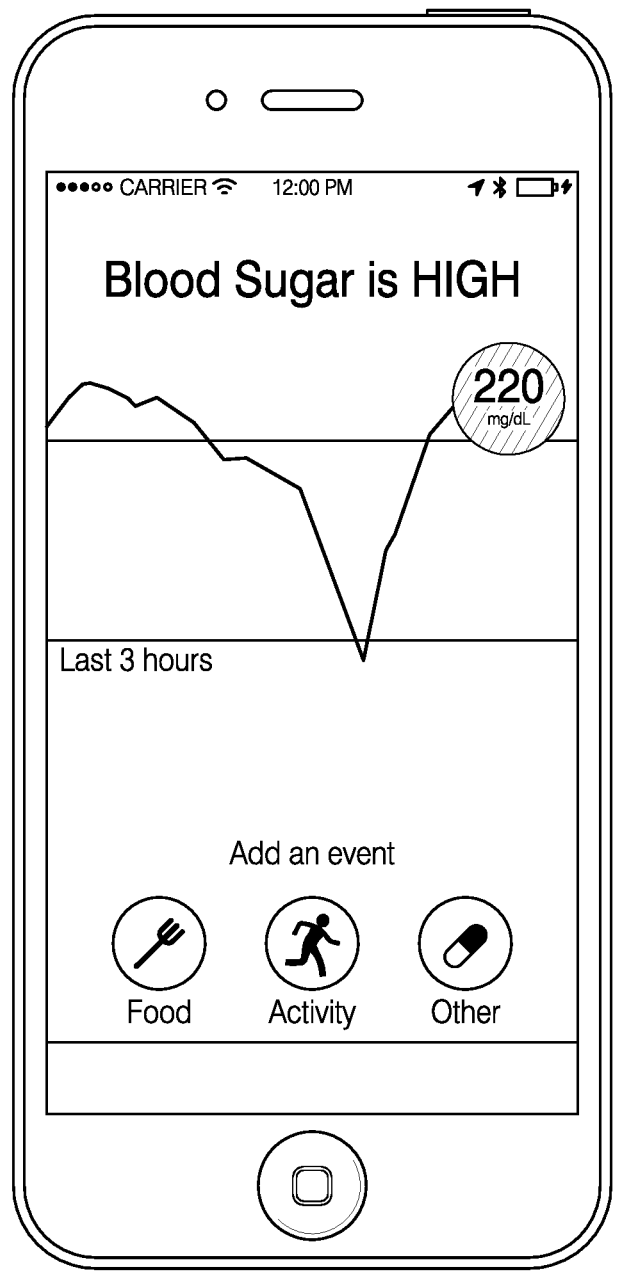

FIGS. 32A-32C are similar, with less emphasis on the colored bands. In addition, the user interface of FIGS. 32A-32C allows convenient user entry of events corresponding to meals, activities, and other events, e.g., ingestion of medication. In this way, the user may be enabled to check the effect of such events on their glucose levels. Having the blood glucose number attached to the graph makes it evident to the user that the number displayed is the current value for the user. In variations, the graph line may also indicate a future trend.

Figure 30A:
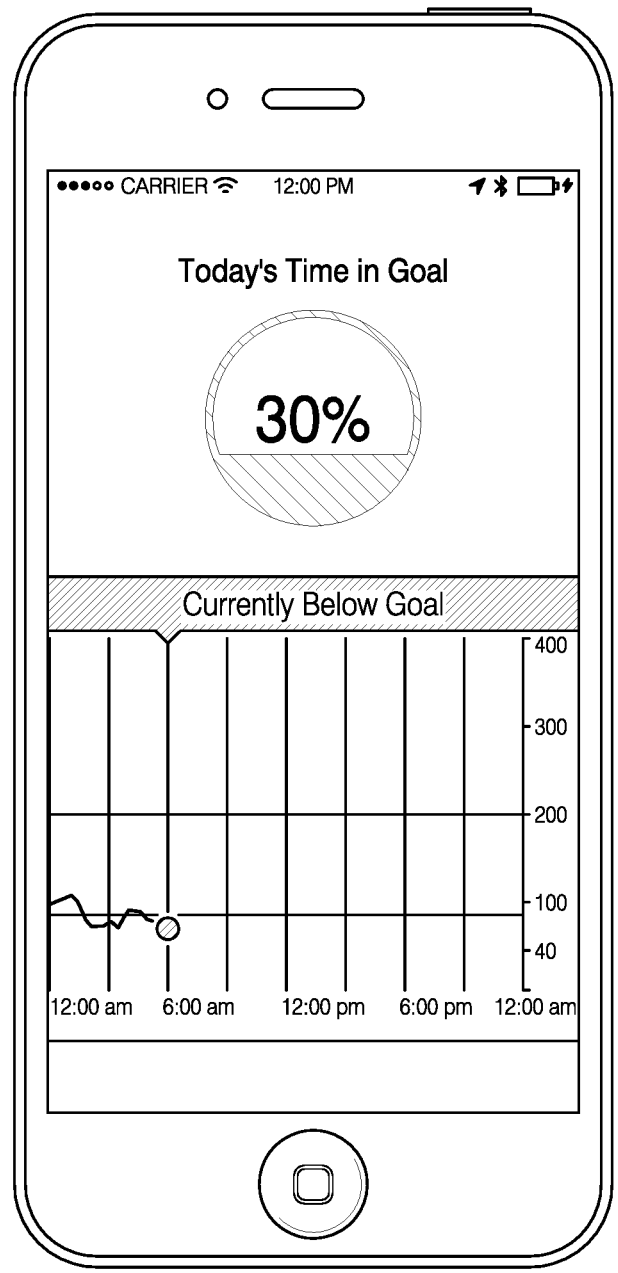
FIGS. 30A-30C illustrate other exemplary user interfaces, particularly suitable for type II users.
Figure 30B:
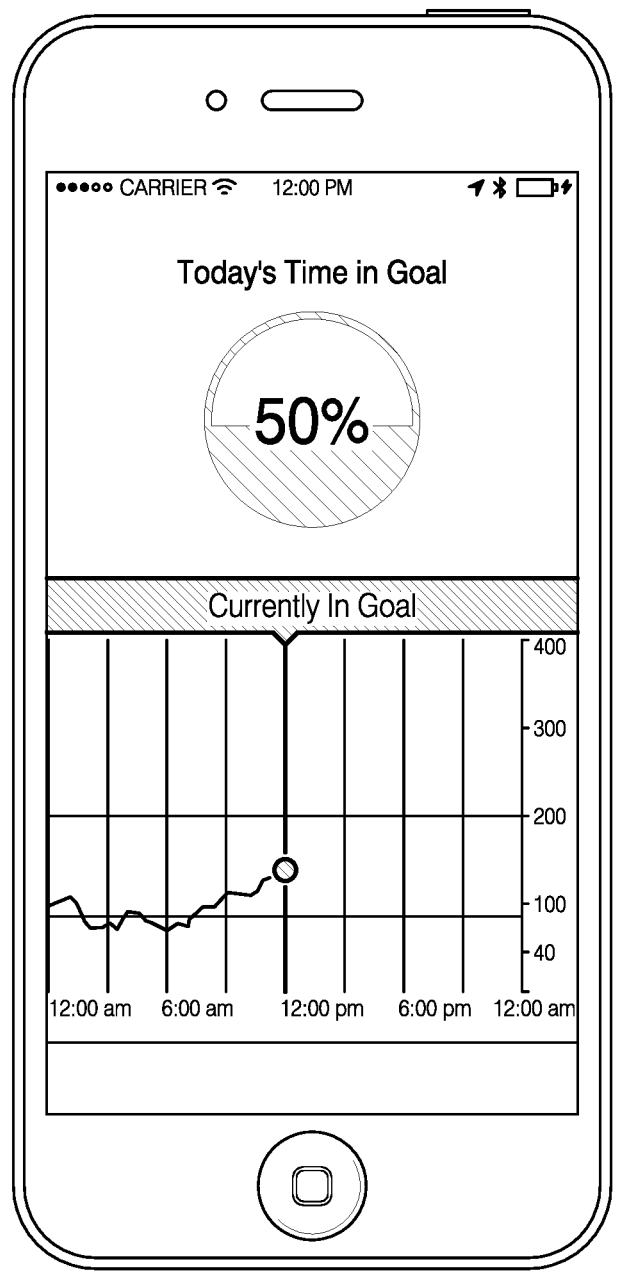
Figure 30C:
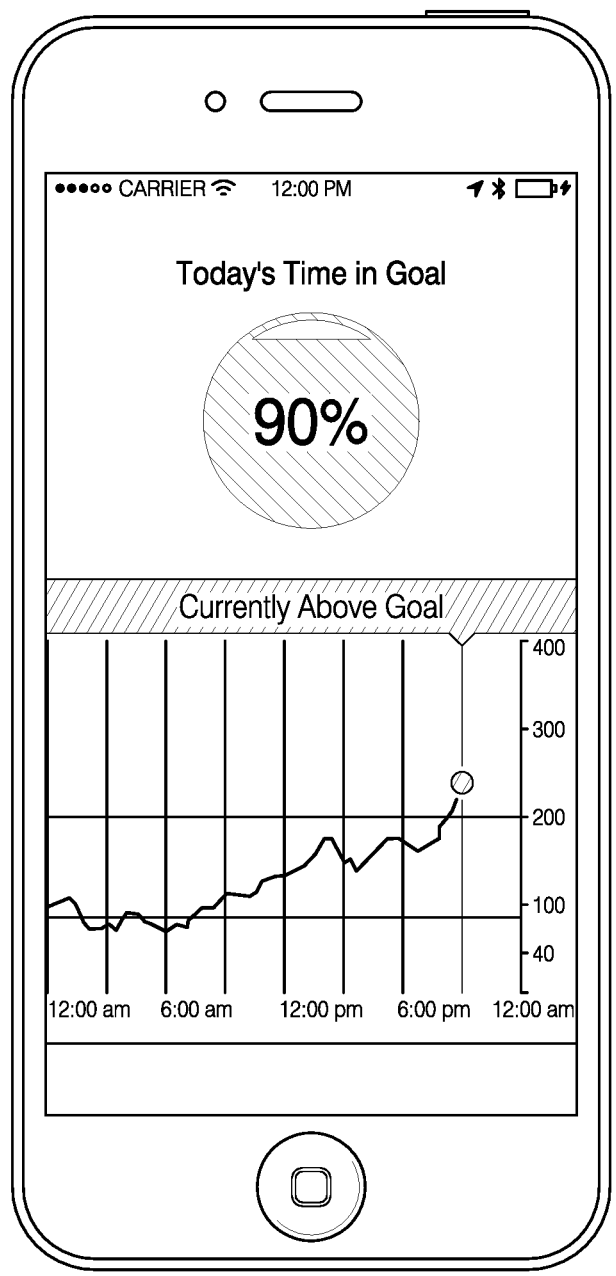

FIGS. 30A-30C provide a variation on the implementations above, in which a trace graph is shown with a terminus at a current time point. Color is again used, and a textual indication may indicate the status of the patient as being in, below, or above goal. A percentage of the day in the goal is also indicated.

Figure 31A:
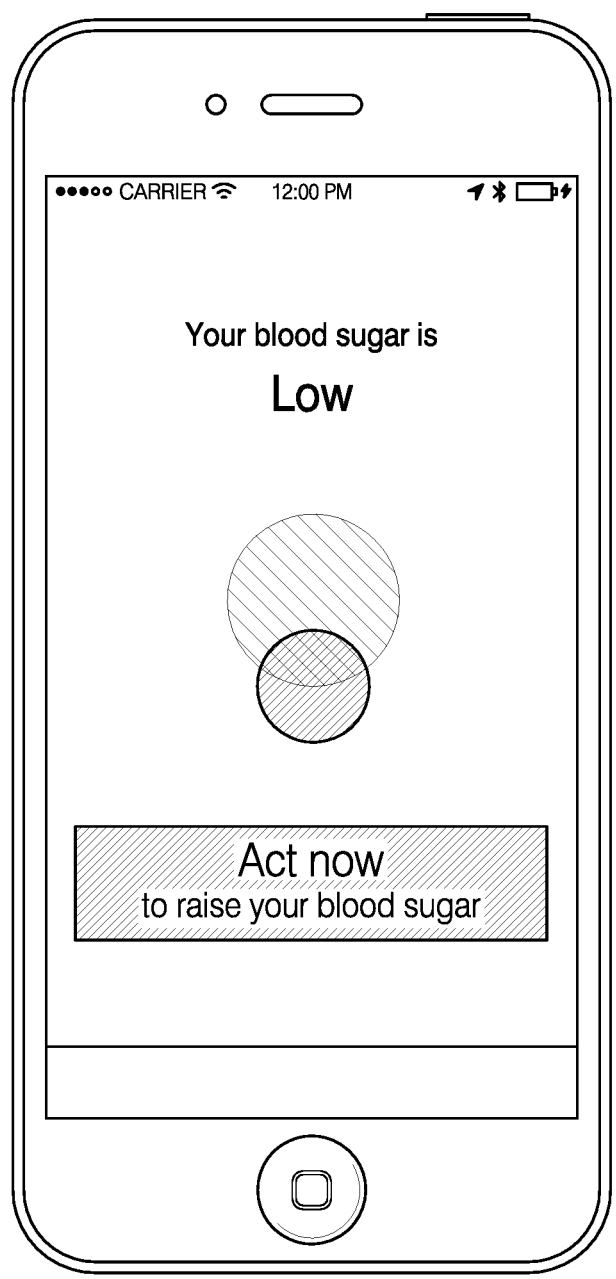
FIGS. 31A-31C illustrate other exemplary user interfaces, particularly suitable for type II users.
Figure 31B:
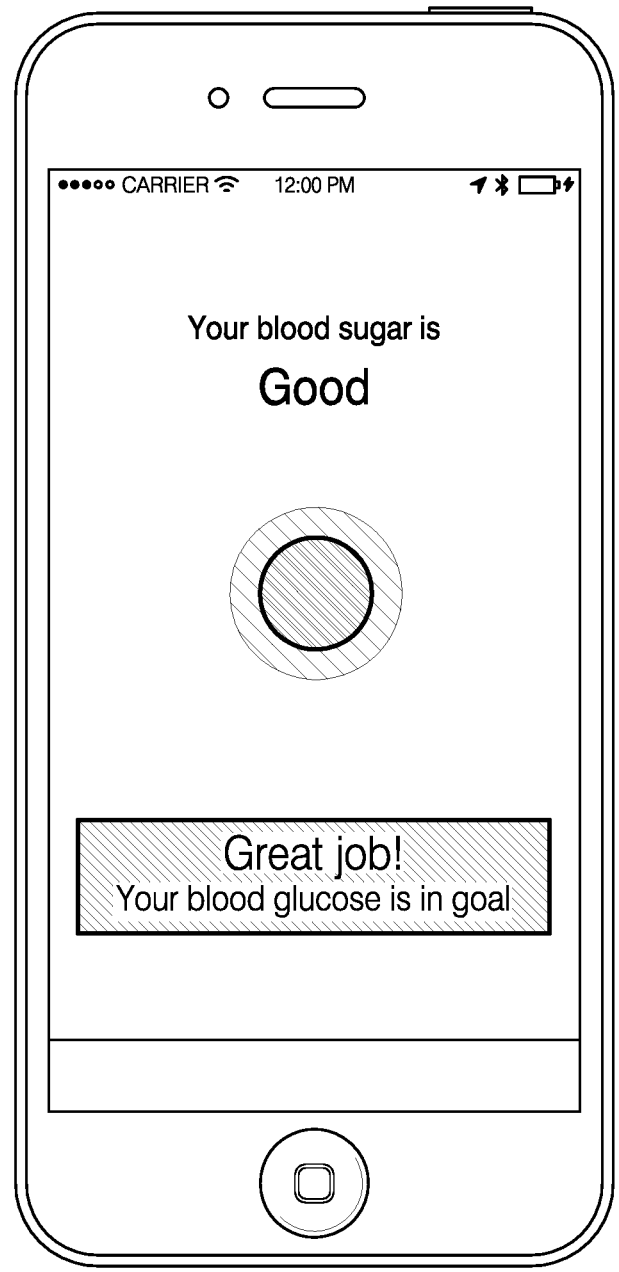
Figure 31C:
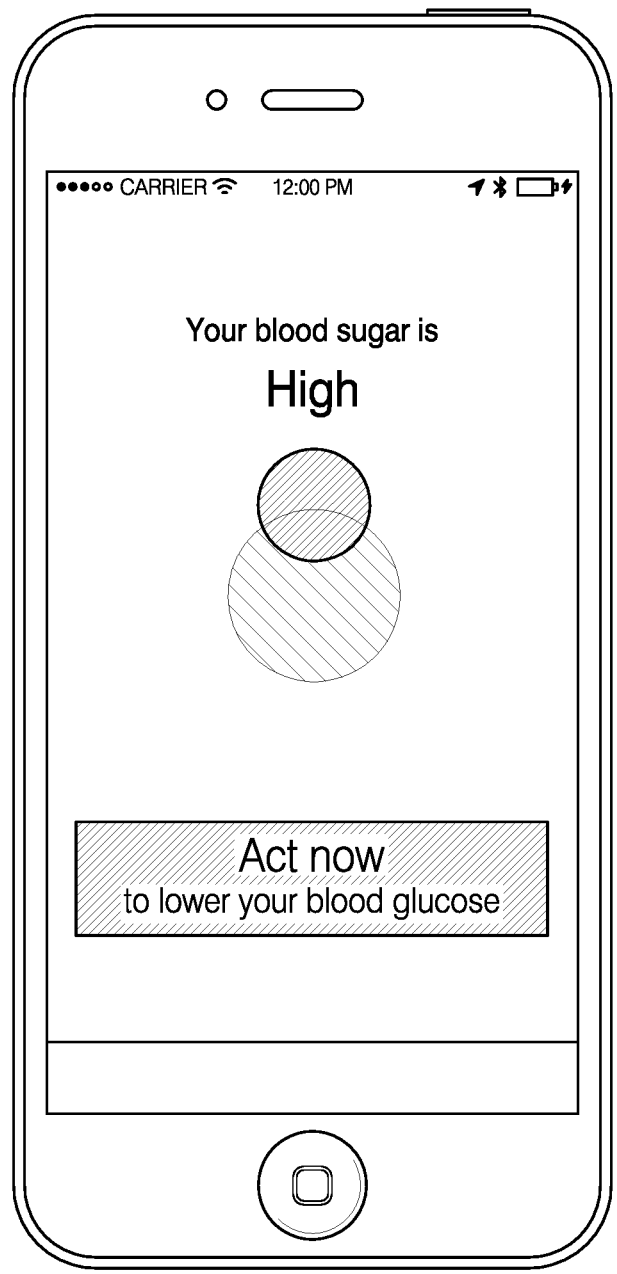

FIGS. 31A-31C provide a further variation on an implementation of the user interface. As in FIG. 28G, a "bubble" or "circle" indicator is employed to indicate to the user whether they are below, at, or above a desired target, the desired target indicated by a larger grey circle. The status message may also be provided in this implementation to provide an indication to the user of steps to take to address the high or the low.

Figure 33A:
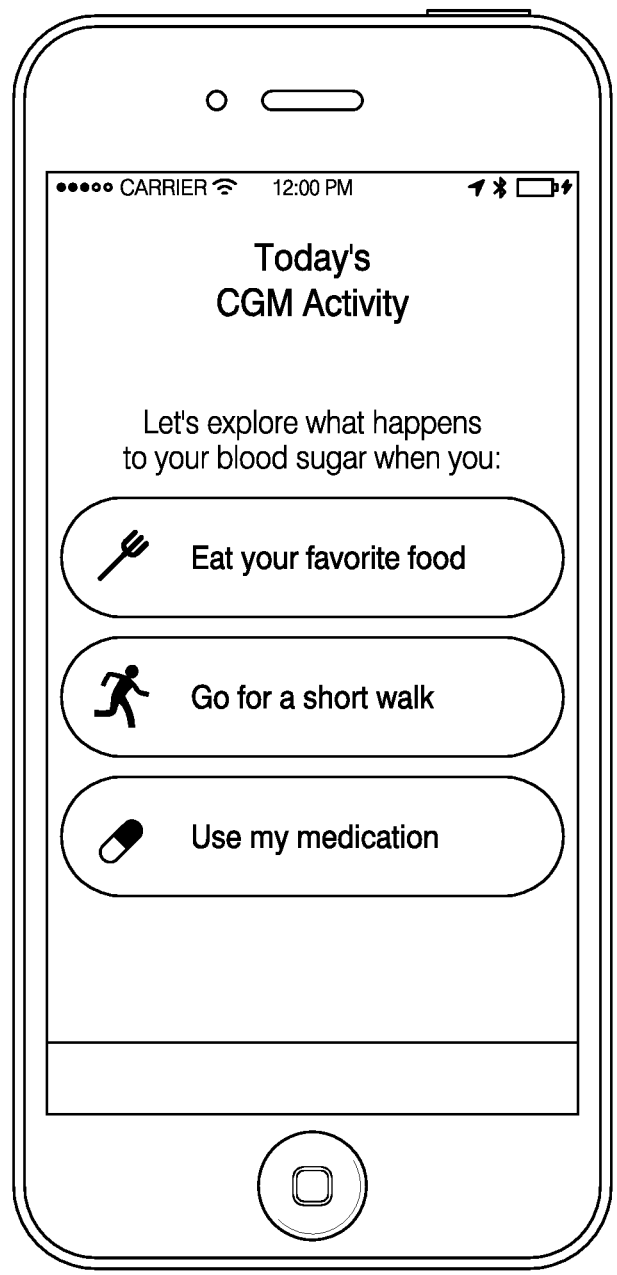
FIGS. 33A-33D illustrate other exemplary user interfaces, particularly suitable for type II users.
Figure 33B:
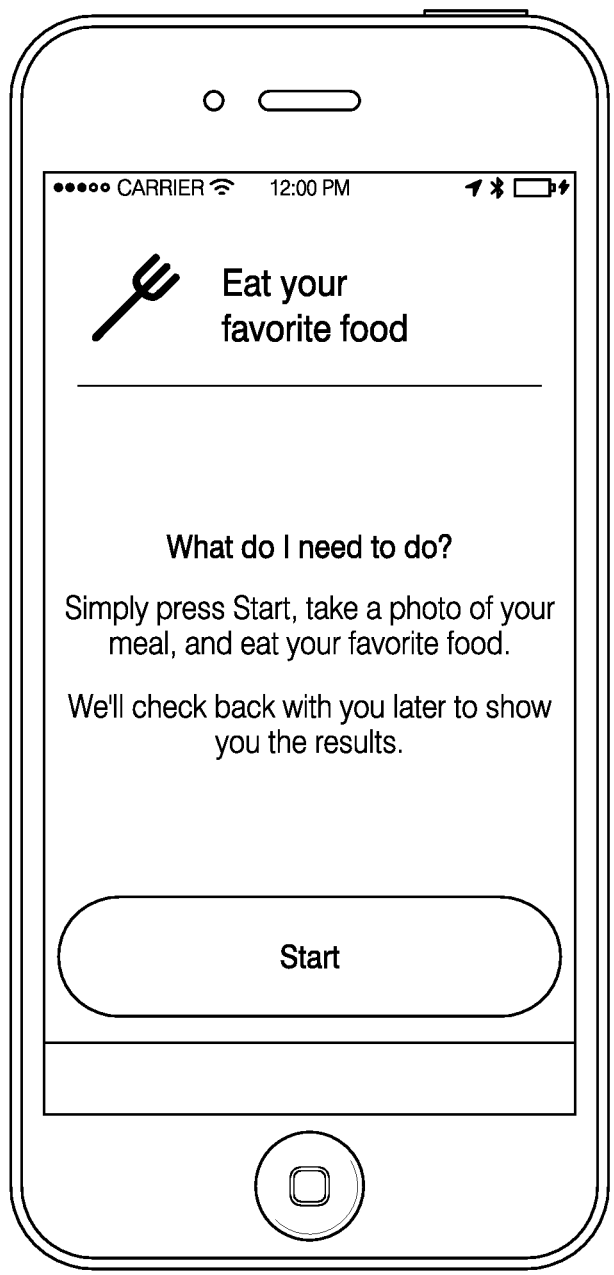
Figure 33C:
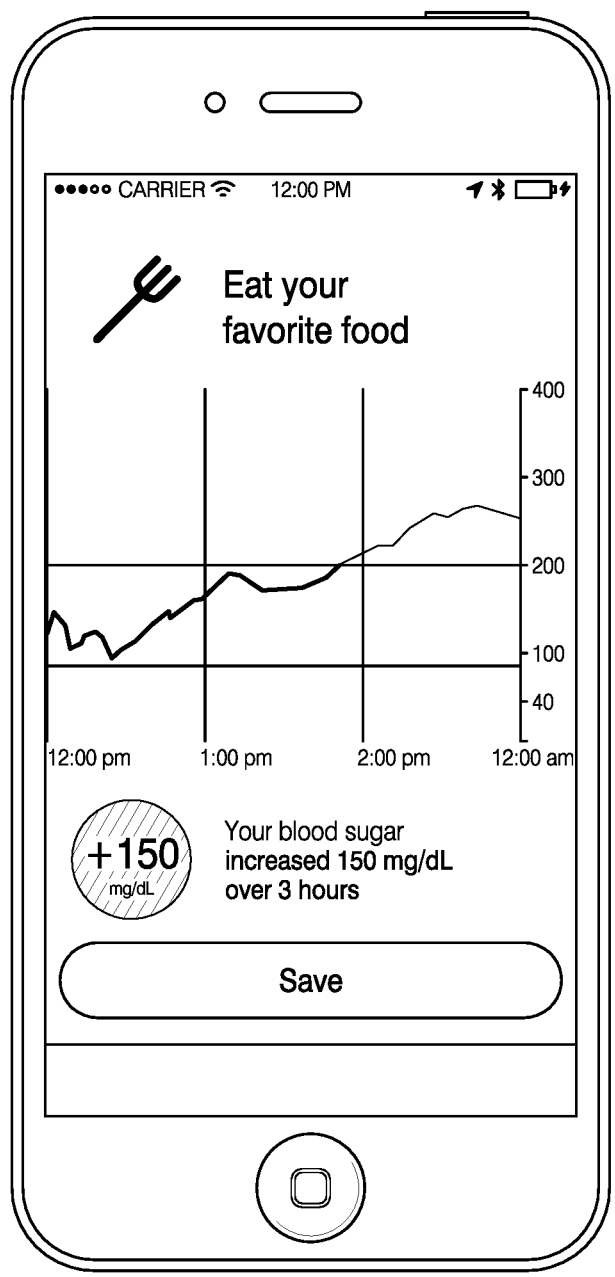

Referring next to FIGS. 33A-33C, a user interface is shown in which activities may be logged in a proactive fashion. FIG. 33A illustrates an initial screen, and FIG. 33B illustrates the effect of tapping one of the entries of the screen of FIG. 33A, i.e., "eat your favorite food". In this implementation the user may press start, take an image of the food they are about to eat, and consume the food. The effect of this consumption is shown in FIG. 33C. In the example shown, the effect of the consumption is to cause the user's glucose value to extend into a warning zone for hyperglycemia.

Figure 33D:
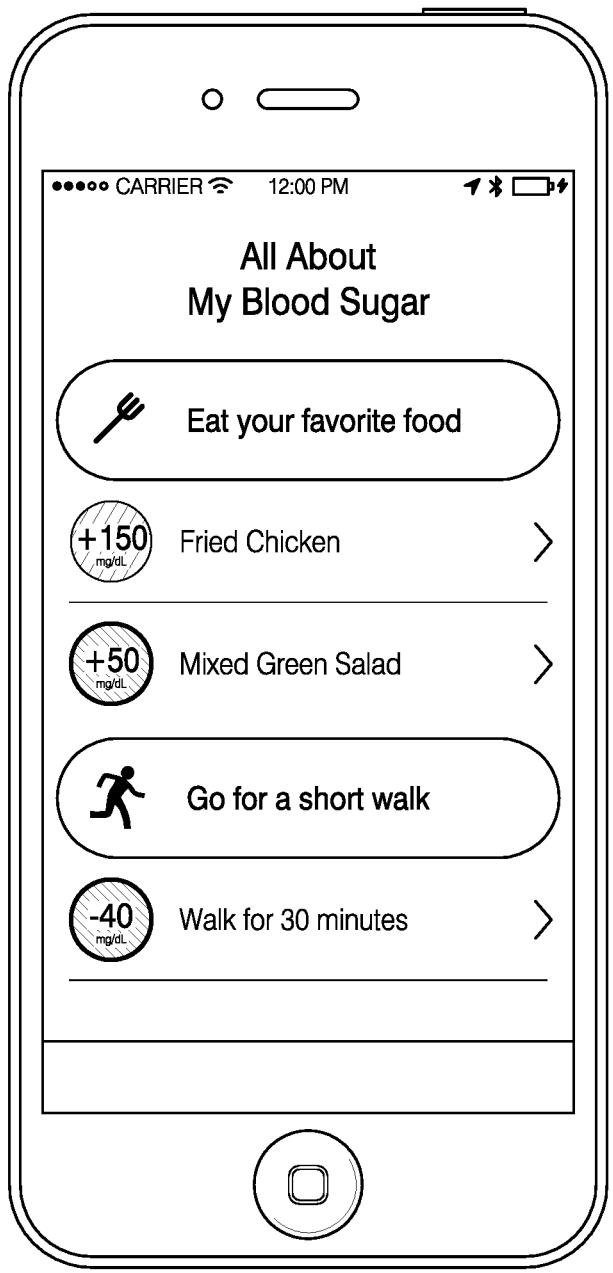

FIG. 33D illustrates another user interface according to this implementation, in which various types of events affecting a user's blood sugar may be investigated further, generally by tapping the appropriate button. For example, under "eat your favorite food", the user's favorite foods may be displayed along with estimated effects on their blood glucose, either with respect to their current glucose value or more generally. For example, as shown in the figure, eating fried chicken may cause the user's blood glucose to rise by 150 mg/dL, and such may be indicated in yellow to notify the user that eating such will cause them to enter a warning zone. The yellow color indicator may alternatively be employed to notify the user that eating such is more generally a less optimum choice.

By displaying options in this manner, less keystrokes or button presses are necessary for a user to enter data important to glucose monitoring calculations. In this way, the overall computing equipment, e.g., smart phone, runs more efficiently and requires less entered button presses for the same output calculation.

Figure 34:
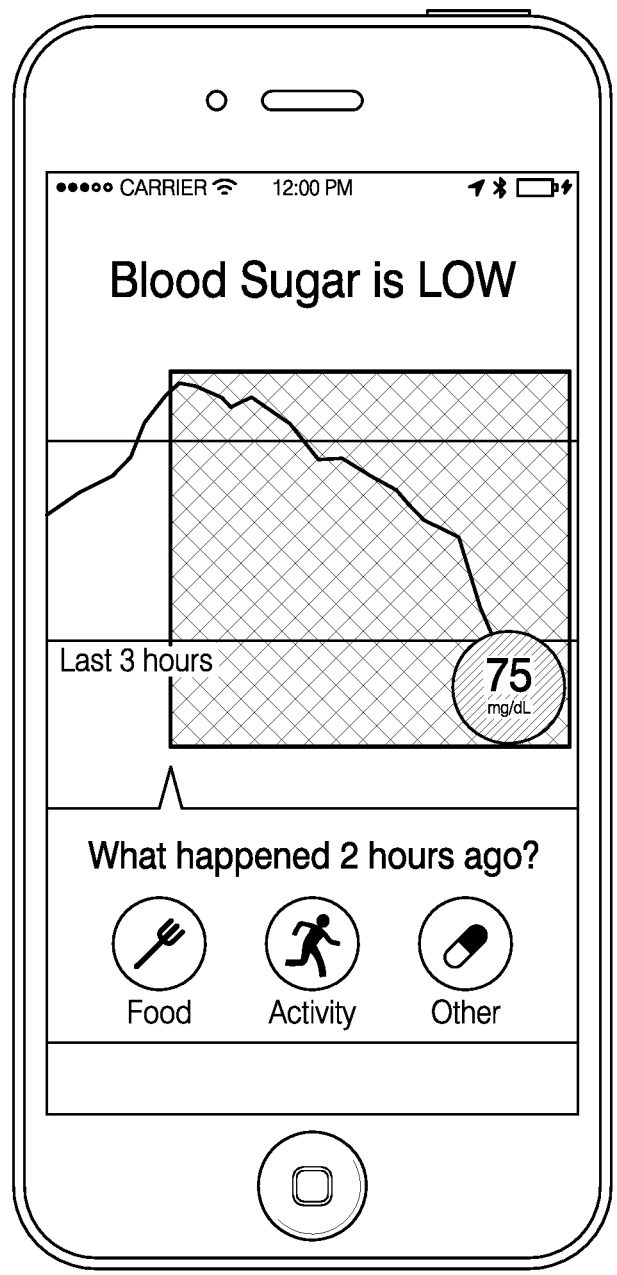
FIG. 34 illustrates an exemplary user interface, particularly suitable for type II users.
Figure 35:
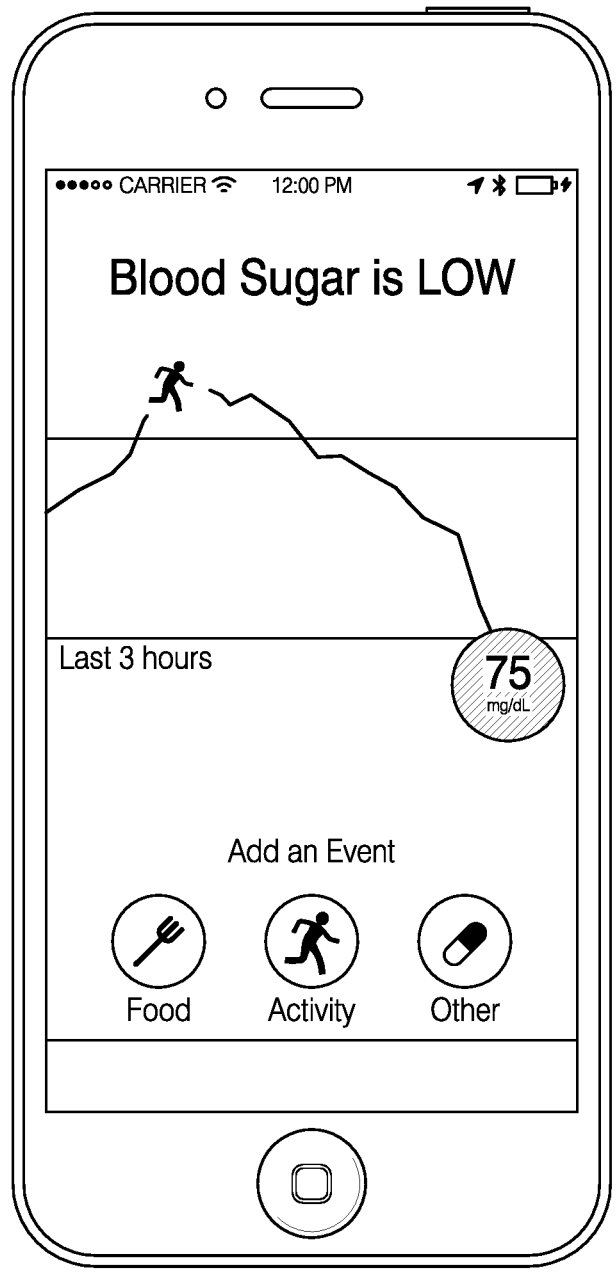
FIG. 35 illustrates the user interface of FIG. 34, in which an event has been added.

FIGS. 34 and 35 illustrate event logging that is not proactive but rather occurs after the fact. Referring first to FIG. 34, the start of a downward trend in blood sugar is indicated along with the ensuing decrease and a current glucose value, displayed in the color red, indicating a dangerous situation for which action needs to be taken immediately. The application automatically prompts the user to enter an event, if any, that might have precipitated the decrease. In this case, potential choices for events are displayed, the same corresponding to meals, activity, or "other", as is also described above. The user may select that they exercised, leading to the interface shown in FIG. 35, in which a "running" icon is used to log the event of activity which caused the decrease, at least as a correlation.

Figure 36:
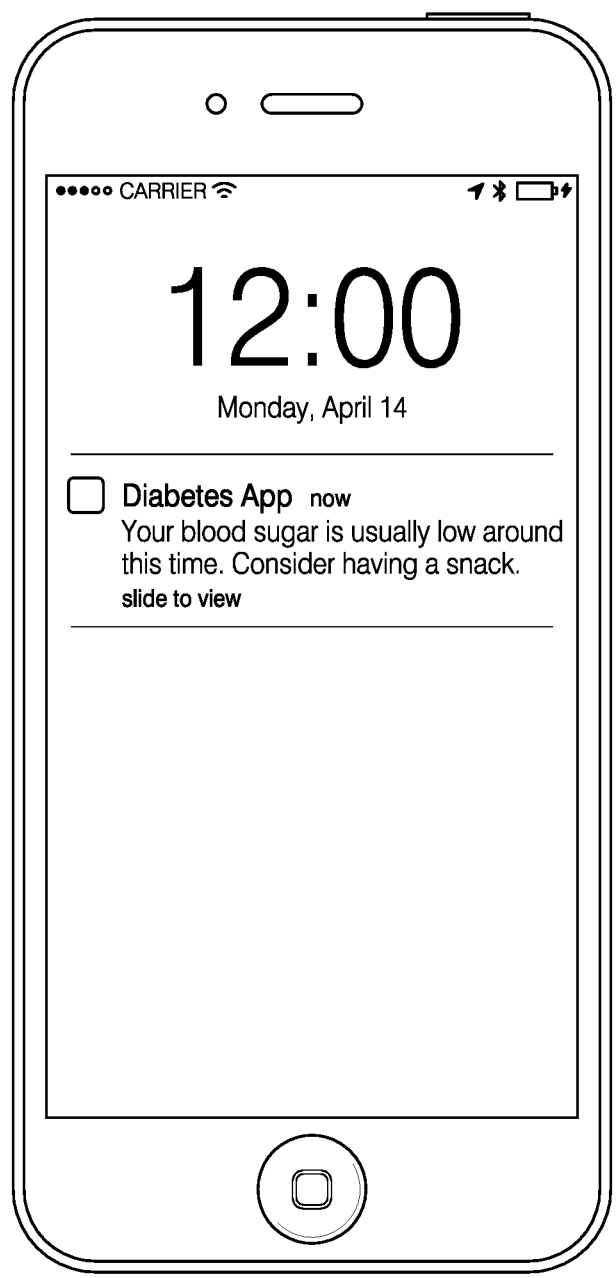
FIG. 36 illustrates an exemplary implementation of a notification on a home screen of a smart phone.

FIG. 36 illustrates an exemplary notification screen. Such notifications may be particularly useful for situations in which users are going low, as such situations have immediate and impactful consequences.

Other variations will also be understood and other types of output mechanisms which can be employed to display the outputs above include output mechanisms described in U.S. Ser. No. 61/978,151, filed Apr. 10, 2014, and U.S. Ser. No. 14/659,263, filed Mar. 16, 2015, both owned by the assignee of the present application and herein incorporated by reference in their entireties.

Figure 37:
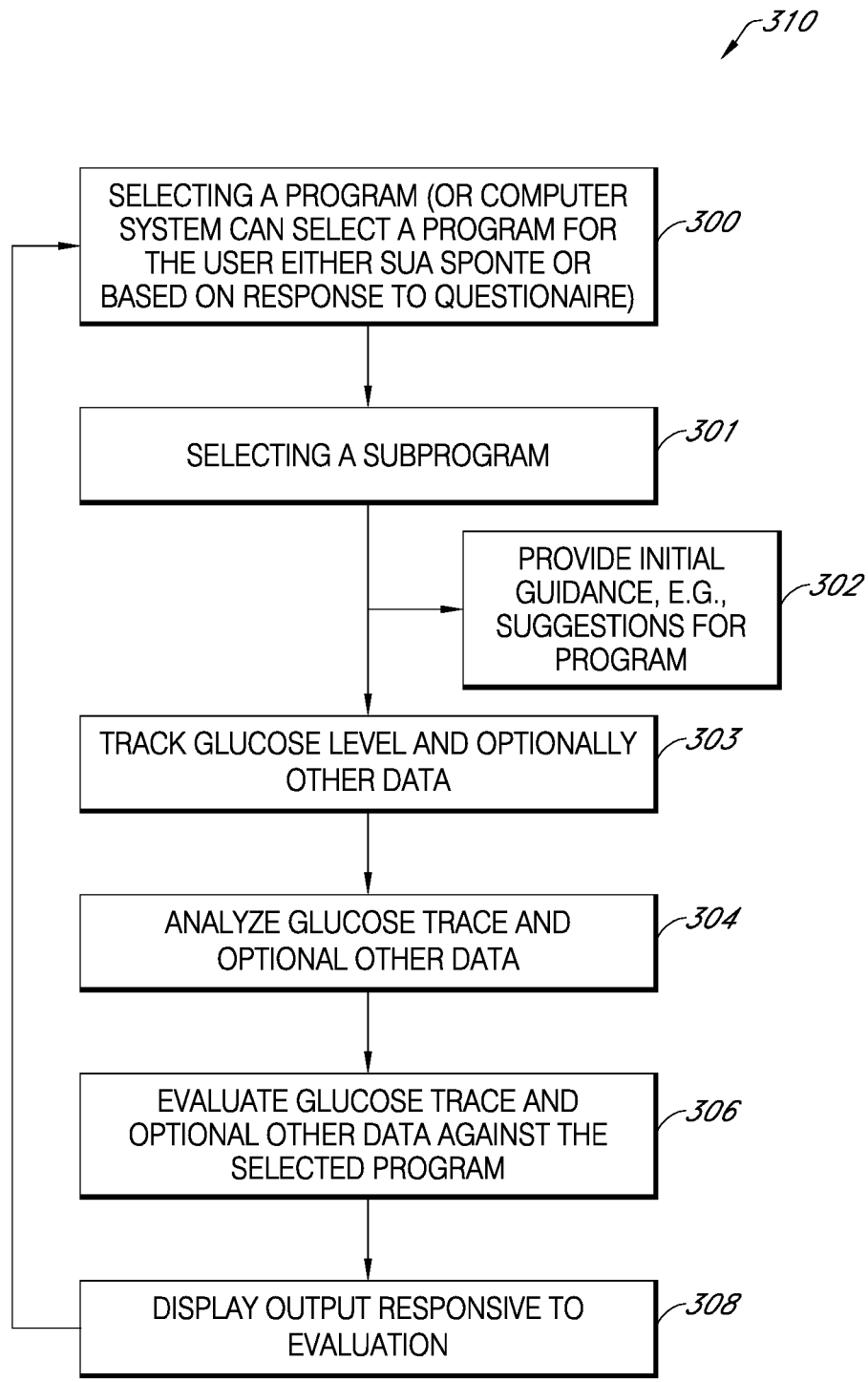
FIG. 37 is a more detailed flowchart indicating an application of the flowchart of FIG. 1, specific to programmatic learning and discovery, and in particular to assist diabetes and pre-diabetes patients in learning how to better manage their health.

FIG. 37 illustrates a particular implementation of the flowchart of FIG. 1. In particular, FIG. 37 relates to a guided start-up program that can serve as an introduction to analyte monitoring for a subject user. For a user with type II diabetes, the systems and methods described according to present principles may provide an introduction to continuous glucose monitoring, and may enable beneficial behavior modification for those users, including newly diagnosed users with type II diabetes.

For example, for such patients, a kit, system, or package may be provided with a glucose sensor and transmitter, along with optional components such as a heart rate monitor (e.g., using an on-skin sensor), ketone test strips or other such ketone sensors, and other types of sensors as described above and further described below. One or more applications running in a mobile device, such as the monitoring device 21 of FIG. 2, may be employed to receive data from the various sources and use the data to help those with diabetes achieve an optimum lifestyle balance incorporating a healthy diet and exercise. The kit, system, or package may also help newly diagnosed type I patients to establish a nutrition and/or exercise plan to meet their body's unique needs.

The application may be employed to receive and evaluate data determined by the multiple devices, e.g., by identifying ratios, correlations, or the like. The application also provides a user-friendly user interface to implement phases of education in both diet and exercise. The sensor systems including CGM may be used to determine how a patient's body uniquely responds to programs including meals and exercise.

In one implementation, a phase 1 program may include a seven-day controlled diet in which different types of foods, e.g., high fat versus high carbohydrate, fat or carbohydrate versus protein, or the like, are prescribed for a user's consumption. CGM may then be employed to determine the effect and interactions of each type of food on the patient. To simplify the implementation of the program for the user, the program may affect only a single meal per day, with the remainder of the user's typical diet and exercise routine unaffected. For example, phase 1 may include a program to try different types of breakfasts, and the systems and methods at the end of the program display an output responsive to the program, e.g., displaying the best breakfasts and the worst breakfasts as determined by the monitored data, e.g., by evaluation of glucose values, glycemic indices, and other known parameters and variables as determined or measured. Continuing with this example, phase 2 of the program could essentially be the same controlled meal plan except portion size may vary, thus showing the user how amounts of food impact their glucose levels. The output may be a graph showing the effect of the selected meal, e.g., and in some implementations a comparison may be illustrated, e.g., with prior baseline data, showing greater or lesser glucose control. In much the same way, the CGM data may be employed to show the impact of exercise, e.g., both type and duration, on each individual. In this way, the type II patient may be enabled to evaluate current behavior and identify particular problems and patterns, learning in the process how to modify their behavior in order to achieve desired results.

As another example, phase 1 may include a program to try different types of breakfasts, and then phase 2 may be for the user to try different exercise routines or regimes. Phase 3 can then go back to address meals. Subsequent phases or levels can also include the addition of other aspects, e.g., to learn or determine the effect of alcohol intake, challenging the user to stay within zones or predetermined durations, limiting excursions, or the like. Numerous variations of these will be understood, and the phases or levels followed by the user may be those so as to best keep the user's interest and to rapidly place the user on a path to better health. In this way, a user can more easily and effectively learn how to modify their behavior based on their own unique physiology and lifestyle patterns in order to improve their health without the complexities and costs associated with a clinical professional.

As a particular example, phase (or level) 1 may be employed to assist the user in better learning about the effects of exercise. Consequently, the program may call for the user to perform a run three times per week and to observe what the effect of the run is on the user's glucose level. The systems and methods can determine an exercise sensitivity, akin to insulin sensitivity, and can note the same to the user. For example, the systems and methods may note that "Walking seems to really work for you.".

As noted in the evaluation step noted above, first-time users or other users who are being introduced to systems and methods according to present principles may be provided with programs that are easy-to-follow and with which it is relatively easy to obtain successful results. As users become more sophisticated, and more knowledgeable about the effects of food and exercise on their lives, "successful" ranges and envelopes may be reduced in size or otherwise tightened so as to make it more difficult for the user to achieve a "successful" result.

In some implementations, the programs may be combined with known weight loss programs having predefined meal plans, such as Jenny Craig® or Weight Watchers®. In more detail, a "mode" may be entered in which the predefined meal plans are defined or consistent with known diets, such as those noted above or others, e.g., the Atkins diet, the South Beach diet, and so on. Alternatively, meal plans may be customized for a user or user type, e.g., including programs specified to a "busy executive", "elite athlete", or the like. In these ways, a doctor may recommend a program for reversing diabetes, preventing diabetes, or continuing to prevent diabetes, in a similar fashion to the way doctors recommend weight loss programs. In some cases, "cheat days" may be situated in the program of such diets, not only as a reward for the user but also for purposes of checking the measured analytes, to ensure that the diet and/or exercise plan is working.

Over time, systems and methods according to present principles may perform "machine learning" to allow significant personalization of programs suggested and therapies prescribed, e.g., by utilizing prior information about the particular host. In this way, the computing environments implementing such systems and methods may be made more efficient, requiring fewer computations to arrive at an appropriate output for display. Such machine learning can be on the basis of feedback by the user, retrospective user data analysis, program selected by the user, and the like.

In this way, by increasing engagement and knowledge of a particular disease, e.g., diabetes, users will become more engaged, more aware of the effect of food and exercise on their lives, and will thus become healthier individuals.

As noted above with respect to, e.g., FIG. 2, data used by computing environments implementing present systems and methods may be obtained from a number of sources, including sensors, cloud or network data, as well as user entry. It is noted here that the systems and methods may operate on whatever data they are provided. For example, assuming the systems and methods have access to analyte level, if a user enters food data, the systems and methods will attempt to provide an evaluation of the food data and the analyte data with respect to the selected program. Similarly, if a user enters exercise data, the systems and methods will attempt to provide an evaluation of the exercise data and the analyte data with respect to the selected program. In addition, data may be received from numerous sources and not just those entered by the user or for which the user gives an explicit acknowledgment. That is, in some cases, the application may request data from a connected device (e.g., via a health data sharing application or "app") and/or from the cloud on its own, and assuming appropriate rights have been granted to the sourcing entities, the data may be received from a network or other cloud-based source, even without the user expressly being aware of the receipt of such data.

The systems and methods may also be adapted to receive data and/or settings from other network sources to further assist personalization of programs to users from personal trainers, nutritionists, HCP's, and the like.

An exemplary implementation of the use of such programs is illustrated by the flowchart 310 in FIG. 37. In a first step, a program is selected by a user (step 300). In some cases, default programs may be provided to the user on the user interface 26 (FIG. 2) as potential programs. The default programs may be based on no prior knowledge of the user or may be determined based on knowledge of the user including retrospective user data analysis, user responses to a questionnaire, or the like. Following selection of a program in step 300, in some cases a sub program may also selected by the user (step 301), the subprogram selected from one or more displayed subprograms related to the program selected in step 300. For example, in step 300, a user may select whether to follow an initial meal program or exercise program. In step 301, if the user selected a meal program in step 300, the user may select whether to follow a breakfast program, a lunch program, or a dinner program. Alternatively, if the user selected an exercise program in step 300, the user may select a running program, walking program, yoga program, or the like, in step 301. Users may be enabled to select known food programs having known steps and meal plans, e.g., such as those provided by Jenny Craig® or Weight Watchers®.

The program selected in step 300, as well as the optional subprogram selected in step 301, may further include a sub-subprogram which is a challenge or scenario of the day. For example, in the case of glucose control, a sub-subprogram may be issued to a user on the user interface such as "Can you stay below 140 today?".

A subject user may select a program and/or subprogram or the system may propose certain programs/subprograms determined to be of potential use to the subject user. Moreover, upon completion of a program or subprogram, the systems and methods in many implementations may propose a new (or modified) program/subprogram, and the same may be similarly chosen to be of potential use to the subject user. In performing the above-noted determinations, machine learning or other sorts of artificial intelligence may be employed. Considerations useful for such machine learning or artificial intelligence may include an effort to create healthy habits for, e.g., type II diabetic users, through the use of CGM. For example, the programs may be designed to create healthy habits and may be further designed to be easy-to-follow by a typical late onset diabetic, e.g., with considerations as to age and other typical characteristics, e.g., typically over 40 years old and in some cases obese. Thus the consideration of the creation of healthy habits may include an attempt to break unhealthy habits, e.g., poor exercise, poor diet, often with high glycemic index foods, as well as an attempt to create new habits, such as easy-to-follow exercise routines and diet plans. Consequently, many of the displayed outputs described above may be employed to further these considerations, e.g., by including the use of positive reinforcement, graphical illustrations of the effects of food and exercise decisions, progress reports, reminders, recognition for accomplishments, and the like.

To create and encourage healthy habits, an obvious trigger may be used as an instigator, e.g., the app 27 may provide a challenge based on a glucose pattern, e.g., and may space challenges apart in time to allow a user to concentrate on just one challenge at a time. For example, the challenge may be for the subject user to maintain their glucose concentration value between 100 and 150 after breakfast. The app may thus provide an attainable goal, and may further provide resources to the user while they are trying to accomplish the goal. For example, as shown in FIG. 6, a link to a food source may provide an easy way for a user to obtain healthy food choices. Accountability for the user's attempt to meet the goal may then be as noted above, by a display of an output including an indicator of success or failure, reinforcement, suitable follow-on programs, and the like. For example, if a user is unsuccessful, a follow-on program may provide more easily-attainable goals. Particular challenges may be related to a glucose goal, a monitoring goal, may be focused on a particular time of day or particular meal, e.g., breakfast, or on a particular activity, e.g., exercise or medication adherence.

The programs may be selected to provide teaching to the user through a process of self-discovery, guided by information, outputs, and new programs as determined by the systems and methods, sometimes in combination with user input. Advantageously, the programs may be particularly customized for the user, without the complexity and cost associated with a clinical professional. Allowing programs to be informed by user data allows significant technological advantages as such programs run more efficiently, decreasing computation time and number of cycles required, saving battery power, and so on.

Returning to the discussion of FIG. 37, systems and methods according to present principles may in some implementations provide initial guidance in following the program (step 302). For example, the systems and methods may provide suggestions to help users, e.g., including textual indicators such as "Here's what you should aim for: X, Y, and Z.". Initial guidance may also be provided by the provision of cookbooks as noted above, e.g., with respect to step 44 of FIG. 3. For new users unfamiliar with reading traces, textual explanations may be provided such as "Try to keep your trace in the good envelope or within the good bounds." For users desiring an even simpler display, the indicator may be, e.g., "Try to keep this color indicator in the green zone.".

The glucose level and optionally other data may then be tracked (step 303). In particular, the glucose (or other analyte) and optional data including meal and activity data may then be monitored via appropriate sensors, and the data stored. In the particular case of food and exercise programs, typically meal data and exercise data will be pertinent and thus the same will be monitored and stored. In some cases glucose and other data may then be analyzed (step 304). Such analysis may include signal processing, analysis to determine related data such as time rates of change, or analysis to combine two or more disparate pieces of data to obtain a new resultant datum. The analysis may also include analysis of retrospective data; in other words, analysis of retrospective data may be combined with analysis of contemporaneous or recently-received data to determine the effect of the program on the user's analyte level, and, by extension, overall health. In some implementations, the analysis may include analyzing the data to determine adherence, or lack thereof, to the program. For example, if the user begins a program but the systems and methods indicate little or no adherence to the same, the systems and methods may prompt the user to enter information such as "Do you recall the present program?" or the like. The analysis may further include receiving and analyzing behavioral and context information, as disclosed in U.S. Publ. No. 2015/0119655 A1, incorporated by reference herein in its entirety.

A next step is the evaluation of the glucose trace, and optional other data, against the selected program and/or subprogram (step 306). In this step, the specific evaluation will be based on the perturbation, i.e. the program, as well as on available pertinent data. In general, the evaluation may include evaluating a parameter X and glucose, where X corresponds to the program's predefined instructions. The evaluation, e.g., which may be a correlation, may be against an expected, modeled, or predicted response, which may also be thought of as an ideal response. For example, where the program constitutes a meal plan intended to maintain a user's glucose level within a predefined envelope, the evaluation may include comparing a series of meal data to the predefined envelope. To enable the application to identify a glucose event with the meal, in this example, the data can be analyzed against the time of day, to determine if an event data is reflecting a meal, and if so, what meal it is reflecting. Other data, including user entered data, may also be employed and analyzed in this regard, for subsequent evaluation in step 306.

As a more specific example, if a program concerns learning the effect of changing a parameter such as the breakfast meal, the evaluation may be to examine the parameter versus the glucose value, i.e., a parameter corresponding to the breakfast meal, e.g., calories, carbohydrate content, glycemic index, or the like, against the glucose response. In a more advanced implementation of such a program, the program may also examine previously-determined baseline values of, e.g., "glucose during and after breakfast". Similarly, if the program concerns learning the effect of an exercise parameter such as going on a run at lunch, the evaluation may be to examine the exercise parameter versus glucose values within a particular timeframe, e.g., 11 AM to 5 PM. Of course, overall glucose control can also be looked at and evaluated.

The evaluating may also include evaluating the effect of activity on the glucose level. Activity level may be measured and quantified in various ways, including using predetermined levels such as: sleeping, sedentary, light activity, medium activity, and high activity levels.

The evaluating may also include evaluating the effect of metabolism on the glucose level. For example, data from a metabolic monitor, described elsewhere here, may be combined with glucose data to identify correlations between metabolism and glucose control. Similar evaluations may correlate cholesterol with glucose data.

Evaluations may also be performed based on effective glycemic index or glycemic impact, or on the impact of fats and proteins. In these cases, a CGM trace may be analyzed to compute effective glycemic index (EGI). Over a period of several weeks, a distribution of the EGI may be determined and the same may be evaluated with respect to food habits, e.g., a correlation drawn, and the correlation may be short-term or long-term. Such considerations may be displayed to the user to indicate the beneficial effects of moderation, by identifying the ensuing EGI following a particular meal. For example, after eating a doughnut, the user may be presented with a suggestion such as, "Perhaps it would be a better glycemic choice to eat half as much next time.".

In a final step, an output is displayed responsive to the evaluation (step 308). The displayed output may be any of the types described above, depending on application, and exemplary displays are noted below with respect to the specific examples.

Figure 38:
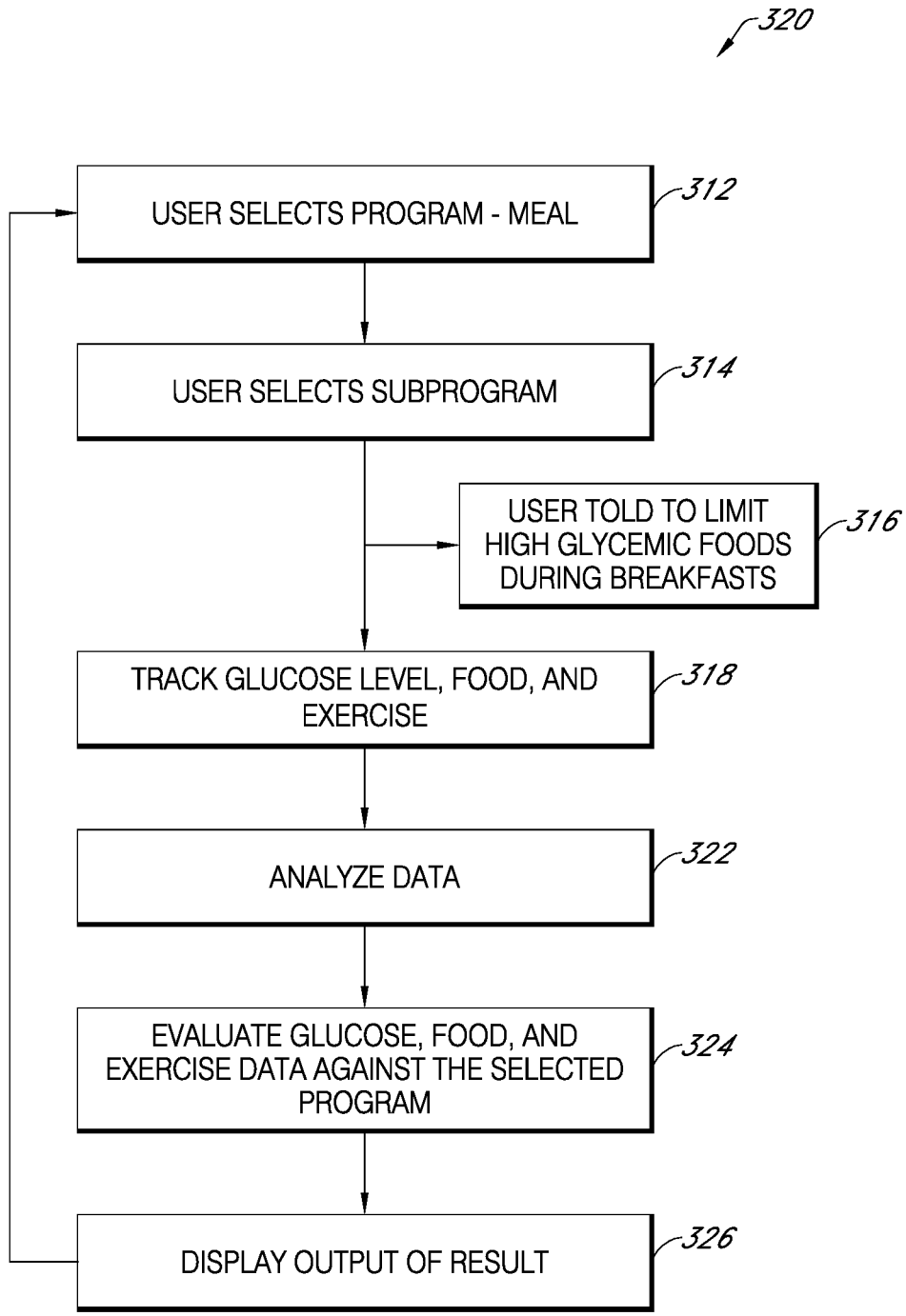
FIG. 38 is an application of the method of FIG. 37, in which a specific program has been suggested for the user.

In one exemplary implementation, illustrated by the flowchart 320 of FIG. 38, a user selects a program to start their engagement with the system, and in this example the user selects a meal program (step 312). The user then selects a subprogram, concentrating on the breakfast meal (step 314). Systems and methods according to present principles then instruct the user to limit high glycemic foods or high carbohydrate foods (or to generally limit foods with significant glycemic load or carbohydrate content) during breakfast, but otherwise to vary the types of breakfasts they eat (step 316). Glucose level is then tracked, along with food data as entered by the user (step 318). In some cases, if desired, exercise data may also be entered by the user (or otherwise obtained) and subsequently tracked. A data analysis step may be performed if desired or needed for subsequent calculations (step 322). Besides limiting high glycemic load foods, other programs may include investigating the impacts of fats and proteins.

The glucose trace is then evaluated along with the entered food data (step 324) against the selected program (again, exercise data may be evaluated as well). Results may then be subsequently displayed (step 326).

For example, the evaluation and displayed output may show to the user that eating eggs for breakfast provides better glucose control than eating doughnuts, and in particular provides better control overall. In other words, it is not just that one meal is shown to be better than another for control, but that overall, as compared to a prescribed program, a pattern of certain meal choices may provide for better health, and systems and methods according to present principles demonstrate such to a user, and further provide for increasing benefits to health, as the programs iterate, and the user becomes increasingly more educated about how to make better choices in meals and exercise.

Figure 39:
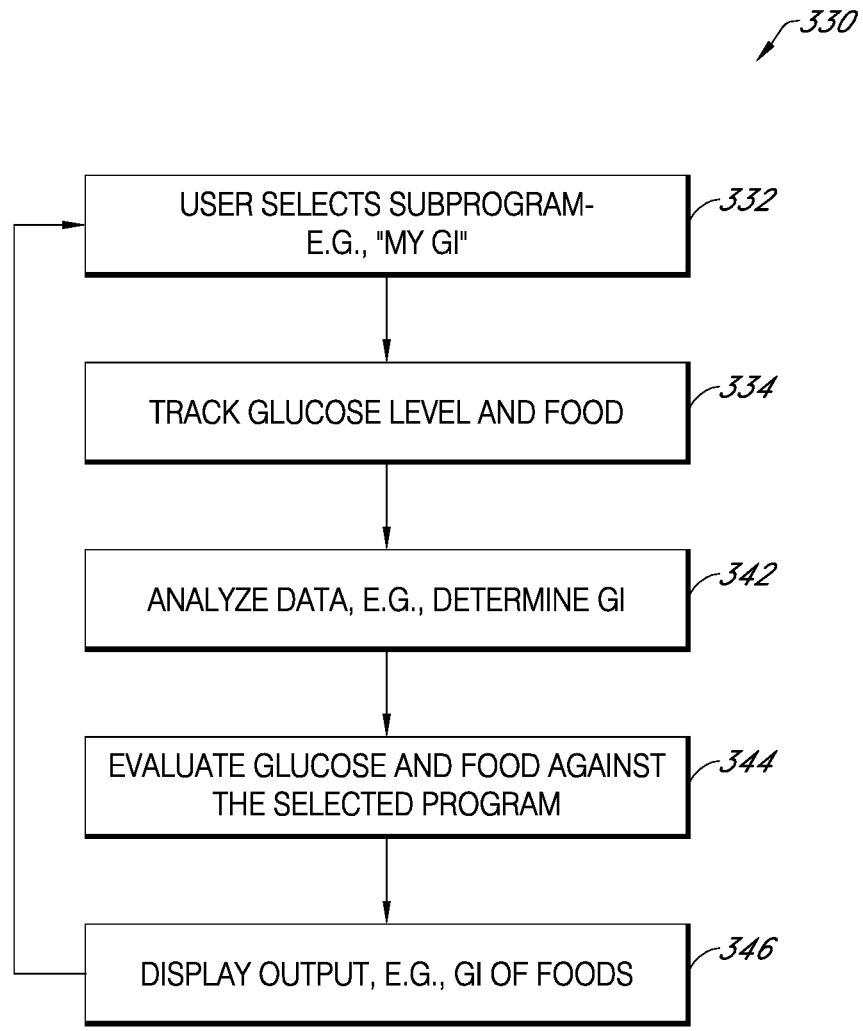
FIG. 39 is an application of the method of FIG. 37, in which a user has selected a specific subprogram.

Another example is illustrated by the flowchart 330 of FIG. 39. Methods according to the flowchart 330 may take various forms, but many may be implemented within the context of an already-selected program as noted above. A first step is that a user selects a particular subprogram, e.g., "MY G.I." (step 332). This particular subprogram is intended to be a training tool, and generally (or in many cases) to be implemented in the course of another program, e.g., to educate the user about the effects of certain food items. This is in contrast to the educational goals of most programs according to present principles, which seek to educate the user with respect to overall patterns of eating, exercise, or the like.

The subprogram of step 332 uses the concept of a glycemic index as noted above, which is a characteristic of an individual food. However, the same may be specified to a particular individual, as the glycemic index may vary depending on the user's particular choice of a specified food. For example, a glycemic index of a medium-sized potato may have a certain value, which can be determined by the user using any number of references. However, what constitutes a "medium" potato may vary from user to user. The particular glycemic index, specified to a user's intended food item, is herein termed a "glycemic impact". Thus, one aspect of the subprogram of step 332 is to determine data about what a user defines as a particular food item, and in so doing, defining the glycemic impact of the particular food item. Advantageously this personalization of glycemic information avoids the complexities associated with standardized regimes, which may be too rigid for many users to utilize practically.

Another aspect is that a beginner may have a certain goal with respect to a food, the food having a certain glycemic impact, while an experienced user might have another goal. For example, the experienced user may be aware that eating smaller portion sizes, eating carbohydrates in combination with proteins, performing exercise before eating, eating more slowly, allowing more time between insulin and a meal, may all lead to enhanced glucose control.

As the final arbiter of glucose control is the measured glucose concentration value, following selection of the subprogram, the glucose level may be tracked, along with data about foods consumed (step 334). The data may be analyzed, e.g., to determine the glycemic impact (step 342). For example, a photograph of the meal may indicate a potato, and the user may enter data indicating that the potato is a medium-sized potato. The glucose level is tracked, and a portion of a subsequent glucose rise may be attributed to a medium-sized potato, this definition being used in subsequent calculations.

As before, the glucose value and food may be evaluated against the selected program (step 344). In this case, if the user provided a "guess" as to the glycemic impact prior to the meal, the guess value may be compared against the actual value. The user's guess may constitute a rise in glucose value, but particularly-experienced users may even guess a glucose trace waveform by dragging their finger or stylus on a touchscreen interface, where such is provided by the monitoring device 21. Even if no guess was made, the entered food data and the resulting glucose level and/or glycemic impact may be evaluated, and an output displayed (step 346). For example, the output may be displayed as a glycemic impact of the entered food, either as an absolute value or as a comparison to other foods consumed by the user, including like meals such as other dinners, or with like constituent elements, such as "meals containing chicken".

Using subprograms such as those selected in step 332, users may be educated as to the glycemic impacts of various foods. Users training on such programs over a time period, e.g., 28 days, may obtain significant information about how to eat to reverse or avoid diabetes. As noted above, such programs may focus a week on breakfast, a week on lunch, a week on dinner, etc.

In an advanced implementation of the above, a user may enter not only meal information but also post-meal bolus information. The application may then ask the user what they guess their glucose level to be after 30 minutes. Subsequent to the expiration of the 30 minute time frame, the application can show the actual glucose level and the guess, thus providing advice on how to make the difference smaller in the future.

In yet another variation, an initial screen of the application 27 maybe configured to not indicate to the user their glucose level, or any sort of trend graph. Instead, every time the user opens the application, or on an occasional basis, the application may ask the user to guess their current glucose value, thus training the user to estimate the glucose value based on how they feel. Such may serve to effectively demonstrate to the user the poor correlation between how they feel and their glucose level.

Figure 40:
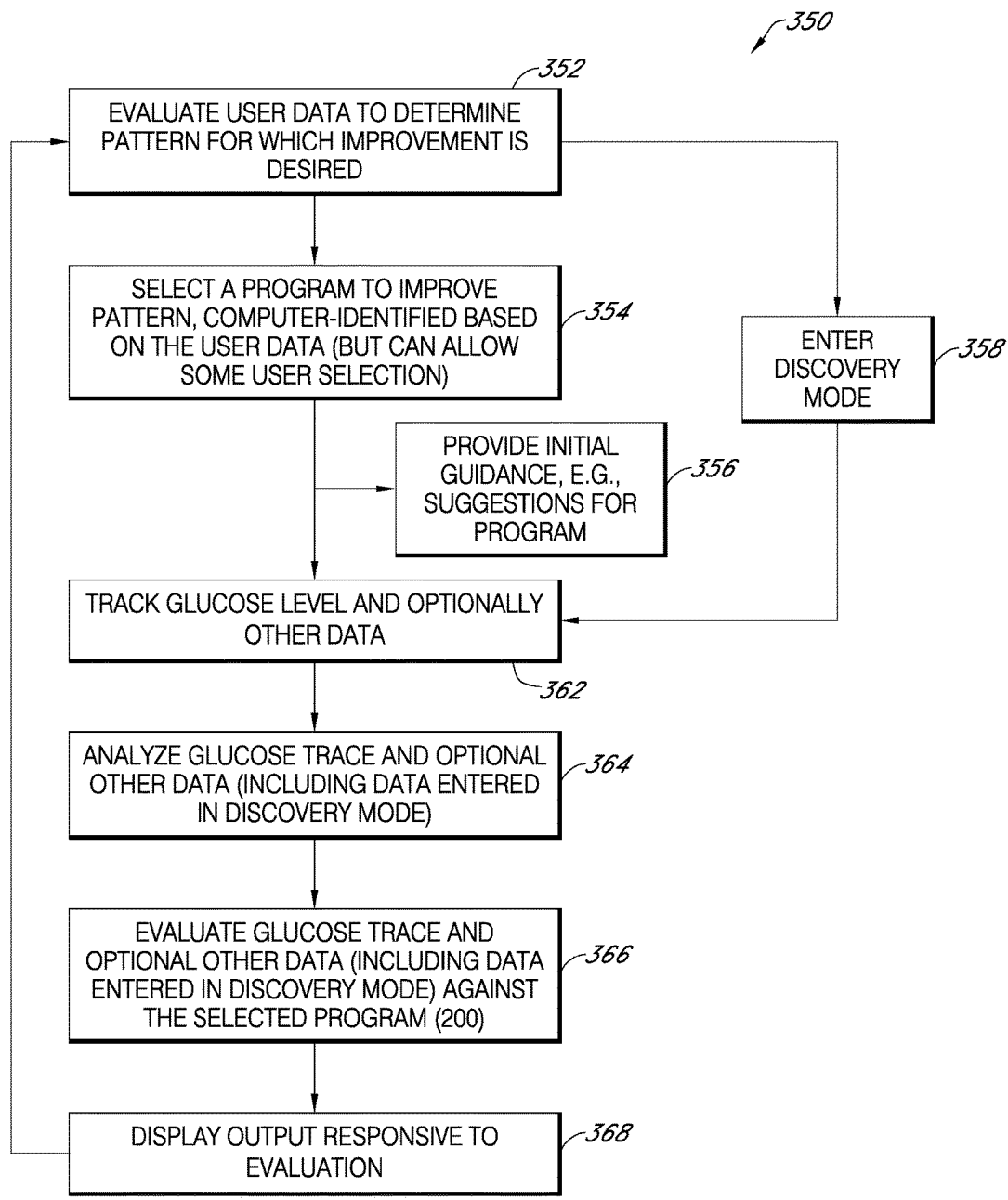
FIG. 40 is another more detailed flowchart indicating an application of the flowchart of FIG. 1, specific to steps following the determination of a pattern within data, e.g., glucose data, and in particular to assist diabetes and pre-diabetes patients in learning how to better manage their health.

The flowchart 350 of FIG. 40 illustrates another implementation of systems and methods according to present principles. In this case, the systems and methods react to a detected pattern, generally a deleterious one, and propose one or more programs to address the pattern. Systems and methods according to the principles of FIG. 40 further allow and enable a "discovery mode", in which additional information may be obtained to better address deleterious events or trends.

In more detail, in a first step, user data is evaluated to determine a pattern for which improvement may be desired (step 352). In this step, generally, retrospective user history is analyzed to detect a problem pattern, e.g., a pattern of overnight lows, weekend highs, postprandial spikes, or the like. As used in this specification a pattern is generally a repeating data arrangement occurring over a time window such as on a daily or weekly basis. While examples of patterns are described above, patterns may generally relate to sudden rises, sudden drops, repeating differences from typical or baseline patterns, or the like.

A next step is that the computer environment, e.g., application 27 of FIG. 2, selects a program to improve the pattern (step 354). In selecting the pattern, the computing environment may base the selection on a number of factors, including the retrospective user data, what the pattern is of, and other factors. For example, look up tables, artificial intelligence, rules-based systems, expert systems, machine learning, or the like, may be employed to make this and other determinations. By basing the selected or suggested programs in this way, a technological efficiency is gained because the user need not tolerate a significant amount of "trial and error" in finding the correct and appropriate program.

In some cases, two or more potential programs may be determined to be appropriate and displayed, and the user may have the option to select one of the displayed programs. As above, the program is generally to be implemented in a patterned or systematic way, e.g., asking a user to eat according to a certain diet or perform a certain pattern of exercises. By so doing, an effect of the program can be determined vis-a-vis the determined pattern, and the effect can also be quantified.

Once a program is selected, initial guidance may be provided for following the program (step 356). In this case, the initial guidance can also indicate additional aspects, e.g., may indicate a potential cause of the deleterious pattern. Additional details about such may be found above, in the discussion of step 302.

In a variation, as the pattern is generally determined on the basis of computing environment observations or determinations of a deleterious event or pattern, a discovery mode may be entered (step 358) in which an attempt is made to glean, infer, or otherwise receive additional information helpful in determining the program of step 354, and in some cases even helping to discover a root cause of the pattern detected in step 352. The discovery mode may prompt the user to answer certain questions over a period of time in order to obtain the noted information. The period of time may be a period of several hours or several days. The discovery mode may automatically generate and pose questions for user data entry based on glucose variations or the like, prompting for data which may relate to events causing or caused by such variations. The discovery mode may ask questions relating to retrospective user data, and may also ask questions relating to current events, e.g., current excursions or recently-experienced excursions. In so doing, the discovery mode can perform analysis on the received data, including previously-known or historical data, and provide an output to the user relating to, e.g., potential causes of the deleterious pattern. In many cases, the determined information may also be used as feedback in order to inform the selected program of step 354, or to better determine the root cause of the pattern (step 352), so as to provide a better program for user self-discovery in step 354.

As one example of the discovery mode, following an unhealthy excursion, e.g., if a glucose concentration value exceeds 200 mg/dL, or a change in glucose concentration value over a predetermined period of time meets a certain criteria, e.g., exceeds a predetermined threshold, the user may be prompted for extra information, e.g., meal details, the last time they exercised, and so on. In this way, the discovery mode provides a prompt for data similar to a log book, but where the user only enters data if a significant event is detected. In a variation, the thresholds may be adjusted so that requests for information do not exceed a certain predetermined threshold, to avoid user interaction fatigue.

The remainder of the flowchart 350 of FIG. 40 is similar to that of the flowchart 310 of FIG. 37. In particular, glucose data (and/or optional other data) is tracked (step 362) and analyzed (step 364). The tracked and optionally-analyzed glucose data is then evaluated against the selected program (step 366), and an output is displayed (step 368).

As a specific implementation of the flowchart 350 of FIG. 3, retrospective user data may be evaluated (step 352) and may determine that the user has a deleterious pattern of overnight lows, e.g., commonly experiences hypoglycemia at night. A discovery mode may be entered (step 358), and the same may determine that the user eats a very small dinner and works out at a gym after dinner. A program may be determined by a computing environment (step 354), and the program may propose that the user eat a larger dinner and work out before dinner instead of after. Initial guidance may be provided (step 356), based automatically on entered data, and the initial guidance may suggest recipes for the user, or may suggest, e.g., a certain level of glycemic impact which may be beneficial for the user to attain at dinner. Over the duration of the program, e.g., a week, the user's glucose level may be tracked (step 362), along with their meal data and activity data. The meal data may be analyzed (step 364) to determine to determine a glycemic impact of the meals eaten. The glucose trace, and other data including, e.g., glycemic impact determined by an analysis step, may then be evaluated against the program. For example, the individual meals may be evaluated against nutritional data of the meals suggested by the program. An output may be displayed (step 368) indicating whether the user met the goals of the program. For example, the output may indicate that overall the user decreased the number of nighttime hypoglycemic events. However, a more granular output may indicate that certain days were better than others. For example, the user may still experience a significant overnight low on Friday, but a subsequent discovery mode (step 358) may reveal that the user takes a long bike ride with coworkers during Friday lunches. A subsequent evaluation of such additional information may lead to a modified program regimen, whereby the user is suggested to consume a high carbohydrate bar before, during, or subsequent to the bike ride. The output of this modified program may then be displayed in a subsequent display step. Such iterative processing provides the user with progressively more information about their disease and its response to therapy, and thus the user achieves greater control over their disease and a subsequently improved healthy lifestyle.

Figure 41:
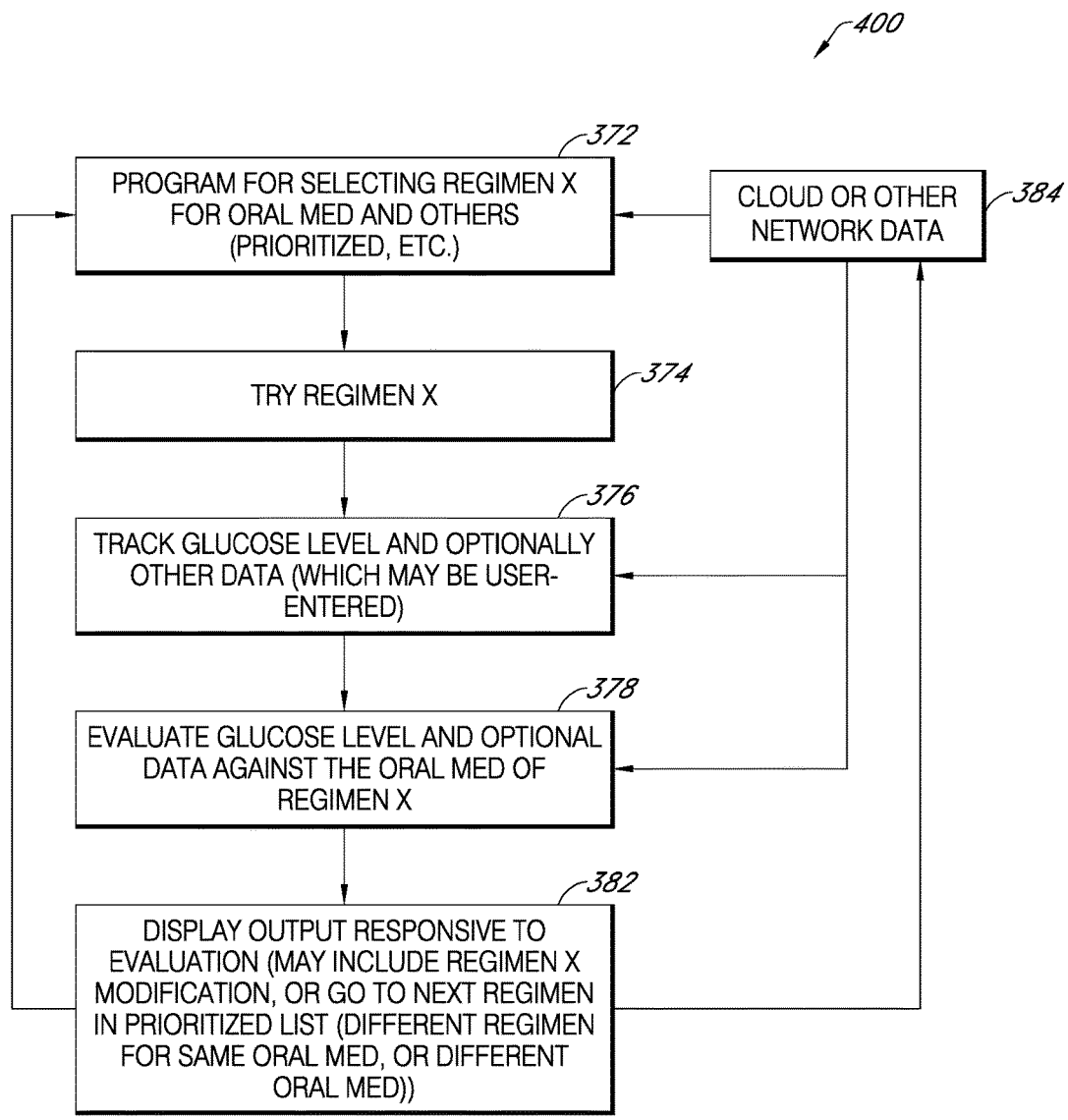
FIG. 41 is another more detailed flowchart indicating an application of the flowchart of FIG. 1, specific to determining an optimal medicament regimen.

FIG. 41 illustrates another application of the flowchart 10 of FIG. 1. In particular, a flowchart 400 is shown which allows for a personalization of therapy, in particular with regard to the administration of medicaments. Systems and methods employing the flowchart 400 can be used to provide suggestions to users of medicament programs to follow, not only with regard to data discovered about the user but also with regard to data about similar users, sourced from the cloud or other network-based system. In particular, if users have similar profiles, it may be assumed that similar programs and medicaments might be appropriate.

It is further noted in this regard the practical impossibility of physicians to be aware of every medication and the details thereof, as well as all of the other aspects affecting user health. Moreover, it is impossible for physicians to be aware of details of all other users of a medicament for a particular disease, or even a subset of such users, e.g., a network-connected subgroup. Systems and methods according to present principles, e.g., shown in one implementation in the flowchart 400, employ aspects of a cloud-based ecosystem to resolve the complexity of information using the principles of numerical computation. In particular, users can be compared for demographic information, and the same may be compared in a number of ways, e.g., using machine learning, artificial intelligence, neural nets, Bayesian analysis, and other known computational techniques, which are required to be performed, in some cases in real time, by a computing environment, and in particular a computing environment connected to other computing environments, and which cannot be performed otherwise. Besides analysis of demographics, glucose (or other analyte) trace data may be analyzed by the system, in combination with patient demographic information.

Besides the optional use of cloud-based or other network data, systems and methods according to present principles may use the above-noted programmatic method to customize a therapy for a patient, including medicament titration, to identify a drug regimen which provides the best results for a user, a drug regimen including an identification of a drug, a dosage amount, and an administration pattern, including times and frequencies. Besides providing a way to resolve the computational complexities noted above, systems and methods according to present principles solve the problem of users spending potentially many years on personally inefficient or ineffective drugs. The drug titration method may also include consideration of meals and exercise, which can also be pre-planned and evaluated along with drug titration to provide the best and optimized therapy for the user.

Turning to FIG. 41, in a first step, a program is selected which may include a regimen, e.g., regimen X, for a medicament. In some cases, a combination or "cocktail" of medicaments is used. In some cases, the program selected may simply be the first prescription provided by an HCP. In other cases, an application, e.g., the application 27, suggests a program to follow, and the same may be based on local data such as patient information and retrospective user data analysis, e.g., including historical glucose data, or the same may also be based on cloud or other network data (step 384). In some cases the program can further be based on user input, either by the user solely or in combination with HCP input or input from application 27, the same employable to analyze user data and provide suggestions. Other such data may include drug cost data, user insurance information, and the like. In all of these data inputs, if there is a lack of response in a defined time period, or a lack of provision of data from the user, the clinician, pharmacy, case manager, may be notified.

In this regard, as well as with respect to "computing—environment—performed" or "computing—environment—assisted" program selection under the flowcharts described here, a cloud-based ecosystem may enable HCPs and their patient users to tailor therapy and care, including, e.g., diet, lifestyle, medications, devices, and the like, to optimize adherence and clinical outcomes. In so doing, the application 27, alone or in combination with a network or cloud sourced application, or an application performed entirely on a network, e.g., a web application, may allow entry of relevant user health and lifestyle information. In some cases, all or a portion of such data entry may be automatic. Based on the information, the HCP and/or user may "walk" along a decision tree. The health information may include genetic information, CGM data, insulin data, demographic data, laboratory data, glucose profile, and other known data as may be required or helpful. Based on the data entered, as well as patient lifestyle preferences, the systems and methods may determine an optimal course of action with regard to the issue in question, e.g., diet, lifestyle, medications, e.g., a starting dose, devices, or the like. Optimality may be determined in terms of adherence, outcomes, and cost. The systems and methods may advantageously employ genotype clustering, discriminating "similar" from "dissimilar" patients with respect to predicted responses to medications or other varied parameters. The systems and methods can also employ "recommender" systems, which can determine from lifestyle preferences what therapy and care is most likely to lead to adherence, and can also employ bio informatics, health informatics, and telemedicine tools. As systems and methods thus improve clinical outcomes and reduce costs, the same are valuable to insurance payers as well as to users and HCPs.

Returning to FIG. 41, following program selection, regimen X is then followed (step 374) by the user. In so doing, a glucose level may be tracked (step 376), and other optional data may be tracked as well. The data may be as noted above, e.g., received from activity sensors or other analyte sensors, received from user entry, including data about food consumed, and so on. Data may also be received from the cloud or other network-based sources.

CGM data may be used, alone or in combination with other data, to determine a starting dose of insulin as well as a starting dose of other medications. The CGM data may also be employed to determine the aggressiveness of adjustments, and the frequency of the same. For example, if all glucose data is below 180, basal insulin may be started at 20 units (e.g., versus 10 units). If some days fall below 150, 10 units may be employed. If the low is between 150 and 180, 15 units may be the starting basal insulin dose. If glucose stays above 180 over two days, insulin may be increased by 10 units. If the glucose concentration value falls below 180 but above 150, the regimen may call for waiting three days and increasing the basal insulin by five units. If the glucose value falls below 130, the regimen may call for waiting a week and potentially titrating by three units. Where oral medications are used, if the glucose value stays above 180, the regimen may call for starting a combination therapy. If in one month the glucose value stays above 150 with no lows, GLP-1 or basal insulin may be added.

As with the other flowcharts, a step may then be employed of evaluating the glucose level and optional other data against the medicament of regimen X (step 378). The evaluation may be as noted above, and this step may further include evaluation of cloud-based data, e.g., about similar users. In this analysis users may be profiled to determine similarities with the subject user, as it may be assumed that, if a drug and drug regimen is successful for users similar to the subject user, the drug, drug dose, and drug regimen (or a close variation thereof) may also be successful for the subject user.

By use of cloud-based data about similar users, data may be collected and analyzed about thousands, tens of thousands, or hundreds of thousands of patients, and a profile may be selected for a subject patient based on significant amounts of data about the subject patient as compared to the stored data about all known patients. A clinician would not be able to perform this analysis manually or in any reasonable amount of time. Moreover, such a therapy optimization database may be constantly updated with new patient data, so the same is always improving, which is also something not humanly possible by a clinician at this scale and detail of data.

An output may then be displayed (step 382), where the output is responsive to the evaluation. The outputs may be as noted above, indicating a degree of success or failure of the drug and regimen on, e.g., the user's glucose profile, and may also include a modification of the program, i.e., a new or modified perturbation. The success or failure of a drug and regimen may include a determination as to whether the patient's results are the same as the expected results. If the response of the patient is not usual or typical or as expected, it may be assumed that the medicine is either ineffective or is not being taken properly. In particular, the modification may suggest a different drug, a different regimen for the same drug, e.g., increasing or decreasing units of the drug, dose titration, frequency of titration, or other such modification. Suggestions may be iterative, e.g., provided daily or periodically. Notifications may be triggered and sent to a pharmacy, clinician, case manager, and so on.

In some cases, a glycemic pattern may be detected and analyzed, in some cases including using data from the cloud or on the device, to determine one or more potential medicaments which may be of particular benefit to the user. The output may further include a step of sending the result to the cloud or other network, so as to allow the data to be used for the benefit of other users and for comparison to other users.

In some cases, to detect patient compliance or lack of compliance, systems and methods may be employed which identify a signature of an oral medication, e.g., by use of a sensor/transmitter within the medication and a health monitor, e.g., a patch, to detect if the user has taken a medication, when it was taken, and so on. In some cases, such systems may further include sensors such as accelerometers to detect exercise, or the like.

By use of the systems and methods noted above, not only can a computing environment more efficiently "hone in on" a preferred or optimum drug and regimen, but the patient benefits by having to take fewer drugs because they are taking the right drugs. Many benefits ensue, as will be understood, including cost savings, more rapid titration to target, and fewer side effects.

Figure 42:
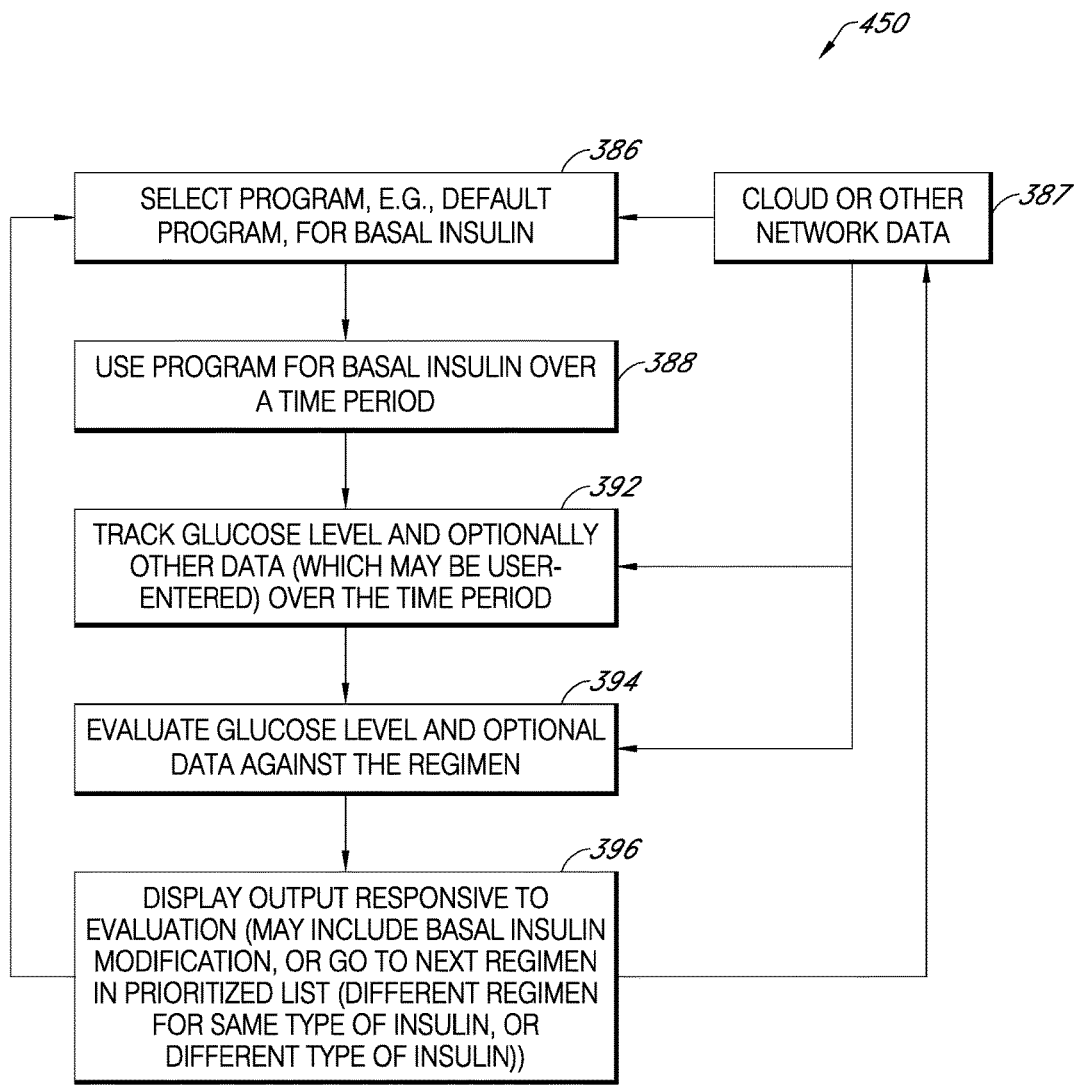
FIG. 42 is another more detailed flowchart indicating an application of the flowchart of FIG. 1, specific to determining an optimal basal insulin regimen.

As a specific example, systems and methods according to present principles may be employed to determine a preferred regimen for controlling glucose levels in Type II diabetes. Referring to FIG. 42, a flowchart 450 is illustrated for such a determination.

In a first step, the program may be selected for type, timing and/or amount of medicament (step 386). As above, such may employ input from the user, from an HCP, and/or from the cloud (step 387). The program may then be employed over a predetermined time period (step 388). Glucose level may then be tracked (step 392), as well as optionally other data, in particular, insulin data, food data, exercise data, previously-measured data, laboratory data, demographics, starting dose, and the like.

The glucose level and optional other data may then be evaluated against the regimen (step 394), and an output displayed (step 396). The output may include a change to the type, timing and/or amount of medicament, when the medicament is insulin, a change to basal insulin dose, an addition to the regimen of insulin sensitizers or secretagogues, a change of type of insulin, and the like, may be included within the scope of recommendation. The process may be iterative, e.g., daily or weekly or the like.

To assist in this method, a direct insulin sensor may be employed to measure the insulin sensitivity of a user. In particular, a user's sensitivity to insulin will determine how much insulin a user needs in order to maintain proper glucose control. Insulin sensitivity can vary between patients and even over time with the same user.

Accordingly, in one specific implementation, the system and method may use a direct insulin sensor to detect the amount of insulin in a user's body. By combining the information of glucose and insulin concentration into the evaluation step 394 of the method of FIG. 42, the insulin sensitivity can be even more effectively calculated. Information about the insulin sensitivity can then be used to determine if an insulin sensitizer, insulin secretagogue, or insulin, should be used to manage the diabetes. The amount of insulin or other medicament can then be increased or decreased in such a way so as to best control the patient's glucose levels.

In another implementation directed to physician and other user interaction with the system, systems and methods according to present principles can address the technical problem that current computing environments are unable to unambiguously determine or calculate a plan or scheme for an HCP to follow in determining a proper medicament regimen for a user. Instead, such HCP's rely on "what worked before", a standard of care laid out by an endocrinologist, or other imprecise measures. In present systems and methods, data inputs, especially CGM data inputs, are used to allow an automatic determination of a drug scheme to follow. Of course, above-noted systems and methods directed to titrating medication may be used to refine the determined drug scheme.

In yet another implementation according to present principles, it is noted that different healthcare professionals help diabetic patients to the extent that their training allows them to. These different HCP's are used to treating patients in different ways and with different types of data. For example, endocrinologists typically treat diabetic patients that have other morbidities besides diabetes. Such HCPs are particularly trained to analyze CGM traces and draw conclusions therefrom.

However, a typical type II or type I patient will be handled by a primary care or family care/internal medicine physician. CGM may still be provided to these doctors, but in a simpler form. In most cases these HCPs are not likely to be able to parse all the nuances of data signatures in the CGM trace; but the data may still be provided to them on a recurring basis so that they may determine longitudinally the effect and success of the drugs they are prescribing to the patient. In most cases generally there will still be an overseeing endocrinologist over the medical care group, determining a preferred drug regime or set of drug regimes. The endocrinologist can provide a detailed report that will go out to all of the family care/internal/primary care doctors, and that will be based in part on reimbursement and the like. But as noted the report will be a simplified version, as such doctors are not specialists with endocrinology and are likely also dealing with other issues of the patient, e.g., high cholesterol, and so on. Because of this way in which most type I and type II patients are cared for, an automatic determination of an initial drug regime, one that is unbiased and personalized to the patient or user, may be of particular benefit.

In prior efforts, most HCP's would start a type II user on the same drug—metformin. If this did not provide satisfactory results by itself, the HCP would add a second therapy, e.g., a second medication. Such may be, e.g., a sulfonylurea, a GLP-1 drug, a DPP-4 inhibitor, or one of several more.

Present systems and methods allow a data-driven approach to determining what this next drug should be, or even if the initial attempt at medicament therapy should be based on metformin, a combination of metformin with another drug, or should start off with a different drug.

Figure 43:
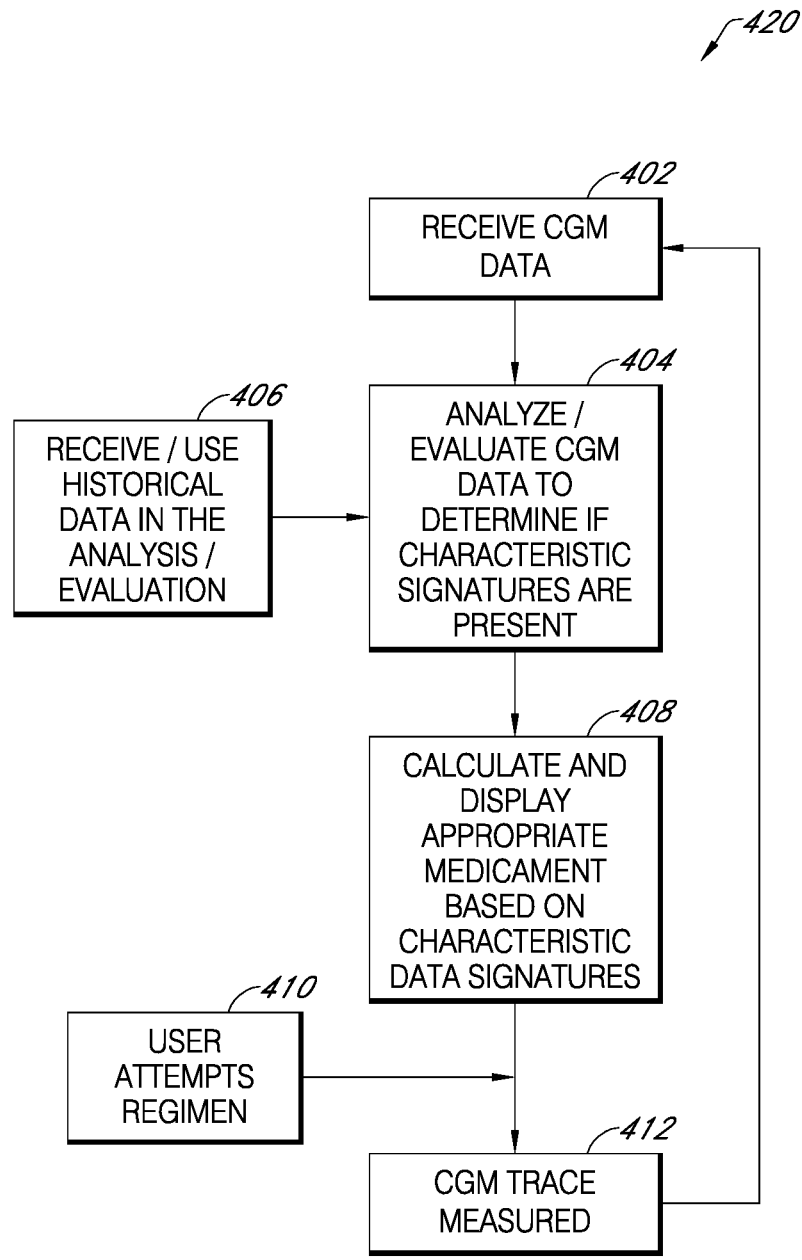
FIG. 43 is a flowchart illustrating an implementation of a method for determining a drug regimen.

For example, referring to the flowchart 420 of FIG. 43, a first step may be seen as receiving CGM data (step 402). This CGM data may constitute currently measured CGM data, or may have been measured in the past. In the same way, a step may include the reception and use of historical data (step 406). A next step is to analyze or evaluate the CGM data to determine if characteristic signatures are present (step 404). In particular, this step involves the numerical evaluation of CGM data, e.g., over the last several months, to determine if one or more particular curve features are present. This step may involve placing curve features in "buckets" or "classifications" as described above. Generally, such characteristic features involve looking at glucose curve trace rises, plateaus, falls, associations with known data about events, e.g., meal data, exercise data, sleep data, and so on, and the construction or calculation of numerical deductions and inferences therefrom.

Such characteristic features may be associated then within the computing environment with certain defects, e.g., in insulin production and use, and the calculation and numerical inference of a defect can lead to a particular drug being suggested, or combination of drugs. In some cases, this data may be used in combination with other data, e.g., event data as noted, or other analyte trace data, other physiological parameter data, and so on. In most cases the use of CGM data, via an indwelling interstitial sensor, is particularly important for the analysis, as the use of data from such a sensor allows the calculation and numerical inference of characteristic signatures and defects, such inferences not possible using prior art devices, e.g., SMBG.

Once an appropriate drug or combination of drugs is determined based on the characteristic signatures, the same is provided to the patient as a prescription for a drug regimen. The user attempts the drug regimen (step 410). Using CGM, a subsequent glucose trace is measured (step 412). Other analytes may also be monitored. Using the CGM glucose traces, and in some cases other analyte traces, systems and methods according to present principles determine if the defect is still present. If it is, the dose may be changed or an additional or different drug or combination of drugs tried, using, e.g., the titration techniques described above. If the defect is no longer present, it may be assumed that the drugs calculated are appropriate. If the defect is present but to a lesser degree, systems and methods according to present principles may calculate that a different dosage is indicated. In any case, the new glucose trace measured in step 412 may be fed back into the general method in step 402. Numerous variations of this technique will be understood.

Figure 44:
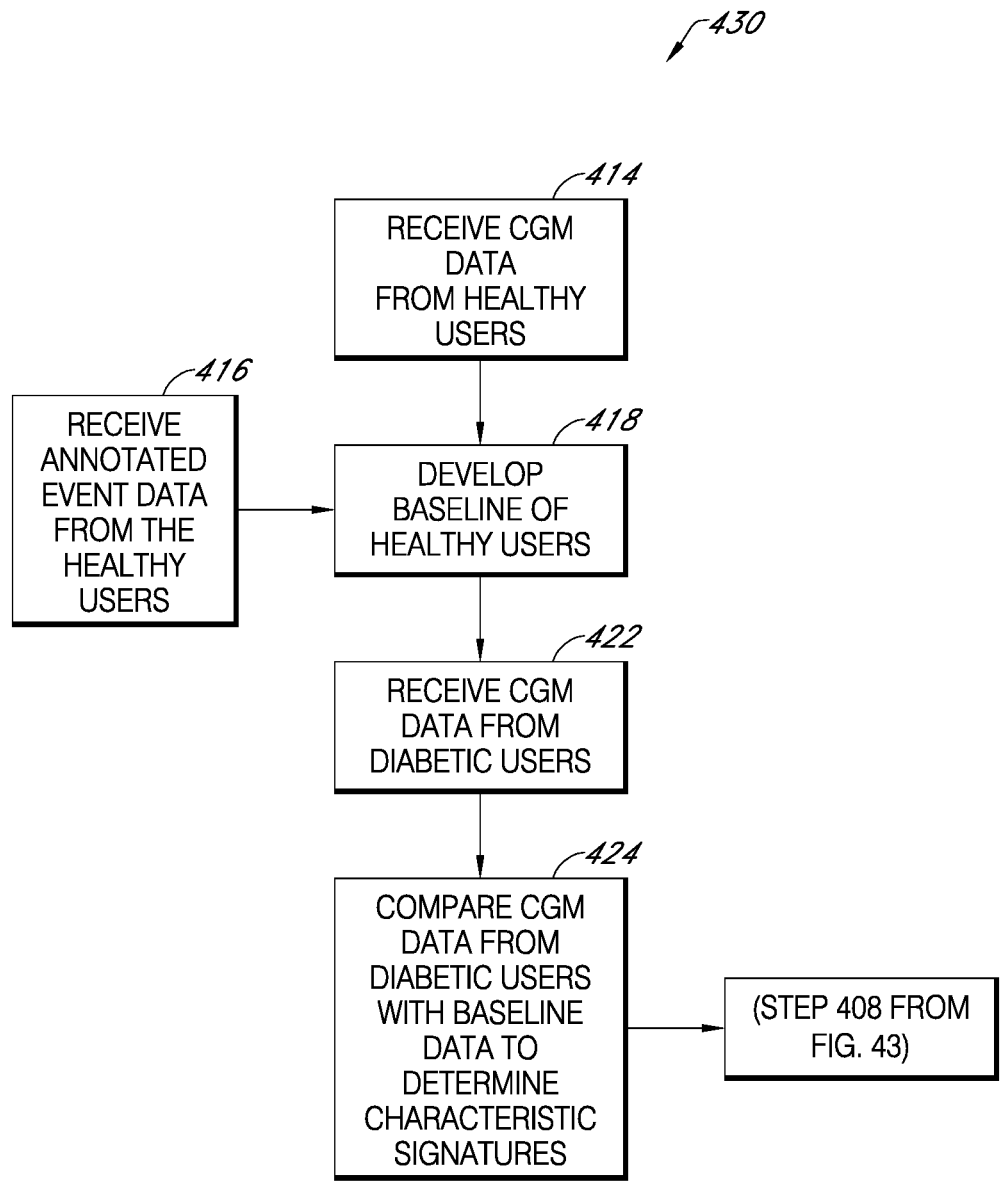
FIG. 44 is a flowchart illustrating an implementation of a method for determining a baseline and characteristic signatures for use in the method of FIG. 43.

In the development of a baseline for such determinations, and referring to the flowchart 430 of FIG. 44, a baseline is generally developed for what constitutes "healthy" or "normal". Such may also be termed a "no defect" model. For example, such data may be determined from users who are young, healthy, and physically active. Such users may wear a CGM and provide CGM data to a computing environment according to present principles (step 414). Such users may also be requested to annotate event data, e.g., events in their lifestyle, e.g., meals, physical activity, sleep, stressful events, and so on, and the same are similarly provided to the computing environment (step 416) so as to determine a set of characteristic healthy glucose trace signatures. In some cases the baseline data will also include other physiological data known about the patient, e.g., other analyte traces, e.g., insulin, glucagon, lactate, and so on. The measured indices from the healthy patients thus provide a baseline for the determination of characteristic signature data from diabetic patients (step 418).

CGM data (and other available data) may then be received from a diabetic user whose medicament regimen is to be determined (step 422). The CGM data is compared with that of the healthy user data. Specific differences may then be identified between an individual who is healthy and one with diabetes. In some implementations, access may be used to public domain human computational models (e.g., the Oral Minimal model) to tie the differences to underlying changes in the biology. If such a model is used, or if another model is used, the parameters of the model may be informed by various analyte measurements. In some cases, such measurements do not even require invasive techniques. For example, some may be based on skin conduction, saliva, and so on.

Systems and methods according to present principles identify on a computational and automatic basis defects or abnormalities by computational analysis of glucose traces, such analysis not being capable of being performed without computational aids.

For example, if the user's postprandial peak is calculated to occur at a later time than in the healthy individual, issues with glucagon may be numerically inferred, and the same may be calculated as being due to incretins not being released fast enough when the person is eating. In contrast, if the postprandial peak is higher but generally follows the same curve, then systems and methods may numerically infer that there is a problem with insulin secretion. Generally, such determinations are performed by numerically overlaying the CGM streamed data on event data as well as overlaying the same on other analyte data, e.g., data associated with C-peptides, insulin, glucagon, and so on.

In medicament determination, systems and methods according to present principles calculate using known drug effects (e.g., via a lookup table or other computational technique) what is necessary to make the user's curve look normal, i.e., what would be necessary to make the diabetic person's curve looked like a nondiabetic person's curve. In this way the systems and methods can automatically and computationally calculate a treatment recommendation. The systems and methods can further provide and display a reason for the recommendation. It should be noted that the calculated drug regimens thus provide a personalized drug regimen for the user, and one that is identified as being optimized and personalized. Generally the calculated drug will be effective for the user, with slight refinements possible related to dosing and perhaps combinations with other drugs or therapies. In this way, significant effort is saved over prior cases where HCPs "tested out" a therapy to determine if it had a reasonable effect on the patient, testing medications by trial and error, and so on.

As noted, the patient may be followed to determine if the patient's response was good, or if additional titration or optimization of the therapy is needed.

Systems and methods according to present principles may be iterative. For example, a first goal of the medicament regimen may be to cause the user's "wake up" or "awakening" glucose level to be lower than a current level. In this case, sulfonylurea may be prescribed. Such a prescription may generally itself lower A1C levels. Next, a user's postprandial peak may be addressed, e.g., using a GLP-1 type drug. Systems and methods according to present principles may rank defects or abnormalities in terms of dangerousness to the user, and automatically calculate drug treatments based on this priority. When a subsequent defect is addressed, the systems and methods may ensure that prior treated defects remain treated and are not caused to reappear given subsequent drug additions or titrations.

Other data may also be employed in the determination of a drug regimen, or indeed any therapy regimen, besides or in addition to CGM data, other analyte data, and so on. For example, such data may include the content and type of apps on the user's smart phone, which can indicate if the user is used to exercising or keeping track of meals. Other data may include what therapies have been tried in the past, and what was the user's adherence to those therapies. Monitoring and using such data may provide substantial predictive power to systems and methods according to present principles, and may indicate, e.g., what users are good candidates to address diabetic issues via exercise and meal control versus via drug regimens. For example, if the user has shown a good ability to control meals and exercise, behavioral therapies may be attempted before an immediate recourse to drug regimens. Other data may include, if available, insurance policy data, so as to determine what drugs are covered by the user's insurance.

In yet another implementation, but based on the description above that different types of HCPs generally perform best when provided with data tailored to them, an HCP login to an EMR system may cause presentation of a user interface that is tailored to a particular type of HCP (but which may also include a degree of user-configurability). In some implementations, a common database is accessed, but the data is transformed into a form using a data accessor or relator to transform the accessed data into a form best suited for the type of HCP as determined by their login data or metadata. For example, an endocrinologist may be provided with glucose trace data. A family care physician may be provided with summary CGM data, e.g., "history of overnight lows". A nurse may be provided with questions to ask the user, e.g., "are you eating before bed?", "can you fit some exercise into your schedule?", and so on.

A benefit of maintaining the common database access is that data is always available. In contrast, transformed data may cause a loss of data, and an attempt to re-transform such transformed data may fail. Thus, access to untouched (by the transformation) "raw data" is desirable, and such is accomplished using a common database scheme.

Figure 45:
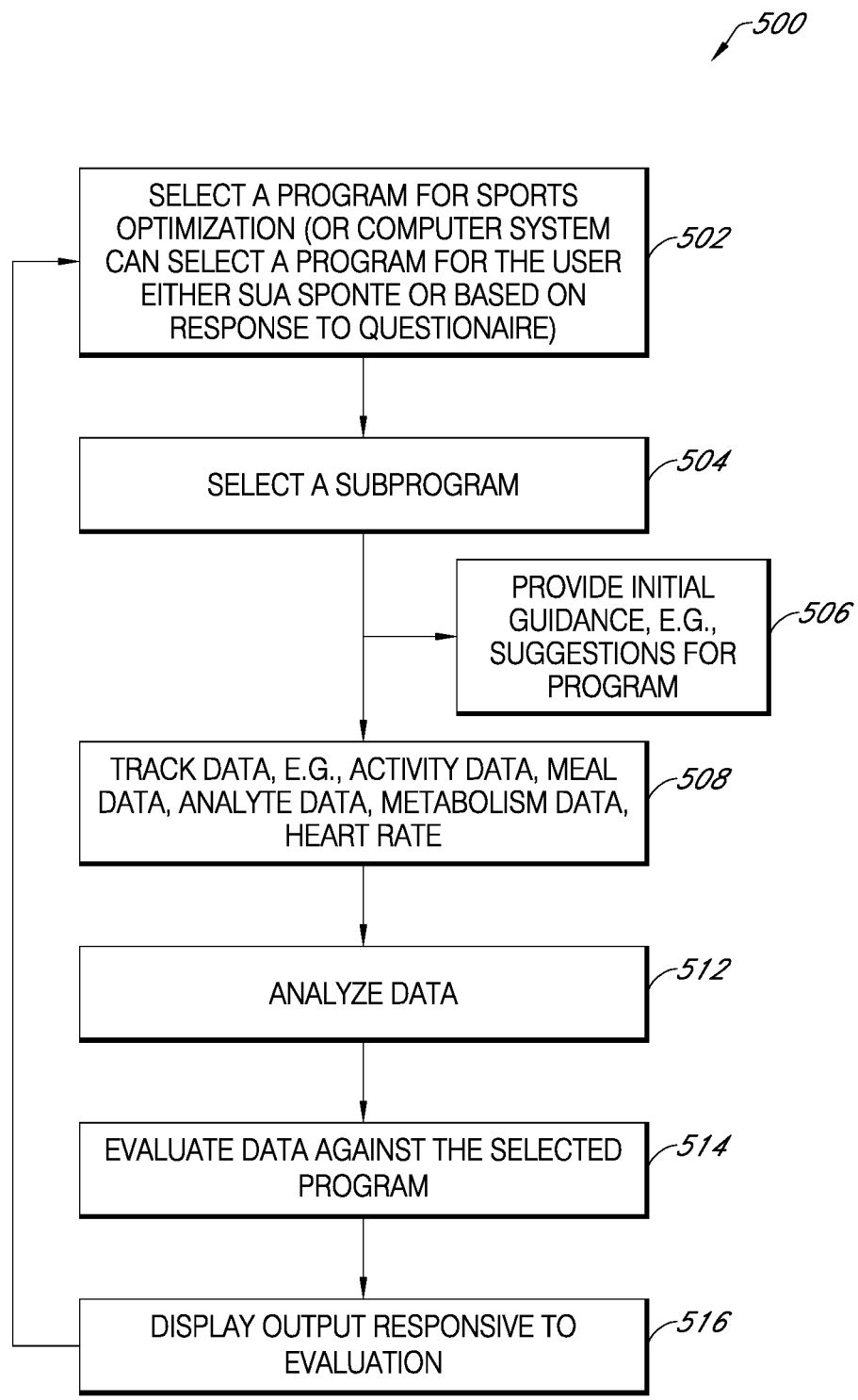
FIG. 45 is another more detailed flowchart indicating an application of the flowchart of FIG. 1, specific to determining optimal parameters for sports, health, or fitness.

FIG. 45 illustrates a flowchart 500 in which the flowchart of FIG. 1 is particularly applied in the area of sports optimization. In particular, it is noted that for athletes training and diet are intimately linked to performance. Tools that provide real-time feedback of physiological parameters may enable individualized optimization of exercise, maximizing the benefit to the athlete. For example, an elite endurance athlete can prevent energy depletion and poor performance by optimizing the type and volume of caloric intake. Additionally, athletes who adequately replenish their energy stores post-workout can avoid triggering adverse hormonal responses from their bodies. Such needs are generally individualized and are not capable of being understood without an appropriate computing environment to measure the individual's response to a sufficient number of performance impact variables. Continuous glucose monitoring in the context of the tools noted here can help guide and inform elite athletes on proper diet and caloric intake in response to different training programs and regimens.

In systems and methods according to present principles as applied to sports optimization, programs are provided to users such as athletes, and iterative use of the programs is intended to lead the user toward a desired goal, i.e., the determination of a fitness regimen in which the user's goal is most closely met, e.g., with regard to muscle building or repair, an optimized intensity level for cardiovascular health, optimized meal plans, optimized endurance, or the like. While glucose may often be measured in such endeavors, the same may in some implementations be replaced or combined with measurements of lactic acid, testosterone, cortisol, and so on.

As with prior flowcharts, a program is selected (step 502), as well as potentially a subprogram (step 504). Programs and subprograms may vary widely, but they may be generally configured to be implemented in a patterned or systematic way. In many cases, they may be associated with a goal, and the goal may be to cause a physiological quantity to achieve a certain level or to be situated within a certain band or envelope. For example, the desire may be to cause a heart rate to increase to a certain percentage of maximum, and to be maintained within a certain band of heart rates. As another example, the goal may be to cause a level of muscle building or repair to be situated within a certain band or envelope of values for a predetermined period of time. In some cases, a single threshold will provide suitable criteria, and it may be desired that a physiological quantity simply stay below or above the threshold. Exemplary physiological quantities include metabolic rate, heart rate, intensity level, and the like.

In some cases, such as with metabolic rate, analytes may be measured from which the quantity may be determined or derived. In other cases, analyte monitoring may be performed for other purposes. As particular examples of analytes which may be useful to monitor for sports optimization purposes, the following examples are provided: a combination of lactate and heart rate monitoring, a ratio R of $VCO_2/VO_2$, glycerol, ketones, a combination of glucose plus lactate, or a combination of glucose plus activity, where activity is shown, e.g., by GPS or accelerometer. Details and examples of the use of such measurements are provided below, as are additional details and examples of sensors to monitor the various analytes.

An optional step of providing initial guidance may be conducted (step 506), and the same may indicate suggestions to achieve success in the program, what "success" constitutes, or the like. Even if such is displayed as part of the program selection, the initial guidance may be employed to reiterate to the user what is expected, e.g., with regards to intensity level, heart rate, and so on.

Data may then be tracked (step 508). The tracked data may include, e.g., activity data (via accelerometer or GPS or other systems noted above), calorie data, meal data, analyte data such as glucose, lactate, or lactic acid, metabolism data, heart rate data, as well as other types of data, and combinations of the above. While certain types of metabolic and other analyte monitors including sensing systems are described in greater detail below, here it is noted that a lactate sensor may be advantageously employed in many implementations to monitor metabolism by calculating a rate of energy expenditure. Appropriate analysis of lactate data may further be employed to separate energy generated from lipid metabolism (fat) versus carbohydrate metabolism (glucose). Details of such distinctions are also described with respect to specific examples below.

A next step is that the data may be analyzed (step 512). In some implementations this step is optional, but the same may be performed to, e.g., perform analyses on the data so as to obtain related data, e.g., to analyze GPS data to determine "miles ran", and to analyze "miles ran" data to determine "calories burned" data, to analyze "calories burned" data to determine "fat burned" data, and so on.

The data is then evaluated against the selected program (step 514). For example, the data may indicate whether the intensity level desired to be achieved as a goal in the program was in fact met by the actual data recorded about intensity during the duration of the program. As another example, a program for sports optimization may desire that exercise be employed to help mediate and control the patient's glucose level, and the evaluation may include determining if the patient's glucose level was sufficiently controlled by the exercise program.

An output may then be displayed responsive to the evaluation (step 516). The outputs may be any of those noted above with respect to FIGS. 4-36, and it is reiterated that the same may be shown via a simple UI. For example, for sports optimization, the same may display one color if the user is maintaining a certain level of lactic acid, heart rate, hydration, or the like.

Figure 46:
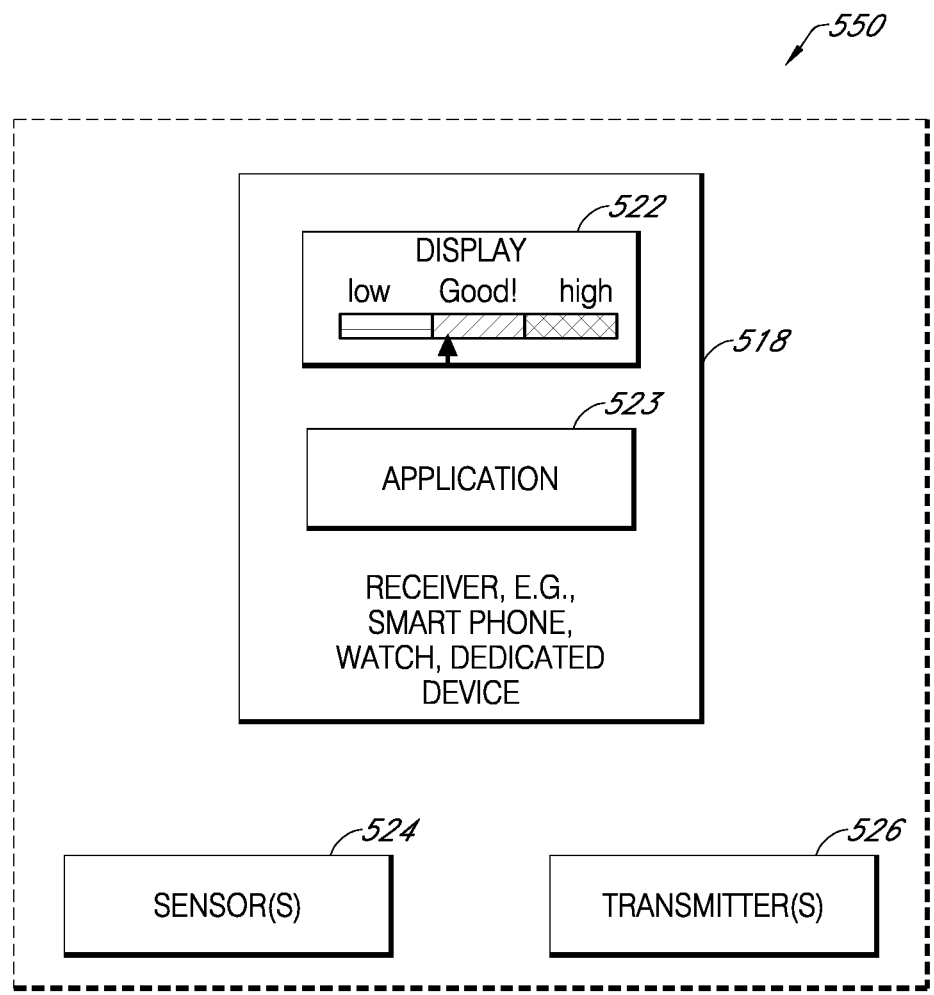
FIG. 46 is a schematic view of a device which may be employed for sports or weight loss optimization.

A system may be provided as illustrated in FIG. 46. In particular, FIG. 46 shows a system 550 in which a device 518 running an application 523 is coupled to a sensor 524 through a transmitter 526.

In one implementation, the sensor may include an optional applicator, a transmitter mount with an adhesive pad, and a sensor probe. The sensor may be inserted into the abdominal subcutaneous tissue using, e.g., a 26-gauge introducer needle encased in the applicator. The sensor probe may be a wire electrode that couples the enzyme glucose oxidase to an electrochemical sensor electrode. The sensor generates an electrical current proportional to the ambient analyte concentration in the interstitial fluid of the subcutaneous tissue surrounding the sensor. The sensor may be held in place by a housing that is adhered to the skin using a standard medical grade adhesive. In one implementation, the sports sensor communicates wirelessly to the sports receiver via the transmitter at a 2.4 GHz frequency.

The transmitter may send the measured electrical analyte signal wirelessly to the device 518 at intermittent intervals. The transmitter may be programmed with a specific identification serial number that is also programmed into the corresponding device in order to establish a secure wireless communication link between the two hardware components. The transmitter may be reusable and may be employed for repeated sessions by a single subject user, up to the lifetime of the battery encased in the device. The device 518 may be a mobile device including a tablet, a smart phone, smart watch, or in some cases a dedicated receiver. The device 518 may perform signal processing algorithms required to convert the sensor electrical signal to values that can be displayed to the user.

In use, the sensor 524 may employ the transmitter 526 to transmit data and other signals to the device 518. In some cases, the sensor 524 will be integral with the transmitter 526. Multiple sensors 524 may couple to multiple transmitters 526 for subsequent transmission, or one transmitter may service two or more sensors 524. The device 518 includes a display 522 in which a user interface provides information to a user, e.g., such as the UI 26 of the monitoring device 21 (see FIG. 2). The display 522 may be of an easy-to-understand design, and may incorporate zones, e.g., colored zones, indicating various values of the physiological quantity to be monitored, and an arrow pointing at the zone in which the parameter is currently situated. As above, such displays may be for intensity levels, lactate levels, heart rate, or the like. In some cases, the tachometer-type outputs of FIG. 15 and FIG. 16 may be of particular use in displaying this type of data. Other displayed outputs as have been described may also be employed.

In one implementation, the device 518 and in particular the application 523 may graphically display whether the user is in zone (which can be user-definable) in a simple graphical color display (green) as well as displaying a current value of the monitored analyte, e.g., glucose. The application 523 may cause the display of zones corresponding to "out-of-zone low" (red) or "out-of-zone high" (yellow or orange). Further information may be created by post-workout retrospective analysis of data with potential further pattern recognition systems. The post-usage analysis may allow for further user-driven refinements of the displayed zones.

Other variations of systems for sports optimization will also be understood given this teaching.

Figure 47:
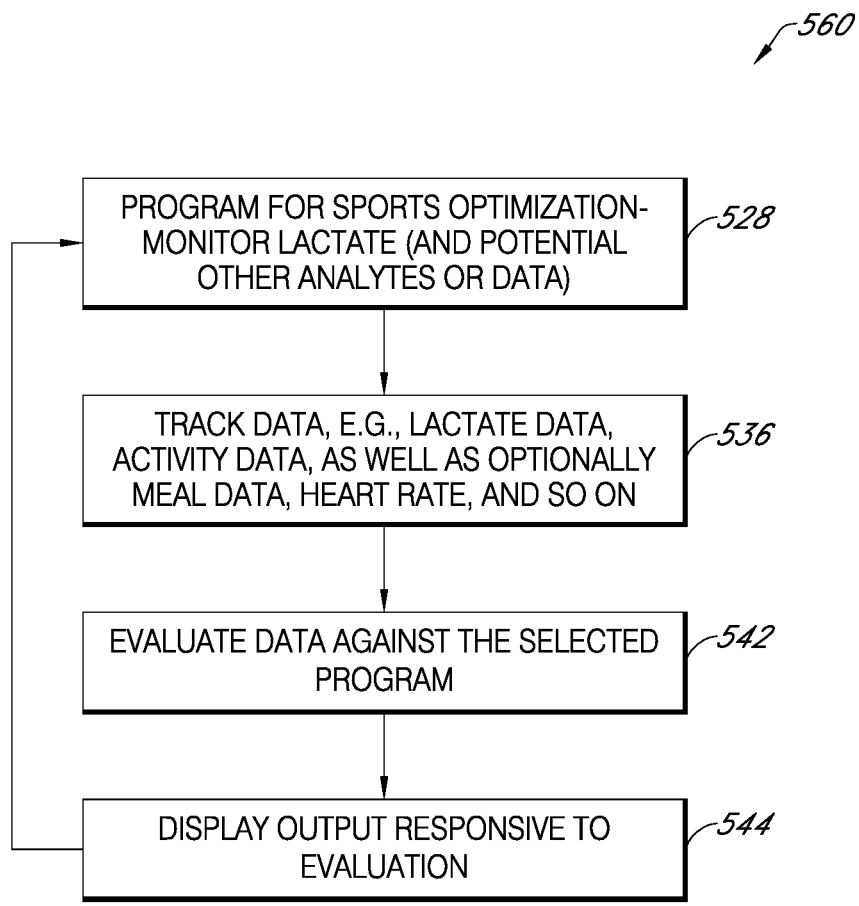
FIG. 47 is another more detailed flowchart related to sports optimization, and in particular for the monitoring of lactate or other analytes.

FIG. 47 is a flowchart 560 illustrating an exemplary implementation of sports optimization. In this implementation, lactate (as well as potential other analytes) is monitored as an indicator of a "body tachometer". Other data may be monitored as well, including activity data so as to determine an intensity level, as well as heart rate data, and so on. In this implementation, comparing heart rate data to lactate data is used as an indicator of fitness level.

In particular, lactate is a byproduct of glucose consumption and becomes elevated during high intensity exercise. A high lactate level indicates pending exhaustion and loss of energy. Athletes often use lactate levels to optimize training, but their use is limited because they require blood draws and analysis equipment. Heart rate monitors have been used as a surrogate for lactate, but the same are indirect. In contrast, lactate is a direct measure of the body's exercise capacity, and in some definitions, a user's fitness level is directly related to a combination of their energy expenditure and their lactate threshold.

Figure 48:
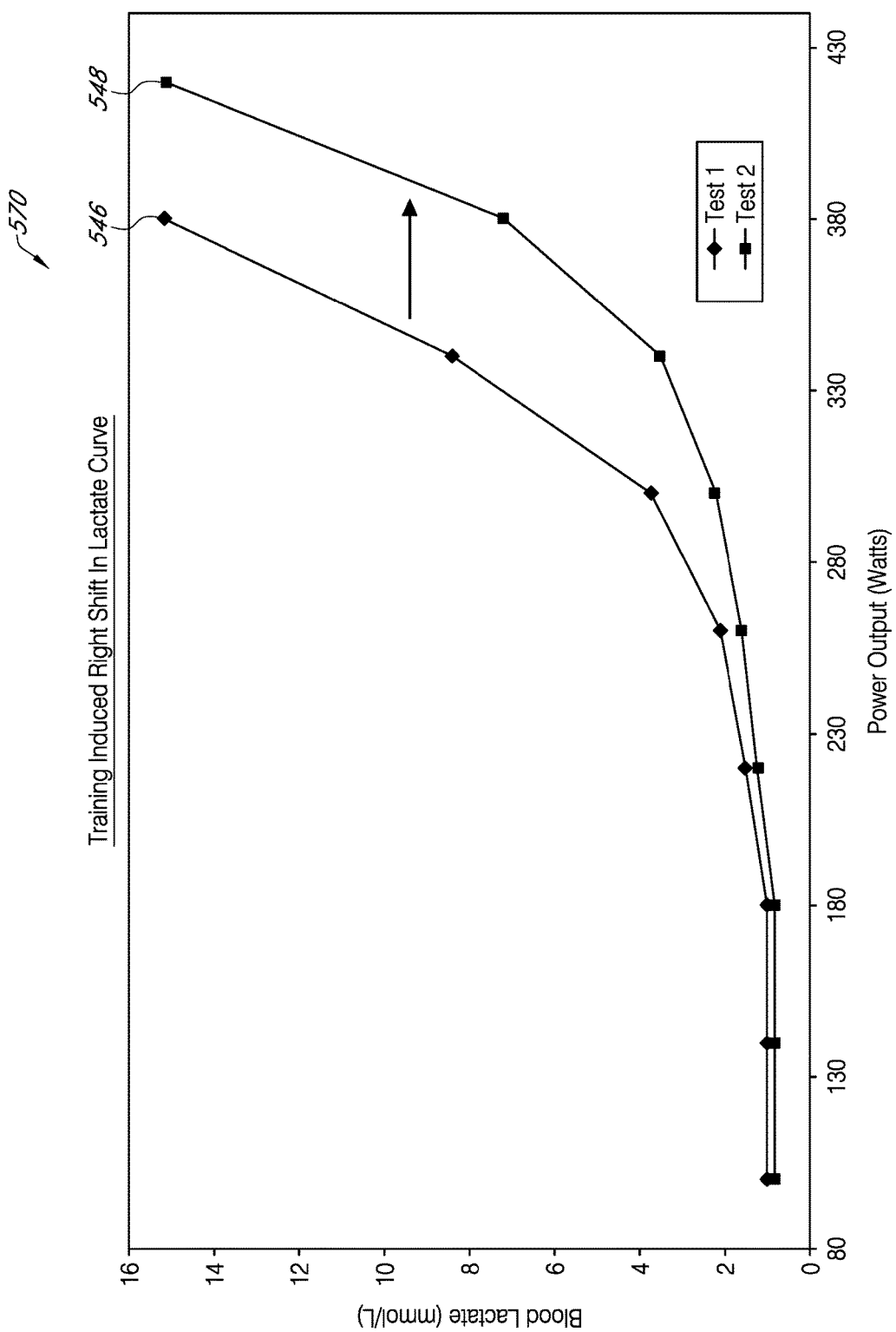
FIG. 48 is a graph showing a training-induced right shift in lactate levels.

Put another way, and referring to the graph 570 of FIG. 48, a user's lactate threshold is a direct indicator of their level of fitness. The data set 546 indicates a lactate curve prior to a training regimen, and the data set 548 indicates a lactate curve subsequent to a training regimen. As can be seen, the more fit a user is, the higher the workout intensity must be before reaching the lactate threshold. In low intensity workouts, lactate levels generally stay stable, while in high-intensity ones, lactate builds up, causing fatigue. Peak performance is achieved when the user stays at but below this lactate threshold.

Figure 49:
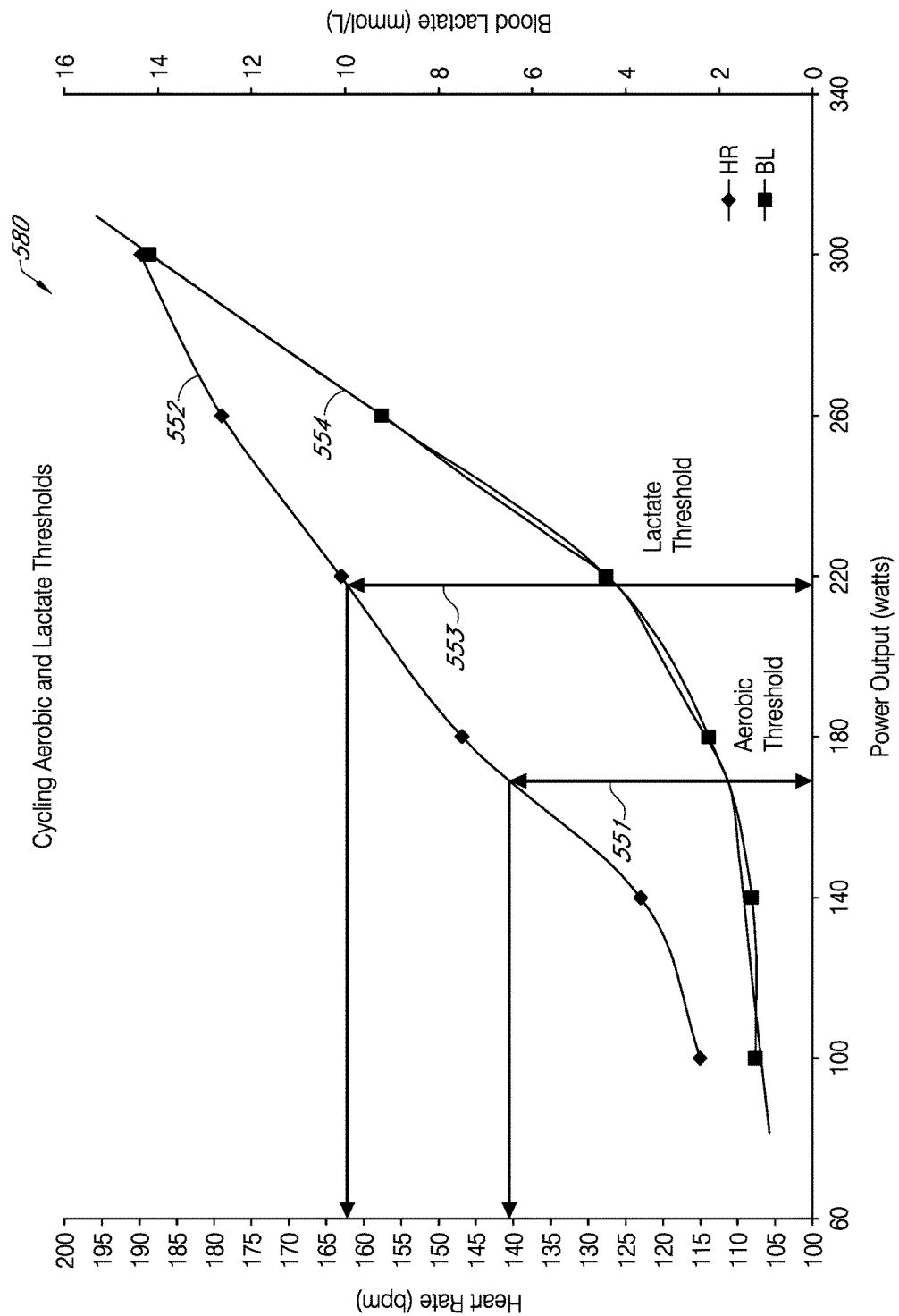
FIG. 49 illustrates aerobic and lactate thresholds.

Referring next to the graph 580 of FIG. 49, data sets are shown for a cycling user. The data set 552 corresponds to heart rate, quantified on the left vertical axis, and data set 554 corresponds to a blood lactate level, quantified on the right vertical axis. The aerobic threshold 551 is indicated, as well as the lactate threshold 553. As noted, peak performance is achieved when the user stays at but below the lactate threshold.

Consequently, and returning to FIG. 47, a program (step 528) may include an attempt to perform exercise in such a way that the user's lactate level is a certain percentage, e.g., 80-98%, of their lactate threshold level. Data may then be tracked, particularly lactate data, and optionally other data such as activity data, meal data, heart rate data, and so on (step 536). The tracked data may then be evaluated against the selected program. For example, the data may be evaluated to determine if the lactate level reached the desired percentage. An output may then be displayed responsive to the evaluation (step 544). And the displayed output may correspond to any of the outputs discussed above in connection with FIGS. 4-36.

Figure 50:
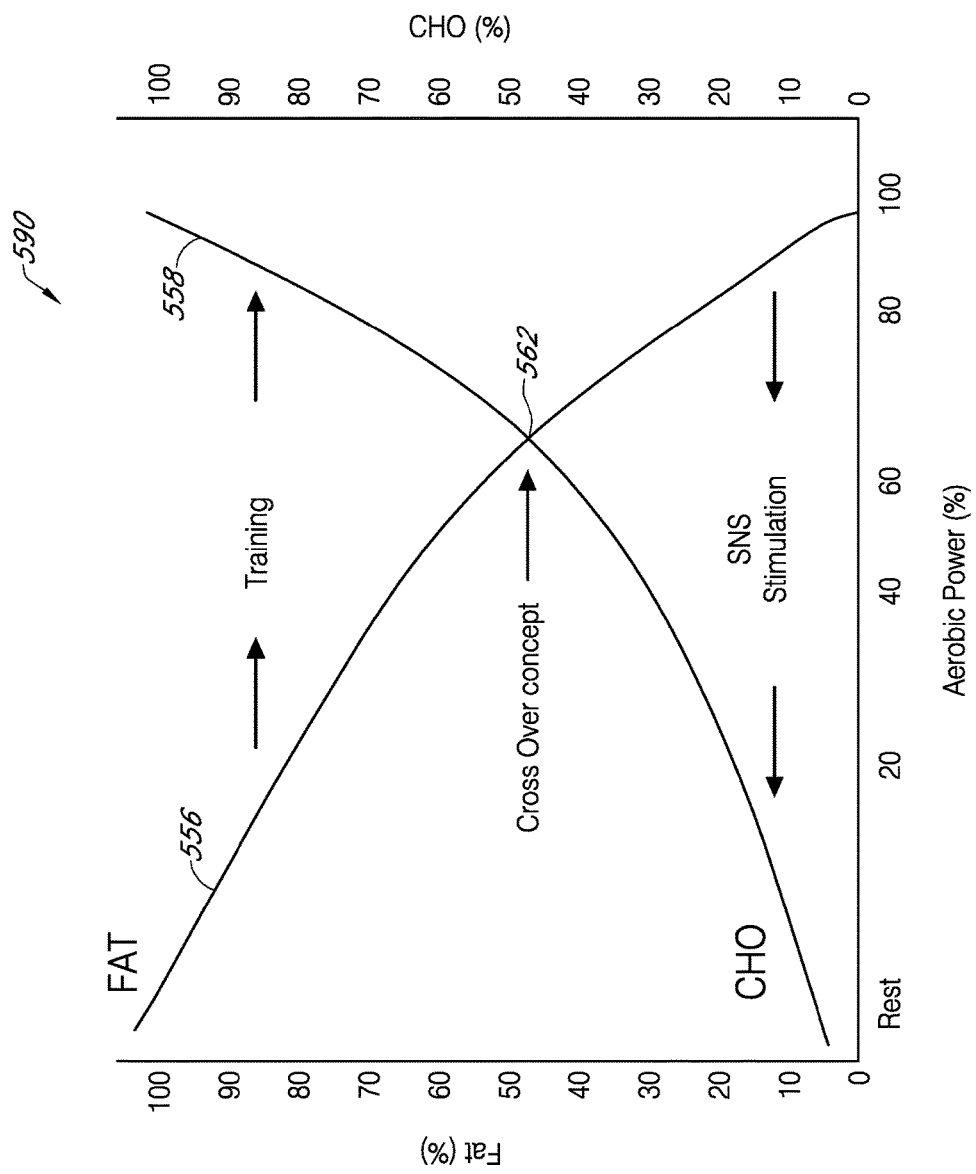
FIG. 50 illustrates a crossover in fat and carbohydrate consumption as a function of aerobic power.

FIG. 50 illustrates another implementation of applications of lactate monitoring. In particular, and which is described in greater detail below with reference to FIG. 51-53, monitoring lactate may be employed to detect regimes in which fat burning may be optimized. In particular, lactate inhibits the breakdown of fat, but an initial rise of lactate levels indicates an intensity known to maximize fat burn (fat is burned at lower intensity exercise (see curve 556), while carbohydrates are burned at higher intensity exercise (see curve 558)). Thus, referring to FIG. 50, the crossover point 562, where the lactate level 558 is seen to significantly rise, may be employed to detect the level at which fat burn is maximized.

In another more general example, and referring again to FIG. 47, a type II diabetic user may desire to optimize their fitness routine but with an eye toward helping control glucose levels as well. In this case, a program may be initiated (step 528) that is a combination of exercise routines, food data, activity data, and at least two monitored analytes including lactate and glucose.

Data may then be tracked (step 536), e.g., with lactate and glucose data being monitored by one or two sensors, meal data tracked by user entry, and activity data tracked by the user's smart phone accelerometer. The tracked data may then be evaluated against the selected program (step 542), and an output displayed responsive to the evaluation (step 544).

If multiple variables are changing, the evaluation may result in ambiguities. In some cases, the computing environment may perform a step of disambiguation by asking the user to maintain one or more variables constant. For example, if it is not known whether an intense exercise workout or a lack of food led to a hypoglycemic event, the user may be prompted to perform similar actions but to include a larger meal or a milder workout. Other variations will be understood given this disclosure.

Exercise Optimization Example

For sports or exercise optimization, whether for diabetics or non-diabetics, exemplary inputs may include those from a lactate sensor, a movement/motion sensor such as an accelerometer or GPS device, and optionally a glucose sensor. Other data may also be entered, including weight, age, and the like. The lactate and glucose sensors may be indwelling sensors as described elsewhere, the accelerometer may be part of a mobile device such as a smart phone, smart watch, or may form part of a wearable analyte sensor, GPS may be provided from a smart phone or smart watch, and other data may be entered manually, retrieved from a profile, or via other similar sensors. If the user is a CGM user already, e.g., is a diabetic using CGM, the same CGM may be employed for exercise optimization. Otherwise, the user can be fitted with a new CGM, or may use other glucose sensing techniques. The accelerometer or motion detector could be incorporated into the body-worn sensor or be part of a separate sensor such as a smart watch, a smart phone, or other sensing device. The devices may be connected wirelessly. A user may also use heart rate as a surrogate for lactate level. However, once a certain level of stamina has been reached, a recalibration of heart rate versus lactate level generally is required.

The lactate sensor may be calibrated using the glucose sensor in the manner described below, or using other calibration techniques described. For example, one or more of the lactate sensor calibration parameters may be keyed to one or more of those of the glucose sensor.

If the user has previously determined a lactate curve with respect to energy expenditure, the same may be used to compare a current level of energy expenditure by the user, and the user may tune their workout to stay in a desired range. For example, a program may be started where a user is instructed to reach a certain heart rate or achieve a certain lactate value. After following the program, results can be evaluated and the program can be modified to iteratively move the user closer to the desired goal.

Other Exercise Optimization Examples

Examples are provided above for exercise and sports optimization, such that a user may be enabled to stay in a preferred "zone" of athletic performance without deleteriously reaching a lactate threshold. Indeed, users may be enabled to stay in any particular zone so given information provided by the system, and in particular a lactate sensor. Use of the lactate sensor may be in combination with that of the glucose sensor, particularly where users such as diabetics or prediabetics are using continuous glucose monitoring. As noted, non-diabetics will also benefit from such techniques for exercise optimization. As will be described, the glucose sensor can be advantageously employed to calibrate the lactate sensor, which would otherwise be uncalibrated or would be difficult to calibrate.

Other sensors may be employed for exercise or sports optimization, besides lactate sensors. For example, testosterone and cortisol may be measured for stress monitoring, determination of fatigue syndrome, and the like. Other exemplary analytes may include epinephrine and norepinephrine.

Examples of sensors for the monitoring of stress, both physical stress as may be encountered by high-intensity athletes, as well as emotional stress, are described below. Such sensors include those that measure stress hormones such as testosterone and cortisol. In many cases such sensors are electrochemical, and may be either invasive or noninvasive. For example, noninvasive sensors include those that may be strapped on the body.

By monitoring such stress hormones along with other data, e.g., motion or accelerometer data, stress may be linked with physical activity or other markers. In this way, users can figure out common stress triggers, and determine ways to avoid stress by avoiding the stressors or performing acts to counteract such determined triggers.

Pertinent "other data" noted above may include other analyte levels if the same are being monitored. In this way, stress may be correlated with certain chemicals in the body. Where a user is taking medications or other drugs, such drug intake may also serve as an input, and the system may determine the effect of the same, or at least a correlation, with stress.

Other data which may be correlated include meal data, which may be entered using hash tags or any of the other techniques noted above or in the applications incorporated by reference. After the system has learned stress responses of the user, the user may be able to indicate that they are eating a particular meal or performing a particular activity, and the system can determine what the likely response will be.

In a particular example, a program may be started in which a user attempts to control their stress hormones to a desired goal level, either in general or with respect to an upcoming event. After following the program, results can be evaluated and the program can be modified to iteratively move the user closer to the desired goal. In this way, a user can more easily and effectively learn how to modify their stress behavior based on their unique physiology and lifestyle patterns, to improve their health, without the complexities and costs associated with a clinical professional. Such needs are generally individualized and are not capable of being understood without an appropriate computing environment to measure the individual's response to a sufficient number of performance impact variables.

Figure 51:
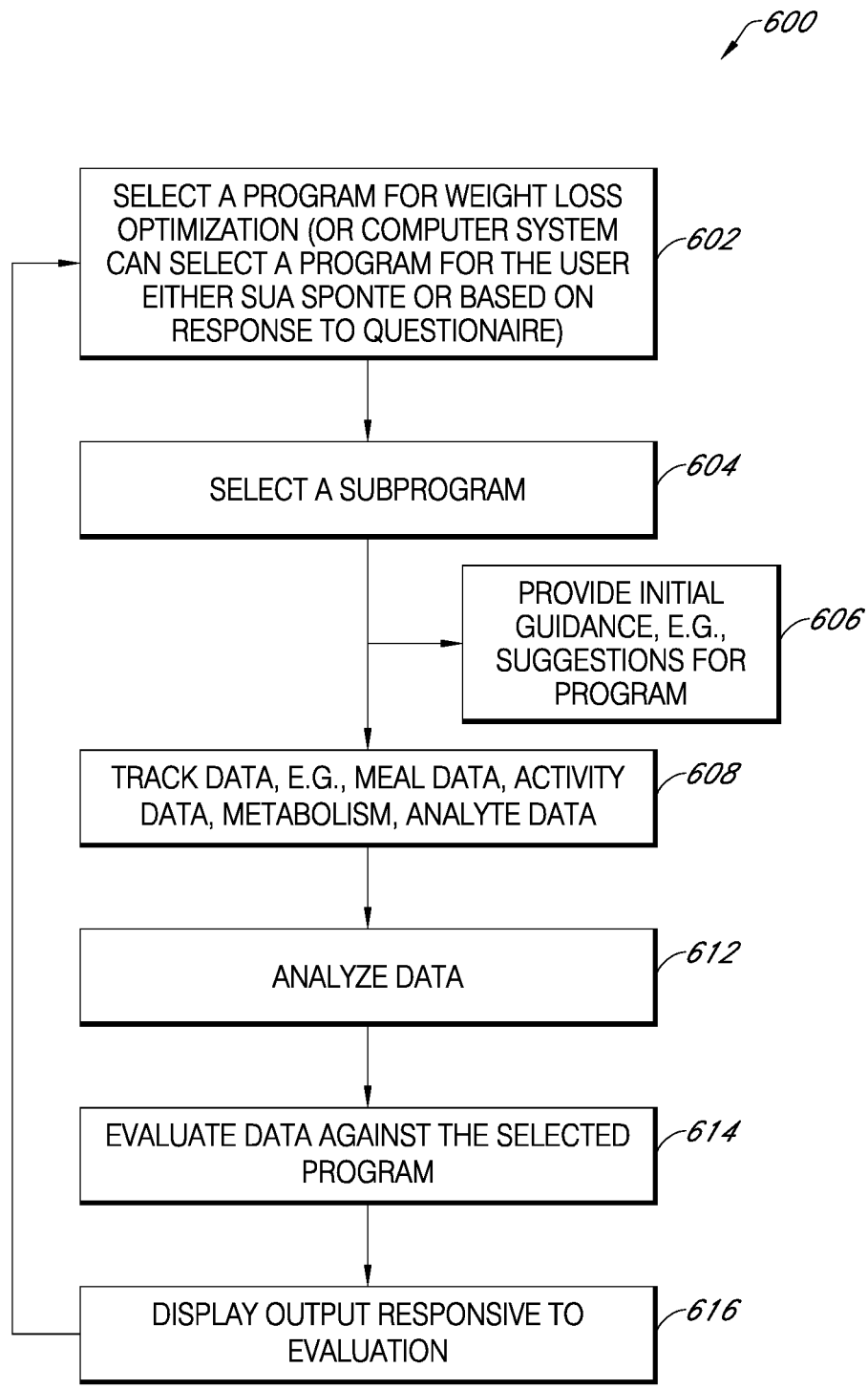
FIG. 51 is another more detailed flowchart indicating an application of the flowchart of FIG. 1, specific to determining optimal parameters for weight loss.

Referring to the flowchart 600 of FIG. 51, another implementation of present principles, e.g., of an application of the flowchart of FIG. 1, is for systems and methods for weight loss optimization. While specific examples are given below, here it is noted that similar steps may be followed as noted in prior flowcharts. A program may be selected for weight loss optimization (step 602), and in some cases a subprogram as well (step 604). Initial guidance may be provided (step 606), such including, e.g., advice on starting the program, potential recipes or a cookbook as noted above with respect to element 44 of FIG. 3, or the like.

Data may then be tracked (step 608). Similar data may be tracked as noted with respect to FIG. 45, however, variations will be seen and certain data given more or less priority. Exemplary data useful in weight loss optimization may include meal data, activity data (e.g., via a smart phone accelerometer), weight data, metabolism data, lactate data (e.g., to calculate a rate of energy expenditure and to differentiate energy generated from lipid (fat) metabolism versus carbohydrate (glucose) metabolism), heart rate data, glucose data, and combinations of the above.

Data may be analyzed (step 612) for various purposes. For example, meal data may be analyzed to obtain calorie data. Pictorial food data may be analyzed to determine an identification of the foods pictured therein. Meal data may further be analyzed to determine glycemic index or other related parameters. Activity data measured by an accelerometer and lactate data measured by a lactate sensor may be combined to calculate the rate of energy expenditure, and this combination may be considered a portion of the analyze data step. Other variations will also be understood of the analyze data step 612.

Data may then be evaluated against the selected program (step 614). For example, data may be evaluated to determine if the program provides an optimized intensity level for fat burn, and if not, an iteration may occur to select a new program that moves the user toward an optimized intensity level for fat burn. Other types of evaluations will also be understood and are described in greater detail below with respect to specific examples.

An output may then be displayed responsive to the evaluation (step 616). The output may be in the forms noted above with respect to FIGS. 4-36, and as noted can be limited in their complexity so as to be easily understood by users. For example, textual indications may be used to provide easily understood instructions to users. As a specific example, if a user's weight increases, but without accompanying significant glucose spikes, a textual recommendation may be displayed to the user to, e.g., lower their fat intake. Other textual recommendations may include, e.g., "You are keeping good control of your glucose; now let's see if you can do the same within the context of a lower fat diet. Here's something to try: X, Y, and Z." where X, Y, and Z are entries or recipes in the cookbook.

One type of sensor of particular use in weight loss optimization schemes according to FIG. 51 include those that measure and report fat metabolism rates. In particular, weight loss optimization, as well as the sports optimization noted above, benefit from knowledge of calorie burn rates, and in particular where such knowledge is specified to the kind of calories being consumed. The weight loss optimization routines of present principles use such knowledge and help users optimize workout regimens and achieve their weight loss goals.

In more detail, the body uses different sources of energy depending on physical exertion, fitness level, rate of energy expenditure, and the body's physical characteristics. During low-to-medium rates of exertion, the body primarily uses fat reserves to supply the needed energy. During more strenuous exercise, the body shifts the energy consumption from fat to carbohydrate metabolism, as noted above with respect to FIG. 50. Optimizing the rate of exertion during exercise shifts the source of energy consumption from carbohydrates to fat, making workouts more effective at eliminating fat, and thus optimizing weight loss. Additionally, where optimizing workouts includes the use of body-worn sensors as noted above with respect to FIG. 46, users may be further motivated by the displayed outputs to modify behavior to continue training regimens and achieve their goals. Thus, use of the sensors described in greater detail below may be advantageously employed to this end.

Figure 52:
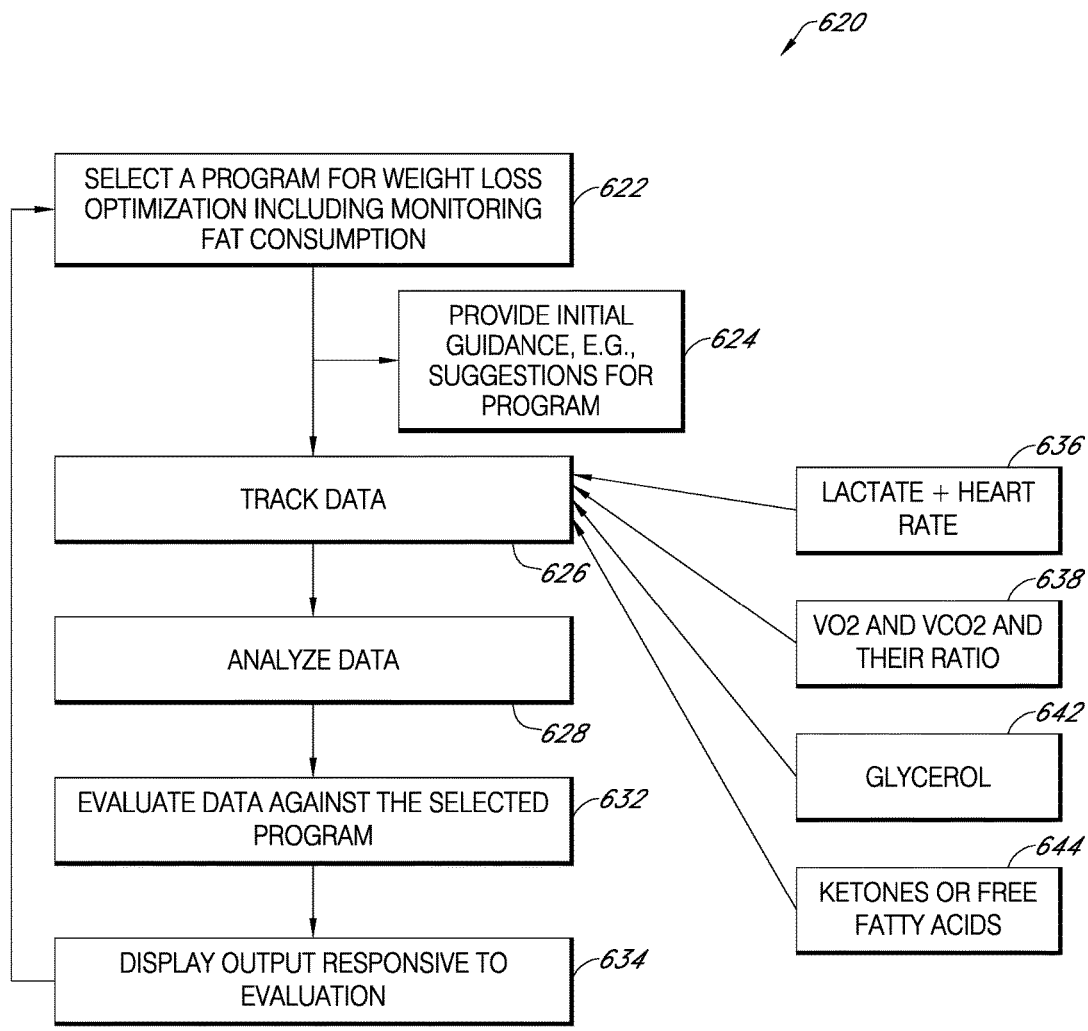
FIG. 52 illustrates a more detailed flowchart corresponding to the flowchart of FIG. 51, in particular showing exemplary types of data which may be tracked.

In applying FIG. 51 to the cause of monitoring and optimizing fat consumption, a program may be selected as indicated in FIG. 52 (step 622), where in particular the selected program is related to fat consumption. Initial guidance may be provided, e.g., specific guidance for exercise and nutrition choices (step 624).

Data may then be tracked (step 626). In one implementation, lactate level and heart rate are tracked (step 636). In particular, heart rate can be employed as a secondary measure of power output and energy expenditure. Computing environments according to present principles can then calculate calorie output by measuring heart rate and incorporating other data such as body weight. As heart rate increases, more calories are consumed. Additionally, there is an observed correlation between blood lactate levels and the crossover from fat metabolism to carbohydrate metabolism. As lactate levels increase, more carbohydrates are consumed, and less fat. It is believed that lactate can counter regulate fat consumption, making it an indicator of the shift to carbohydrate metabolism. Thus, by taking into account heart rate and lactate levels, lipid (fat) burn rates can be calculated and optimized.

In another implementation, VO2 and VCO2 parameters and their ratio can be determined and employed in fat burn optimization (step 638). In particular, the ratio of VCO2 and VO2 (VCO2/VO2 is often referred to as the respiratory exchange ratio, "RER", or just "R") is different between fat metabolism and carbohydrate metabolism. In particular, R is substantially 1.0 for carbohydrate metabolism or glucose metabolism, and R is substantially 0.70 for fat metabolism. The parameters are generally calculated by measuring the concentration of oxygen and carbon dioxide that is inhaled and exhaled, but the same can also be measured by a blood gas analyzer or within tissue using a subcutaneous sensor.

In yet another implementation, glycerol can be employed in fat burn optimization (step 642). In particular, glycerol is a byproduct of lipid metabolism. Direct measurement of blood or subcutaneous glycerol may thus constitute an indirect method of measuring fat metabolism. Such measurements may be by way of electrochemical detection systems using glycerol oxidase, and multi-enzyme cascades.

In yet another implementation, ketones or free fatty acids can be measured as an alternative type of data for measuring metabolism (step 644), particularly as surrogates of fat burning. Ketones are an efficient source of fuel and energy for the human body, and are produced by the liver from fatty acids, which result from the breakdown of body fat in response to the absence of glucose/sugar. Electrochemical detection of ketones can be made via enzymes, e.g., 3-hydroxybuturate dehydrogenase, NADP dependent alcohol aldehyde/ketone oxidoreductase, or NADPH alcohol dehydrogenase.

Using steps 636, 638, 642, and/or 644, data about rates of fat metabolism can be calculated and employed. In doing so, the data may be analyzed (step 628), and the data may be evaluated against the selected program (step 632). In particular, the data may be analyzed to determine if the measured fat consumption rate is that desired by the user, or as set as a goal in the program. An output may be displayed (step 644), such being of the forms noted above with respect to FIGS. 4-36. For example, a tachometer type diagram may indicate a range of fat burning or consumption, as may the use of colored ranges with a bar or needle indicator.

Figure 53:
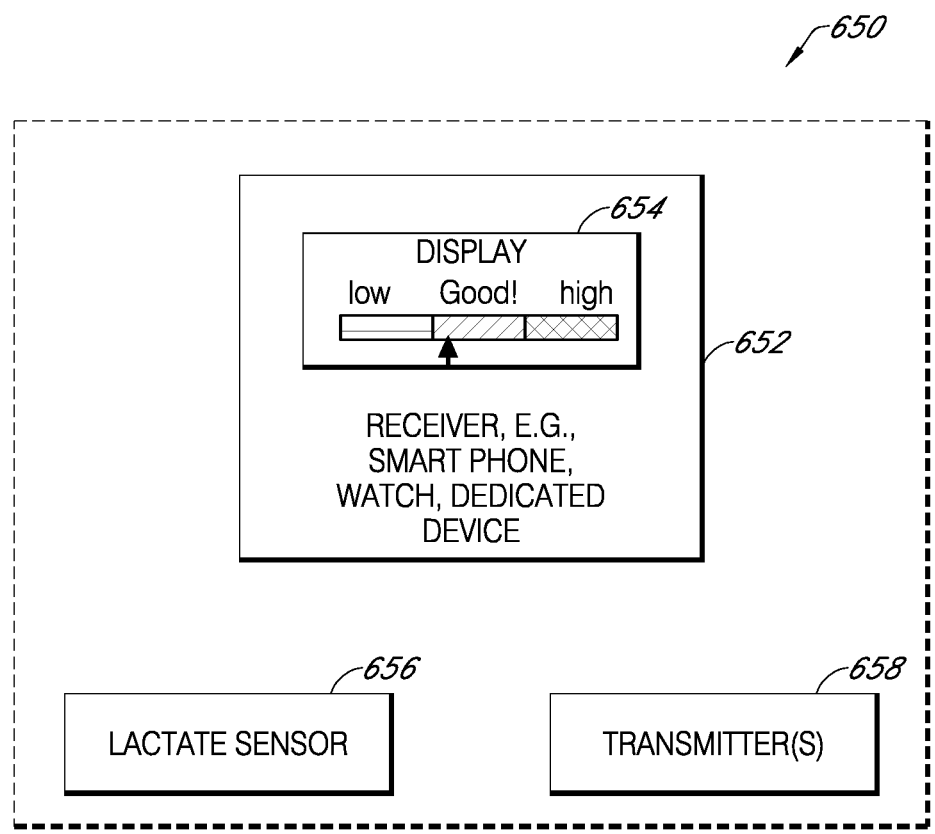
FIG. 53 is a schematic view of a device which may be employed for sports or weight loss optimization, the device including a lactate sensor.

A system may be provided as illustrated in FIG. 53, which is similar to the system illustrated in FIG. 46. In particular, FIG. 53 shows a system 650 in which a device 652 is coupled to a lactate sensor 656 through a transmitter 658. The device 652 may be any of the types of devices noted above with respect to device 518, and the transmitter 658 may perform functions and be otherwise similar to the transmitter 526.

In the use of this system, it is reiterated that users generally wish to maximize weight loss with the least amount of effort. Moreover, low intensity exercise tends to be associated with fat consumption, while moderate-to-high intensity exercise is related to carbohydrate consumption (as energy source). Accordingly, to optimize weight loss it may be desired to display to a user, or to educate a user about, when they are in a preferred fat consumption zone. Optimizing an individual's rate of fat consumption will result in a faster rate of weight loss with less effort from the individual.

The metabolic crossover from fat to carbohydrate consumption is specific to individuals and also to the type of exercise being performed. The optimal exercise intensity for fat burn of an individual who has poor cardiovascular conditioning may be quite low, e.g., 20 to 40% of maximum intensity, while a physically-fit individual may find the optimal intensity for maximum fat burn to be significantly higher, e.g., 60 to 80% of maximum intensity. In addition, rates of fat (lipid) metabolism are also highly specific to the type of exercise. Activities which utilize more diverse muscle groups, e.g., walking or running, are believed to burn fat at a higher rate than activities such as cycling which use more focused muscle groups. Rates of fat metabolism are therefore highly individual and can be influenced by their exercise intensity and type of exercise, such being related to the "exercise sensitivity" noted above.

Thus, the system 650 provides a device that can monitor an individual's metabolic status during exercise and can notify a user of an optimal intensity range of exercise so as to optimize fat loss or cardiovascular training. The device can provide information on the form of energy expenditure, and may be employed as a behavior modification device to help individuals optimize their daily exercise routines. An accelerometer within the device 652 can be employed along with a lactate sensor 656 to calculate a rate of energy expenditure and can differentiate energy that is generated from lipid (fat) metabolism versus that generated from carbohydrate (glucose) metabolism. The accelerometer can be employed to measure caloric burn rate and total caloric consumption for exercises including walking, running, climbing stairs, and so on. Optionally, heart rate monitors may also be employed, and combining information from a heart rate monitor with a lactate sensor can be used for advanced users to improve accuracy or for exercises that cannot be accurately measured using accelerometers, e.g., cycling, rowing, cross-country skiing, or the like.

In use of the device 650 in the method of FIG. 52, a user may select a program calling for a certain metabolic rate to be achieved during exercise (step 622). Initial guidance may be provided (step 624), the initial guidance cautioning the user, e.g., to heed displays, alerts, and warnings from the device regarding optimal intensity workouts. For example, the user may be instructed to work out at an intensity such that the crossover from fat-to-carbohydrate consumption is not reached. Data may be tracked (step 626), this data generally corresponding to metabolic rate but specified to the type of energy being consumed to perform the exercise. Data may be analyzed if necessary (step 628), and the data evaluated (step 632) against the program selected in step 622. For example, the metabolic data may be evaluated against the goal metabolic rate. The display may be output (step 634), generally corresponding to success or failure of the user reaching the goal. For example, during use of the device 650, the displayed output may correspond to whether the user is in a fat-burning range or not.

Besides the above-noted weight loss optimization routines, other examples will also be understood. For example, one such system and method according to present principles may evaluate glucose with respect to weight as measured by a scale, so as to be used to calculate dietary or exercise modifications. Analyzed data may include glucose data from a CGM and weight data from a scale, and the glucose measurement may use any of a number of calibration routines. Evaluation may include evaluating the glucose trace with respect to the weight. In this case the displayed output may include a modified diet plan.

Another example is that glycemic index, or glycemic impact as noted above, may be evaluated with respect to weight. In this way, glycemic index or impact behavior may be paired with weight as measured by a scale. Generally the same should correlate, i.e., their variability should be limited, and their correlation as displayed as an output may indicate to the user that glycemic index/impact is important in weight loss optimization.

Specific examples for optimizing weight loss are described below. Generally inputs to such systems will involve one or more selected from: weight measured by a scale, lactate levels, activity levels, glucose levels, ketone levels, triglyceride levels, glycerol levels, caloric intake, activity level, including activity level over time, and so on. Data received may be processed and determine to either meet requirements of a program or not, e.g., meet a threshold criteria, or not. Outputs may span from the most basic, e.g., a numerical value relating to an analyte being measured, to more significant and/or informative outputs, giving the user a level of insight, e.g., a zone indicator (green, yellow, or red), to actionable outputs informing a user of specific steps to take. Even if the output is just a numerical value, the same can indicate, e.g., rate of fat or calorie burn, rate of carbohydrate burn, percentage or ratio of fat versus calorie burn, or the like.

As with exercise optimization, outputs may be displayed via a simple UI. For example, for metabolic monitoring, the same may display one color if the user is burning more calories than they are consuming, and a different color if the opposite is true.

Weight Loss Optimization Example 1

In one example, which as for other examples may be applied to non-diabetics as well as diabetics, a user may be instructed how to optimize fat reduction through exercise. In this example, weight loss optimization is performed using lactate and accelerometer measurements.

In more detail, many people exercise to lose weight and specifically to lose fat; however, most want to achieve a maximal fat loss with the least amount of effort. A particular use case is a user who has only a half hour to exercise, and who desires to optimize that exercise. Optimizing the type of exercise, the intensity, and the duration, can burn fat more rapidly and more efficiently.

As noted above with respect to exercise optimization, exercise builds up lactate, and at some point as the user increases the intensity of exertion, the body transitions from burning fat to burning carbohydrates. For weight loss optimization, it is thus desired to exercise at a level below this crossover point.

Exemplary inputs will include those from a lactate sensor and an accelerometer. Each of these may have surrogates. For example, the lactate sensor may be replaced with a heart rate sensor, if an appropriate correlation is known. Where a lactate sensor is used, the same may be transcutaneous as with the continuous glucose monitors described here, or the same may be more noninvasive, e.g., using a patch for sweat detection, or optical sensors, e.g., those operating in the near IR. Where the lactate sensor is transcutaneous, it may be similar in structure to those described here, but where glucose oxidase is replaced with lactate oxidase. Where heart rate is used as a surrogate for lactate, the correlation could be incorporated into the algorithm, or alternatively heart rate could be used directly. In the same way, accelerometer data may be replaced with GPS data, particularly where the user exercises by running, hiking, walking, biking, or the like. The accelerometer or other such motion detector may be incorporated into a body-worn sensor or may be part of a separate sensor such as a smart phone, smart watch, or other sensing device. The devices may be connected wirelessly or via wired techniques.

Alternatively, the system may use a glucose sensor as a secondary electrode from which to calibrate, using techniques described below. In some cases, particularly for diabetics employing "finger sticks", a finger stick may be employed to calibrate a glucose sensor, and from that one may determine a lactate sensor calibration. As noted below, various ways of performing factory calibration may also be employed, negating the need for a user to take separate calibration actions.

The lactate signal and accelerometer (or other energy expenditure signal) may be displayed directly on a user interface as a value or as a value and trend. In a more sophisticated implementation, the information may be employed to calculate metrics that are easier for the user to understand. In one case, energy expenditure information may be employed to inform a user as to how many calories are being burned, e.g., as a rate, and also as a cumulative number since the start of an exercise. As noted above, lactate measurements give an indication of what energy source is being used to generate the energy consumed as calories. In particular, lactate is a by-product of carbohydrate consumption. An optimal fat burning exercise expends the most calories without significantly increasing the systemic lactate levels. By measuring the lactate and calorie expenditure, the percent of calories burned caused by fat reduction can be inferred and calculated. If there is low lactate, most is being burned from fat. If there is high lactate, most is being burned by carbohydrates. As noted above with respect to FIG. 50, there is a sliding scale of fat burn ratio between a low and high level. The conversion factor from amount of lactate measured, and fat burn, can be set through conversion factors obtained from literature and experiments.

Alternatively, a rate of energy expenditure may be calculated and energy expended may then be separated into that generated from lipid (fat) metabolism versus that generated from carbohydrate (glucose) metabolism. An accelerometer (and/or heart rate monitor) could measure caloric burn rate and an integration under the curve performed to determine total caloric consumption for exercise.

Outputs may be displayed using user interface elements described above, and the content of the same may include rate of fat burn, which can thus be used to optimize an exercise regimen that is intended to optimize weight loss. The display can be of a fat or calorie burn rate, as well as a total or cumulative value. In addition, the user interface can display the source of energy expended, e.g., fat versus carbohydrates. One way of displaying an individual's rate of fat consumption is to illustrate the percent being burned as fat versus the percent burned as carbohydrates, including as a ratio. For weight loss, the user would generally want to choose a program to maximize the calorie burn rate and the percentage of fat burn. Outputs of the program may advise the user to increase intensity or decrease intensity to achieve the desired output. Optimization of weight loss generally calls for lower exertion than that required for cardiovascular fitness or high-intensity athletics. In many cases, exercise that uses a large number of different muscle groups may be preferable in this regard to exercises that only use a single muscle group in a concentrated way. For example, hiking or walking may be preferable for weight loss as compared to cycling, and this aspect may thus be seen by a user on the display using the program described above.

In some cases, a number of calories consumed may be at least partially inferred from glucose data, and the number of calories expended may be determined from the lactate sensor and/or the accelerometer or other activity sensor. Additional details of ways of determining calories consumed are described below in another example.

Thus, in a particular example, a program may be started in which a user attempts to optimize their weight loss as measured by a desired goal level, e.g., a number of pounds per week. Inputs to the program may include a lactate level and activity data. After following the program, results can be evaluated and the program can be modified to iteratively move the user closer to the desired goal. In this way, a user can more easily and effectively learn how to lose weight based on their unique physiology and lifestyle patterns in order to improve their health, without the complexities and costs associated with a clinical professional. It is further noted that such needs are generally individualized and are not capable of being understood without an appropriate computing environment to measure the individual's response to a sufficient number of performance impact variables.

In one implementation, a "try and learn" approach to optimizing fat loss may be provided as part of a program. The "self-coach" system may recommend types of exercises, e.g., running, swimming, walking, biking, and so on, and may further recommend various types of intensity. The program may suggest different workouts to demonstrate to the user how the different activities impact the fat burn rate. Such would indicate to the user which exercise is the best use of their time if they wish to burn fat, what exercise is the best use of their time if they wish to achieve better cardiovascular fitness, and the like. For example, the system and method may suggest that the user exercise in the morning more, if such is indicated to have a particularly beneficial impact on user health. Heart rate and accelerometer data may be compared with the rate of fat burning to measure how efficient a particular exercise is at fat loss. The program may detect patterns in lactate versus intensity of exercise, and may show progressive levels of fitness. The user goals may be taken as inputs, and used as targets for the program.

Weight Loss Optimization Example 2

In another example, again applicable to non-diabetics and diabetics alike, a user may be instructed how to optimize fat reduction through measurement of glycerol and/or ketones or similar analytes. Glycerol, like triglycerides, is a byproduct of metabolism such as fat digestion. In this example, weight loss optimization is performed using analyte sensors without necessarily measuring user activity.

In more detail, measuring rates of fat burning can help people maintain or optimize their diet. This example uses measurement of glycerol and/or ketones, which are byproducts of fat metabolism, without necessarily requiring exercise. Thus, a user on a low carbohydrate diet could use the system and method of this example to monitor and measure the efficacy of their approach. The fat metabolism itself may be caused by either exercise or diet.

In particular, inputs to this system include data from measurements of glycerol and ketones. Appropriate sensors may include two single analyte sensors or a multi-analyte sensor. While either glycerol or ketones may be employed in the present system, using both enhances accuracy as fat may be burned along different pathways, and the use of both glycerol and ketone measurements allows detection, quantification, and accounting of multiple of these pathways.

In some cases an array of sensors may be employed, with the most common array being those measuring glycerol, ketones, and potentially other parameters such as glucose and/or triglycerides. If the glycerol and ketone sensors are provided under a common enzyme layer, they may be expected to drift in the same way. Generally, implementations may include use of various sensors, including ketone sensors, glucose sensors, accelerometers, and sensors measuring glycerol, as well as combinations of these. Particular implementations of note may include a ketone sensor in isolation, a ketone and glucose sensor combination device, and a ketone, glucose and accelerometer sensor combination device.

Where it is additionally desired to monitor metabolism, and in particular to determine if the same is from fat versus carbohydrates, a lactate sensor as described above may also be employed in the system.

The signal received may be a direct product of the byproduct of metabolism, and may be used to determine that fat metabolism is occurring. In some cases the signal may require an algorithm to correct for background signals, calibration issues, or noise. The signal may be interpreted by an algorithm to convert the data into a measurement of fat metabolism. If two sensors are used, e.g., for glycerol and ketones, the information for each individual sensor can be used together to provide additional information on efficacy of fat burning or as a quality check to have more accurate or reliable information. An algorithm may also be employed to calculate cumulative fat burn over time, as well as daily or weekly statistics.

As in the prior example, a "self-coach" system may be employed which in some cases may be combined with an interactive weight management system. In both cases, programs for exercise and meals may be suggested for a user. Specific meals may be consumed in different amounts and the results evaluated. The individual, using the program, may learn about the impact of different foods and/or exercise and be motivated by an immediate feedback for a suggested lifestyle adjustment.

As above, if glucose measurements are also considered, information may be determined or inferred such as calories ingested, calories expended, calories left on board, as well as calculations of calories in excess or deficit. Historical data may be employed, and past weight gain or loss compared to current values of the same.

Various ketones may be employed, including acetone, acetoacetic acid, and beta-hydroxybutyric acid.

Thus, in a particular example, a program may be started in which a user attempts to optimize their weight loss as measured by a desired goal level, e.g., a number of pounds per week. Inputs to the program may include measured glycerol and ketone levels, including levels over time. In more sophisticated implementations, glucose data may also be considered. After following the program, results can be evaluated and the program can be modified to iteratively move the user closer to the desired goal. In this way, a user can more easily and effectively learn how to lose weight based on their unique physiology and lifestyle patterns in order to improve their health, without the complexities and costs associated with a clinical professional. It is further noted that such needs are generally individualized and are not capable of being understood without an appropriate computing environment to measure the individual's response to a sufficient number of performance impact variables.

Weight Loss Optimization Example 3

In yet another example, again applicable to diabetics and non-diabetics alike, a user may be instructed how to optimize fat reduction through measurement of triglycerides or similar analytes. Such instructions may be calculated or determinable by a number of factors, including measurements of fat storage and fat utilization. Fat storage is measurable or determinable by various effects including high glucose, high insulin, high triglycerides, low glucagon, low ketones, or low free fatty aides Fat utilization is measurable or determinable by various effects including stable glucose, low insulin, low triglycerides, high glucagon, high ketones, and/or high free fatty acids. By measuring and tracking data about these parameters, users may be instructed to optimize fat reduction by suggestion of meals, exercise, and other therapies that emphasize fat utilization and lead to the effects noted above. In this example, weight loss optimization is performed using analyte sensors without necessarily measurement of user activity. This example particularly focuses on user eating habits, and optimizing healthy eating.

In more detail, many people would like real time feedback on how their eating habits impact their health. This system may provide information as to how their diet and exercise levels impact their triglyceride levels, which correlates to the amount of excess food eaten. In particular, triglycerides are created when extra food is eaten that is not being used in energy expenditure. Such "extra calories" are converted to triglycerides prior to being stored as long term fat. Real-time monitoring of triglycerides could give valuable information about eating and exercise habits toward health and weight loss. For example, such information may include whether a user is thinking they are eating well, by eating a salad, but in fact is sabotaging their own efforts by adding too much salad dressing. Accordingly, by measuring triglycerides, a user may be informed as to how much fat they are ingesting.

In this implementation, a resting metabolism may be a useful parameter in calculations, as the same relates to how much energy will be consumed by the user even in the absence of exercise or excess energy expenditure. Resting metabolism may be determined in a number of ways, e.g., using $CO_2$ breath levels as measured in a chamber with known gases, by knowledge of a basal level of lactate production, and the like.

In particular, one input to the system may include a measurement of triglycerides, either in the bloodstream or subcutaneous, or both. In some cases, a level of lipoproteins, which serve to transport lipids such as triglycerides, may be measured. For subcutaneous measurements, a system similar to those described here may be employed, with an appropriate enzyme exchange, e.g., using lipase, which breaks triglycerides into glycerol and three free fatty acids.

In some cases an array of sensors may be employed, with the most common array being those measuring triglycerides and potentially another analyte such as glucose. If the triglycerides and glucose sensors are provided under a common enzyme layer, they may be expected to drift in the same way.

In some cases the signal received may require an algorithm to correct for background signals, calibration issues, or noise. The signal may be interpreted by an algorithm to convert the data into a metric that compares healthy levels to unhealthy levels, rather than against a particular concentration. For example, comparison may be made against a typically acceptable level, in some cases calculating a difference from the normal, and expressed as a number such as a dietary health quotient. Alternatively, a zone diagram may be displayed with, e.g., yellow, red, and green zones. Other helpful metrics may include averages over time, area under the curve, cumulative levels over time, and the like.

As in the prior example, a "self-coaching" system may be employed. Programs for exercise and meals may be suggested for users, such as using recommendations in a cookbook or eating program. Specific meals may be consumed in different amounts and the results evaluated immediately. The individual, using the program, may learn about the impact of different foods and/or exercise and be motivated by an immediate feedback for a suggested lifestyle adjustment. For example, a user may be alerted to excess fat in their diet, and may be suggested to lower their fat intake. In the same way, particularly if glucose is measured at the same time, a user may be alerted to excess sugar in their diet, and may be directed to lower their sugar intake.

In more detail, it has been hypothesized that glucose levels in response to food intake differ with respect to the type of food. If carbohydrates are ingested, the glucose levels follow a normal curve, while if fats are ingested, a normal curve is again seen but with a significant elevation or "tail" on the right side. This aspect may be employed in several of the examples to determine if ingested food contain significant levels of fats or carbohydrates.

It is noted here that triglycerides are a particular type of fat, but multiple types of fat may be measured and employed in systems and methods according to present principles.

The system may be further employed to indicate to a user how healthy their meals are. Using data such as a measurement of free fatty acids, caloric intake, as well as types of calories, the system in this example may indicate to a user how their diet and lifestyle is stressing their body, e.g., in insulin production, glucose effects, or the like.

Thus, in a particular example, a program may be started in which a user attempts to optimize their weight loss as measured by a desired goal level, e.g., a number of pounds per week. Inputs to the program may include measured triglyceride and optionally glucose levels, including levels over time. After following the program, results can be evaluated and the program can be modified to iteratively move the user closer to the desired goal. In this way, a user can more easily and effectively learn how to lose weight based on their unique physiology and lifestyle patterns in order to improve their health, without the complexities and costs associated with a clinical professional. Such needs are generally individualized and are not capable of being understood without an appropriate computing environment to measure the individual's response to a sufficient number of performance impact variables.

Weight Loss Optimization Example 4

In yet a further generally applicable example, a user may be enabled to determine their calories ingested and their calories expended, in many cases termed "calories—calories out". In particular, one potential application for a real-time monitoring system is to measure the amount of calories taken in by the body. Such systems may be combined with those measuring calories expended to give a real-time indicator as to whether a user is losing weight or gaining it.

The determination of calories expended may be made in a number of ways. In some cases, knowledge of activity, combined with knowledge of a user's weight, fitness level, or the like, may be used to estimate calories expended during exercise. Other ways of determining calories expended, or to refine calculations using other methods, is by measurement of lactate as noted above with respect to exercise and sports optimization.

The determination of calories ingested may in a simplest sense be determined by glucose, such as may be determined by a CGM system. Related indices include total daily glucose, total meal glucose, or the like, and the same can generally be obtained by numerical integration under a glucose value curve. A derivative of the glucose value curve can give another type of indicator, in particular, a glucose rate indicator, which can be of particular value after exercise in determining and characterizing glucose drops. The rate of change of the analyte, the value of the analyte concentration, or the cumulative total may be characterized as being above normal, below normal, or at normal, and the same may be characterized as such using the exemplary user interfaces described above.

In a more sophisticated calculation, insulin may also be measured and used in combination with glucose data. Alternatively, insulin analogues or surrogates may be used. Measuring insulin together with glucose allows the determination of insulin action, the ability of insulin to enhance glucose uptake and simultaneously suppress endogenous glucose production. In this way, the combination of glucose measurements and insulin measurements can allow a relatively complete picture to be obtained of a person's metabolic health in relation to calories ingested, i.e., caloric uptake.

In an even more sophisticated and accurate calculation, triglyceride measurements may be employed to determine the amount of fat ingested by a user. Methods of triglyceride measurements are discussed above.

The type of sensors which may be employed for the above measurements are as follows. Glucose measurements may be taken using CGM systems or others described here. Insulin measurements are generally more difficult, as insulin is present in only low quantities, but high sensitivity measurements may be employed to measure the same.

In one implementation, an array of sensors is employed to measure insulin, glucose, and triglycerides. An accelerometer or other motion sensor may be employed to detect user activity. Using the array sensor and the accelerometer, a determination may be made as to total calories ingested and total calories expended, thus giving an indication as to whether the user is losing or gaining weight.

In addition, insulin measurements may be employed to determine progression of disease state. As diabetes progresses, insulin becomes less and less effective, and more and more must accordingly be created and used by the body. If in the course of following programs progressively more insulin becomes required, with relatively equal amounts of food ingested and exercise performed, an inference can be made that insulin is becoming less and less effective. In addition, besides use in determining calories ingested, insulin measurements may be used as part of an "insulin-on-board" calculation for use in diabetes management.

In this example, as in the one above, a resting metabolism may be a useful parameter in calculations, as the same relates to how much energy will be consumed by the user even in the absence of exercise or excess energy expenditure. Resting metabolism may be determined in a number of ways, e.g., using $CO_2$ breath levels as measured in a chamber with known gases, by knowledge of a basal level of lactate production, and the like.

In some cases the insulin signal received may require an algorithm to correct for background signals, calibration issues, or noise. The signal may be interpreted by an algorithm to convert the data into a metric that indicates weight gain or weight loss.

As in the prior example, a "self-coaching" system may be employed. Programs for exercise and meals may be suggested for users, such as using recommendations in a cookbook or eating program. Specific meals may be consumed in different amounts and the results evaluated. The individual, using the program, may learn about the impact of different foods and/or exercise and may be motivated by an immediate feedback for a suggested lifestyle adjustment. For example, a user may be alerted to excess fat in their diet, and may be suggested to lower their fat intake. In the same way, a user may be alerted to excess sugar in their diet, and may be suggested to lower their sugar intake.

Exemplary outputs for the user may be estimated calories input or output versus time, as well as a calculated area under the curve, i.e., total calories consumed or expended, for various time points. One exemplary indicator may be total calories burned over time, showing how much excess (weight gain) or deficit (weight loss) was happening over time. Another output may be an indicator of how much fat is being burned, this output in many cases using a measurement of lactate, glucose, heart rate, accelerometer, or other calorie-burning measures.

Thus, in a particular example, a program may be started in which a user attempts to optimize their weight loss as measured by a desired goal level, e.g., a certain number of calories expended which is greater than the number of calories ingested. Inputs to the program may include measured insulin, glucose, and in some cases triglyceride levels, including levels over time. After following the program, results can be evaluated and the program can be modified to iteratively move the user closer to the desired goal. In this way, a user can more easily and effectively learn how to lose weight based on their unique physiology and lifestyle patterns in order to improve their health, without the complexities and costs associated with a clinical professional.

As a specific example, users may be informed as to the best times to exercise or eat meals to maximize calorie expenditure, or the best times to exercise or eat meals with regard to insulin production. Users can thus condition their bodies to use the insulin they produce in a more effective way. Prediabetics may be enabled to determine their diabetic state and to reverse a trend toward diabetes. For example, by maintaining or losing weight while producing the same or less amounts of insulin, a trend toward diabetes, as measured by pancreas function, may be halted or even reversed.

It is further noted that such needs are generally individualized and are not capable of being understood without an appropriate computing environment to measure the individual's response to a sufficient number of performance impact variables. Moreover, in this and in other examples, measurements within the interstitial space of the indicated analytes provides a data collection regime that is both highly accurate and prolific in that significant quantities of data may be obtained for analysis.

As noted above, systems and methods according to present principles provide ways for users to employ analyte monitors and other sensors as well as control systems for self-education about a disease state or for avoidance of a disease state, as well as to enable a user's education in the optimization of a sports or weight loss regimen. In the specific field of diabetes management, such can include the education of type II diabetic users to better manage their disease. These users, in contrast to type I diabetic users, are in many cases unaccustomed to complicated and/or repetitive calibration routines for continuous analyte (glucose) monitors. Accordingly, for an ideal system and method for the type II diabetic user, as well as for those interested in optimizing their sports and/or weight loss regimens, it is desirable to provide sensors and calibration routines that do not require significant user technical savvy to operate, and that do not require complicated calibration routines. It should be understood, however, that in some cases, particularly for current type I users of CGM systems, current sensor technology and monitoring means may be employed to accomplish the methods and goals described above. In most implementations, any commercially available sensor of current design may be used.

Systems and methods according to present principles may be advantageously used by both diabetics and non-diabetics alike, as noted above. In particular, any of the examples described, whether for sports, exercise, or fitness optimization, or for weight loss, or for other purposes, may be used by non-diabetics, diabetics, and other users as well.

In some cases, sensors not requiring significant calibration steps may be employed because the accuracy requirements of the sensors are often lessened in such implementations. Lessened accuracy and resolution requirements may also allow the use of less expensive sensors. In other words, so long as the sensor is accurate to a given tolerance, it may be employed in such implementations, as the implementation may only require accuracy within a given range. For example, it may only be necessary to know whether the patient is hypoglycemic, hyperglycemic, or euglycemic, rather than a degree of hypoglycemia or hyperglycemia. Using range colors as noted above with respect to, e.g., FIGS. 7, 8, 9, 12, 13, 14, 15, 16, 46, and 53, it may only be required to know if a user's glucose concentration value is within a red/green/yellow zone, or between, e.g., 100 and 200, rather than requiring knowledge of the exact value. Whereas the primary need for a type I patient is accurate glucose information in order to determine trends in glucose, actual glucose levels, and/or predicted glucose states, the broader type II population may benefit from a wider variety of biological information, even at lower resolutions of accuracy, so long as the information is presented in a simple, intuitive, and actionable manner.

Additional details about providing analyte concentration values in ranges rather than strictly in numerical values may be found in U.S. Pat. Publ. No. 2014/0278189-A1, and in U.S. Provisional Application No. 62/053,733, filed Sep. 22, 2014, each of which is incorporated by reference herein in its entirety.

One type of sensor system which may be employed is described in U.S. Publ. No. 2009/0076360-A1, incorporated by reference herein in its entirety.

In some cases, users may find current insertion techniques for CGM sensors to be too complex or painful. In such cases simpler and less painful options may be employed, such as are described in U.S. Pat. Publ. No. 2009/0076360-A1, U.S. Pat. Publ. No. 2011/0077490-A1, U.S. Pat. Publ. No. 2014/0107450-A1, and U.S. Pat. Publ. No. 2014/0213866-A1, each of which is incorporated by reference herein in its entirety.

In some cases, the system may be made even simpler by provision of a power source on board, thus reducing the overall number of components in helping the cause of miniaturization. Certain aspects regarding implementing power on board are described in U.S. Pat. Publ. No. 2009/0076360-A1, incorporated herein by reference in its entirety.

It is also noted that power may be conserved by transmitting data on an "on demand" basis, i.e., only when the user indicates a desire to view the measured data. Provision may still be had for device-initiated transmissions, such as where a glycemic urgency is indicated, e.g., a hypoglycemic state, and in these cases data may be pushed to a nearest connected device and from there to other resources on the internet. For example, data may be pushed to a local network via a Wi-Fi hotspot, or may be pushed to a telecommunications network, e.g., either directly or through a user's cell phone, and subsequently transmitted to a caregiver or other monitor.

Additional details about data transmissions in such cases are described in U.S. Pat. Publ. No. 2014/0118138-A1; U.S. Provisional Patent Application No. 61/978,151, filed Apr. 10, 2014; U.S. patent application Ser. No. 14/659,263, filed Mar. 16, 2015; and U.S. Provisional Appl. No. 62/053,733, filed Sep. 22, 2014, each of which is incorporated herein by reference in its entirety.

Other techniques may also be employed to simplify sensor systems, and thereby make such sensors more appropriate or accessible for more general use.

For example, an exemplary sensor system is described below with respect to FIGS. 54-57.

U.S. Pat. Publ. No. 2011/002712-A1, U.S. Pat. Publ. No. 2008/0119703-A1 and U.S. Pat. Publ. No. 2005/0245799-A1, each of which is incorporated herein by reference in its entirety, describe additional configurations for using the continuous sensor in different body locations. In some embodiments, the sensor is configured for transcutaneous implantation in the host. In alternative embodiments, the sensor is configured for insertion into the circulatory system, such as a peripheral vein or artery. However, in other embodiments, the sensor is configured for insertion into the central circulatory system, such as but not limited to the vena cava. In still other embodiments, the sensor can be placed in an extracorporeal circulation system, such as but not limited to an intravascular access device providing extracorporeal access to a blood vessel, an intravenous fluid infusion system, an extracorporeal blood chemistry analysis device, a dialysis machine, a heart-lung machine (i.e., a device used to provide blood circulation and oxygenation while the heart is stopped during heart surgery), etc. In still other embodiments, the sensor can be configured to be wholly implantable, as described in U.S. Pat. No. 6,001,067.

FIGS. 54 through 57 illustrate an embodiment of the in vivo portion of a continuous analyte sensor 700, which includes an elongated conductive body 702. The elongated conductive body 702 includes a core 710 (see FIG. 55) and a first layer 712 at least partially surrounding the core. The first layer includes a working electrode (for example, located in window 706) and a membrane 708 located over the working electrode. In some embodiments, the core and first layer can be of a single material (such as, for example, platinum). In some embodiments, the elongated conductive body is a composite of at least two materials, such as a composite of two conductive materials, or a composite of at least one conductive material and at least one non-conductive material. In some embodiments, the elongated conductive body comprises a plurality of layers. In certain embodiments, there are at least two concentric or annular layers, such as a core formed of a first material and a first layer formed of a second material. However, additional layers can be included in some embodiments. In some embodiments, the layers are coaxial.

The elongated conductive body may be long and thin, yet flexible and strong. For example, in some embodiments, the smallest dimension of the elongated conductive body is less than about 0.1 inches, 0.075 inches, 0.05 inches, 0.025 inches, 0.01 inches, 0.004 inches, or 0.002 inches. While the elongated conductive body is illustrated in FIGS. 54 through 57 as having a circular cross-section, in other embodiments the cross-section of the elongated conductive body can be ovoid, rectangular, triangular, polyhedral, star-shaped, C-shaped, T-shaped, X-shaped, Y-shaped, irregular, or the like. In one embodiment, a conductive wire electrode is employed as a core. To such a clad electrode, two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

The materials used to form the elongated conductive body (such as, for example, stainless steel, titanium, tantalum, platinum, platinum-iridium, iridium, certain polymers, alloys or combinations thereof, and/or the like) can be strong and hard, and therefore are resistant to breakage. In some embodiments, the sensor's small diameter provides flexibility to these materials, and therefore to the sensor as a whole. Thus, the sensor can withstand repeated forces applied to it by surrounding tissue.

In addition to providing structural support, resiliency and flexibility, in some embodiments, the core 710, or a component thereof, provides electrical conduction for an electrical signal from the working electrode to sensor electronics (not shown). In some embodiments, the core 710 comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is a conductive material selected to provide electrical conduction between the core and the first layer, and/or to attach the first layer to the core (that is, if the first layer is formed of a material that does not attach well to the core material). In another embodiment, the core is formed of a non-conductive material (such as, for example, a non-conductive metal and/or a non-conductive polymer) and the first layer is formed of a conductive material, such as stainless steel, titanium, tantalum, a conductive polymer, and/or the like. The core and the first layer can be of a single (or same) material, such as platinum. One skilled in the art appreciates that additional configurations are possible.

Referring again to FIGS. 54-57, the first layer 712 can be formed of a conductive material and the working electrode can be an exposed portion of the surface of the first layer 712. Accordingly, the first layer 712 can be formed of a material configured to provide a suitable electroactive surface for the working electrode, a material such as, but not limited to, platinum, platinum-iridium, gold, palladium, iridium, graphite, carbon, a conductive polymer, an alloy and/or the like.

Figure 56:
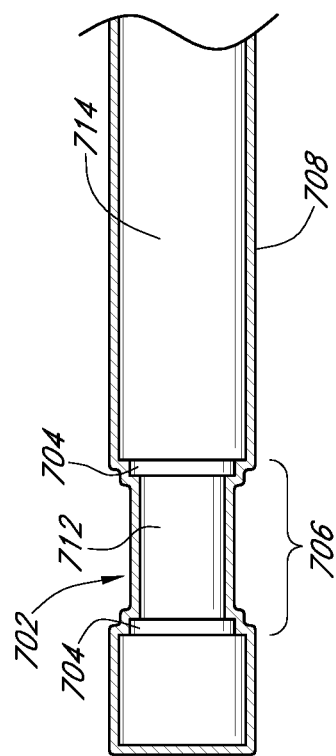
FIGS. 55-57 are other views of the sensor of FIG. 54, illustrating various embodiments of a sensor system.
Figure 55:
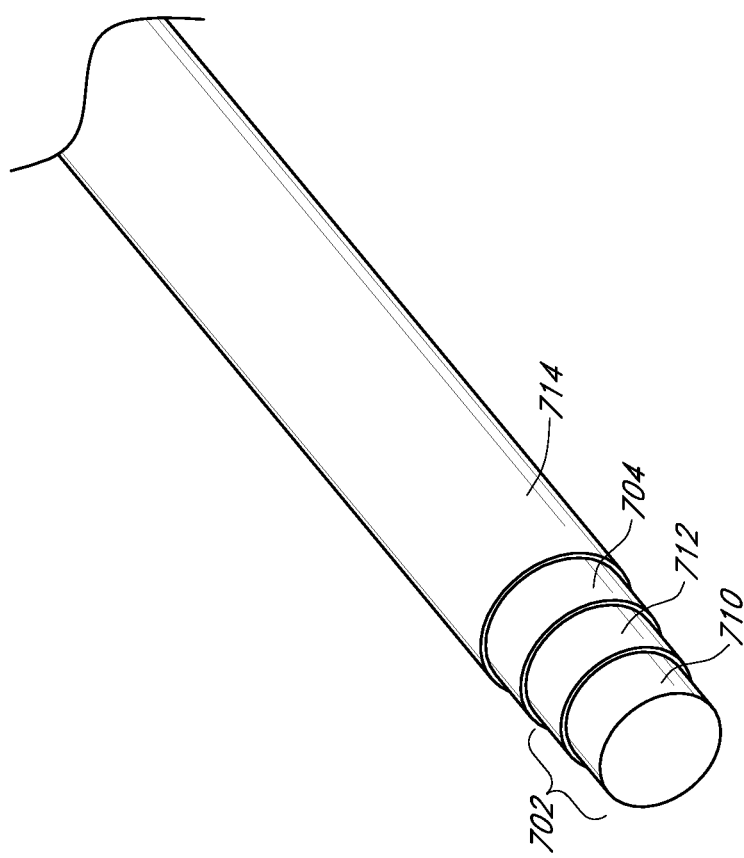

As illustrated in FIGS. 55-56, a second layer 704 surrounds at least a portion of the first layer 712, thereby defining the boundaries of the working electrode. In some embodiments, the second layer 704 serves as an insulator and is formed of an insulating material, such as polyimide, polyurethane, parylene, or any other known insulating materials. For example, in one embodiment the second layer is disposed on the first layer and configured such that the working electrode is exposed via window 706. In some embodiments, an elongated conductive body, including the core, the first layer and the second layer, is provided. A portion of the second layer can be removed to form a window 706, through which the electroactive surface of the working electrode (that is, the exposed surface of the first layer 712) is exposed. In some embodiments, a portion of the second and (optionally) third layers can be removed to form the window 706, thus exposing the working electrode. Removal of coating materials from one or more layers of the elongated conductive body (for example, to expose the electroactive surface of the working electrode) can be performed by hand, excimer lasing, chemical etching, laser ablation, grit-blasting, or the like.

The sensor can further comprise a third layer 714 comprising a conductive material. For example, the third layer 714 may comprise a reference electrode, which may be formed of a silver-containing material that is applied onto the second layer 704 (that is, the insulator).

The elongated conductive body 702 can further comprise one or more intermediate layers (not shown) located between the core 710 and the first layer 712. For example, the intermediate layer can be one or more of an insulator, a conductor, a polymer, and/or an adhesive.

It is contemplated that the ratio between the thickness of the silver/silver chloride layer and the thickness of an insulator (such as, for example, polyurethane or polyimide) layer can be controlled, so as to allow for a certain error margin (that is, an error margin associated with the etching process) that would not result in a defective sensor (for example, due to a defect resulting from an etching process that cuts into a depth more than intended, thereby unintentionally exposing an electroactive surface). This ratio may be different depending on the type of etching process used, whether it is laser ablation, grit blasting, chemical etching, or some other etching method. In one embodiment in which laser ablation is performed to remove a silver/silver chloride layer and a polyurethane layer, the ratio of the thickness of the silver/silver chloride layer and the thickness of the polyurethane layer can be from about 1:5 to about 1:1, or from about 1:3 to about 1:2.

In some embodiments, the core 710 comprises a non-conductive polymer and the first layer 712 comprises a conductive material. Such a sensor configuration can advantageously provide reduced material costs, in that it replaces a typically expensive material with an inexpensive material. For example, the core 710 can be formed of a non-conductive polymer, such as, a nylon or polyester filament, string or cord, which can be coated and/or plated with a conductive material, such as platinum, platinum-iridium, gold, palladium, iridium, graphite, carbon, a conductive polymer, and allows or combinations thereof.

Figure 57:
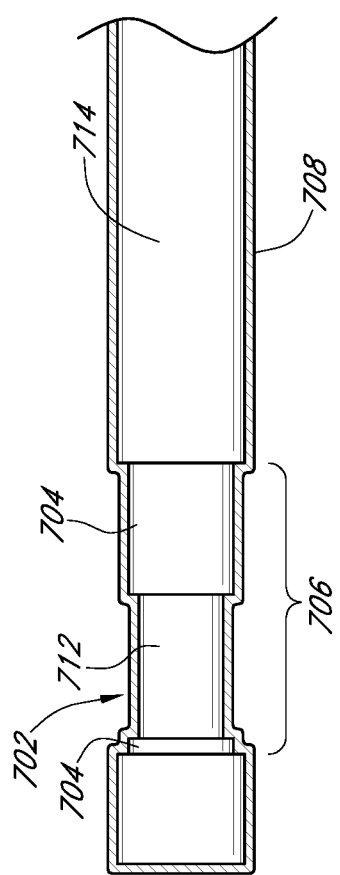

As illustrated in FIGS. 56 and 57, the sensor can also include a membrane 708, such as those discussed elsewhere here. The membrane 708 can include an enzyme layer (not shown), as described elsewhere herein. For example, the enzyme layer can include a catalyst or enzyme configured to react with an analyte. For example, the enzyme layer can be an immobilized enzyme layer including glucose oxidase. In other embodiments, the enzyme layer can be impregnated with other oxidases, including, for example, galactose oxidase, cholesterol oxidase, amino acid oxidase, alcohol oxidase, lactate oxidase, or uricase.

FIG. 55 is a schematic illustrating an embodiment of an elongated conductive body 702, or elongated body, wherein the elongated conductive body is formed from at least two materials and/or layers of conductive material. The term "electrode" can be used herein to refer to the elongated conductive body, which includes the electroactive surface that detects the analyte. In some embodiments, the elongated conductive body provides an electrical connection between the electroactive surface (that is, the working electrode) and the sensor electronics (not shown). In certain embodiments, each electrode (that is, the elongated conductive body on which the electroactive surface is located) is formed from a fine wire with a diameter of from about 0.001 inches or less to about 0.01 inches or more. Each electrode can be formed from, for example, a plated insulator, a plated wire, or bulk electrically-conductive material. For example, in some embodiments, the wire and/or elongated conductive body used to form a working electrode is about 0.002, 0.003, 0.004, 0.005, 0.006, 0.007, 0.008, 0.009, 0.01, 0.015, 0.02, 0.025, 0.03, 0.035, 0.04 or 0.045 inches in diameter.

Furthermore, the first layer can comprise an electroactive surface (that is, the portion exposed through the window 706). The exposed electroactive surface can be the working electrode. For example, if the sensor is an enzymatic electrochemical analyte sensor, the analyte enzymatically reacts with an enzyme in the membrane covering at least a portion of the electroactive surface. The reaction can generate electrons (e) that are detected at the electroactive surface as a measurable electronic current. For example, in the detection of glucose where glucose oxidase produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected.

Figure 54:
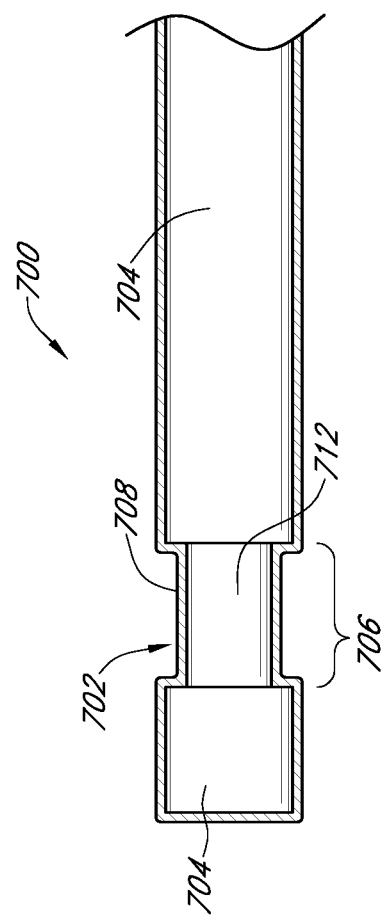
FIG. 54 is a view of an exemplary embodiment of a continuous analyte sensor.

As previously described with reference to FIG. 54 and as illustrated in FIG. 56, an insulator 704 is disposed on at least a portion of the elongated conductive body 702. In some embodiments, the sensor is configured and arranged such that the elongated body includes a core 710 and a first layer 712, and a portion of the first layer 712 is exposed via window 706 in the insulator 704. In other embodiments, the sensor is configured and arranged such that the elongated body 702 includes a core 710 embedded in an insulator 704, and a portion of the core 710 is exposed the window 706 in the insulator 704. For example, the insulating material can be applied to the elongated body 702 (by, for example, screen-, ink-jet and/or block-print) in a configuration designed to leave at least a portion of the first layer's 712 surface (or the core's 710 surface) exposed. For example, the insulating material can be printed in a pattern that does not cover a portion of the elongated body 702. Alternatively, a portion of the elongated body 702 can be masked prior to application of the insulating material. Removal of the mask, after insulating material application, can expose the portion of the elongated body 702.

In some embodiments, the insulating material 704 comprises a polymer, for example, a non-conductive (e.g., dielectric) polymer. Dip-coating, spray-coating, vapor-deposition, printing and/or other thin film and/or thick film coating or deposition techniques can be used to deposit the insulating material on the elongated body 702 and/or core 710. For example, in some embodiments, the insulating material is applied as a layer of from about less than 5 microns, or from 5, 10 or 15-microns to about 20, 25, 30 or 35-microns or more in thickness. The insulator can be applied as a single layer of material, or as two or more layers, which are comprised of either the same or different materials, as described elsewhere herein. Alternatively, the conductive core may not require a coating of insulator. In some embodiments, the insulating material defines an electroactive surface of the analyte sensor (that is, the working electrode). For example, a surface of the conductive core (such as, for example, a portion of the first layer 712) can either remain exposed during the insulator application, or a portion of applied insulator can be removed to expose a portion of the conductive core's surface, as described above.

In some embodiments, in which the sensor has an insulated elongated body or an insulator disposed upon a conductive structure, a portion of the insulating material can be stripped or otherwise removed, for example, by hand, excimer lasing, chemical etching, laser ablation, grit-blasting (such as, for example, with sodium bicarbonate or other suitable grit), or the like, to expose the electroactive surfaces. In one exemplary embodiment, grit blasting is implemented to expose the electroactive surface(s), for example, by utilizing a grit material that is sufficiently hard to ablate the polymer material yet also sufficiently soft so as to minimize or avoid damage to the underlying metal electrode (for example, a platinum electrode). Although a variety of "grit" materials can be used (such as, for example, sand, talc, walnut shell, ground plastic, sea salt, and the like), in some embodiments, sodium bicarbonate is an advantageous grit-material because it is sufficiently hard to ablate, e.g., a parylene coating without damaging, e.g., an underlying platinum conductor. An additional advantage of sodium bicarbonate blasting includes its polishing action on the metal as it strips the polymer layer, thereby eliminating a cleaning step that might otherwise be necessary. Alternatively, a portion of an electrode or other conductive body can be masked prior to depositing the insulator in order to maintain an exposed electroactive surface area.

The electroactive surface of the working electrode can be exposed by formation of a window 706 in the insulator 704. The electroactive window 706 of the working electrode can be configured to measure the concentration of an analyte.

In some embodiments, a silver wire is formed onto and/or fabricated into the sensor and subsequently chloridized to form a silver/silver chloride reference electrode. Advantageously, chloridizing the silver wire as described herein enables the manufacture of a reference electrode, with good in vivo performance. By controlling the quantity and amount of chloridization of the silver to form silver/silver chloride, improved break-in time, stability of the reference electrode and extended life can be obtained in some embodiments. Additionally, use of silver chloride as described above allows for relatively inexpensive and simple manufacture of the reference electrode.

Referring to FIGS. 55-56, the reference electrode 714 can comprise a silver-containing material (e.g., silver/silver chloride) applied over at least a portion of the insulating material 704, as discussed in greater detail elsewhere herein. For example, the silver-containing material can be applied using thin film and/or thick film techniques, such as but not limited to dipping, spraying, printing, electro-depositing, vapor deposition, spin coating, and sputter deposition, as described elsewhere herein. For example, a silver or silver chloride-containing paint (or similar formulation) can be applied to a reel of the insulated conductive core. Alternatively, the reel of insulated elongated body (or core) may be cut into single unit pieces (that is, "singularized"), and silver-containing ink may be pad printed thereon. In still other embodiments, the silver-containing material may be applied as a silver foil. For example, an adhesive can be applied to an insulated elongated body, around which the silver foil can then be wrapped in. Alternatively, the sensor can be rolled in Ag/AgCl particles, such that a sufficient amount of silver sticks to and/or embeds into and/or otherwise adheres to the adhesive for the particles to function as the reference electrode. In some embodiments, the sensor's reference electrode includes a sufficient amount of chloridized silver that the sensor measures and/or detects the analyte for at least three days.

It is contemplated that the electrode may be formed to have any of a variety of cross-sectional shapes. For example, in some embodiments, the electrode may be formed to have a circular or substantially circular cross-sectional shape, but in other embodiments, the electrode may be formed to have a cross-sectional shape that resembles an ellipse, a polygon (e.g., triangle, square, rectangle, parallelogram, trapezoid, pentagon, hexagon, octagon), or the like. In various embodiments, the cross-sectional shape of the electrode may be symmetrical, but in other embodiments, the cross-sectional shape may be asymmetrical. In some embodiments, each electrode may be formed from a fine wire with a diameter of from about 0.001 or less to about 0.050 inches or more, for example, and may be formed from, e.g., a plated insulator, a plated wire, or bulk electrically conductive material. In some embodiments, the wire used to form a working electrode may be about 0.002, 0.003, 0.004, 0.005, 0.006, 0.007, 0.008, 0.009, 0.01, 0.015, 0.02, 0.025, 0.03, 0.035, 0.04, or 0.045 inches in diameter. In some embodiments, the working electrode may comprise a wire formed from a conductive material, such as platinum, platinum-black, platinum-iridium, palladium, graphite, gold, carbon, ruthenium, rhodium, osmium, and oxides or alloys thereof, conductive polymers, or the like. Although the illustrated electrode configuration and associated text describe one method of forming a sensor, any of a variety of known sensor configurations can be employed with the analyte sensor system.

In some alternative embodiments, additional electrodes can be included within the assembly, for example, a three-electrode system (working, reference, and counter electrodes) and an additional working electrode (e.g., an electrode which can be used to generate oxygen, which is configured as a baseline subtracting electrode, or which is configured for measuring additional analytes). U.S. Pat. No. 7,081,195, U.S. Pat. Publ. No. 2005/0143635-A1 and U.S. Pat. Publ. No. 2007/0027385-A1 describe some systems and methods for implementing and using additional working, counter, and reference electrodes. In one implementation wherein the sensor comprises two working electrodes, the two working electrodes are juxtapositioned, around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline signals, and the additional working electrode is configured to measure a baseline signal consisting of the baseline signal only. In these embodiments, the second working electrode may be configured to be substantially similar to the first working electrode, but without an enzyme disposed thereon. In this way, the baseline signal can be determined and subtracted from the first signal to generate a difference signal, i.e., a glucose-only signal that is substantially not subject to fluctuations in the baseline or interfering species on the signal, such as described in U.S. Pat. Publ. No. 2005/0143635-A1, U.S. Pat. Publ. No. 2007/0027385-A1, and U.S. Pat. Publ. No. 2007/0213611-A1, and U.S. Pat. Publ. No. 2008/0083617-A1.

It is contemplated that the sensing region may include any of a variety of electrode configurations. For example, in some embodiments, in addition to one or more glucose-measuring working electrodes, the sensing region may also include a reference electrode or other electrodes associated with the working electrode. In these particular embodiments, the sensing region may also include a separate reference or counter electrode associated with one or more optional auxiliary working electrodes. In other embodiments, the sensing region may include a glucose-measuring working electrode, an auxiliary working electrode, two counter electrodes (one for each working electrode), and one shared reference electrode. In yet other embodiments, the sensing region may include a glucose-measuring working electrode, an auxiliary working electrode, two reference electrodes, and one shared counter electrode.

It is to be understood that sensing membranes modified for other sensors, for example, may include fewer or additional layers. For example, in some embodiments, the membrane system may comprise one electrode layer, one enzyme layer, and two bioprotective layers, but in other embodiments, the membrane system may comprise one electrode layer, two enzyme layers, and one bioprotective layer. In some embodiments, the bioprotective layer may be configured to function as the diffusion resistance domain and control the flux of the analyte (e.g., glucose) to the underlying membrane layers.

In some embodiments, one or more domains of the sensing membranes may be formed from materials such as silicone, polytetrafluoroethylene, polyethylene-co-tetrafluoroethylene, polyolefin, acrylates, poly(vinyl pyridine), polyvinyl/pyrrolidone, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide), zwitterions (e.g., betaines), polyelectrolytes, polysulfones, and copolymers thereof including, for example, di-block, tri-block, alternating, random and graft copolymers, and blends thereof.

In some embodiments, the sensing membrane can be deposited on the electroactive surfaces of the electrode material using known thin or thick film techniques (for example, spraying, electro-depositing, dipping, or the like). It should be appreciated that the sensing membrane located over the working electrode does not have to have the same structure as the sensing membrane located over the reference electrode; for example, the enzyme domain deposited over the working electrode does not necessarily need to be deposited over the reference or counter electrodes.

Although the exemplary embodiments illustrated in the figures involve circumferentially-extending membrane systems, the membranes described herein may be applied to any planar or non-planar surface, for example, the substrate-based sensor structure of U.S. Pat. No. 6,565,509 to Say et al.

Other details of such sensor systems are described in U.S. Pat. Publ. No. 2013/0053665-A1, incorporated herein by reference in its entirety.

In many implementations, including as described above, present glucose sensors measure a glucose surrogate such as hydrogen peroxide, which is a product of the reaction of glucose and oxygen. In particular, such a glucose conversion reaction requires oxygen as a co-reactant, and the same must be present in equi-molar quantities to glucose for the reaction to proceed. Accordingly such sensors are limited by the amount of oxygen present. If at times the oxygen is limited, then the sensor becomes inaccurate in its reading of glucose. In this case the sensors will be detecting oxygen instead of glucose. In practice, this may manifest itself as an end-of-life fault. Additional details about such end-of-life faults are described in U.S. Provisional Application No. 62/053,733, filed Sep. 22, 2014, which is incorporated herein by reference in its entirety.

The amount of glucose can be reduced by the use of the diffusion resistance domain or layer noted above, but using such a mechanism typically lowers the overall amount of signal. Accordingly, in some implementations it would be desirable to reduce sensor dependence on oxygen.

One solution is to have an oxygen-independent enzyme, e.g., glucose dehydrogenase, e.g., GDH, GDH-NAD, GDH- PQQ, or the like, configured to catalyze a reaction with glucose as a reactant. However, past efforts of using an oxygen-independent enzyme have suffered from issues related to the enzyme's lack of specificity to glucose, which can result in cross reactions with other sugars such as galactose or maltose, which in turn results in a signal that includes contributions from non-glucose species. In some embodiments, an oxygen independent enzyme complex is used that is formed by bonding a co-factor (e.g., flavin adenine dinucleotide (FAD)) with the enzyme directly. When bonded to certain enzymes, FAD can increase glucose specificity and substantially lower or eliminate reactivity to other sugars. FAD also increases the temperature stability of the enzyme compared to earlier GDHs. With the GDH-FAD co-enzyme, e.g., within the enzyme domain, glucose-specific sensors may be created that are oxygen-independent.

The GDH enzyme uses an electron acceptor and these have classically been potassium ferrocyanide, dichlorophenylindophenol (DCPIP) or methylene blue. In tailoring the use of these enzymes and acceptors to the system, a polyurethane encapsulation technique may be employed via dissolution within a polyurethane dispersion, and then the subsequent curing may utilize a cross-linker for the polyurethane dispersion, to bind an electron acceptor like a ferredoxin into the polyurethane. Alternatively, the polyurethane may itself be modified with regions incorporating one of the electron acceptors, e.g., potassium ferrocyanide, as the cross-linker, such that it could be used as an electron acceptor as well.

Alternatively, a hybrid dual enzyme system may be employed, in which both the GDH-FAD and GOx enzymes are incorporated into the enzyme domain. Such a hybrid dual enzyme system could be tailored to function more robustly than either enzyme system alone. For example, when an oxygen deficit arises that would ordinarily cause low oxygen performance issues within the GOx system, the GDH-FAD system may take over, thereby allowing the overall sensor system to still function normally and provide accurate data.

Besides enzymatic methods of measuring glucose and other analyte concentrations, systems and methods according to present principles may also employ non-enzymatic methods. For example, colorimetric, fluorometric, and electrochemical sensors may be employed in this way. As one example, boronic acid-based electrochemical sensors have been employed in the detection of glycoproteins, as well as dopamine. These do not rely on enzymes but rather on the boronic acid-diol interaction. Such methods have also shown sensitivity to glucose, and thus such and other like methods may be employed for the detection and quantification of certain analyte concentrations, including glucose.

As noted above in the application of weight loss optimization, measurement of ketone bodies may often be employed to measure metabolism, and in some cases the same can also be used as a secondary indicator of diabetes (ketone bodies are elevated in blood following fasting and episodes of hypoglycemia). Examples of endogenous ketone bodies to be continuously measured by the sensor are acetone, acetoacetic acid, and beta-hydroxybutyric acid, which are three water-soluble molecules that are produced by the liver from fatty acids during periods of low food intake or carbohydrate restriction for cells of the body to use as energy instead of glucose. Measurements of ketone bodies may be useful individually as well as in combination with glucose measurements to provide an indicator of diabetic control.

In certain embodiments, the sensor employs an electrochemical mechanism for measuring ketone. For example, the sensor may comprise an enzyme layer that has an oxidoreductase enzyme (e.g., NADP dependent alcohol aldehyde/ketone oxidoreductase) that reacts with ketone bodies to produce hydrogen peroxide, which is then oxidized by an electrode. Alternatively, through the use of a dehydrogenase enzyme (e.g., 3-hydroxybuturate dehydrogenase or NADPH alcohol dehydrogenase), ketone bodies (e.g., beta-hydroxybutyric acid) can be reacted to generate a reduced electron mediator that can then travel to an electrode to create an electrochemical signal. The enzymes described herein may be cross-linked and/or stabilized and then immobilized in aqueous polyurethane, silicone, or hydrogel materials.

In some embodiments, the sensor has a ketone-specific diffusion resistance layer. A ketone-specific resistance layer may also be constructed by appropriate modification of the diffusion resistance layer noted above. For example, modification may be made of the above-noted polyurethane, silicone, or epoxy membrane systems. In many cases, a polyamide membrane system may be used as limited or no alternative pathways exist for membrane transport in such materials. Improved control of ketone permeability in these membranes may be enabled by control of hydrophilic channels within these membranes, as well as by control of the degree of membrane channel hydration and hydrogen bonding (PVP systems). That is, by control of such hydrophilic channels, e.g., size, density, structure, configuration, and the like, control may be exerted over the ketone permeability. Ketone membrane control may further be enabled by modifying or using a hybrid PEO/PVP hydrophile co-system for permeability across these membranes.

Various sports and fitness optimization routines are discussed above, and the same may benefit in certain programs as called for by flowcharts of FIGS. 1, 37-45, 47, 51, and 53, by the sensing and measurement of certain hormones related to workouts and stress, e.g., testosterone, cortisol, epinephrine, norepinephrine, insulin, and so on. In particular, cortisol is a stress hormone that is released when the body is stressed to physical exertion or emotional stress. Testosterone is a hormone that has significant implications on sports medicine, as well as on physical and emotional status. Real-time or retrospective monitoring of cortisol and/or testosterone, intermittently or continuously, may provide important information on the status of the body under physical and emotional stress. In addition, the ratio of the two parameters may also yield pertinent information. Such sensors can be used for performance athletics to optimize exercise regimens, monitor doping, and optimize muscle building or repair. Besides applications in sports optimization, such sensors may also be used for diagnosis and treatment of stress-related diseases, including chronic fatigue syndrome, irritable bowel syndrome, and post-traumatic stress disorder. The device may further be employed by the general population to monitor biochemical signals that reflect stress levels and impact an individual's mood, personality, and decision-making.

In one implementation, systems and methods according to present principles take such measurements and display the results in real time to a user. In this way, and using the programmatic methods described above with respect to flowcharts of FIGS. 1, 37-45, 47, 51, and 53, the systems and methods can be employed to drive behavioral change and adapt and/or personalize medical treatment.

Several sensing technologies can be employed to measure testosterone and cortisol. Such technologies include immunoelectrochemical sensors, specifically using alkaline phosphatase enzyme and cortisol antigen with detector antibodies. Direct attachment of antibodies on electrochemical surfaces can be used as an amperometric sensor. Antibodies—antigen binding can also be detected using impedance spectroscopy on electrochemical electrodes. Alternatively, optical detection methods can be used such as surface plasmon resonance with molecularly-imprinted films, fluorescence, FRET, Raman spectroscopy, and the like.

Figure 58:
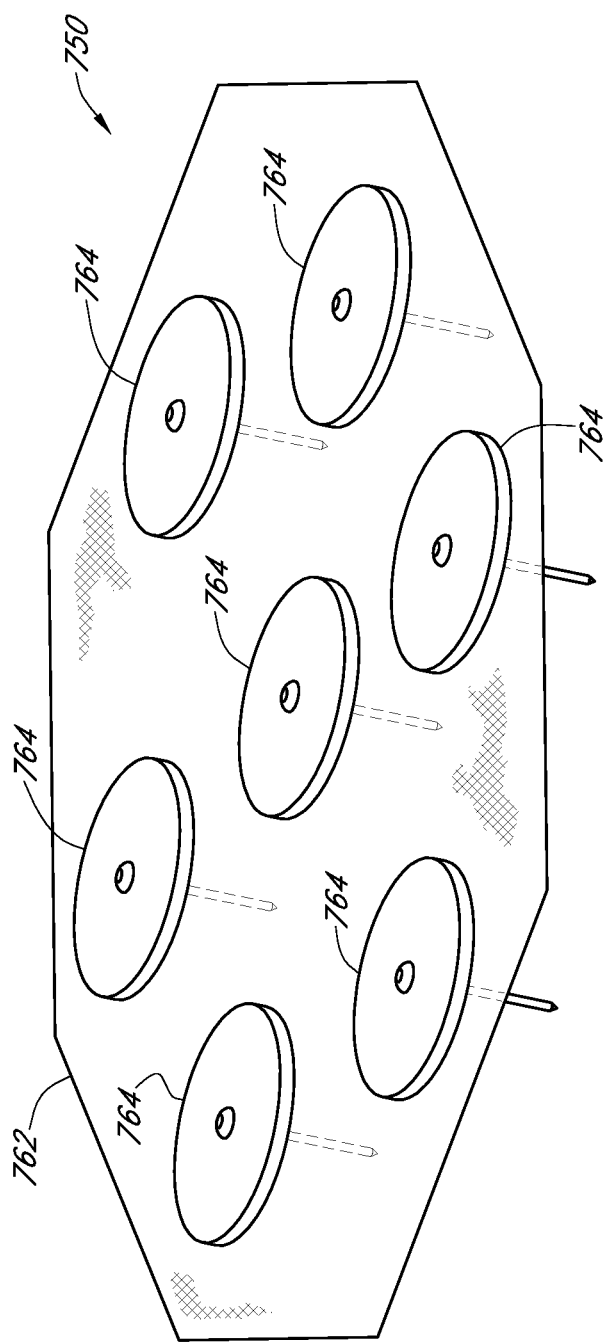
FIG. 58 illustrates one embodiment of a sensor system in which a plurality of sensor devices are grouped together to form a sensor array.

As noted above with respect to flowcharts of FIGS. 1, 37-45, 47, 51, and 53, in some implementations multiple analytes (or other physiological parameters, including heart rate, movement, motion, temperature, skin conductivity, and so on) may be monitored at one time. In some cases the multiple measurements may occur via separate sensors, each coupled to a common monitoring device. In other cases multiple measurements may occur via an array of sensors. One exemplary array of sensors is illustrated in FIG. 58, which illustrates an array 750 of sensors 764 on a framework 762. Additional details of such arrays of sensors may be found in U.S. Pat. Publ. No. 2011/0077490-A1, herein incorporated by reference in its entirety.

In the embodiment of FIG. 58, the individual sensor devices 764 are each attached to a laminate 762 that may comprise sensor electronics, and are thereby grouped together to form a sensor array 750. Alternatively or additionally, the laminate 762 may comprise a transmitter configured to transmit sensor data to a remote computer system. Transmission of sensor data to a remote computer system can be performed wirelessly or alternatively via a tether that provides an electrical connection between the sensor and the sensor electronics unit. The laminate 762 may comprise a plurality of layers, including an adhesive layer, for adhering the laminate to the skin. In certain embodiments, the laminate 762 and the sensor array 750 may be disposable and configured for single use.

In certain embodiments, the sensor devices of the sensor array may differ in a variety of characteristics, other than a difference in the insertion site. For example, some of the sensor devices of the array may be configured to measure glucose, while other sensor devices of the same array may be configured to measure one or more other analytes. For example, one or more of the sensor devices 764 of the array 750 may be configured to detect glucose, while other sensor devices 764 may be configured to detect and measure lactic acid, ketones, testosterone, cortisol, uric acid, or other analytes.

The information collected from the different sensor devices 764, in turn, may be processed, e.g., as input in an algorithm to perform or trigger calibration, to update calibration, and/or to validate or reject inaccurate reference analyte values, and data to generate an analyte concentration value that can be displayed to the user. Other information that may be collected include those corresponding to parameters that can affect sensor characteristics (e.g., sensor sensitivity or baseline). In some embodiments, different sensor devices of the sensor array may be configured to penetrate the skin at different preselected depths and reside in different layers (e.g., the stratum germinativum, dermis, subcutaneous layers) of the skin. For example, in some embodiments, the glucose sensor device measures at a first depth (which is ideal for glucose measurement), while a lactate sensor device measures at a second depth (which is ideal for lactate measurement), wherein the first and second depths are different.

In some embodiments, the plurality of sensor devices 764 are used to provide information regarding differences of a certain parameter along a plane of an area covered by the sensor array 750. The parameter may be related to physiological information, such as analyte concentration, so that an analyte concentration gradient can be measured. In one example, the sensor array 750 may be configured to detect a buildup of lactic acid in a certain locality (e.g. in certain muscles) as a result of exercise. Knowledge of lactic acid levels can allow a person (e.g., an athlete competing in a long distance running event) to determine and set a target pace (e.g., a certain running pace to achieve a goal time). As another example, the parameter may be related to the concentration of a drug, so that the body absorption rate of a drug can be determined.

In one implementation of an array of sensors, a system may be employed for continuous metabolic monitoring for the purpose of monitoring weight loss and gain. The sensing system may contain a sensor or array of sensors that monitors metabolic indicators that are influenced by the body state of fat build up or reduction. The monitors may indicate if the body's caloric intake was more than that used or if the body was burning more calories than consumed, e.g., where one sensor of the array measures insulin and another glucose. In this way, such a device may be employed for real-time information on the effectiveness of diets or exercise. The same can be employed as a behavior modification device or motivational tool for patients who are actively managing their health in accordance with, e.g., the flowcharts of FIGS. 45 and 51.

In a variation, the array may be a microneedle array where there is an array of sensors with one common mounting unit, rather than multiple mounting units. Calibration may be performed based on one sensor but need not be—each sensor may have its own calibration technique. In a particular implementation, all sensors are factory calibrated.

As noted above in connection with FIGS. 8 and 9, and for a particular example of metabolic monitoring, a simple readout may be provided where a threshold of neutral body fat metabolism is displayed and an indicator may be above the line if body fat is being gained or below if reduced. The distance above or below the line may indicate the magnitude or rate of energy storage or reduction. A trend graph may also be employed to indicate the amount and length of time of increasing or decreasing metabolism. Systems and methods according to present principles may allow for integrating the area under the curve to get a measure of total fat build up or reduction over time. The display may read out in real time or data may be stored for retrospective download and analysis.

Using information gained from an array of such sensors, systems and methods according to present principles may modify user behavior by communicating a patient's caloric intake and energy burn, and may motivate the user to balance that ratio or further reduce caloric intake or increase exercise (if the objective is to lose weight). The systems and methods may employ the programmatic functionality noted above, and use of such systems and methods may be of significant use in educating a user on the effects of food and exercise (and other variables) on their health, particularly their weight and fitness.

Particular analytes of interest measurable by the array of FIG. 58 may include those noted as useful above, e.g., involved in the conversion of fat into food storage or intermediaries between dietary inputs and fat, e.g., glucagon, insulin and other hormones involved in metabolic processes, glucose, glycogen, starch, free fatty acids, triglycerides, monoglycerides, troponin, cholesterol, proteins involved in fat storage, glycerol, pyruvate, lipids, and other carbohydrates. Other potential candidates for measurement include those involved in breaking down fat, e.g., glucagon, acetyl Co A, triglycerides, fatty acids, intermediaries in the citric acid cycle, ketone bodies such as acetone, acetoacetic acid and beta hydroxybutyric acid, lactate, and the like. Even further other potential candidates for measurement include molecules involved in aerobic or anaerobic metabolic pathways.

For weight loss optimization, sports optimization, as well as other programs as described above with respect to flowcharts of FIGS. 1, 37-45, 47, 51, and 53, various other analytes of interest will also be understood to be useful measures. For example, and as noted above, sensors may be employed in the measurement of lactate and/or lactic acid, particularly for health and fitness applications, in which the peak performance of an athlete is to be optimized. For example, one implementation of a body-worn lactate sensor may be similar to the CGM system described here but where the glucose oxidase is replaced with lactate oxidase. A small wire may go under the skin to record interstitial lactate levels. Alternatively, the lactate sensor could be noninvasive, and embodied by a patch such as for a sweat detector or an optical sensor, e.g., using near IR.

Such measurements may also be employed in the determination and quantification of a level of fat burning, calorie burning, and the like. Other useful sensors include cholesterol sensors, and sensors that track chemicals that in turn tract ingestion of medications. Such sensors may be employed to track compliance with the medication regimen, and the same may provide a signal indicating if a user has ingested the proper medication. Other sensors may also be employed, including those that measure: blood urea, adiponectin, nitrogen, bicarbonate, oxidizing species, oxidants, glycerol, free fatty acids, biochemical signals of mental health, body temperature, ICF (indicative of pancreas function), and so on.

Calibration

Calibration is the process of determining the relationship between the measured sensor signal and the analyte concentration in clinical units. Current CGM systems require finger stick calibrations and/or confirmations to ensure the accuracy of the system, e.g., for use in dosing. Alternative methods of calibration may be used that are still sufficient to meet the needs of the broader type II population, which may not require the same accuracy, or the same resolution of analyte concentration information, at least because users are not basing medicament dosing on such information. Rather, and as noted by the program-based flowcharts above, systems and methods according to present principles are more generally directed toward education of users and behavior modification.

Additional data may be employed to help the calibration as well. For example, if the user is a diabetic and is measuring their blood glucose several times a day anyway, such values may be employed as calibration values. In some cases it is not necessary to hone in on a particular value. Determination that a user is in a range of values may be sufficient for type II users. The range may be determined and used in providing the user with information about whether goals are being met, or other information about the program they are on.

Systems and methods according to present principles may further be employed to use calibration information about one sensor to calibrate another, e.g., an adjacent sensor, e.g., one under the same membrane. Such calibration may be performed, as drift parameters, if caused by the membrane, may be assumed to be the same for both sensors. For example, if both sensors are under the same membrane layer, e.g., a glucose sensor and a lactate sensor, and if one or more calibration parameters were determined ex vivo, then the calibration parameters may be assumed to bear a similar relationship in vivo, and thus the measurement of one can be used to determine the other. For example, if the lactate sensor has a known offset in calibration from the glucose sensor (or other relationship or scaling or correlation factor), as measured ex vivo, then in vivo, a determination of calibration for that glucose sensor may be employed to calibrate the lactate sensor. For example, if calibration of the glucose sensor is seen to drift by 50%, then the calibration of the lactate sensor may be assumed to have drifted by 50%. Consequently, an update of one or more calibration parameters of one sensor can result in the update of one or more calibration parameters of the other sensor.

Additional details of such aspects may be seen in U.S. Pat. Publ. No. 2010/0198035, U.S. Pat. Publ. No. 2011/0004085; and U.S. Pat. Publ. No. 2011/0024307, each of which is incorporated herein by reference in its entirety.

In addition, systems and methods according to present principles may use factory calibration information to start and then incorporate the automatic calibration technique over time to get more accurate glucose information. If the signal did not follow pre-prescribed parameters, or was outside of pre-prescribed parameters, the system could request a calibration value using known techniques, e.g., SMBG or finger stick calibrations. The systems and methods may then incorporate this glucose information into the original parameters to adjust the setpoint from, e.g., 100 mg/dL, to a more appropriate and accurate value. That is, while the above techniques intended for use in type II applications may be generally configured to avoid the need for finger stick calibrations, if such are available, systems and methods according to present principles may apply the same advantageously, for calibration purposes and otherwise.

Systems and methods according to present principles may be configured to determine a confidence level or range, and as the resolution or accuracy of the data changes, the confidence level or range can change. In more detail, the display could generate a value and a trend graph or the same may show a range or other UI element, as described in greater detail above. The range may also change over time and shrink or expand as a confidence in the accuracy changes. For instance, during initial warm-up, a factory calibration value may be utilized. However, its accuracy may not be as precise as it would be with additional information. During this time, the display may show a range rather than a value.

A further feature of systems and methods according to present principles are that they may request information when a user is set up within the system and adjust which technique to use depending on the information. For example, the system may prompt the user to enter whether they have type I diabetes, type II diabetes, or are nondiabetic, and may select a different technique depending upon the answer. Systems and methods according to present principles may further ask if the user is interested in weight loss optimization, sports and fitness optimization, or other like optimization routine, and may adjust the algorithm accordingly. The device may also, e.g., be used in a "blinded" mode for an extended period of time, e.g., 14 days, and only accept blood glucose values. These blood glucose values could be used to learn what a patient's resting blood glucose is, which could better guide the assumption of the auto calibration blood glucose value. After the extended period of time, the user could then use the device in auto calibration mode.

Other techniques may also be employed to simplify the calibration of sensors. In particular, where multiple sensors are employed, e.g., in a multi-sensor system such as that described in FIG. 58, the calibration of one sensor can be based on the calibration of another. This technique may be distinguished from that described above, where the calibration parameters are determined, and knowledge of their relationship ex vivo leads to knowledge of one implying knowledge of the other in vivo. In this former implementation, two analytes are monitored where one is easier to calibrate than the other. For example, the calibration of a glucose sensor may be based on that of a different analyte of interest, e.g., triglycerides, lactate, ketones, and so on. In a particular embodiment, tears, saliva, interstitial fluid, etc., may be employed as such alternative analytes. Conversely, the calibration of alternate analyte sensors may be based on a glucose calibration.

In general, in such systems, at least two analytes are monitored. One is easier to calibrate than the other. If there is a known relationship between the two analytes' calibrations or sensitivities, then the calibration of the sensor that is more difficult to calibrate can be based on the one that is easier to calibrate. In other words, calibration parameters of an analyte that is relatively easy to calibrate are determined and then used to estimate the calibration parameters of an analyte that is more difficult to calibrate. In some cases these involve steps of determining or estimating the sensitivity of the sensor. In a particular implementation, an analyte that is relatively easy to calibrate, such as glucose, is used to estimate a calibration (or sensitivity) of an analyte sensor that is relatively difficult to calibrate, such as lactate or lactic acid.

It is noted that in most cases the calibration-simplifying routines noted above with respect to glucose sensors may also be employed for other analyte sensors.

What has been described above are systems and methods for programmatically educating users about disease states, e.g., educating type II diabetic users about how to better manage their diabetes. For example, systems and methods have been described in which programs are prescribed for and/or selected by users, including where such programs are suggested based on recognized patterns. Variations and complementary routines will also be understood. For example, applications noted above may help coordinate and record subject user's actions during clinical studies. For example, if a clinical study requires one day with seven finger sticks at 30 minute intervals, then the schedule could be programmed into a digital calendar with alarms to remind the subject user throughout the study. The reminders may be displayed along with program reminders, or otherwise in addition thereto. Also, if the subject user's glucose spikes above a certain threshold, the app could trigger a voluntary survey which asks the subject user what they ate, what activities they took part in, or a request for another finger stick for more thorough analysis later. Such a survey may be performed in conjunction with the "discovery mode" discussed above. If the systems and methods are detecting extreme noise or any other data artifacts, then the same can immediately survey the subject user before the event is forgotten. Such systems and methods help ensure desired participation with clinical trials, e.g., ensuring finger sticks at the right times and intervals, as well as ensuring logging of daily events such as showers and actively capturing finger sticks during excursion events. The systems and methods may also help build a better record of paired events, which could be used to correlate user actions to specific data artifacts. Capturing finger sticks during excursions is particularly important for certain sensor performance metrics, such as sensitivity, baseline, and time lag. Such may be especially true for nondiabetic patients who have excursion events at lower frequencies and over shorter periods.

In another potential variation, systems and methods according to present principles may be used as a diagnostic, e.g., used in diagnostic tests to determine diabetes or other disease states, or to determine a level of progression of such disease states. That is, and in one example, systems and methods according to present principles may be able to provide an indication of the level of diabetes, as well as stages and severity thereof. Greater resolution may similarly be obtained on the progress of the disease, or the stage of progression or severity, as compared to prior metrics.

In yet another variation, a recommendation can be triggered to suggest a user see a physician if glucose (or other analyte) data is outside of set criteria. That is, for either diabetic or non-diabetic users, or users with other diseases or medical challenges, criteria may be programmed (which criteria may vary depending on user and/or condition) and if an appertaining analyte value meets the criteria, e.g., achieves a predetermined threshold, then an alert may be displayed. Similarly, patients may be alerted if relevant measured values are outside of a range or at a percentile in a distribution of individuals. The alert may provide advice on correction, e.g., to eat better, to eat certain foods, or may similarly recommend certain diets or exercise.

In yet another variation, CGM traces and other inputs (passive or active) may be employed to detect onset or progression of various complications, e.g., using CGM tracing to detect worsening of renal failure, sepsis, infection, flu, stress, sleep deprivation, shiftwork patterns for medication adjustment, and so on.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

As used herein, the term "determining" is a broad term, and is to be given its ordinary and customary meaning to a person of ordinary skill in the art (and is not to be limited to a special or customized meaning), and refers without limitation to a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer-readable medium may comprise non-transitory computer-readable medium (e.g., tangible media). In addition, in some aspects a computer-readable medium may comprise transitory computer-readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer-readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained. For example, a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

The system and method may be fully implemented in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or WiFi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where multiple types of data are contemplated, the plural inputs may allow plural devices or users to input relevant data at the same time.

What is claimed is:

1. A method of optimizing a diabetes therapy involving a medicament, comprising:
   receiving data about a first medicament to be ingested by a user in a first regimen, wherein the first regimen indicates a course of treatment for the user including ingestion of the first medicament;
   monitoring and storing glucose concentration data of the user;
   receiving data from a cloud connected source, the data pertaining to medicaments and/or regimens attempted by a plurality of other users, the plurality of other users determined by having similar demographics to the user;
   analyzing the monitored and stored glucose concentration data of the user, wherein the analyzing is based at least in part on the data pertaining to medicaments and/or regimens attempted by the plurality of users;
   evaluating the analyzed glucose concentration data of the user against the first regimen; and
   displaying an output responsive to the evaluating.

2. The method of claim 1, the similar demographics including one or more similar demographic parameters selected from the group consisting of: age, ethnicity, weight, BMI, and type of diabetes.

3. The method of claim 1, wherein the evaluating includes determining either the first medicament or the first regimen to be non-optimal for the user, and further comprising:
   determining a second medicament or a second regimen, or both, for the user; and
   displaying an output indicating the second medicament, or the second regimen, or both.

4. The method of claim 1, wherein the regimen includes data about a dosage of a respective medicament and the timing of ingestion of the respective medicament.

5. The method of claim 1, further comprising monitoring other data about the user, and wherein the analyzing or evaluating steps, or both, are based on the glucose concentration data and the other data.

6. The method of claim 5, wherein the other data includes activity data.

7. The method of claim 5, wherein the other data include data about other analytes.

8. The method of claim 5, wherein the other data include meal data.

9. The method of claim 8, wherein the meal data is received from:
   a social network;
   user entry;
   a food app; or
   photographic data.

10. The method of claim 1, further comprising determining user compliance with the regimen.

11. The method of claim 1, further comprising transmitting an indication of the output to a cloud connected entity, along with demographic data about the user.

* * * * *

UNITED STATES PATENT AND TRADEMARK OFFICE
CERTIFICATE OF CORRECTION

PATENT NO.         : 10,410,538 B2
APPLICATION NO.    : 15/148757
DATED              : September 10, 2019
INVENTOR(S)        : Peter C. Simpson et al.

It is certified that error appears in the above-identified patent and that said Letters Patent is hereby corrected as shown below:

On the Title Page

On page 2, Column 1, item (56), U.S. Patent Documents, Line 1, delete "Karnath et al." and insert -- Kamath et al. --.

In the Drawings

In sheet 46 of 66, FIG. 37, reference numeral 300, Line 4, delete "QUESTIONAIRE)" and insert -- QUESTIONNAIRE) --.

In sheet 54 of 66, FIG. 45, reference numeral 502, Line 5, delete "QUESTIONAIRE)" and insert -- QUESTIONNAIRE) --.

In sheet 60 of 66, FIG. 51, reference numeral 602, Line 5, delete "QUESTIONAIRE)" and insert -- QUESTIONNAIRE) --.

In the Specification

In Column 14, Line 37, delete "di splaying" and insert -- displaying --.

In Column 19, Line 52, delete "tryptophan)" and insert -- tryptophan --.

In Column 19, Line 52, delete "andrenostenedione;" and insert -- androstenedione; --.

In Column 20, Line 1, delete "diptheria" and insert -- diphtheria --.

In Column 20, Line 8, delete "perioxidase;" and insert -- peroxidase; --.

In Column 20, Line 17 approx., delete "sissomicin;" and insert -- sisomicin; --.

Signed and Sealed this
Twenty-fourth Day of December, 2019

Andrei Iancu
*Director of the United States Patent and Trademark Office*

CERTIFICATE OF CORRECTION (continued)
U.S. Pat. No. 10,410,538 B2

In Column 20, Line 22, delete "duodenalisa," and insert -- duodenalis, --.

In Column 20, Line 30, delete "Trepenoma pallidium," and insert -- Treponema pallidum, --.

In Column 20, Line 31, delete "stomatis" and insert -- stomatitis --.

In Column 23, Line 9, delete "L" and insert -- µL --.

In Column 35, Line 39, delete "ACOS," and insert -- ACOs, --.

In Column 49, Line 42, delete "Z."." and insert -- Z". --.

In Column 68, Line 3, delete "Z."" and insert -- Z" --.

In Column 69, Lines 13-14, delete "3-hydroxybuturate" and insert -- 3-hydroxybutyrate --.

In Column 75, Line 31, after "acids." insert -- Noninvasive techniques may also be employed. --.

In Column 83, Line 8, delete "(e)" and insert -- (e-) --.

In Column 87, Lines 18-19, delete "dichlorophenylindophenol" and insert -- dichlorophenolindophenol --.

In Column 91, Line 33, delete "ICF" and insert -- IPF --.